(12) United States Patent
Steyaert et al.

(10) Patent No.: US 12,252,521 B2
(45) Date of Patent: Mar. 18, 2025

(54) BINDING DOMAINS DIRECTED AGAINST GPCR:G PROTEIN COMPLEXES AND USES DERIVED THEREOF

(71) Applicants: VIB VZW, Ghent (BE); Vrije Universiteit Brussel, Brussels (BE); The Board of Trustees of the Leland Stanford Junior University, Palo Alto, CA (US); The Regents of the University of Michigan, Ann Arbor, MI (US)

(72) Inventors: Jan Steyaert, Beersel (BE); Els Pardon, Wezemaal (BE); Toon Laeremans, Dworp (BE); Brian Kobilka, Palo Alto, CA (US); Soren G. F. Rasmussen, Frederiksberg (DK); Sebastien Granier, Menlo Park, CA (US); Roger K Sunahara, Ann Arbor, MI (US)

(73) Assignees: The Board of Trustees of the Leland Stanford Junior University, Palo Alto, CA (US); Vrije Universiteit Brussel, Brussels (BE); The Regens of the University of Michigan, Ann Arbor, MI (US)

( * ) Notice: Subject to any disclaimer, the term of this patent is extended or adjusted under 35 U.S.C. 154(b) by 1322 days.

(21) Appl. No.: 16/852,235

(22) Filed: Apr. 17, 2020

(65) Prior Publication Data

US 2020/0239534 A1    Jul. 30, 2020

Related U.S. Application Data

(63) Continuation of application No. 15/583,540, filed on May 1, 2017, now Pat. No. 10,626,154, which is a continuation of application No. 14/129,100, filed as application No. PCT/EP2012/062036 on Jun. 21, 2012, now Pat. No. 9,695,227.

(60) Provisional application No. 61/571,159, filed on Jun. 21, 2011.

(30) Foreign Application Priority Data

Sep. 15, 2011   (EP) ..................................... 11181357

(51) Int. Cl.
| | |
|---|---|
| C07K 14/47 | (2006.01) |
| C07K 14/435 | (2006.01) |
| C07K 14/705 | (2006.01) |
| C07K 16/28 | (2006.01) |
| G01N 33/74 | (2006.01) |

(52) U.S. Cl.
CPC ........ *C07K 14/4722* (2013.01); *C07K 14/435* (2013.01); *C07K 14/705* (2013.01); *C07K 14/70571* (2013.01); *C07K 16/28* (2013.01); *G01N 33/74* (2013.01); *C07K 2317/22* (2013.01); *C07K 2317/569* (2013.01); *C12N 2799/026* (2013.01); *G01N 2333/726* (2013.01); *G01N 2500/02* (2013.01)

(58) Field of Classification Search
CPC .............. C07K 14/435; C07K 14/4722; C07K 14/705; C07K 14/70571; C07K 16/28; C07K 2317/22; C07K 2317/569; G01N 33/74; G01N 2333/726; G01N 2500/02
See application file for complete search history.

(56) References Cited

U.S. PATENT DOCUMENTS

| | | | |
|---|---|---|---|
| 5,721,121 | A | 2/1998 | Etcheverry et al. |
| 2007/0077597 | A1 | 4/2007 | Gilchrist et al. |
| 2007/0231830 | A1 | 10/2007 | Gilchrist et al. |

FOREIGN PATENT DOCUMENTS

| | | | |
|---|---|---|---|
| EP | 2723764 | A2 | 4/2014 |
| WO | 9404678 | A1 | 3/1994 |
| WO | 9937681 | A2 | 7/1999 |
| WO | 0043507 | A1 | 7/2000 |
| WO | 0190190 | A2 | 11/2001 |
| WO | 02085945 | A2 | 10/2002 |
| WO | 03025020 | A1 | 3/2003 |
| WO | 03035694 | A2 | 5/2003 |
| WO | 2004035614 | A1 | 4/2004 |
| WO | 2004049794 | A2 | 6/2004 |

(Continued)

OTHER PUBLICATIONS

Chung et al. (The Journal of Pharmacology and Experimental Therapeutics, 2005, 313:191-198) (Year: 2005).*

(Continued)

*Primary Examiner* — Jeremy C Flinders
(74) *Attorney, Agent, or Firm* — Patent Law Works LLP

(57) ABSTRACT

The present disclosure relates to the field of G protein coupled receptor (GPCR) structural biology and signaling. In particular, the present disclosure relates to binding domains directed against and/or specifically binding to GPCR:G protein complexes. Also provided are nucleic acid sequences encoding such binding domains and cells expressing or capable of expressing such binding domains. The binding domains of the present disclosure can be used as universal tools for the structural and functional characterization of G-protein coupled receptors in complex with downstream heterotrimeric G proteins and bound to various natural or synthetic ligands, for investigating the dynamic features of G protein activation, as well as for screening and drug discovery efforts that make use of GPCR:G protein complexes.

11 Claims, 23 Drawing Sheets
(23 of 23 Drawing Sheet(s) Filed in Color)
Specification includes a Sequence Listing.

(56) References Cited

FOREIGN PATENT DOCUMENTS

| WO | 2006086883 A1 | 8/2006 |
| --- | --- | --- |
| WO | 2009051633 A1 | 4/2009 |
| WO | 2009138519 A1 | 11/2009 |
| WO | 2009147196 A1 | 12/2009 |
| WO | 2010043650 A2 | 4/2010 |
| WO | 2010066740 A1 | 6/2010 |
| WO | 2012007593 A1 | 1/2012 |
| WO | 2012148586 A1 | 11/2012 |
| WO | 2012175643 A2 | 12/2012 |

OTHER PUBLICATIONS

Mijares et al. (Molecular Pharmacology, 2000, 58:373-379) (Year: 2000).*

Brown et al., Tolerance to single, but not Multiple, Amino Acid Replacements in Antibody VH CDR2, 1996, The American Association of Immunologists, 320, pp. 3285-3291.

European Communication in copending EP application No. 12 730 478.0 dated Feb. 22, 2016.

European Patent Office Communication for Application No. 17209368.4, mailing date Apr. 6, 2018.

Examiners Decision of Rejection for copending Japanese Patent Application No. 2014-516358; mailing date of Nov. 1, 2016.

International Search Report for PCT/EP2012/062036, mailed Apr. 19, 2013, 7 pages.

Japanese Notice of Rejection dated May 17, 2016, Japanese Patent Application No. 2014-516358.

Okuma Yet al., "Immunoprecipitation of Alpha-2-Adrenergic Receptor-GTP-Binding Protein Complexes Using GTP-Singing Protein Selective Antisera Changes in Receptor-GTP-Binding Protein Interaction Following Agonist Binding," Journal of Biological Chemistry, vol. 267, No. 21, 1992, pp. 14826-14831.

Rasmussen, Soren G. F., et al., "Structure of a nanobody-stabilized active state of the .beta.2 adrenoceptor," Nature, Nature Publishing Group, United Kingdom, vol. 469, No. 7329, Jan. 13, 2011, pp. 175-180.

Saini, Vikas, et al. "CXC Chemokine Receptor 4 Is a Cell Surface Receptor for Extracellular Ubiquitin." Journal Of Biological Chemistry, vol. 285, No. 20, 2010, pp. 15566-15576.

Staus et al., Regulation of beta2-Adrenergic Receptor Function by Conformationally Selective Single-Domain Intrabodies, Molecular Pharmacology, Mar. 2014, pp. 472-481, vol. 85, No. 3.

Steyaert et al., Nanobody stabilization of G protein-coupled receptor conformational states, Current Opinion in Structural Biology, 2011, pp. 567-572, vol. 21.

Translation of Text of the First Office Action in copending CN application No. 201280040585.9.

Vajdos et al., Comprehensive functional maps of the antigen-binding site on an anti-ErbB2 antibody with shotgun scanning mutagenesis, J Mol. Biol., 320 pp. 415-428, 2002.

Pardon, Els, et al., "Nanobody-Enabled Reverse Pharmacology on G-Protein-Coupled Receptors" Communications, Angewandte Chemie (2018) vol. 57, 5292-5295.

Rasmussen, Soren G F, et al. Crystal Structure of the B2 Adrenergic Receptor-Gs Protein Complex. Nature, vol. 477, No. 7366, 2011, pp. 549-555.

Saleh, Noureldin, et al. "Differences between G-Protein-Stabilized Agonist-GPCR Complexes and Their Nanobody-Stabilized Equivalents." Angewandte Chemie (International Ed.), vol. 56, No. 31, 2017, pp. 9008-9012.

Steyaert, Jan, and Brian K Kobilka. "Nanobody Stabilization of G Protein-Coupled Receptor Conformational States." Current Opinion in Structural Biology, vol. 21, No. 4, 2011, pp. 567-572.

Triest, Sarah, et al. "Production, Crystallization and Preliminary X-Ray Diffraction of the Gas α-Helical Domain in Complex with a Nanobody." Acta Crystallographica. Section F, Structural Biology Communications, vol. 70, No. 11, 2014, pp. 1504-1507.

* cited by examiner

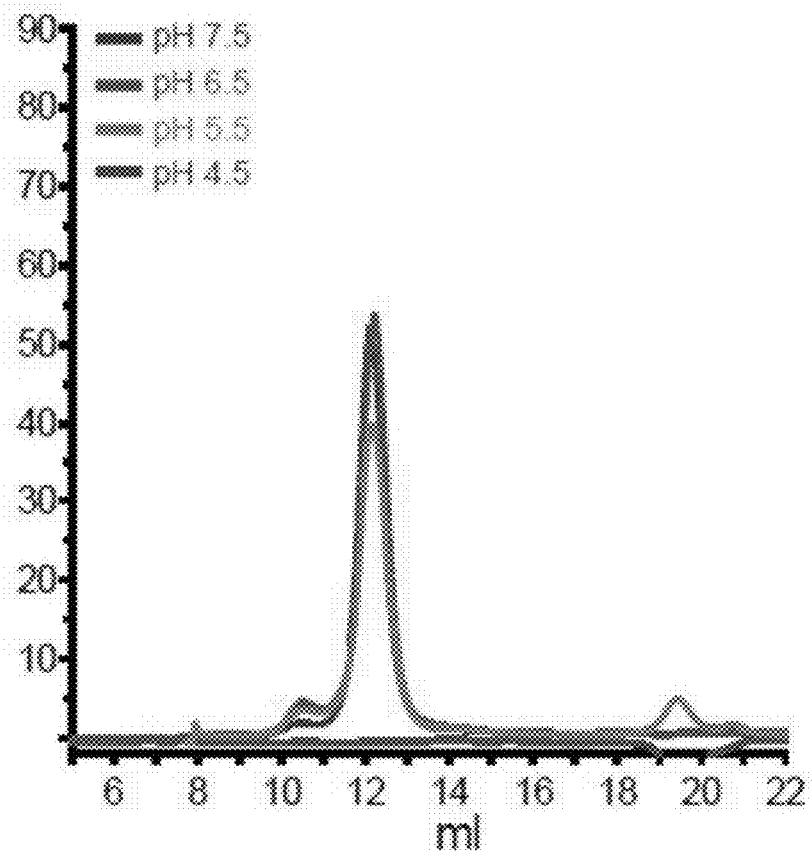

BINDING DOMAINS DIRECTED AGAINST GPCR:G PROTEIN COMPLEXES AND USES DERIVED THEREOF

CROSS-REFERENCE TO RELATED APPLICATIONS

This application is a continuation of U.S. patent application Ser. No. 15/583,540, filed May 1, 2017, pending, which is a continuation of U.S. patent application Ser. No. 14/129,100, filed Jun. 5, 2014, issued on Jul. 4, 2017 as U.S. Pat. No. 9,695,227, which is a national phase entry under 35 U.S.C. § 371 of International Patent Application PCT/EP2012/062036, filed Jun. 21, 2012, designating the United States of America and published in English as International Patent Publication WO 2012/175643 A2 on Dec. 27, 2012, which claims the benefit under Article 8 of the Patent Cooperation Treaty and under 35 U.S.C. § 119(e) to U.S. Provisional Patent Application Ser. No. 61/571,159, filed Jun. 21, 2011, and priority under Article 8 of the PCT to European Patent Application Serial No. 11181357.2, filed Sep. 15, 2011, the entirety of each of which are incorporated herein by this reference.

TECHNICAL FIELD

The present disclosure relates to the field of G protein coupled receptor (GPCR) structural biology and signaling. In particular, the present disclosure relates to binding domains directed against and/or specifically binding to GPCR:G protein complexes. Also provided are nucleic acid sequences encoding such binding domains and cells expressing or capable of expressing such binding domains. The binding domains of the present disclosure can be used as universal tools for the structural and functional characterization of G-protein coupled receptors in complex with downstream G proteins and bound to various natural or synthetic ligands, for investigating the dynamic features of G protein activation, as well as for screening and drug discovery efforts that make use of GPCR:G protein complexes.

STATEMENT ACCORDING TO 37 C.F.R. § 1.821(c) or (e)—SEQUENCE LISTING SUBMITTED AS PDF FILE WITH A REQUEST TO TRANSFER CRF FROM PARENT APPLICATION

Pursuant to 37 C.F.R. § 1.821(c) or (e), a file containing a PDF version of the Sequence Listing has been submitted concomitant with this application, the contents of which are hereby incorporated by reference. The transmittal documents of this application include a Request to Transfer CRF from the parent application.

BACKGROUND

Seven-transmembrane receptors (7TMRs), also called G protein-coupled receptors (GPCRs), are the largest class of receptors in the human genome and are the most commonly targeted protein class for medicinal therapeutics. Substantial progress has been made over the past three decades in understanding diverse GPCRs, from pharmacology to functional characterization in vivo. Recent high-resolution structural studies have provided insights into the molecular mechanisms of GPCR activation and constitutive activity (e.g., Rasmussen et al., 2011). However, the molecular details of how GPCRs interact with and regulate the activity of their downstream targets are still lacking. The structures of GPCRs in complex with their downstream proteins are of great interest not only because these interactions are pharmacologically relevant but also because the atomic understanding of the intermolecular interactions are key to unlocking the secrets of functional selectivity, the ability of different agonists to coerce distinct downstream effects from a single kind of receptor. Recent structural data support the idea that GPCRs, despite their small size, are sophisticated allosteric machines with multiple signaling outputs.

GPCRs, once activated, convey their signals in a GTP dependent manner via a complex of three proteins known as heterotrimeric G proteins, or Gαβγ. Binding of extracellular ligands to GPCRs modulates their capacity to catalyze GDP-GTP exchange in Gαβγ, thereby regulating the intracellular level of secondary messengers. The inactive Gαβγ heterotrimer is composed of two principal elements, Gα-GDP and the Gβγ heterodimer. Gβγ sequesters the switch II element on Gα such that it is unable to interact with second messenger systems, such as those involving cAMP, diacylglycerol and calcium. Activated GPCRs catalyze the release of GDP from Gα, allowing GTP to bind and liberate the activated Gα-GTP subunit. In this state, switch II forms a helix stabilized by the γ-phosphate of GTP allowing it to interact with effectors such as adenylyl cyclase. Although much progress has been made in understanding how Gα subunits interact with and regulate the activity of their downstream targets, it is not clear how activated GPCRs initiate this process by catalyzing nucleotide exchange on Gαβγ.

Drug discovery efforts generally focus on small molecule ligands that competitively bind to a particular catalytic or active site, using static models of the target as a starting point. This method has identified and validated a multitude of viable active-site therapeutics in use today. However, as reflected by the high failure rate of new drug compounds (only an estimated 8% of phase I clinical therapeutics eventually gain Food and Drug Administration approval, at a conservative cost of $800 million per drug), many efforts are unsuccessful and often targets are abandoned once they are deemed undrugable (Lee & Craik, 2009). A considerable part of these failures are due to the fact that the most prominent conformation of the target in question does not correspond to the drugable conformation to which a drug must bind to be effective for the therapeutic indication. For example, efforts to obtain an agonist-bound active-state GPCR structure have proven difficult due to the inherent instability of this state in the absence of a G protein. Recently it became possible to obtain structures of an active state of a GPCR, making use of conformationally selective stabilizing nanobodies or XAPERONES® that mimic G proteins and increase the affinity for agonists at the orthosteric site (Rasmussen et al., 2011). This demonstrates the power of XAPERONES® to lock the structure of the most challenging drug targets in a therapeutically relevant conformation (Steyaert & Kobilka, 2011) and their usefulness for directed drug discovery allowing to specifically screen for potential drugs with higher sensitivity and selectivity towards a particular target (WO2012007593). One limitation of this technological approach is that for each GPCR target a specific stabilizing nanobody needs to be identified, which is not only time-consuming and costly, but also implies the availability of different tools, like biological material for immunization and selection purposes, amongst others.

DISCLOSURE

Unraveling the structural and functional features of GPCRs in complex with their downstream heterotrimeric G proteins and bound to various natural and synthetic ligands is valuable both for understanding the mechanisms of GPCR signal transduction as well as for drug discovery efforts. For example, obtaining the structure of the active state ternary complex composed of the agonist, the GPCR and the G protein was so far unsuccessful but highly desired in the structural biology of signal transduction because of its poorly understood biology. Crystallogenesis of this complex turned out to be extremely difficult because one partner (the receptor) needs detergents to be solubilized while the G protein is unstable in detergents. Also, nucleotides that are required for the formation of the complex also dissociate the complex in a transient process.

Therefore, and very unexpectedly, the inventors identified tools that stabilize complexes of GPCRs and G proteins, which allowed them to capture and purify such complexes, and finally to crystallize such complexes. This will facilitate the identification of ligands or drug compounds by, for example, structure based virtual screening or design, high-throughput screening or fragment-based drug discovery (see, e.g., Example 10). More specifically, the inventors have identified binding domains, in particular immunoglobulin single variable domains, suitable for the structural and functional analysis of an active state complex composed of an agonist, GPCR and G protein (see, e.g., Example 4-7). Interestingly, it was demonstrated that some of these GPCR:G protein complex-selective binding domains are specifically directed against the G protein, and not against the GPCR. For example, binding domains were identified that bind Gs at the interface of G$\alpha$s and G$\beta\gamma$, without making contact with the beta-adrenergic receptor (see, e.g., Example 3), and will thus be useful to capture and stabilize other Gs coupled receptors, as was demonstrated for the arginine vasopressin receptor 2 (V2R) (see, e.g., Example 9). Thus, it is a particular advantage that binding domains are directed against the G protein of a GPCR:G protein complex, since such a binding domain can be used as generic tool to stabilize and capture active state complexes of the range of GPCRs that interact with that particular G protein.

Thus, according to a first aspect, the disclosure relates to a binding domain that is directed against and/or specifically binds to a complex comprising a GPCR and a G protein. More specifically, the binding domain as described herein binds with higher affinity to the GPCR:G protein complex as compared with binding to the G protein alone and/or to the GPCR alone, respectively. Also, the binding domain as described herein enhances the affinity of a G protein for a GPCR. Thus, the present disclosure provides for binding domains directed against and/or specifically binding to a conformational epitope of a complex comprising a GPCR and a G protein, and stabilizes or locks the complex in a particular conformational state, more specifically an active conformational state.

In general, the binding domain as described herein may bind to any conformational epitope that is made available or accessible by a complex of a GPCR and a G protein. These conformational epitopes may be represented by the individual proteins comprised in the complex, and/or may only be represented upon formation of the complex. Further, these conformational epitopes may or may not be represented by the individual proteins alone. According to one particular embodiment, the binding domain as described herein specifically binds to the G protein comprised in the complex, and not to the GPCR.

Typically, in nature, G proteins are in a nucleotide-bound form. More specifically, G proteins (or at least the $\alpha$ subunit) are bound to either GTP or GDP depending on the activation status of a particular GPCR, as described further herein. Agonist binding to a GPCR promotes interactions with the GDP-bound G$\alpha\beta\gamma$ heterotrimer leading to exchange of GDP for GTP on G$\alpha$, and the functional dissociation of the G protein into G$\alpha$-GTP and G$\beta\gamma$ subunits, which is needed for further intracellular signaling. In a specific embodiment, the binding domain as described herein specifically bind to and stabilize a GPCR:G protein complex in the absence of nucleotides, more specifically the binding domains bind to and stabilize a GPCR:G protein complex wherein the G protein is in a nucleotide free from. In a particular embodiment, the binding domain as described herein will specifically bind to a conformational epitope at the interface between the alpha and beta-gamma subunit of the G protein, and as such blocks the GDP/GTP binding site and interferes with GDP/GTP binding. As such, and surprisingly, the binding domain as described herein prevents or inhibits the dissociation of the GPCR:G protein complex in the presence of nucleotides, in particular guanine nucleotides or analogs thereof, such as GTP$\gamma$S. Also, the binding domain as described herein prevents or inhibits binding of nucleotides to the G protein.

Preferably, the binding domain as described herein is directed against and/or specifically binds to a complex comprising a GPCR, a G protein, and one or more receptor ligands. Typically, the receptor ligand will be an agonist or a positive allosteric modulator, or a combination thereof.

According to another preferred embodiment, the binding domain as described herein is directed against and/or specifically binds to a complex comprising a Gs protein coupled receptor and a Gs protein; or to a complex comprising a Gi protein coupled receptor and a Gi protein; or to complex comprising a Gt protein coupled receptor and a Gt protein; or to a complex comprising a Ggust protein coupled receptor and a Ggust protein; or to a complex comprising a Gz protein coupled receptor and a Gz protein; or to a complex comprising a Golf protein coupled receptor and a Golf protein; or to a complex comprising a Gq protein coupled receptor and a Gq protein; or to a complex comprising a G12 coupled receptor and a G12 protein; or to a complex comprising a G13 coupled receptor and a G13 protein. The GPCR and/or the G protein as comprised in the complex may be from the same or different species, in particular from a mammalian species. Preferably the GPCR is a human protein.

In general, a binding domain of the disclosure can be any non-naturally occurring molecule, or part thereof, that is able to specifically bind to a GPCR:G protein complex. Particularly, the binding domain as described herein is an immunoglobulin single variable domain comprising an amino acid sequence that comprises four framework regions (FR1 to FR4) and three complementarity-determining regions (CDR1 to CDR3), according to the following formula (1):

FR1-CDR1-FR2-CDR2-FR3-CDR3-FR4 (1).

Preferably, the binding domain as described herein is an immunoglobulin single variable domain derived from a Camelidae species, and particularly is a nanobody or $V_HH$.

According to specific embodiments, the binding domain as described herein is an immunoglobulin single variable domain comprising an amino acid sequence that comprises four framework regions (FR1 to FR4) and three complementarity-determining regions (CDR1 to CDR3), according to the following formula (1):

FR1-CDR1-FR2-CDR2-FR3-CDR3-FR4 (1);

and wherein CDR1 is chosen from the group consisting of:
a) SEQ ID NOs: 13-18,
b) Polypeptides that have at least 80% amino acid identity with SEQ ID NOs: 13-18,
c) Polypeptides that have 3, 2 or 1 amino acid difference with SEQ ID NOs: 13-18, and wherein CDR2 is chosen from the group consisting of:
a) SEQ ID NOs: 25-30,
b) Polypeptides that have at least 80% amino acid identity with SEQ ID NOs: 25-30,
c) Polypeptides that have 3, 2 or 1 amino acid difference with SEQ ID NOs: 25-30, and wherein CDR3 is chosen from the group consisting of:
a) SEQ ID NOs: 37-42,
b) Polypeptides that have at least 80% amino acid identity with SEQ ID NOs: 37-42,
c) Polypeptides that have 3, 2 or 1 amino acid difference with SEQ ID NOs: 37-42.

In a particularly preferred embodiment, the present disclosure provides for an immunoglobulin single variable domain comprising an amino acid sequence that comprises four framework regions (FR1 to FR4) and three complementarity-determining regions (CDR1 to CDR3), according to the following formula (1):

FR1-CDR1-FR2-CDR2-FR3-CDR3-FR4 (1);

wherein CDR1 is SEQ ID NO: 13;
wherein CDR2 is SEQ ID NO: 25; and
wherein CDR3 is SEQ ID NO: 37.

According to a very specific embodiment, the binding domain, in particular the immunoglobulin single variable domain, has an amino acid sequence selected from the group consisting of consisting of SEQ ID NOs: 1 to 6.

Further the binding domains as described herein may also be comprised in a polypeptide. Also, the binding domains may be immobilized on a solid support.

In one particular aspect, the present disclosure relates to a binding domain that is directed against and/or specifically binds to a G protein.

Another aspect of the disclosure envisages a complex comprising a binding domain as described herein. In particular, the complex comprises a GPCR, a G protein, and optionally a receptor ligand. In certain applications, the complex as described herein is crystalline.

Further, the disclosure also provides for nucleic acid sequences, in particular a nucleic acid sequence encoding any amino acid sequence of any of the binding domains as described herein, as well as recombinant vectors comprising any of the nucleic acid sequences as described herein. Particularly preferred aspects of the disclosure are cells comprising any of the vectors or nucleic acids as described herein, and as such, that can express or are capable of expressing a GPCR and/or a G protein. Cell cultures of cells according to the disclosure as well as membrane preparations derived thereof are also within the scope of the present invention.

The herein described binding domains, complexes and cells may be useful in a variety of contexts and applications. Thus, accordingly, one aspect of the disclosure relates to the use of a binding domain as described herein to stabilize a complex comprising a GPCR and a G protein, and optionally a receptor ligand, in a functional conformational state, more specifically in an active conformational state. In one specific embodiment, the binding domains as described herein can be used to prevent dissociation of the complex in the presence of nucleotides, in particular guanine nucleotides or analogs thereof, such as GTPγS. Binding domains as tools to stabilize GPCR:G protein complexes and block the GPCR in a functional conformational state, preferably an active conformational state, are thus very useful for a range of applications, as outlined hereafter.

Disclosed is the use of a binding domain as described herein to crystallize and/or to solve the structure of a complex comprising a GPCR and a G protein, and optionally a receptor ligand.

Also envisaged within the scope of the present disclosure is to use a binding domain as described herein or a cell or a membrane preparation derived thereof, as described herein, to screen for compounds that modulate the signaling activity of the GPCR.

Further, the binding domains as described herein may be used to capture one or more interacting proteins, in particular proteins that interact with the G protein and/or with the GPCR.

According to specific embodiments, the present disclosure provides for a method of capturing and/or purifying a complex comprising a GPCR and a G protein, the method comprising the steps of:
a) Providing a binding domain as described herein, and
b) Allowing the binding domain to bind to a complex comprising a GPCR and a G protein and optionally a receptor ligand, and
c) Optionally, isolating the complex formed in step b).

In another specific embodiment, the present disclosure relates to a method of determining the crystal structure of a complex comprising a GPCR and a G protein, the method comprising the steps of:
a) Providing a binding domain as described herein, and
b) Allowing the binding domain to bind to a complex comprising a GPCR and a G protein and optionally a receptor ligand, and
c) Crystallizing the complex formed in step b).

Some of the binding domains as described herein may have therapeutic utility. Thus, it is also an object of the disclosure to use the binding domains as described herein to modulate GPCR receptor signaling, in particular G protein-mediated GPCR receptor signaling.

The present disclosure further encompasses a method of producing a binding domain directed against and/or specifically binding to a complex comprising a GPCR and a G protein, the method comprising the steps of:
a) Expressing in a suitable cellular expression system a nucleic acid as described herein, and optionally,
b) Isolating and/or purifying the binding domain.

Another aspect of the present disclosure relates to a method of screening for binding domains directed against and/or specifically binding to a complex comprising a GPCR and a G protein, the method comprising the steps of:
a) Providing a plurality of binding domains, and
b) Screening the plurality of binding domains for a binding domain that binds to a complex comprising a GPCR and a G protein, and
c) Isolating the binding domain that binds to the complex.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 3A-3G: Effect of nucleotide analogs, pH, and nanobodies on the stability of the β2AR:Gs complex. FIG. 3A, Analytical gel filtration showing that nucleotides GDP and GTPγS (0.1 mM) causes dissociation of the $\beta_2AR$-365: Gs complex. FIG. 3B, The phosphates pyrophosphate and forcarnet (used at 5 mM) resembling the nucleotide phosphate groups did not cause disruption of the complex. They served as additives as they improved crystal growth of both the T4L-β2AR:Gs complex (without nanobodies), T4L-β2AR:Gs:Nb37, and T4L-β2AR:Gs:Nb35. FIG. 3C, The pH limit was determined to guide the preparation of crystallization screens. For the same purpose the effect of ionic strength (data not shown) was determined using NaCl at various concentrations. The complex is stable in 20, 100, and 500 mM NaCl but dissociates at 2.5 M NaCl. FIG. 3D, Nanobody 35 (Nb35, red broken line) binds to the T4L-β2AR:Gs:BI167107 ternary complex (blue solid line) to form the R:G:Nb35 complex (red solid line) which is insensitive to GTPγS treatment (green solid line) in contrast to the treated R:G complex (green broken line). Nb35 and Nb37 bind separate epitopes on the Gs heterotrimer to form a R:G:Nb35:Nb37 complex (purple solid line). FIG. 3E, Nanobody 36 (Nb36, red broken line) binds to the to the R:G complex (black solid line) to form the R:G:Nb36 complex (red solid line) which is less sensitive to GTPγS treatment (green solid line). Nb36 and Nb37 bind separate epitopes on the Gs heterotrimer to form a R:G:Nb36:Nb37 complex (purple solid line). FIG. 3F, Nanobody 37 (Nb37, green line) binds to the to the R:G complex (black solid line) to form the R:G:Nb37 complex (red solid line).

FIG. 3G, The R:G:Nb37 complex is insensitive to GTPγS treatment (blue solid line) in contrast to the treated R:G complex (blue broken line).

FIG. 10A, Two representative views on the interactions of CDR1

(space filling representation) of Nb35 (red) with Gβ (space filling, cyan). FIG. 10B, Two representative views on the interactions of CDR3 (space filling representation) of Nb35 (red) with GαS (space filling, orange) and G3 (space filling, cyan). By interacting with GαS and Gβ, Nb35 may reduce the conformational flexibility of the complex. FIG. 10C, Two representative views on the interactions of the framework regions of Nb35 (space filling representation, red) with GαS (orange).

DETAILED DESCRIPTION

Definitions

Figure 1:
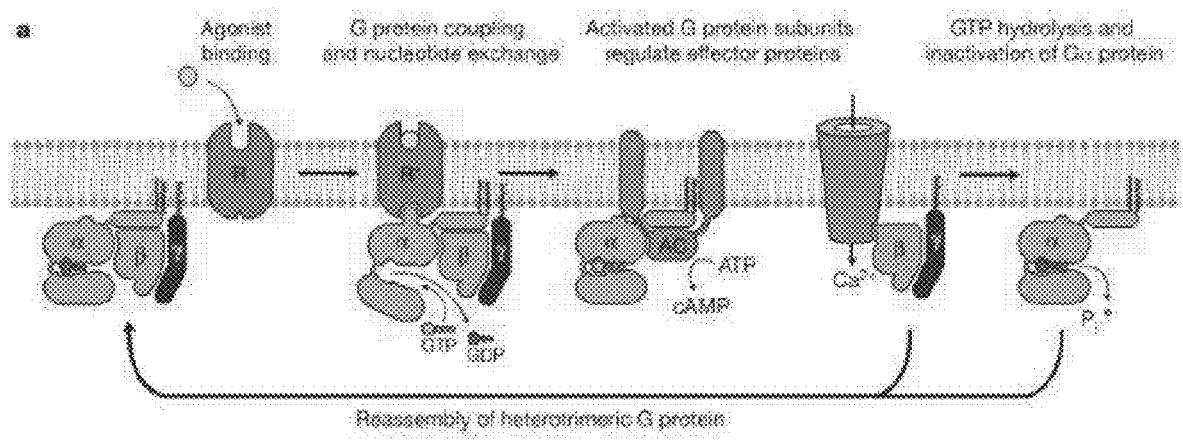
FIG. 1: G protein cycle for the $\beta_2AR$:Gs complex. Panel a, Extracellular agonist binding to the $\beta_2AR$ leads to conformational rearrangements of the cytoplasmic ends of transmembrane segments that enable the Gs heterotrimer ($\alpha$, $\beta$, and $\gamma$) to bind the receptor (R, R*). GDP is released from the $\alpha$ subunit upon formation of R:G complex. The GTP binds to the nucleotide-free $\alpha$ subunit resulting in dissociation of the $\beta$ and $\beta\gamma$ subunits from the receptor. The subunits regulate their respective effector proteins adenylyl cyclase (AC) and $Ca^{2+}$ channels. The Gs heterotrimer reassembles from $\alpha$ and $\beta\gamma$ subunits following hydrolysis of GTP to GDP in the $\alpha$ subunit. Panel b, The purified nucleotide-free $\beta_2AR$:Gs protein complex maintained in detergent micelles. The Gs$\alpha$ subunit consists of two domains, the Ras domain ($\alpha$Ras) and the $\alpha$-helical domain ($\alpha$AH). Both are involved in nucleotide binding. In the nucleotide-free state, the $\alpha$AH domain has a variable position relative the $\alpha$Ras domain.
Figure 1:
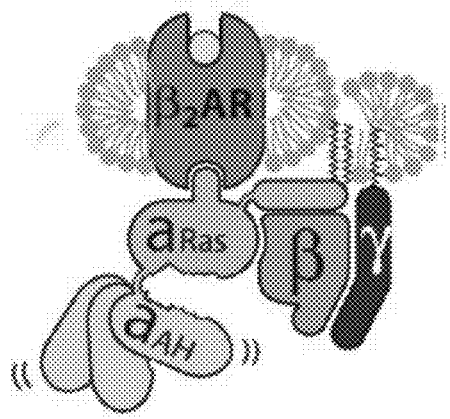

The present disclosure will be described with respect to particular embodiments and with reference to certain drawings but the disclosure is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun, e.g., "a" "an," or "the," this includes a plural of that noun unless something else is specifically stated. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the disclosure described herein are capable of operation in other sequences than described or illustrated herein.

Unless otherwise defined herein, scientific and technical terms and phrases used in connection with the present disclosure shall have the meanings that are commonly understood by those of ordinary skill in the art. Generally, nomenclatures used in connection with, and techniques of molecular and cellular biology, genetics and protein and nucleic acid chemistry and hybridization described herein are those well known and commonly used in the art. The methods and techniques of the present disclosure are generally performed according to conventional methods well known in the art and as described in various general and more specific references that are cited and discussed throughout the present specification unless otherwise indicated. See, for example, Sambrook et al., Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002).

The term "binding domain" or "protein binding domain" refers generally to any non-naturally occurring molecule, or part thereof, that is able to bind a protein or peptide using specific intermolecular interactions. A variety of molecules can function as protein binding domains, including, but not limited to, proteinaceous molecules (protein, peptide, protein-like or protein containing), nucleic acid molecules (nucleic acid, nucleic acid-like, nucleic acid containing), and carbohydrate molecules (carbohydrate, carbohydrate-like, carbohydrate containing). A more detailed description can be found further in the specification.

The terms "polypeptide," "protein," or "peptide" are used interchangeably herein, and refer to a polymeric form of amino acids of any length, which can include coded and non-coded amino acids, chemically or biochemically modified or derivatized amino acids, and polypeptides having modified peptide backbones.

As used herein, the term "protein complex" or simply "complex," refers to a group of two or more associated polypeptide chains. Proteins in a protein complex are linked by non-covalent protein-protein interactions. The "quaternary structure" is the structural arrangement of the associated folded proteins in the protein complex. It will be understood that the complex may be a multimeric complex comprising two, three, four, five, six or more polypeptides. Also, the complex may additionally comprise a non-proteinaceous molecule.

As used herein, the terms "nucleic acid molecule," "polynucleotide," "polynucleic acid," or "nucleic acid" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

As used herein, the term "ligand" or "receptor ligand" means a molecule that specifically binds to a GPCR, either intracellularly or extracellularly. A ligand may be, without the purpose of being limitative, a protein, a (poly)peptide, a lipid, a small molecule, a protein scaffold, an antibody, an antibody fragment, a nucleic acid, a carbohydrate. A ligand may be synthetic or naturally occurring. The term "ligand" includes a "native ligand" which is a ligand that is an endogenous, natural ligand for a native GPCR. In most cases, a ligand is a "modulator" that increases or decreases an intracellular response when it is in contact with, for example binds to, a GPCR that is expressed in a cell. Examples of ligands that are modulators include agonists, partial agonists, inverse agonists, and antagonists, of which a more detailed description can be found further in the specification.

The term "conformation" or "conformational state" of a protein refers generally to the range of structures that a protein may adopt at any instant in time. One of skill in the art will recognize that determinants of conformation or conformational state include a protein's primary structure as reflected in a protein's amino acid sequence (including modified amino acids) and the environment surrounding the protein. The conformation or conformational state of a protein also relates to structural features such as protein secondary structures (e.g., α-helix, β-sheet, among others), tertiary structure (e.g., the three dimensional folding of a polypeptide chain), and quaternary structure (e.g., interactions of a polypeptide chain with other protein subunits). Post-translational and other modifications to a polypeptide chain such as ligand binding, phosphorylation, sulfation, glycosylation, or attachments of hydrophobic groups, among others, can influence the conformation of a protein. Furthermore, environmental factors, such as pH, salt concentration, ionic strength, and osmolality of the surrounding solution, and interaction with other proteins and co-factors, among others, can affect protein conformation. The conformational state of a protein may be determined by either functional assay for activity or binding to another molecule or by means of physical methods such as X-ray crystallography, NMR, or spin labeling, among other methods. For a general discussion of protein conformation and conformational states, one is referred to Cantor and Schimmel, Biophysical Chemistry, Part I: The Conformation of Biological Macromolecules, W.H. Freeman and Company, 1980, and Creighton, Proteins: Structures and Molecular Properties, W.H. Freeman and Company, 1993. A "specific conformation" or "specific conformational state" is any subset of the range of conformations or conformational states that a protein may adopt.

As used herein, a "functional conformation" or a "functional conformational state," refers to the fact that proteins possess different conformational states having a dynamic range of activity, in particular ranging from no activity to maximal activity. Examples of functional conformational states include active conformations and inactive conformations. It should be clear that "a functional conformational state" is meant to cover any conformational state of a GPCR, having any activity, including no activity; and is not meant to cover the denatured states of proteins. A particular class of functional conformations that is envisaged here is a "drugable conformation" and generally refers to a unique therapeutically relevant conformational state of a target protein. As an illustration, the active conformation of the β2 adrenergic receptor corresponds to the drugable conformation of this receptor for the treatment of asthma. It will thus be understood that drugability is confined to particular conformations depending on the therapeutic indication.

The wording "locking" or "trapping" or "fixing" or "freezing" with respect to a functional conformational state of a GPCR (as defined herein), as used herein, refers to the retaining or holding of a GPCR in a subset of the possible conformations that it could otherwise assume, due to the effects of the interaction of the GPCR:G protein complex with the binding domain according to the invention. Accordingly, a protein that is "conformationally trapped" or "conformationally fixed" or "conformationally locked" or "conformationally frozen," as used herein, is one that is held in a subset of the possible conformations that it could otherwise assume, due to the effects of the interaction of the GPCR:G protein complex with the binding domain according to the invention. Within this context, a binding domain that specifically or selectively binds to a specific conformation or conformational state of a protein refers to a binding domain that binds with a higher affinity to a protein in a subset of conformations or conformational states than to other conformations or conformational states that the protein may assume. One of skill in the art will recognize that binding domains that specifically or selectively bind to a specific conformation or conformational state of a protein will stabilize this specific conformation or conformational state.

As used herein, the terms "complementarity-determining region" or "CDR" within the context of antibodies refer to variable regions of either H (heavy) or L (light) chains (also abbreviated as $V_H$ and $V_L$, respectively) and contains the amino acid sequences capable of specifically binding to antigenic targets. These CDR regions account for the basic specificity of the antibody for a particular antigenic determinant structure. Such regions are also referred to as "hypervariable regions." The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all canonical antibodies each have three CDR regions, each non-contiguous with the others (termed L1, L2, L3, H1, H2, H3) for the respective light (L) and heavy (H) chains. In particular, immunoglobulin single variable domains, such as nanobodies (as defined further herein), generally comprise a single amino acid chain that comprises four "framework sequences or regions" or FRs (termed FR1, FR2, FR3, FR4) and three complementarity-determining regions" or CDRs (termed CDR1, CDR2, CDR3), each non-contiguous with the others. The delineation of the CDR sequences (and thus also of the FR sequences) is based on the IMGT unique numbering system for V-domains and V-like domains (Lefranc et al., 2003).

An "epitope," as used herein, refers to an antigenic determinant of a polypeptide. An epitope could comprise three amino acids in a spatial conformation, which is unique to the epitope. Generally an epitope consists of at least 4, 5, 6, 7 such amino acids, and more usually, consists of at least 8, 9, 10 such amino acids. Methods of determining the spatial conformation of amino acids are known in the art, and include, for example, x-ray crystallography and multidimensional nuclear magnetic resonance.

A "conformational epitope," as used herein, refers to an epitope comprising amino acids in a spatial conformation that is unique to a folded 3-dimensional conformation of the polypeptide. Generally, a conformational epitope consists of amino acids that are discontinuous in the linear sequence that come together in the folded structure of the protein. However, a conformational epitope may also consist of a linear sequence of amino acids that adopts a conformation that is unique to a folded 3-dimensional conformation of the polypeptide (and not present in a denatured state). In protein complexes, conformational epitopes consist of amino acids that are discontinuous in the linear sequences of one or more polypeptides that come together upon folding of the different folded polypeptides and their association in a unique quaternary structure. Similarly, conformational epitopes may here also consist of a linear sequence of amino acids of one or more polypeptides that come together and adopt a conformation that is unique to the quaternary structure.

The term "specificity," as used herein, refers to the ability of a binding domain, in particular an immunoglobulin, such as an antibody, or an immunoglobulin fragment, such as a nanobody, to bind preferentially to one antigen, versus a different antigen, and does not necessarily imply high affinity (as defined further herein). A binding domain, in particular an immunoglobulin, such as an antibody, or an immunoglobulin fragment, such as a nanobody, that can specifically bind to and/or that has affinity for a specific antigen or antigenic determinant (e.g., epitope) is said to be "against" or "directed against" the antigen or antigenic determinant. A binding domain according to the disclosure is said to be "cross-reactive" for two different antigens or antigenic determinants if it is specific for both these different antigens or antigenic determinants.

The term "affinity," as used herein, refers to the degree to which a binding domain, in particular an immunoglobulin, such as an antibody, or an immunoglobulin fragment, such as a nanobody, binds to an antigen so as to shift the equilibrium of antigen and binding domain toward the presence of a complex formed by their binding. Thus, for example, where an antigen and antibody (fragment) are combined in relatively equal concentration, an antibody (fragment) of high affinity will bind to the available antigen so as to shift the equilibrium toward high concentration of the resulting complex. The dissociation constant ($K_d$) is commonly used to describe the affinity between the protein binding domain and the antigenic target. Typically, the dissociation constant is lower than $10^{-5}$ M. Preferably, the dissociation constant is lower than $10^{-6}$ M, more preferably, lower than $10^{-7}$ M. Most preferably, the dissociation constant is lower than $10^{-8}$ M.

The terms "specifically bind" and "specific binding," as used herein, generally refers to the ability of a binding domain, in particular an immunoglobulin, such as an antibody, or an immunoglobulin fragment, such as a nanobody, to preferentially bind to a particular antigen that is present in a homogeneous mixture of different antigens. In certain embodiments, a specific binding interaction will discriminate between desirable and undesirable antigens in a sample, in some embodiments more than about 10 to 100-fold or more (e.g., more than about 1000- or 10,000-fold).

The terms "specifically bind," "selectively bind," "preferentially bind," and grammatical equivalents thereof, are used interchangeably herein. The terms "conformational specific" or "conformational selective" are also used interchangeably herein.

A "deletion" is defined here as a change in either amino acid or nucleotide sequence in which one or more amino acid or nucleotide residues, respectively, are absent as compared to an amino acid sequence or nucleotide sequence of a parental polypeptide or nucleic acid. Within the context of a protein or a fragment thereof, a deletion can involve deletion of about 2, about 5, about 10, up to about 20, up to about 30 or up to about 50 or more amino acids. A protein or a fragment thereof may contain more than one deletion. Within the context of a GPCR, a deletion may in particular be a loop deletion, or an N- and/or C-terminal deletion.

An "insertion" or "addition" is that change in an amino acid or nucleotide sequence which has resulted in the addition of one or more amino acid or nucleotide residues, respectively, as compared to an amino acid sequence or nucleotide sequence of a parental protein. "Insertion" generally refers to addition to one or more amino acid residues within an amino acid sequence of a polypeptide, while "addition" can be an insertion or refer to amino acid residues added at an N- or C-terminus, or both termini. Within the context of a protein or a fragment thereof, an insertion or addition is usually of about 1, about 3, about 5, about 10, up to about 20, up to about 30 or up to about 50 or more amino acids. A protein or fragment thereof may contain more than one insertion.

A "substitution," as used herein, results from the replacement of one or more amino acids or nucleotides by different amino acids or nucleotides, respectively as compared to an amino acid sequence or nucleotide sequence of a parental protein or a fragment thereof. It is understood that a protein or a fragment thereof may have conservative amino acid substitutions which have substantially no effect on the protein's activity. By conservative substitutions is intended combinations such as gly, ala; val, ile, leu, met; asp, glu; asn, gln; ser, thr; lys, arg; cys, met; and phe, tyr, trp.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Determining the percentage of sequence identity can be done manually, or by making use of computer programs that are available in the art.

"Crystal" or "crystalline structure," as used herein, refers to a solid material, whose constituent atoms, molecules, or ions are arranged in an orderly repeating pattern extending in all three spatial dimensions. The process of forming a crystalline structure from a fluid or from materials dissolved in the fluid is often referred to as "crystallization" or "crystallogenesis." Protein crystals are almost always grown in solution. The most common approach is to lower the solubility of its component molecules gradually. Crystal growth in solution is characterized by two steps: nucleation of a microscopic crystallite (possibly having only 100 molecules), followed by growth of that crystallite, ideally to a diffraction-quality crystal.

"X-ray crystallography," as used herein, is a method of determining the arrangement of atoms within a crystal, in which a beam of X-rays strikes a crystal and diffracts into many specific directions. From the angles and intensities of these diffracted beams, a crystallographer can produce a three-dimensional picture of the density of electrons within the crystal. From this electron density, the mean positions of the atoms in the crystal can be determined, as well as their chemical bonds, their disorder and various other information, as will be known by those skilled in the art.

The term "atomic coordinates," as used herein, refers to a set of three-dimensional co-ordinates for atoms within a molecular structure. In one embodiment, atomic-co-ordinates are obtained using X-ray crystallography according to methods well-known to those of ordinarily skill in the art of biophysics. Briefly described, X-ray diffraction patterns can be obtained by diffracting X-rays off a crystal. The diffraction data are used to calculate an electron density map of the unit cell comprising the crystal; the maps are used to establish the positions of the atoms (i.e., the atomic co-ordinates) within the unit cell. Those skilled in the art understand that a set of structure co-ordinates determined by X-ray crystallography contains standard errors. In other embodiments, atomic co-ordinates can be obtained using other experimental biophysical structure determination methods that can include electron diffraction (also known as electron crystallography) and nuclear magnetic resonance (NMR) methods. In yet other embodiments, atomic coordinates can be obtained using molecular modeling tools which can be based on one or more of ab initio protein folding algorithms, energy minimization, and homology-based modeling. These techniques are well known to persons of ordinary skill in the biophysical and bioinformatic arts.

"Solving the structure" as used herein refers to determining the arrangement of atoms or the atomic coordinates of a protein, and is often done by a biophysical method, such as X-ray crystallography.

The term "compound" or "test compound" or "candidate compound" or "drug candidate compound" as used herein describes any molecule, either naturally occurring or synthetic that is tested in an assay, such as a screening assay or drug discovery assay. As such, these compounds comprise organic and inorganic compounds. The compounds include polynucleotides, lipids or hormone analogs that are characterized by low molecular weights. Other biopolymeric organic test compounds include small peptides or peptide-like molecules (peptidomimetics) comprising from about 2 to about 40 amino acids and larger polypeptides comprising from about 40 to about 500 amino acids, such as antibodies, antibody fragments or antibody conjugates. Test compounds can also be protein scaffolds. For high-throughput purposes, test compound libraries may be used, such as combinatorial or randomized libraries that provide a sufficient range of diversity. Examples include, but are not limited to, natural compound libraries, allosteric compound libraries, peptide libraries, antibody fragment libraries, synthetic compound libraries, fragment-based libraries, phage-display libraries, and the like. A more detailed description can be found further in the specification.

As used herein, the terms "determining," "measuring," "assessing," "monitoring," and "assaying" are used interchangeably and include both quantitative and qualitative determinations.

The term "biologically active," with respect to a GPCR, refers to a GPCR having a biochemical function (e.g., a binding function, a signal transduction function, or an ability to change conformation as a result of ligand binding) of a naturally occurring GPCR.

The terms "therapeutically effective amount," "therapeutically effective dose" and "effective amount," as used herein, mean the amount needed to achieve the desired result or results.

The term "pharmaceutically acceptable," as used herein, means a material that is not biologically or otherwise undesirable, i.e., the material may be administered to an individual along with the compound without causing any undesirable biological effects or interacting in a deleterious manner with any of the other components of the pharmaceutical composition in which it is contained.

DETAILED DESCRIPTION

Despite the great diversity of ligands that may activate GPCRs, they interact with a relatively small number of intracellular proteins to induce profound physiological change. Heterotrimeric G proteins, β-arrestins and GPCR kinases are well known for their ability to specifically recognize GPCRs in their active state, though poorly understood both from a structural as well as functional point of view. Therefore, surprisingly and advantageously, binding domains were identified that specifically bind to GPCR:G protein complexes and are capable of stabilizing or locking the complex in a functional conformational state, in particular an active conformational state. Moreover, the binding domains are generic tools for stabilization and capturing of a GPCR of choice in its G protein-bound state, which is generally assumed to represent an active state of a GPCR (as defined herein).

Accordingly, a first aspect of the disclosure relates to a binding domain that is directed against and/or specifically binds to a complex comprising a GPCR and a G protein.

The binding domain of the present disclosure can be any non-naturally occurring molecule or part thereof (as defined hereinbefore) that is capable of specifically binding to a complex comprising a GPCR and a G protein. According to a preferred embodiment, the binding domains as described herein are protein scaffolds. The term "protein scaffold" refers generally to folding units that form structures, particularly protein or peptide structures, that comprise frameworks for the binding of another molecule, for instance a protein (See, e.g., Skerra (2000), for review). A binding domain can be derived from a naturally occurring molecule, e.g., from components of the innate or adaptive immune system, or it can be entirely artificially designed. A binding domain can be immunoglobulin-based or it can be based on domains present in proteins, including but not limited to microbial proteins, protease inhibitors, toxins, fibronectin, lipocalins, single chain antiparallel coiled coil proteins or repeat motif proteins. Examples of binding domains which are known in the art include, but are not limited to: antibodies, heavy chain antibodies (hcAb), single domain antibodies (sdAb), minibodies, the variable domain derived from camelid heavy chain antibodies (VHH or nanobodies), the variable domain of the new antigen receptors derived from shark antibodies (VNAR), alphabodies, protein A, protein G, designed ankyrin-repeat domains (DARPins), fibronectin type III repeats, anticalins, knottins, engineered CH2 domains (nanoantibodies), peptides and proteins, lipopeptides (e.g., pepducins), DNA, and RNA (see, e.g., Gebauer & Skerra, 2009; Skerra, 2000; Starovasnik et al., 1997; Binz et al., 2004; Koide et al., 1998; Dimitrov, 2009; Nygren et al., 2008; WO2010066740). Frequently, when generating a particular type of binding domain using selection methods, combinatorial libraries comprising a consensus or framework sequence containing randomized potential interaction residues are used to screen for binding to a molecule of interest, such as a protein.

The binding domain of the present disclosure may be directed against and/or specifically bind any GPCR:G protein complex of choice. Preferred target complexes are complexes of a GPCR and a G protein that occur in nature or, alternatively, for example in case of non-naturally occurring variants (as described further herein) of GPCRs and G protein, complexes wherein the GPCR and the G protein will associate under the appropriate physiological conditions. It will be understood by the person skilled in the art that the structural relationship between GPCR and G protein determines whether a particular GPCR:G protein complex can be formed, which will be detailed further below for members of the G protein family and members of the GPCR family.

With "G proteins" are meant the family of guanine nucleotide-binding proteins involved in transmitting chemical signals outside the cell, and causing changes inside the cell. G proteins are key molecular components in the intracellular signal transduction following ligand binding to the extracellular domain of a GPCR. They are also referred to as "heterotrimeric G proteins," or "large G proteins." G proteins consist of three subunits: alpha ($\alpha$), beta ($\beta$), and gamma ($\gamma$) and their classification is largely based on the identity of their distinct $\alpha$ subunits, and the nature of the subsequent transduction event. Further classification of G proteins has come from cDNA sequence homology analysis. G proteins bind either guanosine diphosphate (GDP) or guanosine triphosphate (GTP), and possess highly homologous guanine nucleotide binding domains and distinct domains for interactions with receptors and effectors. Different subclasses of G$\alpha$ proteins, such as G$\alpha$s, G$\alpha$i, G$\alpha$q and G$\alpha$12, amongst others, signal through distinct pathways involving second messenger molecules such as cAMP, inositol triphosphate (IP3), diacylglycerol, intracellular $Ca^{2+}$ and RhoA GTPases. To illustrate this further, the $\alpha$ subunit (39-46 kDa) contains the guanine nucleotide binding site and possesses GTPase activity; the $\beta$ (37 kDa) and $\gamma$ (8 kDa) subunits are tightly associated and function as a $\beta\gamma$ heterodimer. There are 23 types (including some splicing isoforms) of $\alpha$ subunits, 6 of $\beta$, and 11 of $\gamma$ currently described. The classes of G protein and subunits are subscripted: thus, for example, the a subunit of Gs protein (which activates adenylate cyclase) is Gs$\alpha$; other G proteins include Gi, which differs from Gs structurally (different type of a subunit) and inhibits adenylate cyclase. Further examples are provided in Table 1.

Typically, in nature, G proteins are in a nucleotide-bound form. More specifically, G proteins (or at least the a subunit) are bound to either GTP or GDP depending on the activation status of a particular GPCR. Agonist binding to a GPCR promotes interactions with the GDP-bound G$\alpha\beta\gamma$ heterotrimer leading to the exchange of GDP for GTP on G$\alpha$, and the functional dissociation of the G protein into G$\alpha$-GTP and G$\beta\gamma$ subunits. The separate G$\alpha$-GTP and G$\beta\gamma$ subunits can modulate, either independently or in parallel, downstream cellular effectors (channels, kinases or other enzymes, see Table 1). The intrinsic GTPase activity of G$\gamma$ leads to hydrolysis of GTP to GDP and the re-association of G$\alpha$-GDP and G$\beta\gamma$ subunits, and the termination of signaling. Thus, G proteins serve as regulated molecular switches capable of eliciting bifurcating signals through $\alpha$ and $\beta\gamma$ subunit effects. The switch is turned on by the receptor and it turns itself off within a few seconds, a time sufficient for considerable amplification of signal transduction.

"G-protein coupled receptors," or "GPCRs," as used herein, are polypeptides that share a common structural motif, having seven regions of between 22 to 24 hydrophobic amino acids that form seven alpha helices, each of which spans the membrane. Each span is identified by number, i.e., transmembrane-1 (TM1), transmembrane-2 (TM2), etc. The transmembrane helices are joined by regions of amino acids between transmembrane-2 and transmembrane-3, transmembrane-4 and transmembrane-5, and transmembrane-6 and transmembrane-7 on the exterior, or "extracellular" side, of the cell membrane, referred to as "extracellular" regions 1, 2 and 3 (EC1, EC2 and EC3), respectively. The transmembrane helices are also joined by regions of amino acids between transmembrane-1 and transmembrane-2, transmembrane-3 and transmembrane-4, and transmembrane-5 and transmembrane-6 on the interior, or "intracellular" side, of the cell membrane, referred to as "intracellular" regions 1, 2 and 3 (IC1, IC2 and IC3), respectively. The "carboxy" ("C") terminus of the receptor lies in the intracellular space within the cell, and the "amino" ("N") terminus of the receptor lies in the extracellular space outside of the cell. Any of these regions are readily identifiable by analysis of the primary amino acid sequence of a GPCR.

GPCR structure and classification is generally well known in the art and further discussion of GPCRs may be found in Probst et al., 1992; Marchese et al., 1994; Lagerström & Schiöth, 2008; Rosenbaum et al., 2009; and the following books: Jurgen Wess (Ed) Structure-Function Analysis of G Protein-Coupled Receptors published by Wiley-Liss (1 st edition; Oct. 15, 1999); Kevin R. Lynch (Ed) Identification and Expression of G Protein-Coupled Receptors published by John Wiley & Sons (March 1998) and Tatsuya Haga (Ed), G Protein-Coupled Receptors, published by CRC Press (Sep. 24, 1999); and Steve Watson (Ed) G-Protein Linked Receptor Factsbook, published by Academic Press (1st edition; 1994). GPCRs can be grouped on the basis of sequence homology into several distinct families. Although all GPCRs have a similar architecture of seven membrane-spanning α-helices, the different families within this receptor class show no sequence homology to one another, thus suggesting that the similarity of their transmembrane domain structure might define common functional requirements. A comprehensive view of the GPCR repertoire was possible when the first draft of the human genome became available. Fredriksson and colleagues divided 802 human GPCRs into families on the basis of phylogenetic criteria. This showed that most of the human GPCRs can be found in five main families, termed Rhodopsin, Adhesion, Secretin, Glutamate, Frizzled/Taste2 (Fredriksson et al., 2003).

Members of the Rhodopsin family (corresponding to class A (Kolakowski, 1994) or Class 1 (Foord et al. (2005) in older classification systems) only have small extracellular loops and the interaction of the ligands occurs with residues within the transmembrane cleft. This is by far the largest group (>90% of the GPCRs) and contains receptors for odorants, small molecules such as catecholamines and amines, (neuro)peptides and glycoprotein hormones. Rhodopsin, a representative of this family, is the first GPCR for which the structure has been solved (Palczewski et al., 2000). β2-AR, the first receptor interacting with a diffusible ligand for which the structure has been solved (Rosenbaum et al., 2007) also belongs to this family. Based on phylogenetic analysis, class B GPCRs or Class 2 (Foord et al., 2005) receptors have recently been subdivided into two families: adhesion and secretin (Fredriksson et al., 2003). Adhesion and secretin receptors are characterized by a relatively long amino terminal extracellular domain involved in ligand-binding. Little is known about the orientation of the transmembrane domains, but it is probably quite different from that of rhodopsin. Ligands for these GPCRs are hormones, such as glucagon, secretin, gonadotropin-releasing hormone and parathyroid hormone. The Glutamate family receptors (Class C or Class 3 receptors) also have a large extracellular domain, which functions like a "Venus fly trap" since it can open and close with the agonist bound inside. Family members are the metabotropic glutamate, the $Ca^{2+}$-sensing and the γ-aminobutyric acid (GABA)-B receptors.

GPCRs include, without limitation, serotonin olfactory receptors, glycoprotein hormone receptors, chemokine receptors, adenosine receptors, biogenic amine receptors, melanocortin receptors, neuropeptide receptors, chemotactic receptors, somatostatin receptors, opioid receptors, melatonin receptors, calcitonin receptors, PTH/PTHrP receptors, glucagon receptors, secretin receptors, latrotoxin receptors, metabotropic glutamate receptors, calcium receptors, GABA-B receptors, pheromone receptors, the protease-activated receptors, the rhodopsins and other G-protein coupled seven transmembrane segment receptors. GPCRs also include these GPCR receptors associated with each other as homomeric or heteromeric dimers or as higher-order oligomers. The amino acid sequences (and the nucleotide sequences of the cDNAs which encode them) of GPCRs are readily available, for example by reference to GenBank (on the World Wide Web at ncbi.nlm.nih.gov/entrez).

Thus, according to specific embodiments, the present disclosure provides for binding domains that are directed against and/or specifically bind GPCR:G protein complexes wherein the G protein is selected from the group consisting of Gs, Gi, Go, Gt, Ggust, Gz, Golf, Gq, G12 and G13. In one preferred embodiment, the G protein is Gs. In another preferred embodiment, the G protein is Gi. In still another preferred embodiment, the G protein is Gt, more specifically transducin. In correspondence thereto, the GPCR comprised within the complex is selected from the group consisting of a Gs coupled receptor, a Gi coupled receptor, a Go coupled receptor, a Gt coupled receptor, a Ggust coupled receptor, a Golf coupled receptor, a Gq coupled receptor, a G12 coupled receptor and a G13 coupled receptor. In one preferred embodiment, the GPCR is a Gs coupled receptor. In another preferred embodiment, the GPCR is a Gi coupled receptor. In still another preferred embodiment, the GPCR is a Gt coupled receptor, more specifically rhodopsin. Particular non-limiting examples are provided in Table 1.

TABLE 1

Non-limiting examples of the relationship of G protein-coupled receptors and signaling pathways.

| G protein family | | Effectors/Signaling pathways | Use/Receptors |
|---|---|---|---|
| Gi family | α subunit | | |
| Gi | αi | Inhibition of adenylate cyclase (cAMP ↓) Closing $Ca^{2+}$ channels ($Ca^{2+}$↓) | Acetylcholine M2 & M4 receptors |
| Go | αo | | Adenosine A1 & A3 receptors |
| | | | Adrenergic α2A, α2B, & α2C receptors |
| | | | Apelin receptors |
| | | | Calcium-sensing receptor |
| | | | Chemokine CXCR4 receptor |
| | | | Dopamine D2, D3, D4 |
| | | | GABAB receptor |
| | | | Glutamate mGluR2, mGluR3, mGluR4, mGluR6, mGluR7, & mGluR8 receptors |
| | | | Histamine H2 & H3 & H4 receptors |
| | | | Melatonin MT1, MT2, & MT3 receptors |
| | | | Muscarinic M2 & M4 receptors |
| | | | Opioid δ, κ, μ, & nociceptin receptors |
| | | | Prostaglandin EP1, EP3, FP, & TP receptors |
| | | | Serotonin 5-HT1 & 5-HT5 receptors |

TABLE 1-continued

Non-limiting examples of the relationship of G protein-coupled receptors and signaling pathways.

| G protein family | | Effectors/Signaling pathways | Use/Receptors |
|---|---|---|---|
| Gt | αt (transducin) | Activation phosphodiesterase 6 (vision) | Rhodopsin |
| Ggust | αgust (gustducin) | Activation phosphodiesterase 6 (vision) | Taste receptors |
| Gz | αz | Inhibition adenylate cyclase (cAMP ↓) | unknown |
| Gs family | | | |
| Gs | αs | Activation adenylate cyclase (cAMP ↑) | 5-HT receptors types 5-HT4 and 5-HT7<br>ACTH receptor<br>Adenosine receptor types A2a and A2b<br>Arginine vasopressin receptor 2<br>β-adrenergic receptors types β1, β2 and β3<br>Calcitonin receptor<br>Calcitonin gene-related peptide receptor<br>Corticotropin-releasing hormone receptor<br>Dopamine receptors D1-like family (D1 and D5)<br>FSH-receptor<br>Gastric inhibitory polypeptide receptor<br>Glucagon receptor<br>Histamine H2 receptor<br>Luteinizing hormone/choriogonadotropin receptor<br>Melanocortin receptor<br>Parathyroid hormone receptor 1<br>Prostaglandin receptor types D2 and I2<br>Secretin receptor<br>Thyrotropin receptor |
| Golf | αolf | Activation adenylate cyclase (cAMP ↑) | Olfactory receptors |
| Gq family | | | |
| Gq | αq | Activation of phospholipase C (IP$_3$ ↑) | 5-HT2 serotonergic receptors<br>Alpha-1 adrenergic receptor<br>Vasopressin type 1 receptor<br>Angiotensin II receptor type 1<br>Calcitonin receptor<br>Histamine H1 receptor<br>Metabotropic glutamate receptor, Group I<br>M1, M3, and M5 muscarinic receptors |
| G12/13 family | | | |
| G12 | α12 | | |
| G13 | α13 | | |
| | βγ subunit | Na$^+$/H$^+$ exchange ↑ | |
| | βγ | Opening K$^+$ channels (K$^+$ ↑) | |
| | βγ | Adenylate cyclase (cAMP) ↑ or ↓ | |
| | βγ | Phospholipase C (IP$_3$) | |

Generally, binding domains of the disclosure will at least bind to those forms of GPCR:G protein complexes that are most relevant from a biological and/or therapeutic point of view, as will be clear to the skilled person. It will thus be understood that, depending on the purpose and application, the GPCR and G protein comprised in the target complex may be naturally occurring or non-naturally occurring (i.e., altered by man). The term "naturally occurring," as used herein, means a GPCR or a G protein that is naturally produced. In particular, wild type polymorphic variants and isoforms of GPCRs and G proteins, as well as orthologs across different species are examples of naturally occurring proteins, and are found for example, and without limitation, in a mammal, more specifically in a human, or in a virus, or in a plant, or in an insect, amongst others). Thus, such GPCRs or G proteins are found in nature. The term "non-naturally occurring," as used herein, means a GPCR or a G protein that is not naturally occurring. In certain circumstances, it may be advantageous that the GPCR and/or G protein comprised in the complex are non-naturally occurring proteins. For example, and for illustration purposes only, to increase the probability of obtaining crystals of a GPCR:G protein complex stabilized by the binding domains of the present invention, it might be desired to perform some protein engineering without or only minimally affecting ligand binding affinity. Or, alternatively or additionally, to increase cellular expression levels of a GPCR and/or a G protein, or to increase the stability, one might also consider to introduce certain mutations in the GPCR and/or the G protein of interest. Non-limiting examples of non-naturally occurring GPCRs include, without limitation, GPCRs that have been made constitutively active through mutation, GPCRs with a loop deletion, GPCRs with an N- and/or C-terminal deletion, GPCRs with a substitution, an insertion or addition, or any combination thereof, in relation to their amino acid or nucleotide sequence, or other variants of naturally occurring GPCRs. Similarly, non-limiting examples of non-naturally occurring G proteins include, without limitation, G proteins with an N- and/or C-terminal deletion, G proteins with a substitution, an insertion or addition, or any combination thereof, in relation to their amino acid or nucleotide sequence, or other variants of naturally occurring G proteins. Also comprised within the scope of the present disclosure are target GPCR:G protein complexes comprising a chimeric or hybrid GPCR, for example a chimeric GPCR with an N- and/or C-terminus from one GPCR and loops of a second GPCR, or comprising a GPCR fused to a moiety, such as T4 lysozyme (see also Example section).

According to specific embodiments, a non-naturally occurring GPCR or G protein, as comprised in the GPCR:G protein complex, may have an amino acid sequence that is at least 80% identical to, at least 90% identical to, at least 95% identical to, at least 97% identical to, or at least 99% identical to, a naturally occurring GPCR or G protein. To illustrate this further, and taking the β2-adrenergic receptor as a particular non-limiting example of a GPCR within the scope hereof, it should be clear from the above that in addition to the human $β_2$ adrenergic receptor (e.g., the sequence described by GenBank accession number NP_000015), the mouse $β_2$ adrenergic receptor (e.g., as described by GenBank accession no. NM 007420) or other mammalian $β_2$ adrenergic receptor are encompassed. Also envisaged are wild-type polymorphic variants and certain other active variants of the $β_2$ adrenergic receptor from a particular species. For example, "human $β_2$ adrenergic receptor" has an amino acid sequence that is at least 80% identical to, at least 90% identical to, at least 95% identical to, at least 97% identical to, or at least 99% identical to the naturally occurring "human $β_2$ adrenoreceptor" of GenBank accession number NP_000015.

Analogously, and taking Gαs, Gαi and Gαt as particular non-limiting examples of subunits of G proteins within the scope of the present invention, it should be clear from the above that in addition to the human Gαs or Gαi or Gαt, the mouse Gαs or Gαi or Gαt proteins or other mammalian Gαs or Gαi or Gαt proteins are encompassed. Also envisaged are wild-type polymorphic variants and certain other active variants of the Gαs or Gαi or Gαt from a particular species. For example, a "human Gαs" or a "human Gαi" or a "human Gαt" has an amino acid sequence that is at least 80% identical to, at least 90% identical to, at least 95% identical to, at least 97% identical to, or at least 99% identical to the naturally occurring "human Gαs" or "human Gαi" or "human Gαt" of Genbank accession number P63092, P63096 and P11488, respectively. Further, many isoforms of G protein subunits exist, including for example isoforms of Gs and Gi proteins (Gαs: GNAS; Gα0: GNAO1; Gαi: GNAI1 or GNAI2 or GNAI3; Gβ: GNB1 or GNB2 or GNB3 or GNB4 or GNB5 or GNB1L or GNB2L; Gγ: GNGT1 or GNGT2 or GNG2 or GNG3 or GNG4 or GNG5 or GNG7 or GNG8 or GNG10 or GNG11 or GNG12 or GNG13; according to HGNC standardized nomenclature to human genes; accession numbers of different isoforms from different organisms are available from the World Wide Web at uniprot.org).

Some particular examples of isoforms of G protein subunits are provided in Table 5. The skilled person will appreciate that the amino acid sequences of the different G protein subunits are almost 100%, if not 100%, conserved across species and organisms. Notably, sequence alignment of the amino acid sequence of the human, bovine, rat and mouse f subunit of the G protein reveals that the amino acid sequences between these organisms are 100% conserved. Analogously, the amino acid sequences of the human, mouse, and bovine y subunit of the G protein are 100% identical. The rat and mouse Gαs amino acid sequences are also 100% identical, whereas human and bovine Gαs only differ in 1 or 2 amino acids, respectively. Thus, the binding domains directed against and/or specifically binding to a GPCR:G protein complex, and particularly binding to the G protein comprised in the complex, are expected to be cross-reactive. It will also be clear that the GPCR and G protein comprised in the target complex may be from the same or different species. Preferably, the GPCR and/or the G protein is a mammalian protein, or a plant protein, or a microbial protein, or a viral protein, or an insect protein. More preferably, the GPCR is a human protein.

It is also expected that binding domains of the disclosure will generally be capable of binding to GPCR:G protein complexes comprising all naturally occurring or synthetic analogs, variants, mutants, alleles, parts, fragments, and isoforms of a particular GPCR and/or G protein comprised in the complex; or at least to those analogs, variants, mutants, alleles, parts, fragments, and isoforms of a particular GPCR and/or G protein comprised in the complex that contain one or more antigenic determinants or epitopes that are essentially the same as the antigenic determinant(s) or epitope(s) to which the binding domains of the disclosure bind to a particular GPCR and/or G protein comprised in the complex.

Various methods may be used to determine specific binding (as defined hereinbefore) between the binding domain and a target GPCR:G protein complex, including for example, enzyme linked immunosorbent assays (ELISA), surface Plasmon resonance assays, phage display, and the like, which are common practice in the art, for example, in discussed in Sambrook et al. (2001), Molecular Cloning, A Laboratory Manual. Third Edition. Cold Spring Harbor Laboratory Press, Cold Spring Harbor, NY, and are further illustrated in the Example section. It will be appreciated that for this purpose often a unique label or tag will be used, such as a peptide label, a nucleic acid label, a chemical label, a fluorescent label, or a radio frequency tag, as described further herein.

According to a specific embodiment, the binding domain against a GPCR:G protein complex binds with higher affinity to the complex compared with binding to the G protein alone and/or to the GPCR alone, respectively. In one embodiment, the binding domain against a GPCR:G protein complex specifically binds to the GPCR comprised in the complex, and not to the G protein. Preferably, in another embodiment, the binding domain against a GPCR:G protein complex specifically binds to the G protein comprised in the complex, and not to the GPCR. More specifically, the binding domain against a GPCR:G protein complex specifically binds to the G protein which is a Gs protein comprised in a complex of a Gs coupled receptor and a Gs protein.

It is well-known that GPCRs are conformationally complex membrane proteins that exhibit a spectrum of functional behavior in response to natural and synthetic ligands. In nature, a ligand-bound GPCR may associate with a G protein into a complex which will represent a particular functional conformational state, more specifically an active conformational state, resulting in a particular biological activity. The present disclosure offers the particular advantage that the binding domains as described herein can stabilize various of these active conformations of GPCRs in complex with a G protein and bound to various natural or synthetic ligands. One of skill in the art will recognize that binding domains that specifically bind to a ligand:GPCR:G protein complex, will stabilize the specific conformation of the GPCR comprised in the complex. In a preferred embodiment, the binding domain is capable of stabilizing, or otherwise, increasing the stability of a particular functional conformational state of a GPCR:G protein complex, preferably wherein the GPCR is in an active conformational state. Generally, a functional conformation state of the GPCR can be a basal conformational state, or an active conformational state or an inactive conformational state. Preferably, the binding domain of the disclosure is capable of stabilizing a GPCR in its active conformational state and/or is capable of locking the GPCR in an active conformational state upon binding the GPCR:G protein complex, whether or not in the presence of a receptor ligand.

In a particularly preferred embodiment, it is envisaged that the binding domain is directed against and/or specifically binds to a complex comprising a GPCR, a G protein and a receptor ligand (as defined herein). More preferably, the binding domain is directed against and/or specifically binds to a complex consisting of a GPCR, a G protein and a receptor ligand. A receptor ligand may be a small compound, a peptide, an antibody, or an antibody fragment, and the like, which triggers a response upon binding. Receptor ligands, or simply ligands, as used herein may be orthosteric ligands (both natural and synthetic) that bind to the receptor's active site and are classified according to their efficacy or in other words to the effect they have on receptor signaling through a specific pathway. As used herein, an "agonist" refers to a ligand that, by binding a receptor, increases the receptor's signaling activity. Full agonists are capable of maximal receptor stimulation; partial agonists are unable to elicit full activity even at saturating concentrations. Partial agonists can also function as "blockers" by preventing the binding of more robust agonists. An "antagonist" refers to a ligand that binds a receptor without stimulating any activity. An "antagonist" is also known as a "blocker" because of its ability to prevent binding of other ligands and, therefore, block agonist-induced activity. Further, an "inverse agonist" refers to an antagonist that, in addition to blocking agonist effects, reduces receptors' basal or constitutive activity below that of the unliganded receptor. Preferably, the binding domain of the disclosure is directed against and/or specifically binds to a complex comprising a GPCR, a G protein and a receptor ligand, wherein the receptor ligand is an agonist. More specifically, the agonist binds the receptor at the orthosteric site.

The signaling activities of GPCRs (and thus their conformational behavior) may also be affected by the binding of another kind of ligands known as allosteric regulators. "Allosteric regulators" or otherwise "allosteric modulators" or "effector molecules" bind at an allosteric site of a GPCR (that is, a regulatory site physically distinct from the protein's active site). In contrast to orthosteric ligands, allosteric modulators are non-competitive because they bind receptors at a different site and modify receptor function even if the endogenous ligand also is binding. Because of this, allosteric modulators are not limited to simply turning a receptor on or off, the way most drugs are. Instead, they act more like a dimmer switch, offering control over the intensity of activation or deactivation, while allowing the body to retain its natural control over initiating receptor activation, by altering the affinity of the receptor for its (endogenous) ligand. Allosteric regulators that enhance the protein's activity are referred to herein as "allosteric activators" or "positive allosteric modulators," whereas those that decrease the protein's activity are referred to herein as "allosteric inhibitors" or otherwise "negative allosteric modulators." Thus, in one particular embodiment, the binding domain of the disclosure is directed against and/or specifically binds to a complex comprising a GPCR, a G protein and a receptor ligand, wherein the receptor ligand is an allosteric modulator, preferably a positive allosteric modulator. More specifically, the positive allosteric modulator binds the receptor at an allosteric site.

As explained, the canonical view of how GPCRs regulate cellular physiology is that the binding of ligands (such as hormones, neurotransmitters or sensory stimuli) stabilizes an active conformational state of the receptor, thereby allowing interactions with heterotrimeric G proteins. In addition to interacting with G proteins, agonist-bound GPCRs associate with GPCR kinases (GRKs), leading to receptor phosphorylation. A common outcome of GPCR phosphorylation by GRKs is a decrease in GPCR interactions with G proteins and an increase in GPCR interactions with arrestins, which sterically interdict further G protein signaling, resulting in receptor desensitization. As β-arrestins turn off G protein signals, they can simultaneously initiate a second, parallel set of signal cascades, such as the MAPK pathway. GPCRs also associate with various proteins outside the families of general GPCR-interacting proteins (G proteins, GRKs, arrestins and other receptors). These GPCR-selective partners can mediate GPCR signaling, organize GPCR signaling through G proteins, direct GPCR trafficking, anchor GPCRs in particular subcellular areas and/or influence GPCR pharmacology (Ritter and Hall 2009). In this regard, ligands as used herein may also be "biased ligands" with the ability to selectively stimulate a subset of a receptor's signaling activities, for example the selective activation of G protein or β-arrestin function. Such ligands are known as "biased ligands," "biased agonists," or "functionally selective agonists." More particularly, ligand bias can be an imperfect bias characterized by a ligand stimulation of multiple receptor activities with different relative efficacies for different signals (non-absolute selectivity) or can be a perfect bias characterized by a ligand stimulation of one receptor activity without any stimulation of another known receptor activity. Thus, in one particular embodiment, the binding domain of the disclosure is directed against and/or specifically binds to a complex comprising a GPCR, a G protein and a receptor ligand, wherein the receptor ligand is a biased ligand.

Further, according to a preferred embodiment, it is particularly envisaged that the binding domain of the disclosure directed against and/or specifically binding to a GPCR:G protein complex, as described hereinbefore, is derived from an innate or adaptive immune system. Preferably, the binding domain is derived from an immunoglobulin. Preferably, the binding domain according to the disclosure is an antibody or an antibody fragment. The term "antibody" (Ab) refers generally to a polypeptide encoded by an immunoglobulin gene, or a functional fragment thereof, that specifically binds and recognizes an antigen, and is known to the person skilled in the art. A conventional immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain (VL) and variable heavy chain (VH) refer to these light and heavy chains respectively. The term "antibody" is meant to include whole antibodies, including single-chain whole antibodies, and antigen-binding fragments. In some embodiments, antigen-binding fragments may be antigen-binding antibody fragments that include, but are not limited to, Fab, Fab' and F(ab')2, Fd, single-chain Fvs (scFv), single-chain antibodies, disulfide-linked Fvs (dsFv) and fragments comprising or consisting of either a VL or VH domain, and any combination of those or any other functional portion of an immunoglobulin peptide capable of binding to the target antigen. The term "antibodies" is also meant to include heavy chain antibodies, or functional fragments thereof, such as single domain antibodies, more specifically, immunoglobulin single variable domains such as VHHs or nanobodies, as defined further herein.

Preferably, the binding domain of the disclosure is an immunoglobulin single variable domain. More preferably, the binding domain is an immunoglobulin single variable domain that comprises an amino acid sequence comprising four framework regions (FR1 to FR4) and three complementarity-determining regions (CDR1 to CDR3), preferably according to the following formula (1):

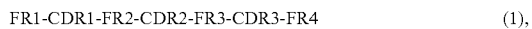

FR1-CDR1-FR2-CDR2-FR3-CDR3-FR4   (1), or any suitable fragment thereof (which will then usually contain at least some of the amino acid residues that form at least one of the complementarity-determining regions).

Binding domains comprising 4 FRs and 3 CDRs are known to the person skilled in the art and have been described, as a non-limiting example, in Wesolowski et al. (2009, Med. Microbiol. Immunol. 198:157). Typical, but non-limiting, examples of immunoglobulin single variable domains include light chain variable domain sequences (e.g., a $V_L$ domain sequence), or heavy chain variable domain sequences (e.g., a $V_H$ domain sequence), which are usually derived from conventional four-chain antibodies. Preferably, the immunoglobulin single variable domains are derived from camelid antibodies, preferably from heavy chain camelid antibodies, devoid of light chains, and are known as $V_HH$ domain sequences or nanobodies (as described further herein).

The term "nanobody" (Nb), as used herein, refers to the smallest antigen binding fragment or single variable domain ($V_HH$) derived from naturally occurring heavy chain antibody and is known to the person skilled in the art. They are derived from heavy chain only antibodies, seen in camelids (Hamers-Casterman et al., 1993; Desmyter et al., 1996). In the family of "camelids" immunoglobulins devoid of light polypeptide chains are found. "Camelids" comprise old world camelids (*Camelus bactrianus* and *Camelus dromedarius*) and new world camelids (for example, *Lama paccos, Lama glama, Lama guanicoe* and *Lama vicugna*). The single variable domain heavy chain antibody is herein designated as a Nanobody or a $V_HH$ antibody. Nanobody™ and Nanobodies™ are trademarks of Ablynx NV (Belgium). The small size and unique biophysical properties of Nbs excel conventional antibody fragments for the recognition of uncommon or hidden epitopes and for binding into cavities or active sites of protein targets. Further, Nbs can be designed as multispecific and/or multivalent antibodies or attached to reporter molecules (Conrath et al., 2001). Nbs are stable and rigid single domain proteins that can easily be manufactured and survive the gastro-intestinal system. Therefore, Nbs can be used in many applications including drug discovery and therapy (Saerens et al., 2008) but also as a versatile and valuable tool for purification, functional study and crystallization of proteins (Conrath et al., 2009). A particular class of nanobodies that act as crystallization chaperones binding conformational epitopes of native targets are called XAPERONES™ and are particularly envisaged here. XAPERONES™ are unique tools in structural biology. XAPERONE™ is a trademark of VIB and VUB (Belgium). Major advantages for the use of camelid antibody fragments as crystallization aid are that XAPERONES™ (1) bind cryptic epitopes and lock proteins in unique native conformations, (2) increase the stability of soluble proteins and solubilized membrane proteins, (3) reduce the conformational complexity of soluble proteins and solubilized membrane proteins, (4) increase the polar surface enabling the growth of diffracting crystals, (5) sequester aggregative or polymerizing surfaces, (6) allow to affinity-trap active protein.

Thus, the immunoglobulin single variable domains hereof, in particular the nanobodies hereof, generally comprise a single amino acid chain that typically comprises 4 "framework sequences" or FRs and three "complementarity-determining regions" or CDRs according to formula (1):

FR1-CDR1-FR2-CDR2-FR3-CDR3-FR4   (1).

The term "complementarity-determining region" or "CDR" refers to variable regions in immunoglobulin single variable domains and contains the amino acid sequences capable of specifically binding to antigenic targets. These CDR regions account for the basic specificity of the nanobody for a particular antigenic determinant structure. Such regions are also referred to as "hypervariable regions." The immunoglobulin single variable domains have 3 CDR regions, each non-contiguous with the others (termed CDR1, CDR2, CDR3). It should be clear that framework regions of immunoglobulin single variable domains may also contribute to the binding of their antigens (Desmyter et al., 2002; Korotkov et al., 2009). Non-limiting examples of such immunoglobulin single variable domains according to the present disclosure as well as particular combinations of FRs and CDRs are as described herein (see Tables 2 and 3). The delineation of the CDR sequences (and thus also the FR sequences) is based on the IMGT unique numbering system for V-domains and V-like domains (Lefranc et al., 2003). Alternatively, the delineation of the FR and CDR sequences can be done by using the Kabat numbering system as applied to $V_HH$ domains from Camelids in the article of Riechmann and Muyldermans (2000). As will be known by the person skilled in the art, the immunoglobulin single variable domains, in particular the nanobodies, can in particular be characterized by the presence of one or more Camelidae hallmark residues in one or more of the framework sequences (according to Kabat numbering), as described for example in WO 08/020079, on page 75, Table A-3, incorporated herein by reference).

In a preferred embodiment, the disclosure provides immunoglobulin single variable domains with an amino acid sequence selected from the group consisting of amino acid sequences that essentially consist of four framework regions (FR1 to FR4, respectively) and three complementarity-determining regions (CDR1 to CDR3, respectively), in which the CDR sequences of the amino acid sequences have at least 70% amino acid identity, preferably at least 80% amino acid identity, more preferably at least 90% amino acid identity, such as at least 95%, at least 96%, at least 97%, at least 98%, at least 99%, or even 100% amino acid identity with the CDR sequences (see Table 3) of at least one of the immunoglobulin single variable domains of SEQ ID NO:s 1-6, preferably SEQ ID NO: 1 and/or 4. It will be understood that for determining the degree of amino acid identity of the amino acid sequences of the CDRs of one or more sequences of the immunoglobulin single variable domains, the amino acid residues that from the framework regions are disregarded. Some preferred, but non-limiting, examples of immunoglobulin single variable domains of the disclosure are given in SEQ ID NO:s 1 to 6, preferably SEQ ID NO: 1 and/or SEQ ID NO: 4 (see Table 2).

It should be noted that the immunoglobulin single variable domains, in particular the nanobodies, of the disclosure in their broadest sense are not limited to a specific biological source or to a specific method of preparation. For example, the immunoglobulin single variable domains hereof, in particular the nanobodies, can generally be obtained: (1) by isolating the $V_HH$ domain of a naturally occurring heavy chain antibody; (2) by expression of a nucleotide sequence encoding a naturally occurring $V_HH$ domain; (3) by "humanization" of a naturally occurring $V_HH$ domain or by expression of a nucleic acid encoding a such humanized $V_HH$ domain; (4) by "camelization" of a naturally occurring VH domain from any animal species, and in particular from a mammalian species, such as from a human being, or by expression of a nucleic acid encoding such a camelized VH domain; (5) by "camelization" of a "domain antibody" or "Dab" as described in the art, or by expression of a nucleic acid encoding such a camelized VH domain; (6) by using synthetic or semi-synthetic techniques for preparing proteins, polypeptides or other amino acid sequences known per se; (7) by preparing a nucleic acid encoding a nanobody using techniques for nucleic acid synthesis known per se, followed by expression of the nucleic acid thus obtained; and/or (8) by any combination of one or more of the foregoing.

One preferred class of immunoglobulin single variable domains corresponds to the $V_HH$ domains of naturally occurring heavy chain antibodies directed against a target complex of a GPCR and a G protein. Although naive or synthetic libraries of immunoglobulin single variable domains may contain conformational binders against the target complex, a preferred embodiment of this disclosure includes the immunization of a Camelidae with a target complex to expose the immune system of the animal with the conformational epitopes that are unique to the complex. Animals can be immunized with mixtures of the interacting monomers. Optionally, the complex can be stabilized by chemical cross-linking or by adding cooperative/allosteric ligands/metabolites that stabilize the complex (orthosteric agonists, allosteric activators, $Ca^{++}$, ATP, etc.). The complex can also be stabilized by covalent modification (phosphorylation, etc.) of (one of) the members of the complex. In an alternatively embodiment, one might also immunize Camelidae with the GPCR and/or the G protein alone, thus not in complex with each other. Optionally, the GPCR and/or the G protein may also be stabilized, for example, by adding cooperative/allosteric ligands/metabolites that stabilize the GPCR and/or G protein (orthosteric agonists, allosteric activators, $Ca^{++}$, ATP, amongst others).

Thus, such $V_HH$ sequences can generally be generated or obtained by suitably immunizing a species of Camelid with a target complex comprising a GPCR and a G protein, or with either one or both of its constituting member proteins (i.e., so as to raise an immune response and/or heavy chain antibodies directed against a target complex), by obtaining a suitable biological sample from the Camelid (such as a blood sample, or any sample of B-cells), and by generating $V_HH$ sequences directed against a target complex, starting from the sample, using any suitable technique known per se. Such techniques will be clear to the skilled person. Alternatively, such naturally occurring $V_HH$ domains can be obtained from naive libraries of Camelid $V_HH$ sequences, for example by screening such a library using a target complex or at least one part, fragment, antigenic determinant or epitope thereof using one or more screening techniques known per se. Such libraries and techniques are for example described in WO9937681, WO0190190, WO03025020 and WO03035694. Alternatively, improved synthetic or semi-synthetic libraries derived from naive $V_HH$ libraries may be used, such as $V_HH$ libraries obtained from naive $V_HH$ libraries by techniques such as random mutagenesis and/or CDR shuffling, as for example described in WO0043507. Yet another technique for obtaining $V_HH$ sequences directed against a target involves suitably immunizing a transgenic mammal that is capable of expressing heavy chain antibodies (i.e., so as to raise an immune response and/or heavy chain antibodies directed against a target), obtaining a suitable biological sample from the transgenic mammal (such as a blood sample, or any sample of B-cells), and then generating $V_HH$ sequences directed against a target starting from the sample, using any suitable technique known per se. For example, for this purpose, the heavy chain antibody-expressing mice and the further methods and techniques described in WO02085945 and in WO04049794 can be used.

A particularly preferred class of immunoglobulin single variable domains hereof, in particular nanobodies hereof, comprises immunoglobulin single variable domains with an amino acid sequence that corresponds to the amino acid sequence of a naturally occurring $V_HH$ domain, but that has been "humanized," i.e., by replacing one or more amino acid residues in the amino acid sequence of the naturally occurring $V_HH$ sequence (and in particular in the framework sequences) by one or more of the amino acid residues that occur at the corresponding position(s) in a VH domain from a conventional 4-chain antibody from a human being. This can be performed in a manner known per se, which will be clear to the skilled person, for example on the basis of the further description herein and the prior art on humanization referred to herein. Again, it should be noted that such humanized immunoglobulin single variable domains of the disclosure can be obtained in any suitable manner known per se (i.e., as indicated under points (1)-(8) above) and thus are not strictly limited to polypeptides that have been obtained using a polypeptide that comprises a naturally occurring $V_HH$ domain as a starting material. Humanized immunoglobulin single variable domains, in particular nanobodies, may have several advantages, such as a reduced immunogenicity, compared to the corresponding naturally occurring $V_HH$ domains. Such humanization generally involves replacing one or more amino acid residues in the sequence of a naturally occurring $V_HH$ with the amino acid residues that occur at the same position in a human VH domain, such as a human VH3 domain. The humanizing substitutions should be chosen such that the resulting humanized immunoglobulin single variable domains still retain the favorable properties of immunoglobulin single variable domains as defined herein. The skilled person will be able to select humanizing substitutions or suitable combinations of humanizing substitutions which optimize or achieve a desired or suitable balance between the favorable properties provided by the humanizing substitutions on the one hand and the favorable properties of naturally occurring $V_HH$ domains on the other hand.

Another particularly preferred class of immunoglobulin single variable domains hereof, in particular nanobodies hereof, comprises immunoglobulin single variable domains with an amino acid sequence that corresponds to the amino acid sequence of a naturally occurring VH domain, but that has been "camelized," i.e., by replacing one or more amino acid residues in the amino acid sequence of a naturally occurring VH domain from a conventional 4-chain antibody by one or more of the amino acid residues that occur at the corresponding position(s) in a $V_HH$ domain of a heavy chain antibody. Such "camelizing" substitutions are preferably inserted at amino acid positions that form and/or are present at the VH-VL interface, and/or at the so-called Camelidae hallmark residues, as defined herein (see for example WO9404678). Preferably, the VH sequence that is used as a starting material or starting point for generating or designing the camelized nanobody is preferably a VH sequence from a mammal, more preferably the VH sequence of a human being, such as a VH3 sequence. However, it should be noted that such camelized immunoglobulin single variable domains of the disclosure can be obtained in any suitable manner known per se (i.e., as indicated under points (1)-(8) above) and thus are not strictly limited to polypeptides that have been obtained using a polypeptide that comprises a naturally occurring VH domain as a starting material.

For example both "humanization" and "camelization" can be performed by providing a nucleotide sequence that encodes a naturally occurring $V_HH$ domain or VH domain, respectively, and then changing, in a manner known per se, one or more codons in the nucleotide sequence in such a way that the new nucleotide sequence encodes a "humanized" or "camelized" immunoglobulin single variable domains hereof, respectively. This nucleic acid can then be expressed in a manner known per se, so as to provide the desired immunoglobulin single variable domains hereof. Alternatively, based on the amino acid sequence of a naturally occurring $V_HH$ domain or VH domain, respectively, the amino acid sequence of the desired humanized or camelized immunoglobulin single variable domains hereof, respectively, can be designed and then synthesized de novo using techniques for peptide synthesis known per se. Also, based on the amino acid sequence or nucleotide sequence of a naturally occurring $V_HH$ domain or VH domain, respectively, a nucleotide sequence encoding the desired humanized or camelized immunoglobulin single variable domains hereof, respectively, can be designed and then synthesized de novo using techniques for nucleic acid synthesis known per se, after which the nucleic acid thus obtained can be expressed in a manner known per se, so as to provide the desired immunoglobulin single variable domains hereof. Other suitable methods and techniques for obtaining the immunoglobulin single variable domains of the disclosure and/or nucleic acids encoding the same, starting from naturally occurring VH sequences or preferably $V_HH$ sequences, will be clear from the skilled person, and may for example comprise combining one or more parts of one or more naturally occurring VH sequences (such as one or more FR sequences and/or CDR sequences), one or more parts of one or more naturally occurring $V_HH$ sequences (such as one or more FR sequences or CDR sequences), and/or one or more synthetic or semi-synthetic sequences, in a suitable manner, so as to provide a nanobody of the disclosure or a nucleotide sequence or nucleic acid encoding the same.

Also within the scope of the disclosure are natural or synthetic analogs, mutants, variants, alleles, parts or fragments (herein collectively referred to as "variants") of the immunoglobulin single variable domains, in particular the nanobodies, of the disclosure as defined herein, and in particular variants of the immunoglobulin single variable domains of SEQ ID NOs: 1-6 (see Tables 2-3). Thus, according to one embodiment hereof, the term "immunoglobulin single variable domain hereof" or "nanobody hereof" in its broadest sense also covers such variants. Generally, in such variants, one or more amino acid residues may have been replaced, deleted and/or added, compared to the immunoglobulin single variable domains of the disclosure as defined herein. Such substitutions, insertions or deletions may be made in one or more of the FRs and/or in one or more of the CDRs and, in particular, variants of the FRs and CDRs of the immunoglobulin single variable domains of SEQ ID NOS:1-6 (see Tables 2 and 3). Variants, as used herein, are sequences wherein each or any framework region and each or any complementarity-determining region shows at least 80% identity, preferably at least 85% identity, more preferably 90% identity, even more preferably 95% identity or, still even more preferably 99% identity with the corresponding region in the reference sequence (i.e., FR1_variant versus FR1_reference, CDR1_variant versus CDR1_reference, FR2_variant versus FR2_reference, CDR2_variant versus CDR2_reference, FR3_variant versus FR3_reference, CDR3_variant versus CDR3_reference, FR4_variant versus FR4_reference), as can be measured electronically by making use of algorithms such as PILEUP and BLAST (50, 51). Software for performing BLAST analyses is publicly available through the National Center for Biotechnology Information (on the World Wide Web at ncbi.nlm.nih.gov). It will be understood that for determining the degree of amino acid identity of the amino acid sequences of the CDRs of one or more sequences of the immunoglobulin single variable domains, the amino acid residues that form the framework regions are disregarded. Similarly, for determining the degree of amino acid identity of the amino acid sequences of the FRs of one or more sequences of the immunoglobulin single variable domains hereof, the amino acid residues that form the complementarity regions are disregarded. Such variants of immunoglobulin single variable domains may be of particular advantage since they may have improved potency/affinity.

By means of non-limiting examples, a substitution may for example be a conservative substitution (as described herein) and/or an amino acid residue may be replaced by another amino acid residue that naturally occurs at the same position in another $V_HH$ domain. Thus, any one or more substitutions, deletions or insertions, or any combination thereof, that either improve the properties of the immunoglobulin single variable domains of the disclosure or that at least do not detract too much from the desired properties or from the balance or combination of desired properties of the nanobody of the disclosure (i.e., to the extent that the immunoglobulin single variable domains is no longer suited for its intended use) are included within the scope hereof. A skilled person will generally be able to determine and select suitable substitutions, deletions or insertions, or suitable combinations of thereof, based on the disclosure herein and optionally after a limited degree of routine experimentation, which may for example involve introducing a limited number of possible substitutions and determining their influence on the properties of the immunoglobulin single variable domains thus obtained.

According to particularly preferred embodiments, variants of the immunoglobulin single variable domains, in particular the nanobodies, of the present disclosure may have a substitution, deletion or insertion, of 1, 2 or 3 amino acids in either one, two or three of the CDRs, more specifically a substitution, deletion or insertion of 1, 2 or 3 amino acids (i) in CDR1 or CDR2 or CDR3; (ii) in CDR1 and CDR2, or, in CDR1 and CDR3, or, in CDR2 and CDR3; (iii) in CDR1 and CDR2 and CDR3, of which the amino acid sequences of CDRs are as listed in Table 3. More preferably, variants of the immunoglobulin single variable domains, in particular the nanobodies, of the present disclosure may have a conservative substitution (as defined herein) of 1, 2 or 3 amino acids in one, two or three of the CDRs, more specifically (i) in CDR1 or CDR2 or CDR3; (ii) in CDR1 and CDR2, or, in CDR1 and CDR3, or, in CDR2 and CDR3; (iii) in CDR1 and CDR2 and CDR3, as listed in Table 3.

According to a specific embodiment, the present disclosure provides for an immunoglobulin single variable domain comprising an amino acid sequence that comprises four framework regions (FR1 to FR4) and three complementarity-determining regions (CDR1 to CDR3), according to the following formula (1):

FR1-CDR1-FR2-CDR2-FR3-CDR3-FR4   (1);

and wherein CDR1 is chosen from the group consisting of:
a) SEQ ID NOs: 13-18,
b) Polypeptides that have at least 80% amino acid identity with SEQ ID NOs: 13-18,
c) Polypeptides that have 3, 2 or 1 amino acid difference with SEQ ID NOs: 13-18,
and wherein CDR2 is chosen from the group consisting of:
a) SEQ ID NOs: 25-30,
b) Polypeptides that have at least 80% amino acid identity with SEQ ID NOs: 25-30,
c) Polypeptides that have 3, 2 or 1 amino acid difference with SEQ ID NOs: 25-30,
and wherein CDR3 is chosen from the group consisting of:
a) SEQ ID NOs: 37-42,
b) Polypeptides that have at least 80% amino acid identity with SEQ ID NOs: 37-42,
c) Polypeptides that have 3, 2 or 1 amino acid difference with SEQ ID NOs: 37-42.

In a particularly preferred embodiment, the present disclosure provides for an immunoglobulin single variable domain comprising an amino acid sequence that comprises four framework regions (FR1 to FR4) and three complementarity-determining regions (CDR1 to CDR3), according to the following formula (1):

FR1-CDR1-FR2-CDR2-FR3-CDR3-FR4   (1);

wherein CDR1 is SEQ ID NO: 13; wherein CDR2 is SEQ ID NO: 25; and wherein CDR3 is SEQ ID NO: 37.

Further, and depending on the host organism used to express the binding domain, in particular the immunoglobulin single variable domain hereof, deletions and/or substitutions may be designed in such a way that one or more sites for post-translational modification (such as one or more glycosylation sites) are removed, as will be within the ability of the person skilled in the art. Alternatively, substitutions or insertions may be designed so as to introduce one or more sites for attachment of functional groups (as described herein), for example to allow site-specific pegylation.

Examples of modifications, as well as examples of amino acid residues within the binding domain, in particular the immunoglobulin single variable domain of the disclosure that can be modified (i.e., either on the protein backbone but preferably on a side chain), methods and techniques that can be used to introduce such modifications and the potential uses and advantages of such modifications will be clear to the skilled person. For example, such a modification may involve the introduction (e.g., by covalent linking or in another suitable manner) of one or more functional groups, residues or moieties into or onto the binding domain, in particular the immunoglobulin single variable domain hereof, and in particular of one or more functional groups, residues or moieties that confer one or more desired properties or functionalities to the binding domain hereof.

Examples of such functional groups and of techniques for introducing them will be clear to the skilled person, and can generally comprise all functional groups and techniques mentioned in the art as well as the functional groups and techniques known per se for the modification of pharmaceutical proteins, and in particular for the modification of antibodies or antibody fragments (including ScFvs and single domain antibodies), for which reference is for example made to Remington's Pharmaceutical Sciences, 16th ed., Mack Publishing Co., Easton, PA (1980). Such functional groups may for example be linked directly (for example covalently) to the binding domain, in particular the immunoglobulin single variable domain hereof, or optionally via a suitable linker or spacer, as will again be clear to the skilled person.

One of the most widely used techniques for increasing the half-life and/or reducing immunogenicity of pharmaceutical proteins comprises attachment of a suitable pharmacologically acceptable polymer, such as poly(ethylene glycol) (PEG) or derivatives thereof (such as methoxypoly(ethylene glycol) or mPEG). Generally, any suitable form of pegylation can be used, such as the pegylation used in the art for antibodies and antibody fragments (including but not limited to (single) domain antibodies and ScFvs); reference is made to for example Chapman, Nat. Biotechnol., 54, 531-545 (2002); by Veronese and Harris, Adv. Drug Deliv. Rev. 54, 453-456 (2003), by Harris and Chess, Nat. Rev. Drug. Discov., 2, (2003) and in WO04060965. Various reagents for pegylation of proteins are also commercially available, for example from Nektar Therapeutics, USA. Preferably, site-directed pegylation is used, in particular via a cysteine-residue (see for example Yang et al., Protein Engineering, 16, 10, 761-770 (2003). For example, for this purpose, PEG may be attached to a cysteine residue that naturally occurs in a immunoglobulin single variable domain hereof, a immunoglobulin single variable domain of the disclosure may be modified so as to suitably introduce one or more cysteine residues for attachment of PEG, or an amino acid sequence comprising one or more cysteine residues for attachment of PEG may be fused to the N- and/or C-terminus of a nanobody hereof, all using techniques of protein engineering known per se to the skilled person. Preferably, for the immunoglobulin single variable domain hereof, a PEG is used with a molecular weight of more than 5000, such as more than 10,000 and less than 200,000, such as less than 100,000; for example in the range of 20,000-80,000.

Another, usually less preferred modification comprises N-linked or O-linked glycosylation, usually as part of co-translational and/or post-translational modification, depending on the host cell used for expressing the binding domain, in particular the immunoglobulin single variable domain hereof. Another technique for increasing the half-life of a binding domain may comprise the engineering into bifunctional binding domains (for example, one immunoglobulin single variable domain against the target GPCR:G protein complex and one against a serum protein such as albumin) or into fusions of binding domains, in particular immunoglobulin single variable domains, with peptides (for example, a peptide against a serum protein such as albumin).

Yet another modification may comprise the introduction of one or more detectable labels or other signal-generating groups or moieties, depending on the intended use of the labeled binding domain. Suitable labels and techniques for attaching, using and detecting them will be clear to the skilled person, and for example include, but are not limited to, fluorescent labels (such as fluorescein, isothiocyanate, rhodamine, phycoerythrin, phycocyanin, allophycocyanin, o-phthaldehyde, and fluorescamine and fluorescent metals such as Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes, metals, metals chelates or metallic cations or other metals or metallic cations that are particularly suited for use in in vivo, in vitro or in situ diagnosis and imaging, as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase).

Other suitable labels will be clear to the skilled person, and for example include moieties that can be detected using NMR or ESR spectroscopy. Such labeled binding domains of the disclosure may for example be used for in vitro, in vivo or in situ assays (including immunoassays known per se such as ELISA, RIA, EIA and other "sandwich assays," etc.) as well as in vivo diagnostic and imaging purposes, depending on the choice of the specific label. As will be clear to the skilled person, another modification may involve the introduction of a chelating group, for example to chelate one of the metals or metallic cations referred to above. Suitable chelating groups for example include, without limitation, diethyl-enetriaminepentaacetic acid (DTPA) or ethylenediaminetetraacetic acid (EDTA).

Yet another modification may comprise the introduction of a functional group that is one part of a specific binding pair, such as the biotin-(strept)avidin binding pair. Such a functional group may be used to link the binding domain of the disclosure to another protein, polypeptide or chemical compound that is bound to the other half of the binding pair, i.e., through formation of the binding pair. For example, a immunoglobulin single variable domain of the disclosure may be conjugated to biotin, and linked to another protein, polypeptide, compound or carrier conjugated to avidin or streptavidin. For example, such a conjugated immunoglobulin single variable domain may be used as a reporter, for example in a diagnostic system where a detectable signal-producing agent is conjugated to avidin or streptavidin. Such binding pairs may for example also be used to bind the immunoglobulin single variable domain of the disclosure to a carrier, including carriers suitable for pharmaceutical purposes. One non-limiting example are the liposomal formulations described by Cao and Suresh, Journal of Drug Targetting, 8, 4, 257 (2000). Such binding pairs may also be used to link a therapeutically active agent to the binding domain hereof.

Also encompassed within the scope of the present disclosure are the binding domains, in particular the immunoglobulin single variable domains of the disclosure that are in a "multivalent" form and are formed by bonding, chemically or by recombinant DNA techniques, together two or more monovalent immunoglobulin single variable domains. Non-limiting examples of multivalent constructs include "bivalent" constructs, "trivalent" constructs, "tetravalent" constructs, and so on. The immunoglobulin single variable domains comprised within a multivalent construct may be identical or different. In another particular embodiment, the immunoglobulin single variable domains of the disclosure are in a "multi-specific" form and are formed by bonding together two or more immunoglobulin single variable domains, of which at least one with a different specificity. Non-limiting examples of multi-specific constructs include "bi-specific" constructs, "tri-specific" constructs, "tetra-specific" constructs, and so on. To illustrate this further, any multivalent or multispecific (as defined herein) immunoglobulin single variable domain of the disclosure may be suitably directed against two or more different epitopes on the same antigen, for example against two or more different parts of the G protein as comprised in the GPCR:G protein complex; or may be directed against two or more different antigens, for example against an epitope of the GPCR and an epitope of the G protein. In particular, a monovalent immunoglobulin single variable domain of the disclosure is such that it will bind to the target GPCR:G protein complex (as described herein) with an affinity less than 500 nM, preferably less than 200 nM, more preferably less than 10 nM, such as less than 500 µM. Multivalent or multispecific immunoglobulin single variable domains of the disclosure may also have (or be engineered and/or selected for) increased avidity and/or improved selectivity for the desired GPCR:G protein complex, and/or for any other desired property or combination of desired properties that may be obtained by the use of such multivalent or multispecific immunoglobulin single variable domains.

Further, the binding domain hereof, in particular the immunoglobulin single variable domain hereof, may generally be directed against or specifically binding to any conformational epitope that is represented by or accessible on or part of a complex comprising a GPCR and a G protein. A binding domain that specifically binds to a "three dimensional" epitope or "conformational" epitope is a binding domain that specifically binds to a tertiary or quaternary structure of a folded protein or protein complex. Such a binding domain binds at much reduced (i.e., by a factor of at least 2, 5, 10, 50 or 100) affinity to the linear (i.e., unfolded, denatured) polypeptide chain. The structure to which such a binding domain binds usually contains amino acids that are discontinuous in the linear sequence of the protein (complex). In other words, binding of such a binding domain to a polypeptide is dependent upon the polypeptide being folded into a particular three dimensional conformation. It should be clear that the conformational epitopes selectively recognized by the binding domains of the disclosure can be GPCR specific epitopes, or G protein specific epitopes, or otherwise GPCR:G protein complex-specific epitopes, which are only formed upon association of the constituting proteins, and thus by combining amino acid residues of the GPCR and the G protein. In one embodiment, the binding domain hereof, in particular the immunoglobulin single variable domain, specifically binds to any conformational epitope of any desired G protein or parts thereof. In another embodiment, the conformational epitope can be part of an intracellular or extracellular region, or an intramembraneous region, or a domain or loop structure of any desired GPCR. It is clear that some of these conformational epitopes will be accessible in the GPCR and/or the G protein in the non-associated form, while others will only be accessible once the complex is formed. According to one specific embodiment, the binding domain hereof, in particular the immunoglobulin single variable domain, specifically binds a conformational epitope at the interface between the α and β subunit of a G protein, as is specified as a non-limiting example further herein (see Example section).

According to other specific embodiments, the binding domain binds to a GPCR:G protein complex wherein the G protein is in its nucleotide free from. According to further specific embodiments, the binding domain hereof, in particular the immunoglobulin single variable domain, inhibits or prevents the dissociation of the GPCR:G protein in the presence of nucleotides, in particular guanine nucleotides, such as GDP or GTP, or analogs thereof, such as nonhydrolyzable GTP analogs, such as GTPγS, or GDP in combination with aluminum or beryllium fluoride species, or minimal nucleotide analogs such as pyrophosphate or forcarnet. In the absence of the binding domains hereof, dissociation of the GPCR:G protein complex normally occurs in the presence of these nucleotides.

According to one particular aspect, the disclosure also provides for a binding domain that is directed against or specifically binds to a G protein (i.e., a G protein alone, thus not in complex with a GPCR). In specific embodiments, the binding domain as described herein is directed against and/or specifically binds to a Gs protein. According to specific embodiments of this aspect, the binding domain of the disclosure prevents or inhibits the binding of nucleotides, in particular guanine nucleotides or analogs (as described hereinbefore), to the G protein. Or also, the binding domain of the disclosure is capable of displacing a guanine nucleotide or analog from the G protein. Non-limiting examples of assays to determine the degree of inhibition of binding or displacement of guanine nucleotides to a protein are provided in the Example section, for example in Example 3 and 8. Further, it will be appreciated that all particular embodiments related to the binding domains hereof, as described hereinbefore, also apply for this particular aspect hereof.

The functional versatility of GPCRs is inherently coupled to the flexibility of these proteins resulting in a spectrum of conformations. The conformational energy landscape is intrinsically coupled to such factors as the presence of bound ligands (effector molecules, agonists, antagonists, inverse agonists, etc.), the lipid environment or the binding of interacting proteins. Thus, in one embodiment, the binding domains hereof, in particular the immunoglobulin single variable domains increase the stability of the complex comprising a GPCR and a G protein upon binding of the binding domain. In still a further embodiment, binding of the binding domain of the disclosure to any conformational epitope that is represented by or accessible on or part of a complex comprising a GPCR:G protein complex, induces the formation of a functional conformational state of a GPCR, in particular an active conformational state of the GPCR. More specifically, the binding domain of the disclosure is capable of stabilizing the active state of the GPCR comprised in the GPCR:G protein complex, by increasing the affinity of the G protein for the receptor. Likewise, the binding domain of the present disclosure is capable of stabilizing an agonist-bound GPCR:G protein complex and/or enhances the affinity of an agonist for a GPCR:G protein complex. Preferably, the binding domain is capable of increasing the affinity of the G protein for the GPCR and/or the affinity of the agonist for the GPCR:G protein complex at least twofold, at least fivefold, and more preferably at least tenfold as measured by a decrease in $K_d$. Alternatively, the binding domain is capable of inducing a shift in $EC_{50}$ or $IC_{50}$ by at least twofold, at least fivefold, and more preferably at least tenfold in any assay set-up comparing the interaction strength of the receptor and the G protein in presence of the complex stabilizing binding domain versus a condition where this binding domain is absent or any other measure of affinity or potency known to one of skill in the art.

The term "a functional conformational state," as used herein, refers to the fact that proteins, in particular membrane proteins such as GPCRs, possess many different conformational states having a dynamic range of activity, in particular ranging from no activity to maximal activity (reviewed in Kobilka and Deupi, 2007). It should be clear that "a functional conformational state" is not meant to cover the denatured states of proteins. For example, a basal conformational state can be defined as a low energy state of the receptor in the absence of a ligand. The probability that a protein will undergo a transition to another conformational state is a function of the energy difference between the two states and the height of the energy barrier between the two states. In the case of a receptor protein, such as a GPCR, the energy of ligand binding can be used either to alter the energy barrier between the two states, or to change the relative energy levels between the two states, or both. Changing of the energy barrier would have an effect on the rate of transition between the two states, whereas changing the energy levels would have an effect on the equilibrium distribution of receptors in two states. Binding of an agonist or partial agonist would lower the energy barrier and/or reduce the energy of the more active conformational state relative to the inactive conformational state. An inverse agonist would increase the energy barrier and/or reduce the energy of the inactive state conformation relative to the active conformation. Coupling of the receptor to its G protein could further alter the energy landscape. Cooperative interactions of β2AR and Gs observed in ligand binding assays formed the foundation of the ternary complex model of GPCR activation (Delean et al., 1980). In the ternary complex consisting of agonist, receptor, and G protein, the affinity of the receptor for agonist is enhanced and the specificity of the G protein for guanine nucleotides changes in favor of GTP over GDP.

It should be noted that the activities of integral membrane proteins, including GPCRs are also affected by the structures of the lipid molecules that surround them in the membrane. Membrane proteins are not rigid entities, and deform to ensure good hydrophobic matching to the surrounding lipid bilayer. One important parameter is the hydrophobic thickness of the lipid bilayer, defined by the lengths of the lipid fatty acyl chains. Also, the structure of the lipid headgroup region is likely to be important in defining the structures of those parts of a membrane protein that are located in the lipid headgroup region. Among other lipids, palmitoylation and binding of cholesterol to GPCRs may also play a structural role inside monomeric receptors and contribute to the formation/stabilization of receptor oligomers (Lee 2004; Chini and Parenti 2009).

A further aspect of the present disclosure relates to a complex comprising a binding domain hereof. More specifically, a complex is provided comprising a binding domain hereof, a GPCR, a G protein, and optionally a receptor ligand. As a non-limiting example, a stable complex may be purified by gel filtration, as was done for example for the quaternary complex containing a nanobody, a GPCR, a G protein, and a receptor ligand (see Example section). In a particular embodiment, the complex can be crystalline. Accordingly, a crystal of the complex is also provided, as well as methods of making the crystal, which are described in more detail further herein.

In another aspect, a nucleic acid sequence encoding an amino acid sequence of any of the binding domains hereof, in particular immunoglobulin single variable domains, is also part of the present disclosure and non-limiting examples are provided in Table 4. According to preferred embodiments, the disclosure relates to nucleic acid sequences of binding domains hereof, in particular immunoglobulin single variable domains, in which the sequences have more than 80%, preferably more than 90%, more preferably more than 95%, such as 99% or more sequence identity (as defined herein) with the sequences of at least one of the nucleic acid sequences of the binding domains of SEQ ID NO:s 49-54 (see Table 4). For the calculation of the percentage sequence identity, the nucleic acid sequences of tags (e.g., His tag or EPEA tag) should be disregarded. Also, the nucleic acid sequences as described herein may be comprised in a nucleic acid sequence.

Further, the present disclosure also envisages expression vectors comprising nucleic acid sequences encoding any of binding domains hereof, in particular immunoglobulin single variable domains, as well as host cells expressing such expression vectors. Suitable expression systems include constitutive and inducible expression systems in bacteria or yeasts, virus expression systems, such as baculovirus, semliki forest virus and lentiviruses, or transient transfection in insect or mammalian cells. The cloning, expression and/or purification of the binding domains hereof, in particular the immunoglobulin single variable domains, can be done according to techniques known by the skilled person in the art.

Thus, the present disclosure encompasses a cell or a culture of cells expressing a binding domain hereof, in particular an immunoglobulin single variable domain that is directed against and/or capable of specifically binds to a complex comprising a GPCR and a G protein. The cells according to the present disclosure can be of any prokaryotic or eukaryotic organism. Preferably, cells are eukaryotic cells, for example yeast cells, or insect cells, or cultured cell lines, for example mammalian cell lines, preferably human cell lines, that endogenously or recombinantly express a GPCR and/or G protein of interest. The nature of the cells used will typically depend on the ease and cost of producing the native protein(s), the desired glycosylation properties, the origin of the target protein, the intended application, or any combination thereof. Eukaryotic cell or cell lines for protein production are well known in the art, including cell lines with modified glycosylation pathways, and non-limiting examples will be provided hereafter.

Animal or mammalian host cells suitable for harboring, expressing, and producing proteins for subsequent isolation and/or purification include Chinese hamster ovary cells (CHO), such as CHO-K1 (ATCC CCL-61), DG44 (Chasin et al., 1986, Som. Cell Molec. Genet., 12:555-556; and Kolkekar et al., 1997, Biochemistry, 36:10901-10909), CHO-K1 Tet-On cell line (Clontech), CHO designated ECACC 85050302 (CAMR, Salisbury, Wiltshire, UK), CHO clone 13 (GEIMG, Genova, IT), CHO clone B (GEIMG, Genova, IT), CHO-K1/SF designated ECACC 93061607 (CAMR, Salisbury, Wiltshire, UK), RR-CHOK1 designated ECACC 92052129 (CAMR, Salisbury, Wiltshire, UK), dihydrofolate reductase negative CHO cells (CHO/−DHFR, Urlaub and Chasin, 1980, Proc. Natl. Acad. Sci. USA, 77:4216), and dp12.CHO cells (U.S. Pat. No. 5,721,121); monkey kidney CV1 cells transformed by SV40 (COS cells, COS-7, ATCC CRL-1651); human embryonic kidney cells (e.g., 293 cells, or 293T cells, or 293 cells subcloned for growth in suspension culture, Graham et al., 1977, J. Gen. Virol., 36:59, or GnTI KO HEK293S cells, Reeves et al., 2002, PNAS, 99: 13419); baby hamster kidney cells (BHK, ATCC CCL-10); monkey kidney cells (CV1, ATCC CCL-70); African green monkey kidney cells (VERO-76, ATCC CRL-1587; VERO, ATCC CCL-81); mouse sertoli cells (TM4, Mather, 1980, Biol. Reprod., 23:243-251); human cervical carcinoma cells (HELA, ATCC CCL-2); canine kidney cells (MDCK, ATCC CCL-34); human lung cells (W138, ATCC CCL-75); human hepatoma cells (HEP-G2, HB 8065); mouse mammary tumor cells (MMT 060562, ATCC CCL-51); buffalo rat liver cells (BRL 3A, ATCC CRL-1442); TRI cells (Mather, 1982, Annals N.Y. Acad. Sci., 383:44-68); MCR 5 cells; FS4 cells. According to a particular embodiment, the cells are mammalian cells selected from Hek293 cells or COS cells.

Exemplary non-mammalian cell lines include, but are not limited to, Sf9 cells, baculovirus-insect cell systems (e.g., review Jarvis, Virology Volume 310, Issue 1, 25-5-2003, Pages 1-7), plant cells such as tobacco cells, tomato cells, maize cells, algae cells, or yeasts such as *Saccharomyces* species, *Schizosaccharomyces* species, *Hansenula* species, *Yarrowia* species or *Pichia* species. According to particular embodiments, the eukaryotic cells are yeast cells from a *Saccharomyces* species (e.g., *Saccharomyces cerevisiae*), *Schizosaccharomyces* sp. (for example *Schizosaccharomyces pombe*), a *Hansenula* species (e.g., *Hansenula polymorpha*), a *Yarrowia* species (e.g., *Yarrowia lipolytica*), a *Kluyveromyces* species (e.g., *Kluyveromyces lactis*), a *Pichia* species (e.g., *Pichia pastoris*), or a Komagataella species (e.g., Komagataella *pastoris*). According to a specific embodiment, the eukaryotic cells are *Pichia* cells, and in a most particular embodiment *Pichia pastoris* cells.

Transfection of target cells (e.g., mammalian cells) can be carried out following principles outlined by Sambrook and Russel (Molecular Cloning, A Laboratory Manual, 3$^{rd}$ Edition, Volume 3, Chapter 16, Section 16.1-16.54). In addition, viral transduction can also be performed using reagents such as adenoviral vectors. Selection of the appropriate viral vector system, regulatory regions and host cell is common knowledge within the level of ordinary skill in the art. The resulting transfected cells are maintained in culture or frozen for later use according to standard practices.

Accordingly, another aspect of the disclosure relates to a method for producing a binding domain according to the invention, the method comprising at least the steps of:

a) Expressing in a suitable cellular expression system (as defined hereinabove) a nucleic acid according to the invention, and optionally b) Isolating and/or purifying the binding domain.

The herein described binding domains, complexes, cells or cell lines can be can be used in a variety of contexts and applications, for example, and without limitation, for capturing and/or purification of GPCR:G protein complexes, and in crystallization studies and high-resolution structural analysis of GPCR:G protein complexes. It is thus one of the aims of the disclosure to use the binding domain according to the invention, in particular immunoglobulin single variable domains, such as nanobodies, as tools to stabilize GPCR:G protein complexes and further to use these binding domains as co-crystallization aids for GPCRs in complex with a G protein, or in other words to facilitate crystallogenesis of GPCR:G protein complexes. Additionally, and/or alternatively, the binding domains and preferably cellular systems expressing the binding domains, as described herein, can be useful for other applications such as ligand screening, drug discovery, immunization, all of which will be described into further detail below.

Stabilization of a GPCR:G Protein Complex and Locking the GPCR in the G Protein-Bound State Thus, according to one aspect, the disclosure relates to the use of a binding domain as described hereinbefore to stabilize a complex comprising a GPCR and a G protein. According to a preferred embodiment, the complex that is stabilized further comprises a receptor ligand, more specifically an agonist. The term "stabilize," "stabilizing," or "increasing the stability," as used herein, refers to increasing the stability of a GPCR:G protein complex with respect to the structure (conformational state) and/or particular biological activity (intracellular signaling activity) of one or both of the constituting proteins of the complex, in particular the GPCR and/or the G protein. In one particularly preferred embodiment, the binding domain of the disclosure can be used to stabilize the GPCR:G protein complex so that the GPCR is locked or fixed in an active or G protein-bound state. A GPCR that adopts such an active or G protein-bound state will exert its biological activity in nature. Ways to determine the (increased) stability of a GPCR:G protein complex have been described hereinbefore and are further illustrated in the Examples section.

It will be appreciated that having increased stability with respect to structure and/or a particular biological activity of a GPCR includes the stability to other denaturants or denaturing conditions including heat, a detergent, a chaotropic agent and an extreme pH. Accordingly, in a further embodiment, the binding domain according to the disclosure is capable of increasing the stability of a GPCR:G protein complex under non-physiological conditions induced by dilution, concentration, buffer composition, heating, cooling, freezing, detergent, chaotropic agent, pH, amongst others. Accordingly, the term "thermostabilize," "thermostabilizing," "increasing the thermostability of," refers to the functional rather than to the thermodynamic properties of a GPCR:G protein complex and to the constituting protein's resistance to irreversible denaturation induced by thermal and/or chemical approaches including but not limited to heating, cooling, freezing, chemical denaturants, pH, detergents, salts, additives, proteases or temperature. Irreversible denaturation leads to the irreversible unfolding of the functional conformations of the protein, loss of biological activity and aggregation of the denatured protein. The term "(thermo)stabilize," "(thermo)stabilizing," "increasing the (thermo)stability of," as used herein, applies to GPCR:G protein complexes embedded in lipid particles or lipid layers (for example, lipid monolayers, lipid bilayers, and the like) and to GPCR:G protein complexes that have been solubilized in detergent.

In relation to an increased stability to heat, this can be readily determined by measuring ligand binding or by using spectroscopic methods such as fluorescence, CD or light scattering that are sensitive to unfolding at increasing temperatures. It is preferred that the binding domain is capable of increasing the stability as measured by an increase in the thermal stability of a GPCR:G protein complex with at least 2° C., at least 5° C., at least 8° C., and more preferably at least 10° C. or 15° C. or 20° C. According to another preferred embodiment, the binding domain is capable of increasing the thermal stability of a GPCR:G protein complex with a receptor ligand, more specifically an agonist or positive allosteric modulator of the GPCR dependent signaling pathway. According to another preferred embodiment, the binding domain according to the disclosure is capable of increasing the stability of a GPCR:G protein complex in the presence of a detergent or a chaotrope. Preferably, the binding domain is capable of increasing the stability of a GPCR:G protein complex to denaturation induced by thermal or chemical approaches. In relation to an increased stability to heat, a detergent or to a chaotrope, typically the GPCR:G protein is incubated for a defined time in the presence of a test detergent or a test chaotropic agent and the stability is determined using, for example, ligand binding or a spectroscoptic method, optionally at increasing temperatures as discussed above. According to still another preferred embodiment, the binding domain according to the disclosure is capable of increasing the stability to extreme pH of a functional conformational state of a GPCR. Preferably, the binding domain is capable of increasing the stability of a GPCR:G protein complex to extreme pH. In relation to an extreme of pH, a typical test pH would be chosen for example in the range 6 to 8, the range 5.5 to 8.5, the range 5 to 9, the range 4.5 to 9.5, more specifically in the range 4.5 to 5.5 (low pH) or in the range 8.5 to 9.5 (high pH).

In a particularly preferred embodiment, the binding domain according to the disclosure can be used to prevent the dissociation of the complex in the presence of nucleotides, in particular guanine nucleotides or analogs thereof. More specifically, guanine nucleotides include GDP and GTP, and analogs of guanine nucleotides include, without being limitative, GTPγS or GDP in combination with aluminum or beryllium fluoride species or nucleotide fragments such as pyrophosphate or foscarnet.

Capturing and/or Purifying a GPCR:G Protein Complex

It will thus be understood that the ability of forming a stable GPCR:G protein complex is particularly useful for capturing and/or purifying a GPCR:G protein complex, which will allow subsequent crystallization, ligand characterization and compound screening, immunizations, amongst others. Moreover, it is of particular advantage that the binding domains of the disclosure can be useful generic tools that may be applicable for a range of GPCR:G protein complexes.

Accordingly, the present disclosure also envisages a method of capturing and/or purifying a complex comprising a GPCR and a G protein, the method comprising the steps of:
a) Providing a binding domain according to the invention, and
b) Allowing the binding domain to bind to a complex comprising a GPCR and a G protein, and
c) Optionally, isolating the complex formed in step b).

In a specific embodiment, the disclosure provides for a method of capturing a complex comprising a GPCR and a G protein comprising the steps of:
a) applying a solution containing a plurality of GPCRs and G proteins to a solid support possessing an immobilized binding domain according to the invention, and
b) Forming a complex of the binding domain, the GPCR and the G protein, and
c) Removing weakly bound or unbound molecules, The present disclosure also envisages a method of purifying a complex comprising a GPCR and a G protein, the method comprising the steps of:

a) Contacting a solution containing a GPCR and a G protein with a binding domain according to the invention, and
b) Forming a complex comprising the binding domain, the GPCR and the G protein, and
c) Isolating the complex of step b)
wherein a complex of a GPCR and a G protein is essentially purified.

According to a particular embodiment, the binding domain as described herein can also be used to capture a target GPCR:G protein complex further comprising a receptor ligand and/or one or more other interacting proteins.

The above methods for capturing/purifying target GPCR:G protein complexes include, without limitation, affinity-based methods such as affinity chromatography, affinity purification, immunoprecipitation, protein detection, immunochemistry, surface-display, amongst others, and are all well-known in the art.

Crystallization and Resolving the Structure of a GPCR:G Protein Complex

Crystallization of membrane proteins including GPCRs remains a formidable challenge. Although expression and purification methods are appearing that allow for the generation of milligram quantities, achieving stability with these molecules is perhaps the most difficult hurdle to overcome. First of all, binding domains according to the disclosure may increase the stability of detergent solubilized GPCR:G protein complexes, protecting them from proteolytic degradation and/or aggregation and facilitating the purification and concentration of homogenous samples of correctly folded proteins. Persons of ordinary skill in the art will recognize that such samples are the preferred starting point for the generation of diffracting crystals.

Crystallization is another major bottleneck in the process of macromolecular structure determination by X-ray crystallography. Successful crystallization requires the formation of nuclei and their subsequent growth to crystals of suitable size. Crystal growth generally occurs spontaneously in a supersaturated solution as a result of homogenous nucleation. Proteins may be crystallized in a typical sparse matrix screening experiment, in which precipitants, additives and protein concentration are sampled extensively, and supersaturation conditions suitable for nucleation and crystal growth can be identified for a particular protein. Related to the sparse matrix screening approach is to generate structural variation in the protein itself, for example by adding ligands that bind the protein, or by making different mutations, preferentially in surface residues of the target protein or by trying to crystallize different species orthologues of the target protein (Chang 1998). One unexpected finding of the present disclosure is the usefulness of binding domains that specifically bind to a GPCR:G protein complex to introduce a degree of structural variation upon binding while preserving the overall fold of the complex.

Because crystallization involves an unfavorable loss of conformational entropy in the molecule to be assembled in the crystal lattice, methods that reduce the conformational entropy of the target while still in solution should enhance the likelihood of crystallization by lowering the net entropic penalty of lattice formation. The "surface entropy reduction" approach has proved to be highly effective (Derewenda 2004). Likewise, binding partners such as ions, small molecule ligands, and peptides can reduce the conformational heterogeneity by binding to and stabilizing a subset of conformational states of a protein. Although such binding partners are effective, not all proteins have a known binding partner, and even when a binding partner is known, its affinity, solubility, and chemical stability may not be compatible with crystallization trials. Therefore, it was surprisingly found that the binding domains of the present disclosure can be used as tools to increase the probability of obtaining well-ordered crystals by minimizing the conformational heterogeneity in the target GPCR:G protein complex by binding to a specific conformation of G protein.

Crystallization of GPCRs for high-resolution structural studies is particularly difficult because of the amphipathic surface of these membrane proteins. Embedded in the membrane bilayer, the contact sites of the protein with the acyl chains of the phospholipids are hydrophobic, whereas the polar surfaces are exposed to the polar head groups of the lipids and to the aqueous phases. To obtain well-ordered three-dimensional crystals—a prerequisite to X-ray structural analysis at high resolution—GPCRs are solubilized with the help of detergents and purified as protein-detergent complexes. The detergent micelle covers the hydrophobic surface of the membrane protein in a belt-like manner (Hunte and Michel 2002; Ostermeier et al., 1995). GPCR-detergent complexes form three-dimensional crystals in which contacts between adjacent protein molecules are made by the polar surfaces of the protein protruding from the detergent micelle (Day et al., 2007). Obviously, the detergent micelle requires space in the crystal lattice. Although attractive interactions between the micelles might stabilize the crystal packing (Rasmussen et al., 2007; Dunn et al., 1997), these interactions do not lead to rigid crystal contacts.

Because many membrane proteins, including GPCRs contain relatively small or highly flexible hydrophilic domains, a strategy to increase the probability of getting well-ordered crystals is to enlarge the polar surface of the protein and/or to reduce their flexibility. The most physiologic approach is to use a native signaling partner such as a G protein or arrestin. Unfortunately, interactions of GPCRs with G proteins or arrestins are highly lipid dependent, and it has been difficult to form complexes of sufficient stability for crystallography. So, the binding domains of the present disclosure can be used to enlarge the polar surfaces of the GPCRs through binding of a G protein, supplementing the amount of protein surface that can facilitate primary contacts between molecules in the crystal lattice with the polar surfaces of the G protein and the nanobody. Binding domains of the present disclosure can also reduce the flexibility of its extracellular regions to grow well-ordered crystals. Immunoglobulin single variable domains, including nanobodies, are especially suited for this purpose because they bind conformational epitopes and are composed of one single rigid globular domain, devoid of flexible linker regions unlike conventional antibodies or fragments derived such as Fabs.

Thus, according to a preferred embodiment, the present disclosure provides for binding domains useful as tools to crystallize a complex comprising a GPCR and a G protein, and eventually to solve the structure. More preferably, the complex which is crystallized by making using of a binding domain of the present disclosure further comprises a receptor ligand, more specifically an agonist. In a particularly preferred embodiment, the GPCR comprised in the complex is in an active state or conformation.

Thus, the binding domain in complex with the GPCR:G protein complex and optionally receptor ligand may be crystallized using any of a variety of specialized crystallization methods for membrane proteins, many of which are reviewed in Caffrey (2003 & 2009). In general terms, the methods are lipid-based methods that include adding lipid to the complex prior to crystallization. Such methods have previously been used to crystallize other membrane proteins. Many of these methods, including the lipidic cubic phase crystallization method and the bicelle crystallization method, exploit the spontaneous self-assembling properties of lipids and detergent as vesicles (vesicle-fusion method), discoidal micelles (bicelle method), and liquid crystals or mesophases (in meso or cubic-phase method). Lipidic cubic phases crystallization methods are described in, for example: Landau et al., 1996; Gouaux 1998; Rummel et al., 1998; Nollert et al., 2004, Rasmussen et al., 2011, which publications are incorporated by reference for disclosure of those methods. Bicelle crystallization methods are described in, for example: Faham et al., 2005; Faham et al., 2002, which publications are incorporated by reference for disclosure of those methods.

According to another embodiment, the disclosure relates to the use of a binding domain as described herein to solve a structure of a target complex comprising a GPCR and a G protein, and optionally further comprising a receptor ligand. "Solving the structure" as used herein refers to determining the arrangement of atoms or the atomic coordinates of a protein, and is often done by a biophysical method, such as X-ray crystallography.

In x-ray crystallography, the diffraction data when properly assembled gives the amplitude of the 3D Fourier transform of the molecule's electron density in the unit cell. If the phases are known, the electron density can be simply obtained by Fourier synthesis. For a protein complex, the success to derive phase information from molecular replacement (MR) alone is questionable when the fraction of proteins with a known structure (the search models) is low (less than 50% of the amino acid content) and/or when the crystals exhibit limited diffraction quality. While the combination of multiple isomorphous replacement (MIR) and MR phasing has proven successful for protein complexes (e.g., Ostermeier et al., 1995; Li et al., 1997; Hunte et al., 2000), the requirement of producing a good heavy atom derivative is almost always problematic. Over the past decade, classical MIR approaches have generally been superseded by the use of anomalous dispersion data principally using selenomethionine (SeMet) incorporation (MAD or SAD) (Hendrickson 1991). In fact, the anomalous experimental data using Se-edge energies generally provide superior and less biased phase information compared with either MIR or model-based MR phasing data. Accordingly, one specific embodiment relates to the use of a binding domain according to the disclosure for the phasing of GPCR:G complexes by MR or MAD. In particular, immunoglobulin single variable domains, including nanobodies, generally express robustly and are suitable for SeMet incorporation. To illustrate this further, and without being limitative, phasing a complex comprising a GPCR, G protein, and a nanobody by introducing all the SeMet sites in the nanobody alone circumvents the need to incorporate SeMet sites in the GPCR or the G protein.

In many cases, obtaining a diffraction-quality crystal is the chief barrier to solving its atomic-resolution structure. Thus, according to specific embodiments, the herein described binding domains can be used to improve the diffraction quality of the crystals so that the crystal structure of the target complex can be solved.

Further, obtaining structural information of GPCR targets, for example to help guide GPCR drug discovery, is highly desired. Beyond the crystallization of more GPCRs, especially methods for acquiring structures of receptors bound to different classes of ligands including agonists, antagonists, allosteric regulators and/or G proteins are needed. The present disclosure particularly provides general tools to obtain crystals of GPCR:G protein complexes. In particular, agonist-bound GPCR:G protein complex crystals may provide three-dimensional representations of the active states of GPCRs. These structures will help clarify the conformational changes connecting the ligand-binding and G protein-interaction sites, and lead to more precise mechanistic hypotheses and eventually new therapeutics. Given the conformational flexibility inherent to ligand-activated GPCRs and the greater heterogeneity exhibited by agonist-bound receptors, stabilizing such a state is not easy. Thus, such efforts can benefit from the stabilization of a complex of an agonist-bound receptor conformation bound to its heterotrimeric G protein by the addition of binding domains that are specific for such a complex. Especially suited are binding domains that bind to the G protein that forms part of such a complex, since these binding domains can be used as general tools to stabilize all GPCRs that signal through the same G protein (e.g., Gs coupled receptors, Gi coupled receptors, etc.).

According to an alternative embodiment, the present disclosure encompasses a method of determining the crystal structure of a complex comprising a GPCR and a G protein, the method comprising the steps of:
a) Providing a binding domain according to the invention, and
b) Allowing the binding domain to bind to a complex comprising a GPCR and a G protein, and
c) Crystallizing the complex formed in step b).

In particular embodiments of the above method of determining the crystal structure, the target complex comprising a GPCR and a G protein further comprises a receptor ligand, more specifically an agonist, bound to the GPCR.

The determining of the crystal structure may be done by a biophysical method such as X-ray crystallography. The method may further comprise a step for obtaining the atomic coordinates of the crystal (as defined hereinbefore).

Identification of Compounds Targeting a GPCR:G Protein Complex

In the process of compound screening, drug discovery and lead optimization, there is a requirement for faster, more effective, less expensive and especially information-rich screening assays that provide simultaneous information on various compound characteristics and their affects on various cellular pathways (i.e., efficacy, specificity, toxicity and drug metabolism). Thus, there is a need to quickly and inexpensively screen large numbers of compounds in order to identify new specific ligands of a GPCR of interest, preferably conformation specific ligands, which may be potential new drug candidates. The present disclosure solves this problem by providing binding domains that stabilize a GPCR:G protein complex in a functional conformational state, that can then be used as immunogen or selection reagent for screening in a variety of contexts.

A major advantage of the binding domains according to the disclosure is that the GPCR as comprised in the GPCR:G protein complex can be kept in a stabilized functional conformation, particularly in an active state conformation. For example, library compounds that selectively bind this active conformation of the receptor have a higher propensity to behave as agonists because orthosteric or allosteric stabilization of the active conformation of the GPCR elicits biological responses.

Another advantage is that the binding domain increases the thermostability of the active conformation of the GPCR comprised in the complex, thus protecting the GPCR against irreversible or thermal denaturation induced by the non-native conditions used in compound screening and drug discovery, without the need to rely on mutant GPCRs with increased stability.

Another major advantage of the conformation-selective binding domains according to the disclosure is that they allow to quickly and reliably screen for and differentiate between receptor agonists, inverse agonists, antagonists and/or modulators as well as inhibitors of GPCRs and GPCR-dependent pathways, so increasing the likelihood of identifying a ligand with the desired pharmacological properties.

To illustrate this further, it is a well-established concept that most GPCRs exhibit higher agonist binding affinity when complexed with G protein. This is attributed to the cooperative interaction between agonist occupied receptor and G protein. Binding domains of the present disclosure that inhibit the dissociation of a complex of a GPCR and a G protein thus will stabilize an active conformational state of the R:G protein complex, thus increasing the affinity of the GPCR for agonists and decreasing the affinity for inverse agonists. It follows that binding domains that recognize the active functional conformation of the R:G complex can for example be used in high-throughput screening assays to screen for agonists because they increase the affinity of the receptor for agonists, relative to inverse agonists. Binding domains that recognize the active functional conformation of the G:R complex can also be used in high-throughput screening assays to screen for biased agonists with the ability to selectively stimulate a subset of a receptor's signaling activities, for example the selective activation of G protein, relative to β-arrestin function.

According to a specific embodiment, a binding domain which specifically binds to the G protein in complex with a GPCR (e.g., Tables 2 and 3) can be used as a universal tool for screening programs targeting a plurality of GPCRs, since a particular G protein (e.g., Gs) will form a complex with a plurality of GPCRs (e.g., Gs coupled receptors, including 5-HT receptors types $5-HT_4$ and $5-HT_7$, ACTH receptor, Adenosine receptor types $A_{2a}$ and $A_{2b}$, Arginine vasopressin receptor 2, β-adrenergic receptors types βc1, $β_2$ and $β_3$, Calcitonin receptor, Calcitonin gene-related peptide receptor, Corticotropin-releasing hormone receptor, Dopamine receptors $D_1$-like family ($D_1$ and $D_5$), FSH-receptor, Gastric inhibitory polypeptide receptor, Glucagon receptor, Histamine $H_2$ receptor, Luteinizing hormone/choriogonadotropin receptor, Melanocortin receptor, Parathyroid hormone receptor 1, Prostaglandin receptor types $D_2$ and $I_2$, Secretin receptor, Thyrotropin receptor, etc.; see also Table 1).

Thus, another aspect according to the present disclosure encompasses the use of a binding domain, or the use of a complex, a cell, a membrane preparation comprising a binding domain, all as described hereinbefore, in screening and/or identification programs for conformation-specific binding partners of a GPCR:G protein complex, which ultimately might lead to potential new drug candidates.

According to one embodiment, the disclosure envisages a method of identifying compounds capable of selectively binding to a GPCR:G protein complex, the method comprising the steps of:
 (i) Providing a complex comprising a GPCR and a G protein
 (ii) Contacting the complex with a binding domain that is directed against and/or specifically binds to the complex and allowing the binding domain to bind to the complex, and
 (iii) Providing a test compound, and
 (iv) Evaluating whether the test compound binds to the complex, and
 (v) Selecting a compound that selectively binds to the complex.

It will be clear that the binding domain as used in any of the above methods is capable of stabilizing the functional conformational state of the GPCR:G protein complex and prevents the dissociation of the complex. Preferably, the GPCR:G protein complex is in an active conformational state (as defined hereinbefore). According to particularly preferred embodiments of the above screening methods, the GPCR:G protein complex further comprises a receptor ligand.

It should be noted that particularly preferred embodiments of the binding domains are as described hereinbefore with respect to the earlier aspects of the disclosure.

Thus, the binding domains of the present disclosure can be useful in screening assays. Screening assays for drug discovery can be solid phase or solution phase assays, e.g., a binding assay, such as radioligand binding assays. It will be appreciated that in some instances high throughput screening of test compounds is preferred and that the methods as described above may be used as a "library screening" method, a term well known to those skilled in the art. Thus, the test compound may be a library of test compounds. In particular, high-throughput screening assays for therapeutic compounds such as agonists, antagonists or inverse agonists and/or modulators form part hereof. For high-throughput purposes, compound libraries may be used such as allosteric compound libraries, peptide libraries, antibody libraries, fragment-based libraries, synthetic compound libraries, natural compound libraries, phage-display libraries and the like.

Methodologies for preparing and screening such libraries are known in the art. In one preferred embodiment, high throughput screening methods involve providing a combinatorial chemical or peptide library containing a large number of potential therapeutic ligands. Such "combinatorial libraries" or "compound libraries" are then screened in one or more assays, as described herein, to identify those library members (particular chemical species or subclasses) that display a desired characteristic activity. A "compound library" is a collection of stored chemicals usually used ultimately in high-throughput screening A "combinatorial library" is a collection of diverse chemical compounds generated by either chemical synthesis or biological synthesis, by combining a number of chemical "building blocks" such as reagents. Preparation and screening of combinatorial libraries are well known to those of skill in the art. The compounds thus identified can serve as conventional "lead compounds" or can themselves be used as potential or actual therapeutics. Thus, in one further embodiment, the screening methods as described herein above further comprises modifying a test compound which has been shown to bind to a conformationally active GPCR:G protein complex, and determining whether the modified test compound binds to the GPCR when residing in the particular conformation.

In cases where high-throughput screening of target GPCR:G protein complexes for conformation-specific binding partners will be preferred, this will be facilitated by immobilization of the binding domain according to the invention, or the GPCR:G protein complex stabilized by the binding domain, onto a suitable solid surface or support that can be arrayed or otherwise multiplexed. Non-limiting examples of suitable solid supports include beads, columns, slides, chips or plates. More specifically, the solid supports may be particulate (e.g. beads or granules, generally used in extraction columns) or in sheet form (e. g. membranes or filters, glass or plastic slides, microtiter assay plates, dipstick, capillary fill devices or such like) which can be flat, pleaied, or hollow fibers or tubes, The following matrices are given as examples and are not exhaustive, such examples could include silica. (porous amorphous silica), i. e. the FLASH series of cartridges containing 60 A irregular silica (32-63 um or 35-70 um) supplied by Biotage (a division of Dyax Corp.), agarose or polyacrylamide supports, for example the Sepharose range of products supplied by Amersham Pharmacia Biotech. or the Affi-Gel supports supplied by Bio-Rad. In addition there are macroporous polymers, such as the pressure-stable Affi-Prep supports as supplied by Bio-Rad. Other supports that could be utilized include; dextran, collagen, polystyrene, metbacrYlate, calcium alginate, controlled pore glass, aluminium, titanium and porous ceramics. Alternatively, the solid surface may comprise part of a mass dependent sensor, for example, a surface plasmon resonance deiector. Further examples of commercially available supports are discussed in, for example, Protein Immobilization, R. F. Taylor cd., Marcel Dekker, Inc. New York. (1991).

Immobilization may be either non-covalent or covalent. In particular, non-covalent immobilization or adsorption on a solid surface of the binding domain, or the GPCR:G protein complex stabilized by the binding domain, according to the disclosure may occur via a surface coating with any of an antibody, or streptavidin or avidin, or a metal ion, recognizing a molecular tag attached to the binding domain or the GPCR, according to standard techniques known by the skilled person (e.g., biotin tag, Histidine tag, etc.). Alternatively, the binding domain, or the GPCR:G protein complex stabilized by the binding domain, according to the invention, may be attached to a solid surface by covalent cross-linking using conventional coupling chemistries. A solid surface may naturally comprise cross-linkable residues suitable for covalent attachment or it may be coated or derivatized to introduce suitable cross-linkable groups according to methods well known in the art.

In one particular embodiment, sufficient functionality of the immobilized protein is retained following direct covalent coupling to the desired matrix via a reactive moiety that does not contain a chemical spacer arm. Further examples and more detailed information on immobilization methods of antibody (fragments) on solid supports are discussed in Jung et al. (2008); similarly, membrane receptor immobilization methods are reviewed in Cooper (2004); both herein incorporated by reference. Notably, the mutation of a particular amino acid (in a protein with known or inferred structure) to a lysine or cysteine (or other desired amino acid) can provide a specific site for covalent coupling, for example. It is also possible to reengineer a specific protein to alter the distribution of surface available amino acids involved in the chemical coupling (Kallwass et al, 1993), in effect controllirg the orientation of the coupled protein. A similar approach can be applied to the binding domains according to the invention, as well as to the conformationally stabilized GPCR:G protein complexes, so providing a means of oriented immobilization without the addition of other peptide tails or domains containing either natural or unnatural amino acids. In case of a antibody or an antibody fragment, such as a nanobody, introduction of mutations in the framework region is preferred, mnininiizing disruption to the anigenbinding activity of the antibody (fragment).

Conveniently, the immobilized proteins may be used in immunoadsorption processes such as imnoassays, for example ELISA, or imnnmoaffinity purification processes by contacting the immobilized proteins according to the disclosure with a test sample (i.e., comprising the test compound, amongst other) accrodiig to standard methods conventional in the art. Akernatively, and particularly for high-throughput purposes, the irnunobilized proteins can be arrayed or otherwise iultiplexed. Preferably the imrmobilized proteins according to the disclosure are used for the screening and selection of compounds that specifically bind to a conformationally stabilized GPCR:G protein complex, wherein in particular the GPCR is in an active conformational state.

It will be appreciated that either the binding domain, or the (conformationally stabilized) GPCR:G protein complex, or its constituting proteins may be immobilized, depending on the type of application or the type of screening that needs to be done. Also, the choice of the GPCR:G protein stabilizing binding domain (targeting a particular conformational epitope of the GPCR:G protein complex), will determine the orientation of the proteins and accordingly, the desired outcome of the compound identification, e.g., compounds specifically binding to extracellular parts, intramembranal parts or intracellular parts of the conformationally stabilized GPCR or compounds specifically binding to the conformationally stabilized G protein.

Alternatively, the test compound (or a library of test compounds) may be immobilized on a solid surface, such as a chip surface, whereas the binding domain and the GPCR:G protein complex are provided, for example, in a detergent solution or in a membrane-like preparation (see below).

Most preferably, neither the binding domain, nor the GPCR:G protein complex or its constituting proteins, nor the test compound are immobilized, as is the case for example in phage-display selection protocols in solution, or radioligand binding assays. In a preferred embodiment, the binding domain, the GPCR:G protein complex (or separately, the constituting proteins) as used in any of the above screening methods, are provided as whole cells, or cell (organelle) extracts such as membrane extracts or fractions thereof, or may be incorporated in lipid layers or vesicles (comprising natural and/or synthetic lipids), high-density lipoparticles, or any nanoparticle, such as nanodisks, or are provided as VLPs, so that sufficient functionality of the respective proteins is retained. Preparations of GPCRs formed from membrane fragments or membrane-detergent extracts are reviewed in detail in Cooper (2004), incorporated herein by reference. Alternatively, binding domains, GPCR:G protein complexes, or the constituting proteins may also be solubilized in detergents. Non-limiting examples of solubilized receptor preparations are further provided in the Example section.

Various methods may be used to determine binding between the stabilized GPCR:G protein complex and a test compound, including for example, enzyme linked immunosorbent assays (ELISA), surface Plasmon resonance assays, chip-based assays, immunocytofluorescence, yeast two-hybrid technology and phage display which are common practice in the art, for example, in Sambrook et al. (2001), Molecular Cloning, A Laboratory Manual. Third Edition. Cold Spring Harbor Laboratory Press, Cold Spring Harbor, NY. Other methods of detecting binding between a test compound and a GPCR include ultrafiltration with ion spray mass spectroscopy/HPLC methods or other (bio) physical and analytical methods. Fluorescence Energy Resonance Transfer (FRET) methods, for example, well known to those skilled in the art, may also be used. It will be appreciated that a bound test compound can be detected using a unique label or tag associated with the compound, such as a peptide label, a nucleic acid label, a chemical label, a fluorescent label, or a radio frequency tag, as described further herein.

The efficacy of the compounds and/or compositions comprising the same, can be tested using any suitable in vitro assay, cell-based assay, in vivo assay and/or animal model known per se, or any combination thereof, depending on the specific disease or disorder involved.

In one particular embodiment, it is determined whether the compound alters the binding of the GPCR to a receptor ligand (as defined herein). Binding of a GPCR to its ligand can be assayed using standard ligand binding methods known in the art as described herein. For example, a ligand may be radiolabeled or fluorescently labeled. The assay may be carried out on whole cells or on membranes obtained from the cells or aqueous solubilized receptor with a detergent. The compound will be characterized by its ability to alter the binding of the labeled ligand (see also Example section). The compound may decrease the binding between the GPCR and its ligand, or may increase the binding between the GPCR and its ligand, for example by a factor of at least 2 fold, 3 fold, 4 fold, 5 fold, 10 fold, 20 fold, 30 fold, 50 fold, 100 fold. Thus, according to more specific embodiments, the complex as used in any of the above screening methods further comprises a receptor ligand. Preferably, the receptor ligand is chosen from the group comprising a small molecule, a polypeptide, an antibody or any fragment derived thereof, a natural product, and the like. More preferably, the receptor ligand is a full agonist, or a partial agonist, or an inverse agonist, or an antagonist, as described hereinbefore.

In addition to establishing binding to a target GPCR:G protein complex in a functional conformational state, it will also be desirable to determine the functional effect of a compound on the GPCR:G protein complex, in particular on the biological activity of the GPCR and downstream interacting partners. In particular, the binding domains according to the disclosure can be used to screen for compounds that modulate (increase or decrease) the biological activity of the GPCR:G protein complex, or its constituents, being the GPCR or the G protein. The desired modulation in biological activity will depend on the GPCR of choice. The compounds may bind to the target GPCR:G protein complex, in particular to one or both of its constituents, resulting in the modulation (activation or inhibition) of downstream receptor signaling. This modulation of GPCR signaling can occur ortho- or allosterically. The compounds may bind to the target complex comprising a GPCR bound to a G protein or its constituents so as to activate or increase receptor signaling; or alternatively so as to decrease or inhibit receptor signaling. The compounds may also bind to the target complex in such a way that they block off the constitutive activity of the GPCR. The compounds may also bind to the target complex in such a way that they mediate allosteric modulation (e.g., bind to the GPCR or G protein at an allosteric site). In this way, the compounds may modulate the receptor function by binding to different regions in the GPCR; G protein complex (e.g., at allosteric sites). Reference is for example made to George et al. (2002), Kenakin (2002) and Rios et al. (2001). The compounds of the disclosure may also bind to the target complex in such a way that they prolong the duration of the GPCR-mediated signaling or that they enhance receptor signaling by increasing receptor-ligand affinity. Further, the compounds may also bind to the target complex in such a way that they inhibit or enhance the assembly of GPCR functional homomers or heteromers.

Also, cell-based assays are critical for assessing the mechanism of action of new biological targets and biological activity of chemical compounds. Current cell-based assays for GPCRs include measures of pathway activation ($Ca^{2+}$ release, cAMP generation or transcriptional activity); measurements of protein trafficking by tagging GPCRs and downstream elements with GFP; and direct measures of interactions between proteins using Förster resonance energy transfer (FRET), bioluminescence resonance energy transfer (BRET) or yeast two-hybrid approaches. Introducing the binding domains of the present invention, inside the cell to the relevant compartment of the cell (intra- or extracellularly) by any means well known and commonly used in the art, may lead to new or better cell-based assays.

In particular, there is a need to "de-orphanize" those GPCRs for which a natural activating ligand has not been identified. The stabilization of GPCRs in a functional conformational state using the binding domains according to the disclosure enables screening approaches that may be used to identify ligands of "orphan" GPCRs where the natural ligand is unknown. For example, various approaches to "de-orphanization" have been adopted including array-screening against families of known ligands. Ligands of orphan GPCRs may be identified from biological samples. Thus, in a particular embodiment, the test compound is provided as a biological sample. In particular, the sample can be any suitable sample taken from an individual. For example, the sample may be a body fluid sample such as blood, serum, plasma, spinal fluid. Alternatively, the sample is tissue or cell extract.

The test compound as used in any of the above screening methods may be selected from the group comprising a polypeptide, a peptide, a small molecule, a natural product, a peptidomimetic, a nucleic acid, a lipid, lipopeptide, a carbohydrate, an antibody or any fragment derived thereof, such as Fab, Fab' and F(ab')2, Fd, single-chain Fvs (scFv), single-chain antibodies, disulfide-linked Fvs (dsFv) and fragments comprising either a VL or VH domain, a heavy chain antibody (hcAb), a single domain antibody (sdAb), a minibody, the variable domain derived from camelid heavy chain antibodies (VHH or nanobody), the variable domain of the new antigen receptors derived from shark antibodies (VNAR), a protein scaffold including an alphabody, protein A, protein G, designed ankyrin-repeat domains (DARPins), fibronectin type III repeats, anticalins, knottins, engineered CH2 domains (nanoantibodies), as defined hereinbefore.

The test compound may optionally be covalently or non-covalently linked to a detectable label. Suitable detectable labels and techniques for attaching, using and detecting them will be clear to the skilled person, and include, but are not limited to, any composition detectable by spectroscopic, photochemical, biochemical, immunochemical, electrical, optical or chemical means. Useful labels include magnetic beads (e.g., dynabeads), fluorescent dyes (e.g., all Alexa Fluor dyes, fluorescein isothiocyanate, Texas red, rhodamine, green fluorescent protein and the like), radiolabels (e.g., $^3H$, $^{125}S$, $^{14}C$, or $^{32}P$), enzymes (e.g., horse radish peroxidase, alkaline phosphatase), and colorimetric labels such as colloidal gold or colored glass or plastic (e.g., polystyrene, polypropylene, latex, etc.) beads. Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label. Other suitable detectable labels were described earlier within the context of the first aspect of the disclosure relating to a binding domain.

According to a specifically preferred embodiment, the test compound is an antibody or any fragment derived thereof, as described above, including a nanobody. For example, and without the purpose of being limitative, test compounds may be antibodies (as defined herein in its broadest sense) that have been raised against a GPCR:G protein complex stabilized by a binding domain according to the invention. Methods for raising antibodies in vivo are known in the art. Preferably, immunization of an animal will be done in a similar way as described herein before. The disclosure also relates to methods for selecting antibodies specifically binding to a conformationally stabilized GPCR:G protein complex, involving the screening of expression libraries encoding immunoglobulin genes, or portions thereof, expressed in bacteria, yeast, filamentous phages, ribosomes or ribosomal subunits or other display systems on the GPCR:G protein complex.

A particular aspect of the present disclosure relates to a solid support to which is immobilized a binding domain according to the invention. Such a solid support (as described hereinbefore) may thus be used in any of the above screening methods.

Modulating GPCR Receptor Signaling

The binding domains of the present disclosure can also be used to modulate GPCR signaling, in particular G protein-mediated GPCR signaling, including abolishing G protein-mediated GPCR signaling. The terms "modulating," "modulation," and "modulated" means an increase or decrease in activity of a protein or a protein complex, in particular a GPCR:G protein complex. In particular, the binding domains of the present disclosure can be allosteric modulators or allosteric inhibitors. The terms "allosteric modulator" or "allosteric inhibitor" in the context of the present disclosure refer to noncompetitive modulators or inhibitors, which exert their effect by binding to a site other than the active site of the receptor, and modulate the activity of the receptor or render the receptor ineffective in terms of signal transduction. A "positive allosteric modulator (PAM)" increases signal transduction, whereas a "negative allosteric modulator (NAM)" reduces signal transduction. In particular, an allosteric inhibitor may also abolish signal transduction. Assays to evaluate the modulation in GPCR signaling by the binding domains of the disclosure are as described hereinbefore.

In that regard, according to a specific embodiment, the binding domains of the present invention, in particular immunoglobulin single variable domains, can also be useful for lead identification and the design of peptidomimetics. Using a biologically relevant peptide or protein structure as a starting point for lead identification represents one of the most powerful approaches in modern drug discovery. Peptidomimetics are compounds whose essential elements (pharmacophore) mimic a natural peptide or protein in 3D space and which retain the ability to interact with the biological target and produce the same biological effect. Peptidomimetics are designed to circumvent some of the problems associated with a natural peptide: for example stability against proteolysis (duration of activity) and poor bioavailability. Certain other properties, such as receptor selectivity or potency, often can be substantially improved.

Therapeutic and Diagnostic Applications

Certain of the above-described binding domains may have therapeutic utility and may be administered to a subject having a condition in order to treat the subject for the condition. The therapeutic utility for a binding domain is determined by the target GPCR:G protein complex to which the binding domain binds in that signaling via that GPCR is linked to the condition. In certain cases, the GPCR may be activated in the condition by binding to a ligand. In other embodiments, the GPCR may be mutated to make it constitutively active, for example. A subject binding domain may be employed for the treatment of a GPCR-mediated condition such as schizophrenia, migraine headache, reflux, asthma, bronchospasm, prostatic hypertrophy, ulcers, epilepsy, angina, allergy, rhinitis, cancer, e.g., prostate cancer, glaucoma and stroke. Further exemplary GPCR-related conditions at the On-line Mendelian Inheritance in Man database found at the world wide website of the NCBI. So, a particular embodiment of the present disclosure also envisages the binding domain hereof, or a pharmaceutical composition comprising the binding domain, for use in the treatment of a GPCR-related disease or disorder. It will be appreciated that the therapeutic utility will also depend on the particular conformational epitope of the GPCR:G protein complex against which the binding domain is directed to.

A subject binding domain may be mixed with another drug substance in a fixed pharmaceutical composition or it may be administered separately, before, simultaneously with or after the other drug substance. In general terms, these protocols involve administering to an individual suffering from a GPCR-related disease or disorder an effective amount of a binding domain that modulates the signaling activity of a GPCR in the host and treat the individual for the disorder.

In some embodiments, where a reduction in activity of a certain GPCR is desired, one or more compounds that decrease the activity of the GPCR may be administered, whereas when an increase in activity of a certain GPCR is desired, one or more compounds that increase the activity of the GPCR activity may be administered.

A variety of individuals are treatable according to the subject methods. Generally such individuals are mammals or mammalian, where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the individuals will be humans. Subject treatment methods are typically performed on individuals with such disorders or on individuals with a desire to avoid such disorders.

In another aspect, the disclosure also relates to a pharmaceutical composition comprising a therapeutically effective amount of the binding domains of the disclosure and at least one pharmaceutically acceptable carrier, adjuvant or diluent.

A "carrier" or "adjuvant," in particular, a "pharmaceutically acceptable carrier" or "pharmaceutically acceptable adjuvant," is any suitable excipient, diluent, carrier and/or adjuvant which, by themselves, do not induce the production of antibodies harmful to the individual receiving the composition nor do they elicit protection. So, pharmaceutically acceptable carriers are inherently non-toxic and nontherapeutic, and they are known to the person skilled in the art. Suitable carriers or adjuvantia typically comprise one or more of the compounds included in the following non-exhaustive list: large slowly metabolized macromolecules such as proteins, polysaccharides, polylactic acids, polyglycolic acids, polymeric amino acids, amino acid copolymers and inactive virus particles. Carriers or adjuvants may be, as a non-limiting example, Ringer's solution, dextrose solution or Hank's solution. Non aqueous solutions such as fixed oils and ethyl oleate may also be used. A preferred excipient is 5% dextrose in saline. The excipient may contain minor amounts of additives such as substances that enhance isotonicity and chemical stability, including buffers and preservatives.

The administration of a binding domain as described herein or a pharmaceutically acceptable salt thereof may be by way of oral, inhaled or parenteral administration. In particular embodiments the nanobody is delivered through intrathecal or intracerebroventricular administration. The active compound may be administered alone or preferably formulated as a pharmaceutical composition. An amount effective to treat a certain disease or disorder that express the antigen recognized by the binding domain depends on the usual factors such as the nature and severity of the disorder being treated and the weight of the mammal. However, a unit dose will normally be in the range of 0.01 to 50 mg, for example 0.01 to 10 mg, or 0.05 to 2 mg of binding domain or a pharmaceutically acceptable salt thereof. Unit doses will normally be administered once or more than once a day, for example 2, 3, or 4 times a day, more usually 1 to 3 times a day, such that the total daily dose is normally in the range of 0.0001 to 1 mg/kg; thus a suitable total daily dose for a 70 kg adult is 0.01 to 50 mg, for example 0.01 to 10 mg or more usually 0.05 to 10 mg. It is greatly preferred that the compound or a pharmaceutically acceptable salt thereof is administered in the form of a unit-dose composition, such as a unit dose oral, parenteral, or inhaled composition. Such compositions are prepared by admixture and are suitably adapted for oral, inhaled or parenteral administration, and as such may be in the form of tablets, capsules, oral liquid preparations, powders, granules, lozenges, reconstitutable powders, injectable and infusable solutions or suspensions or suppositories or aerosols.

Tablets and capsules for oral administration are usually presented in a unit dose, and contain conventional excipients such as binding agents, fillers, diluents, tabletting agents, lubricants, disintegrants, colorants, flavorings, and wetting agents. The tablets may be coated according to well-known methods in the art. Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate. These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavoring or coloring agents. Oral formulations also include conventional sustained release formulations, such as tablets or granules having an enteric coating.

Preferably, compositions for inhalation are presented for administration to the respiratory tract as a snuff or an aerosol or solution for a nebulizer, or as a microfine powder for insufflation, alone or in combination with an inert carrier such as lactose. In such a case the particles of active compound suitably have diameters of less than 50 microns, preferably less than 10 microns, for example between 1 and 5 microns, such as between 2 and 5 microns. A favored inhaled dose will be in the range of 0.05 to 2 mg, for example 0.05 to 0.5 mg, 0.1 to 1 mg or 0.5 to 2 mg.

For parenteral administration, fluid unit dose forms are prepared containing a compound of the present disclosure and a sterile vehicle. The active compound, depending on the vehicle and the concentration, can be either suspended or dissolved. Parenteral solutions are normally prepared by dissolving the compound in a vehicle and filter sterilizing before filling into a suitable vial or ampoule and sealing. Advantageously, adjuvants such as a local anesthetic, preservatives and buffering agents are also dissolved in the vehicle. To enhance the stability, the composition can be frozen after filling into the vial and the water removed under vacuum. Parenteral suspensions are prepared in substantially the same manner except that the compound is suspended in the vehicle instead of being dissolved and sterilized by exposure to ethylene oxide before suspending in the sterile vehicle. Advantageously, a surfactant or wetting agent is included in the composition to facilitate uniform distribution of the active compound. Where appropriate, small amounts of bronchodilators for example sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included. As is common practice, the compositions will usually be accompanied by written or printed directions for use in the medical treatment concerned.

Delivery of binding domains, in particular immunoglobulin single variable domains, into cells may be performed as described for peptides, polypeptides and proteins. If the antigen is extracellular or an extracellular domain, the binding domain may exert its function by binding to this domain, without need for intracellular delivery. The binding domains of the present disclosure as described herein may target intracellular conformational epitopes of GPCR:G proteins of interest. To use these binding domains as effective and safe therapeutics inside a cell, intracellular delivery may be enhanced by protein transduction or delivery systems know in the art. Protein transduction domains (PTDs) have attracted considerable interest in the drug delivery field for their ability to translocate across biological membranes. The PTDs are relatively short (1 1-35 amino acid) sequences that confer this apparent translocation activity to proteins and other macromolecular cargo to which they are conjugated, complexed or fused (Sawant and Torchilin 2010). The HIV-derived TAT peptide (YGRKKRRQRRR), for example, has been used widely for intracellular delivery of various agents ranging from small molecules to proteins, peptides, range of pharmaceutical nanocarriers and imaging agents. Alternatively, receptor-mediated endocytic mechanisms can also be used for intracellular drug delivery. For example, the transferrin receptor-mediated internalization pathway is an efficient cellular uptake pathway that has been exploited for site-specific delivery of drugs and proteins (Qian et al., 2002). This is achieved either chemically by conjugation of transferrin with therapeutic drugs or proteins or genetically by infusion of therapeutic peptides or proteins into the structure of transferrin. Naturally existing proteins (such as the iron-binding protein transferrin) are very useful in this area of drug targeting since these proteins are biodegradable, nontoxic, and non-immunogenic. Moreover, they can achieve site-specific targeting due to the high amounts of their receptors present on the cell surface. Still other delivery systems include, without the purpose of being limitative, polymer- and liposome-based delivery systems.

The efficacy of the binding domains hereof, and of compositions comprising the same, can be tested using any suitable in vitro assay, cell-based assay, in vivo assay and/or animal model known per se, or any combination thereof, depending on the specific disease or disorder involved.

Screening, Selection, Production of Binding Domains

In still another aspect, the disclosure also encompasses a method of screening for binding domains directed against and/or specifically binding to a complex comprising a GPCR and a G protein, comprising the steps of:
 a) Providing a plurality of binding domains, and
 b) Screening the plurality of binding domains for a binding domain that binds to a complex comprising a GPCR and a G protein, and
 c) Isolating the binding domain that binds to the complex.

In a preferred embodiment of this aspect hereof, binding domains are generated and screened for their specific binding to a complex comprising a GPCR and a G protein and optionally a receptor ligand. The binding domains may also be generated and screened for their specific binding to a G protein. As described herein, binding domains can be generated in many ways. In the case of immunoglobulin single variable domains, such as nanobodies, typically, immunization of an animal will be done with a target complex comprising a GPCR bound to a G protein and a receptor ligand, as described hereinbefore (e.g., for $V_HH$ sequences, as a non-limiting example) and also exemplified further herein.

For the immunization of an animal with a target complex, the proteins of the target complex (i.e., GPCR and G protein) may be produced and purified using conventional methods that may employ expressing a recombinant form of the proteins in a host cell, and purifying the proteins using affinity chromatography and/or antibody-based methods. In particular embodiments, the bactulovirus/Sf-9 system may be employed for expression, although other expression systems (e.g., bacterial, yeast or mammalian cell systems) may also be used. Exemplary methods for expressing and purifying GCPRs are described in, for example, Kobilka (1995), Eroglu et al. (2002), Chelikani et al. (2006) and the book "Identification and Expression of G Protein-Coupled Receptors" (Kevin R. Lynch (Ed.), 1998), among many others. A functional GPCR:G protein complex may also be reconstituted by using purified receptor (e.g., β2-AR or MOR) reconstituted into recombinant HDL particles with a stoichiometric excess of the G protein (Gs or Gi) as described in Whorton et al. (2009) for β2-AR:Gs or in Kuszak et al. (2009) for MOR:Gi. A GPCR may also be reconstituted in phospholipid vesicles and loaded with a stoichiometric excess of the G protein. Likewise, methods for reconstituting an active GPCR in phospholipid vesicles are known, and are described in: Luca et al. (2003), Mansoor et al. (2006), Niu et al. (2005), Shimada et al. (2002), and Eroglu et al. (2003), among others. In certain cases, the GPCR and phospholipids may be reconstituted at high density (e.g., 1 mg receptor per mg of phospholipid). In many cases, a GPCR may be present in the phospholipid vesicle in both orientations (in the normal orientation, and in the "upside down" orientation in which the intracellular loops are on the outside of the vesicle). Other immunization methods with a GPCR include, without limitation, the use of complete cells expressing a GPCR and/or a G protein or membranes derived thereof.

In a particular embodiment, the animal is immunized with a target complex that is cross-linked with a bifunctional cross-linker (see also Example section). Chemical crosslinking can be done using standard techniques that are well-known by the skilled person in the art (see, e.g., Hermanson, G. T. (2008) Bioconjugate Techniques, 2nd ed., Elsevier Inc., 1202 pages).

Any suitable animal, e.g., a warm-blooded animal, in particular a mammal such as a rabbit, mouse, rat, camel, sheep, cow or pig or a bird such as a chicken or turkey, may be immunized using any of the techniques well known in the art suitable for generating an immune response.

The screening for binding domains specifically binding to a conformational epitope of a target complex may for example be performed by screening a set, collection or library of cells that express the binding domains on their surface (e.g., B-cells obtained from a suitably immunized Camelid), by screening of a (naïve or immune) library of binding domains, or by screening of a (naïve or immune) library of nucleic acid sequences that encode amino acid sequences of the binding domains, which may all be performed in a manner known per se, and which method may optionally further comprise one or more other suitable steps, such as, for example and without limitation, a step of affinity maturation, a step of expressing the desired amino acid sequence, a step of screening for binding and/or for activity against the desired antigen, a step of determining the desired amino acid sequence or nucleotide sequence, a step of introducing one or more humanizing substitutions, a step of formatting in a suitable multivalent and/or multispecific format, a step of screening for the desired biological and/or physiological properties (i.e., using a suitable assay known in the art), and/or any combination of one or more of such steps, in any suitable order.

Yet another aspect of the disclosure relates to a kit comprising a binding domain according to the invention. The kit may further comprise a combination of reagents such as buffers, molecular tags, vector constructs, reference sample material, as well as a suitable solid supports, cells, nucleic acids, and the like. Such a kit may be useful for any of the applications of the present disclosure as described herein. For example, the kit may comprise (a library of) test compounds useful for compound screening applications.

Finally, a last aspect of the disclosure is the use of any binding domain according to the disclosure to isolate amino acid sequences that are responsible for specific binding to a conformational epitope of a GPCR:G protein complex and to construct artificial binding domains based on the amino acid sequences. It will be appreciated that in the binding domains according to the invention, the framework regions and the complementarity-determining regions are known, and the study of derivatives of the binding domain, binding to the same conformational epitope of a GPCR:G protein complex, will allow deducing the essential amino acids involved in binding the conformational epitope. This knowledge can be used to construct a minimal binding domain and to create derivatives thereof, which can routinely be done by techniques known by the skilled in the art.

The following examples are intended to promote a further understanding of the present invention. While the present disclosure is described herein with reference to illustrated embodiments, it should be understood that the disclosure is not limited hereto. Those having ordinary skill in the art and access to the teachings herein will recognize additional modifications and embodiments within the scope thereof. Therefore, the present disclosure is limited only by the claims attached herein.

EXAMPLES

Figure 2:
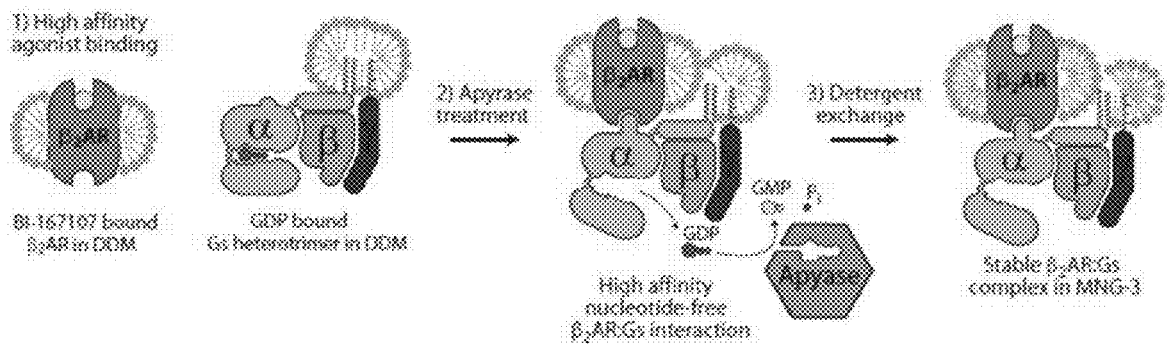
FIG. 2: Formation of a stable $\beta_2AR$:Gs complex. A stable $\beta_2AR$:Gs complex was achieved by the combined effects of: 1) binding a high affinity agonist to the receptor with an extremely slow dissociation rate (as described in Rasmussen et al., 2011); 2) formation of a nucleotide free complex in the presence of apyrase that hydrolyses released GDP preventing it from rebinding and causing a less stable R:G interaction; and 3) detergent exchange of DDM for MNG-3 that stabilizes the complex.
Figure 3A:
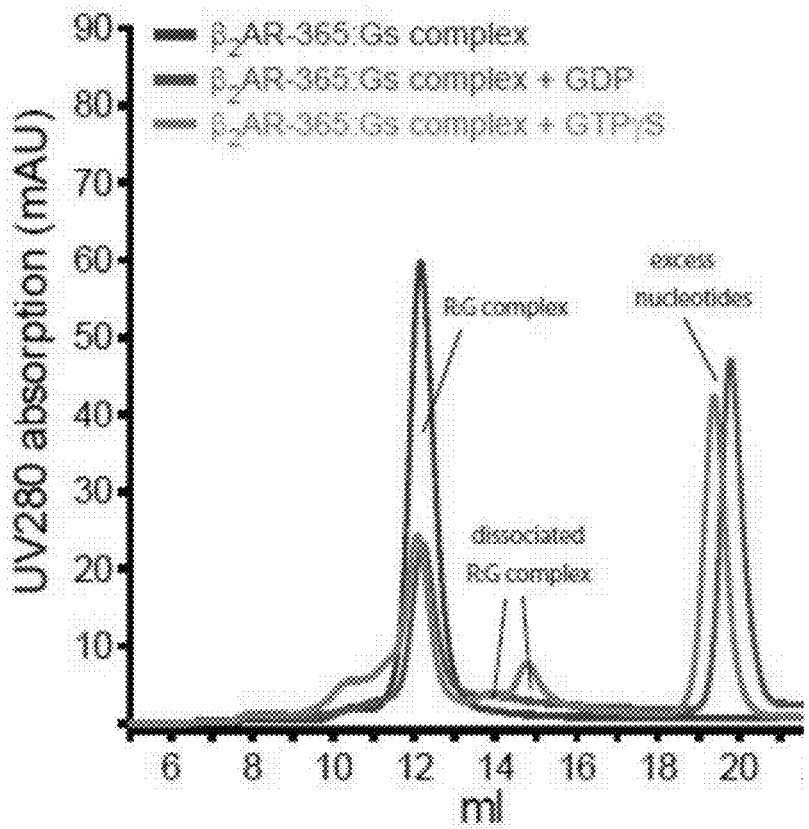

Example 1: Formation and Purification of a Stable Agonist-β2AR-Gs Ternary Complex Formation of a stable complex (see FIG. 2) was accomplished by mixing Gs heterotrimer at approximately 100 µM concentration with BI-167107 bound T4L-$β_2$AR (or $β_2$AR-365) in molar excess (approximately 130 µM) in 2 ml buffer (10 mM HEPES, pH 7.5, 100 mM NaCl, 0.1% DDM, 1 mM EDTA, 3 mM $MgCl_2$, 10 µM BI-167107) and incubating for 3 hours at room temperature. BI-167107, which was identified from screening and characterizing approximately 50 different $β_2$AR agonists, has a dissociation half-time of approximately 30 hours providing higher degree of stabilization to the active G protein-bound receptor than other full agonists such as isoproterenol (Rasmussen et al., 2011). To maintain the high-affinity nucleotide-free state of the complex, apyrase (25 mU/ml, NEB) was added after 90 min to hydrolyze residual GDP released from Gαs upon binding to the receptor. GMP resulting from hydrolysis of GDP by apyrase has very poor affinity for the G protein in the complex. Rebinding of GDP can cause dissociation of the R:G complex (FIG. 3A).

Figure 4:
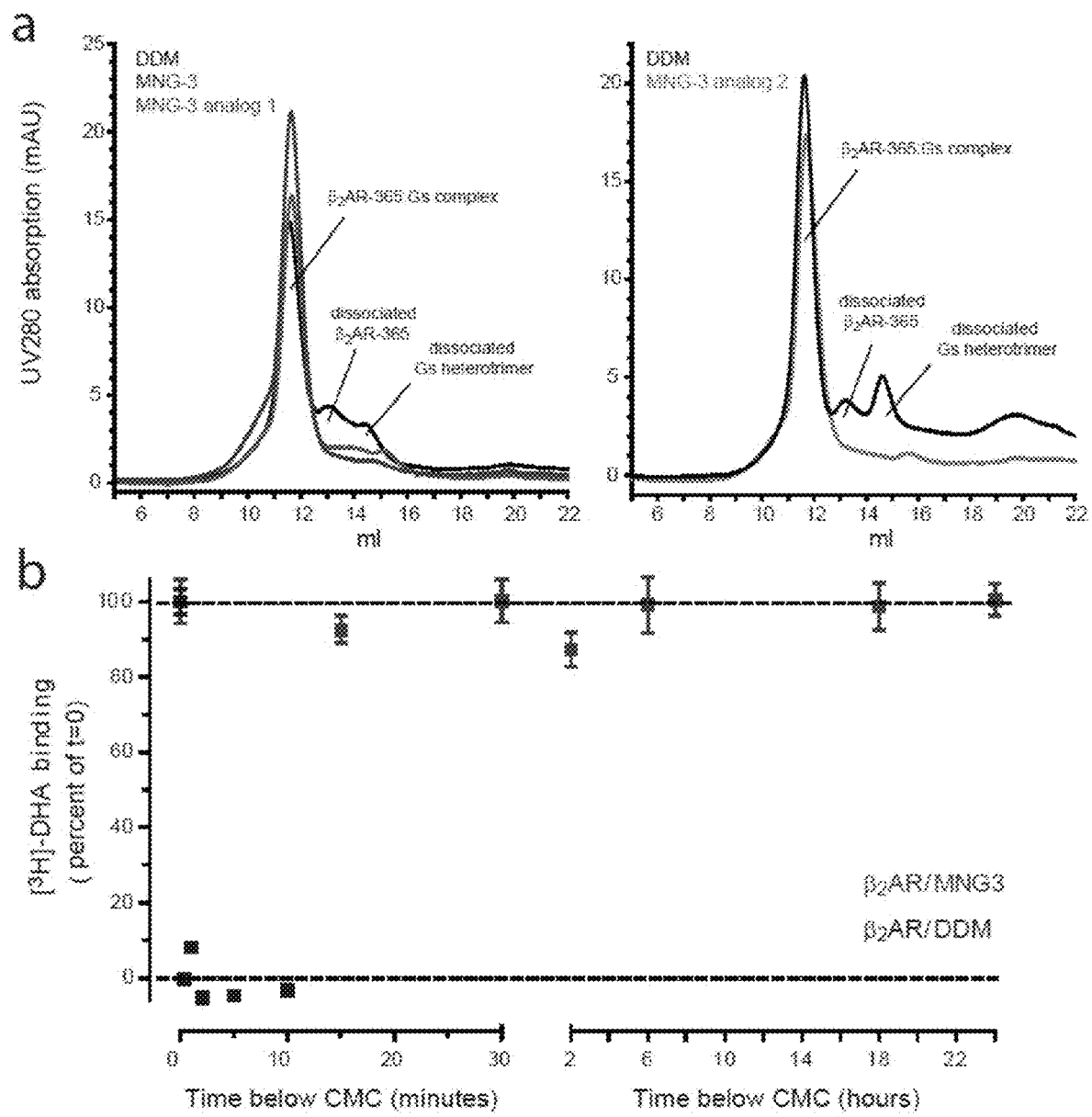
FIG. 4: Stabilizing effect of MNG-3 on the R:G complex. Panel a) Analytical gel filtration of $\beta_2AR$-365:Gs complexes purified in DDM (in black), MNG-3 (in blue), or two MNG-3 analogs (in red and green) following incubation for 48 hrs at 4° C. In contrast to DDM the R:G complexes are stable in the MNG detergents. Panel b) Effect of diluting unliganded purified β2AR in DDM or MNG-3 below the critical micelle concentration (CMC) of the detergent as assayed by 3H-dihydro alprenolol (3H-DHA) saturation binding. Diluting β2AR maintained in DDM 1000-fold below the CMC cause loss in 3H-DHA binding (black data points) after 20 sec. In contrast β2AR in MNG-3 diluted 1000-fold below the CMC maintained full ability to bind the radioligand after 24 hrs.

The R:G complex in DDM shows significant dissociation after 48 hours at 4° C. (FIG. 4, Panel a). We screened and characterized over 50 amphiphiles (data not shown) and identified MNG-3 (NG-310, Affymetrix-Anatrace; Chae et al., 2011) and its closely related analogs as detergents that substantially stabilize the complex (FIG. 4, Panels a and b). The complex was exchanged into MNG-3 by adding the R:G mixture (2 ml) to 8 ml buffer (20 mM HEPES, pH 7.5, 100 mM NaCl, 10 µM BI-167107) containing 1% MNG-3 for 1 hour at room temperature.

Figure 5:
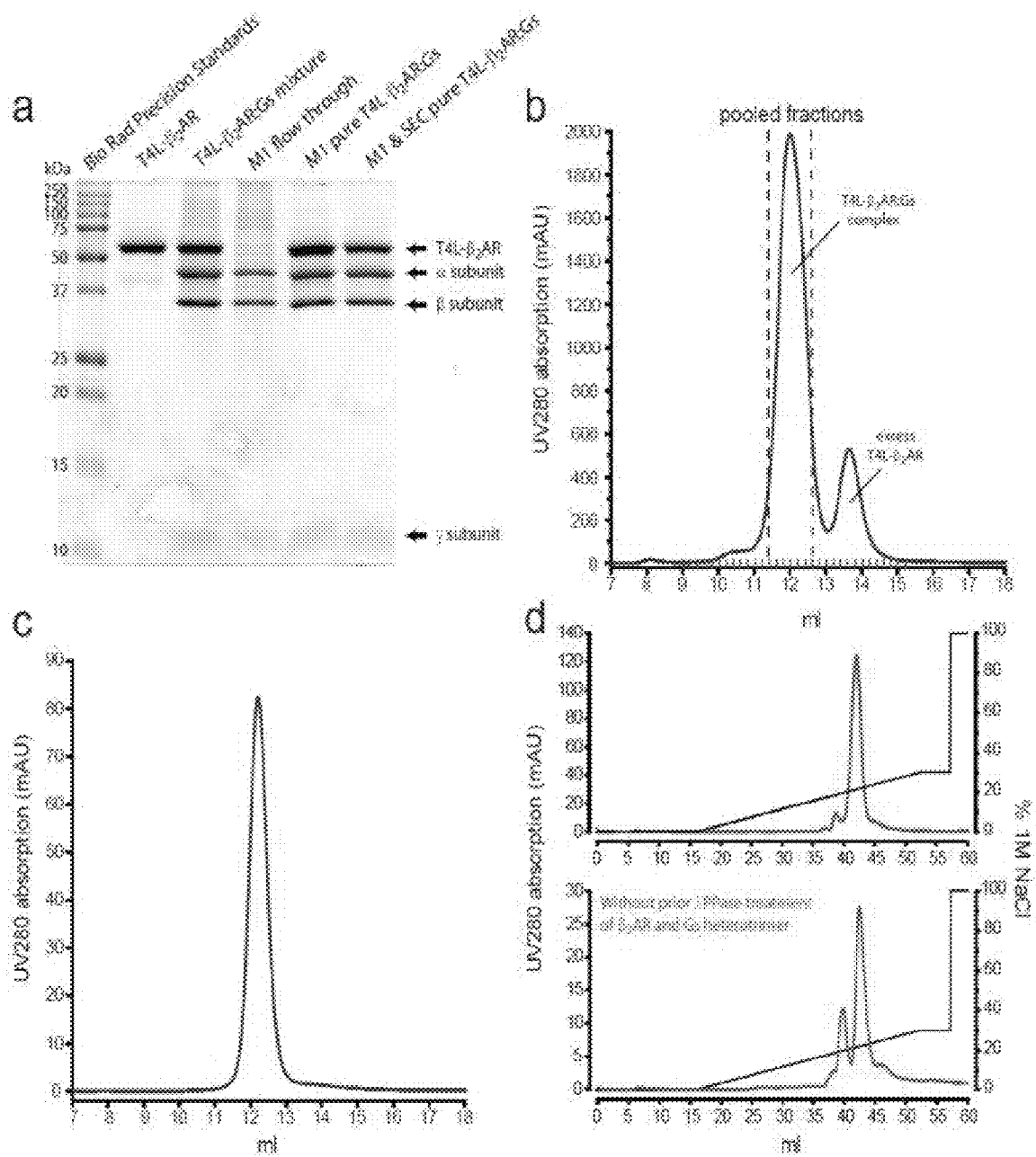
FIG. 5: Purity and homogeneity of the R:G complex. Panel a) Analytical SDS-PAGE/Coomassie blue stain of samples obtained at various stages of T4L-$\beta_2AR$:Gs purification. BI167107 agonist bound, dephosphorylated, and deglycosylated receptor in excess amount of Gs heterotrimer is used for optimal coupling efficiency with the functional fraction of the G protein. Functional purification of Gs is archived through its interaction with the immobilized receptor on the M1 resin while non-functional/non-binding Gs washes out. Panel b) A representative elution profile of one of four consecutive preparative gel filtrations with fractionation indicated in red. Fractions containing the R:G complex were pooled within the indicated dashed lines, spin concentrated and analyzed for purity and homogeneity by SDS-PAGE/Coomassie blue (a, second last lane to the right), gel filtration in Panel c), and by anion exchange chromatography in Panel d). Upper panel shows elution profile from analytical IEC of β2AR-365:Gs complex that was treated with XPPase prior to complex formation in comparison with complex which was not dephosphorylated resulting in a heterogeneous preparation (lower panel). The less homogeneous material in the fractions outside the indicated dashed lines in Panel b) were used for analytical gel filtration experiments of the R:G complex in presence of various chemicals (examples in FIG. 1).

At this stage the mixture contains the R:G complex, non-functional Gs, and an excess of $β_2$AR. To separate functional R:G complex from non-functional Gs, and to complete the detergent exchange, the R:G complex was immobilized on M1 Flag resin and washed in buffer (20 mM HEPES, pH 7.5, 100 mM NaCl, 10 µM BI-167107, and 3 mM $CaCl_2$) containing 0.2% MNG-3. To prevent cysteine bridge-mediated aggregation of R:G complexes, 100 µM TCEP was added to the eluted protein prior to concentrating it with a 50 kDa MWCO Millipore concentrator. The final size exclusion chromatography procedure to separate excess free receptor from the R:G complex (FIG. 5, Panel b) was performed on a Superdex 200 10/300 GL column (GE Healthcare) equilibrated with buffer containing 0.02% MNG-3, 10 mM HEPES pH 7.5, 100 mM NaCl, 10 µM BI-167107, and 100 µM TCEP. Peak fractions were pooled (FIG. 5, Panel b) and concentrated to approximately 90 mg $ml^{-1}$ with a 100 kDa MWCO Viva-spin concentrator and analyzed by SDS-PAGE/Coomassie brilliant blue staining (FIG. 5, Panel a) and gel filtration (FIG. 5, Panel c). To confirm a pure, homogeneous, and dephosphorylated preparation, the R:G complex was routinely analyzed by ion exchange chromatography (FIG. 5, Panel d).

Example 2: Generation of Nanobodies Binding to the Agonist: β2AR:Gs Ternary Complex From negative stain EM imaging (data not shown), we observed that the alpha helical domain of Gαs was flexible. Targeted stabilization of this domain was addressed by generating nanobodies that bind to the agonist-β2AR-Gs ternary complex. Nanobodies are single domain antibodies, derived from heavy chain only antibodies from llamas (Muyldermans, 2001). To identify Nanobodies that bind the (agonist loaded) receptor coupled Gs-protein, we immunized two llamas (Llama glama) with the bis(sulfosuccinimidyl)glutarate (BS2G, Pierce) cross-linked β2AR:Gs:BI167107 ternary complex. Both animals were immunized with 4 bi-weekly shots of 50 to 100 µg. After completing the immunization, peripheral blood lymphocytes were isolated from the immunized animals to extract total RNA and prepare cDNA. Total RNA was isolated from about $10^7$ lymphocytes as described by Chomczynski and Sacchi (1987). First strand cDNA synthesis was prepared using a dN6 primer and the superscript RT according to the manufacturers (Invitrogen) instructions. Fragments encoding VHH genes were amplified from this cDNA by PCR using specific primers as described previously (Conrad et al., 2001).

Using nested PCR, Pst1 and BstEII were engineered at the start and the end of the VHH open reading frame, respectively. VHHs were cloned as Pst1-BstEII fragments into the phage display vector pMESy4. For each llama, a separate phage display library was constructed harboring the respective Nanobody repertoire as a geneIII fusion (Domanska et al., 2011). R:G complex specific nanobodies were enriched by two rounds of biopanning on i) the β2AR:Gs:BI167107 ternary complex embedded in ApoL biotinylated high-density lipoprotein particles (rHDL, Whorton et al., 2007) or ii) on the BS2G cross-linked β2AR:Gs:BI167107 ternary complex. For the first biopanning strategy, biotinylated rHDL particles containing the β2AR:Gs:BI167107 ternary complex were immobilized on a neutravidin coated Maxisorp plate (Nunc) at 1 µg/well in 20 mM Hepes (pH 8.0), 100 mM NaCl, 1 mM EDTA, 100 µM TCEP, and 100 nM BI167107. For the second biopanning strategy the BS2G cross-linked β2AR:Gs:BI167107 ternary complex was solid phase coated on a Maxisorp plate at 1 µg/well. For each round of biopanning, $10^{11}$ phage was added to immobilized antigens and incubated for one to two hours. Next, non-bound phage was removed from the antigen containing wells and the wells were washed 14 times with 20 mM HEPES, 100 mM NaCl, pH8 and finally incubated for 10 minutes with 200 µL of 20 mM Hepes (pH 8.0), 100 mM NaCl, 1 mM EDTA, 100 µM TCEP, and 100 nM BI167107 to remove a specific phages. To elute complex specific phage, the wells were treated with trypsin, phage was recovered and used to infect exponentially growing TG1 cells (OD600±0.5).

From each enriched library, 48 colonies were randomly picked and grown in 1 ml 2×TY containing ampicillin and glucose. Cultures were induced with IPTG to induce the expression of the nanobodies and periplasmatic extracts containing a partially purified nanobody were prepared. Nanobodies contained in these periplasmic extracts were analyzed for binding to the agonist:β2AR:Gs ternary complex by ELISA.

Nanobodies enriched on biotinylated rHDL particles containing the β2AR:Gs:BI167107 ternary complex were analyzed by comparative ELISA on the same complex immobilized on neutravidin coated Maxisorb plates versus empty rHDL particles. Nanobodies enriched on solid phase coated BS2G cross-linked β2AR:Gs:BI167107 ternary complex were analyzed by comparative ELISA on the same solid phase coated complex versus non-coated wells. From colonies that scored positive in comparative ELISA, single clones were prepared, DNA was extracted and the sequences of the encoded nanobody genes were analyzed using routine methods (amino acid sequences shown in Tables 2 and 3). For Nb35, Nb36 and Nb37, binding to the β2AR:Gs:BI167107 ternary complex was further confirmed by analytical gel filtration (FIGS. 3D, 3E, 3F, 3G).

Figure 3B:
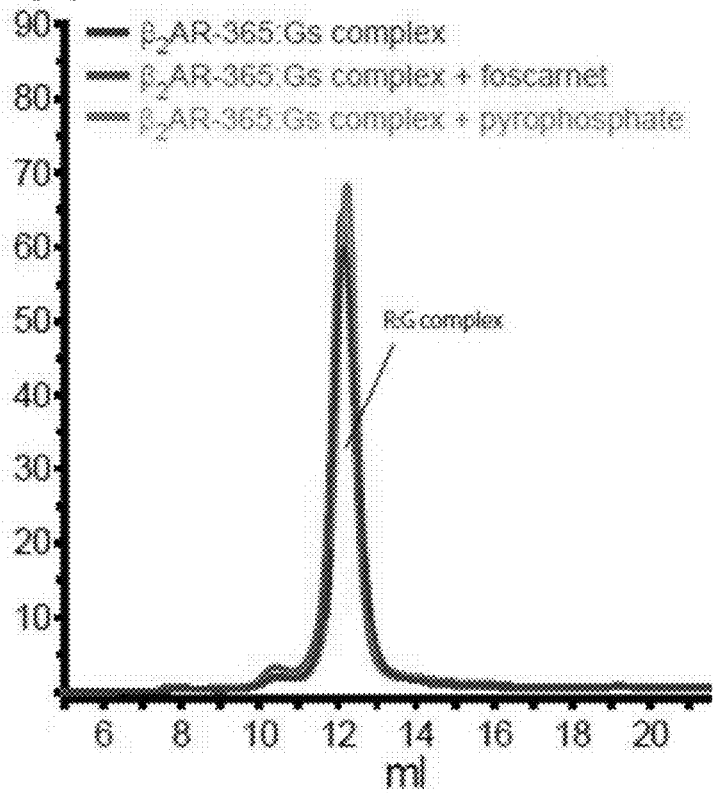
Figure 3D:
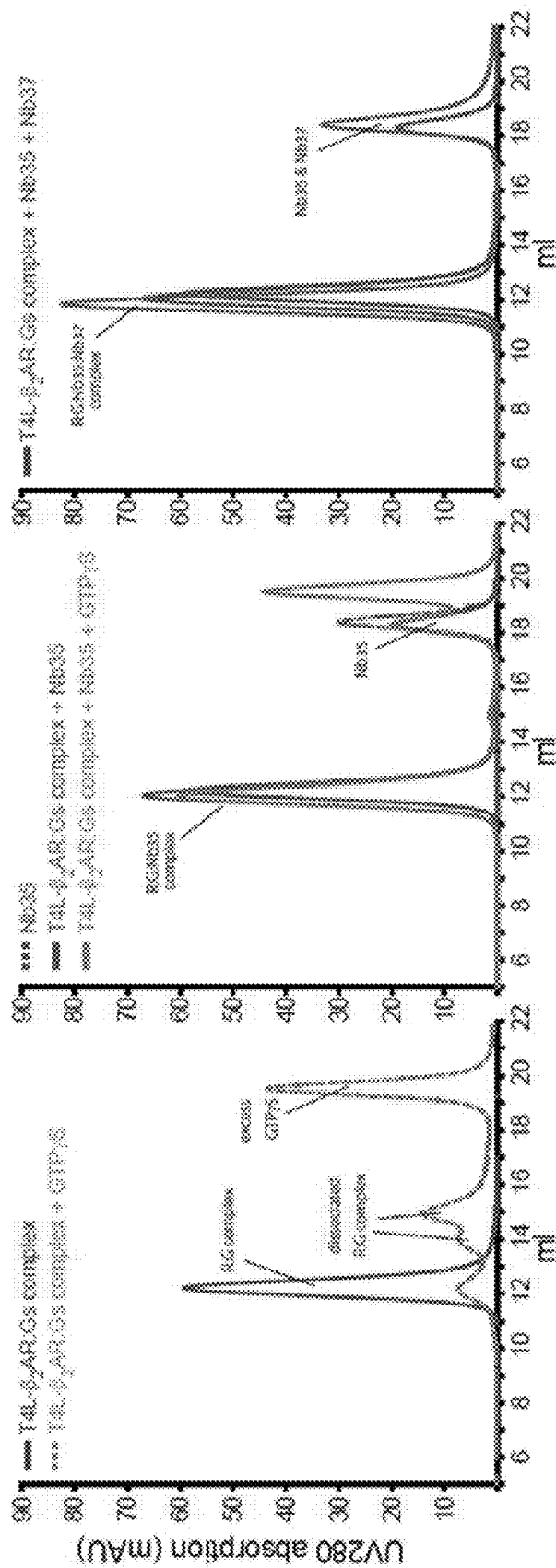
Figure 3E:
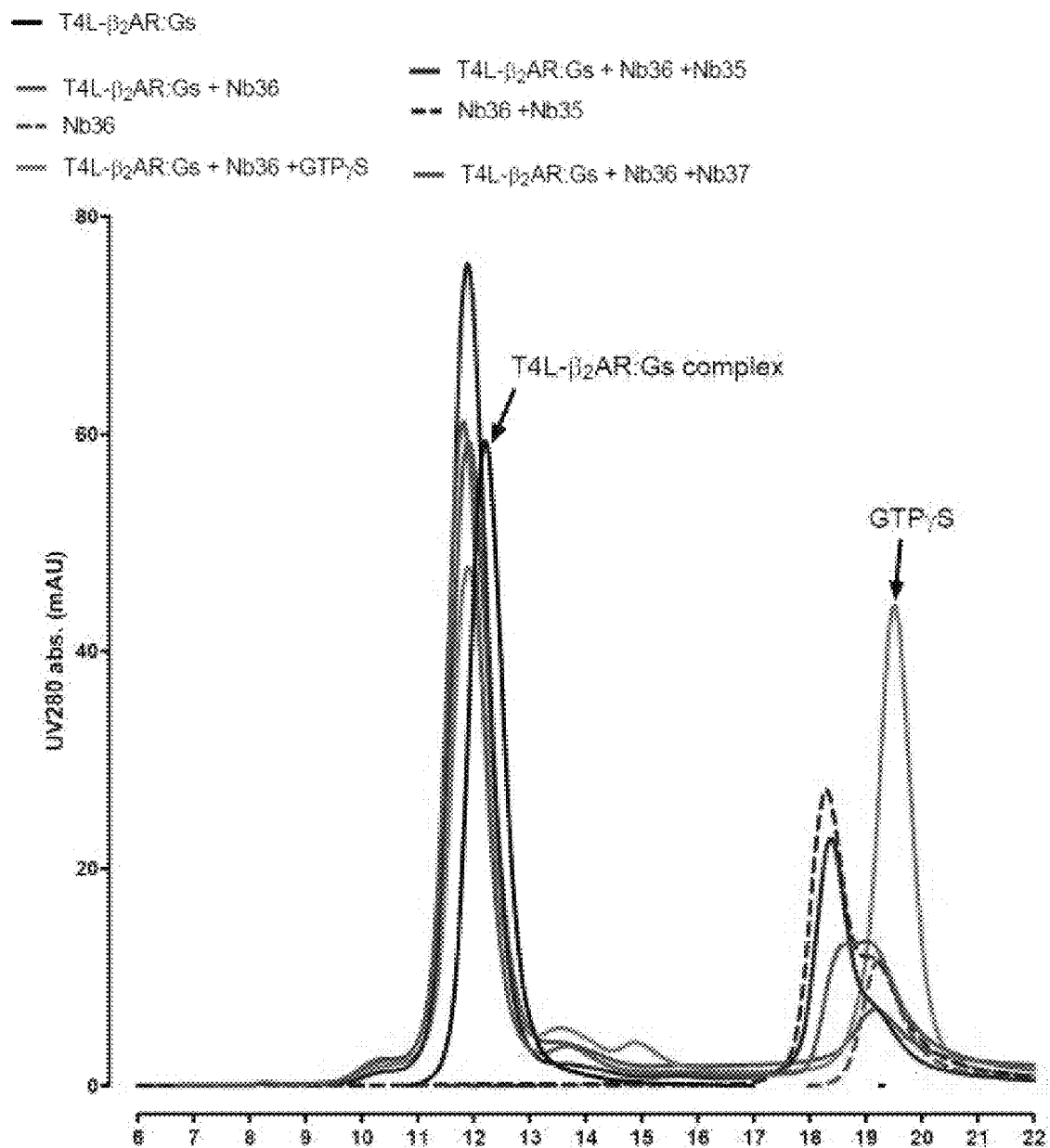
Figure 3F:
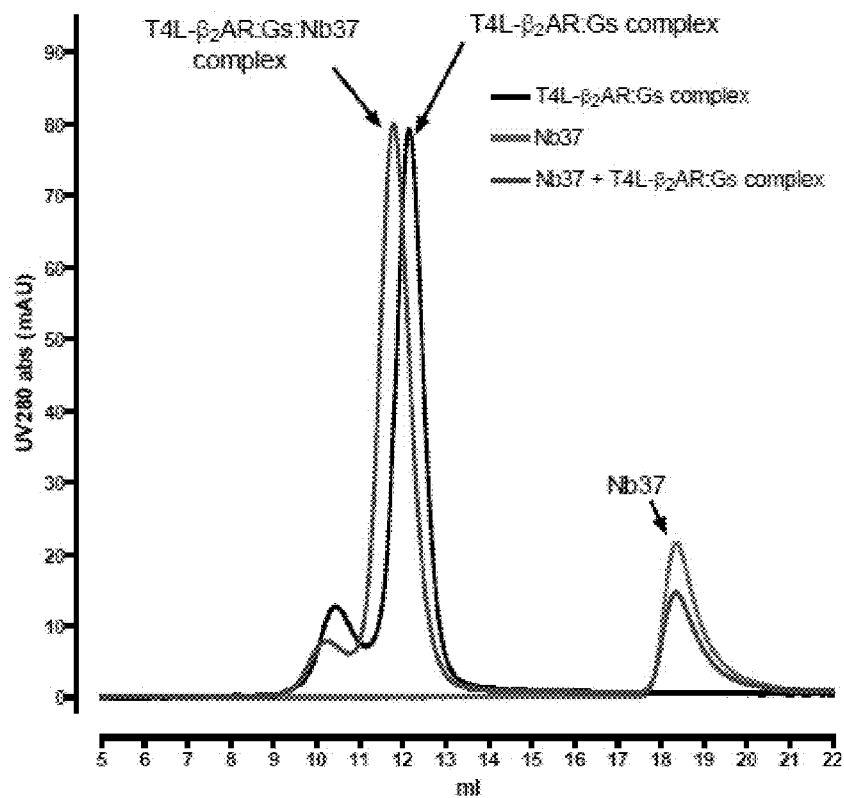

Example 3: Nb35, Nb36 and Nb37 Bind to Gs and Prevent Dissociation of the Complex by GTPγS To determine if the Nanobodies raised against the β2AR:Gs:BI167107 ternary complex (Table 2) bind to the receptor or to Gs, we next monitored binding of these nanobodies in ELISA on purified receptor alone. All nanobodies from Table 2 scored negative in solid phase coated (Maxisorb, Nunc) agonist-bound β2AR-356 reconstituted at high density into phospholipid vesicles (Rasmussen et al., 2011). Nb80, a β2AR specific nanobody (Rasmussen et al., 2011) scored positive in this ELISA. None of the β2AR:Gs:BI167107 binders described in Table 2 bind the reconstituted receptor alone, indicating that they bind epitopes contained on Gs. Size exclusion chromatography shows that Nb35 and Nb37 bind separate epitopes on the Gs heterotrimer to form a R:G:Nb35:Nb37 complex (FIG. 3D). Similarly, Nb36 and Nb37 bind separate epitopes on the Gs heterotrimer to form a R:G:Nb36:Nb37 complex (FIG. 3E).

Figure 3G:
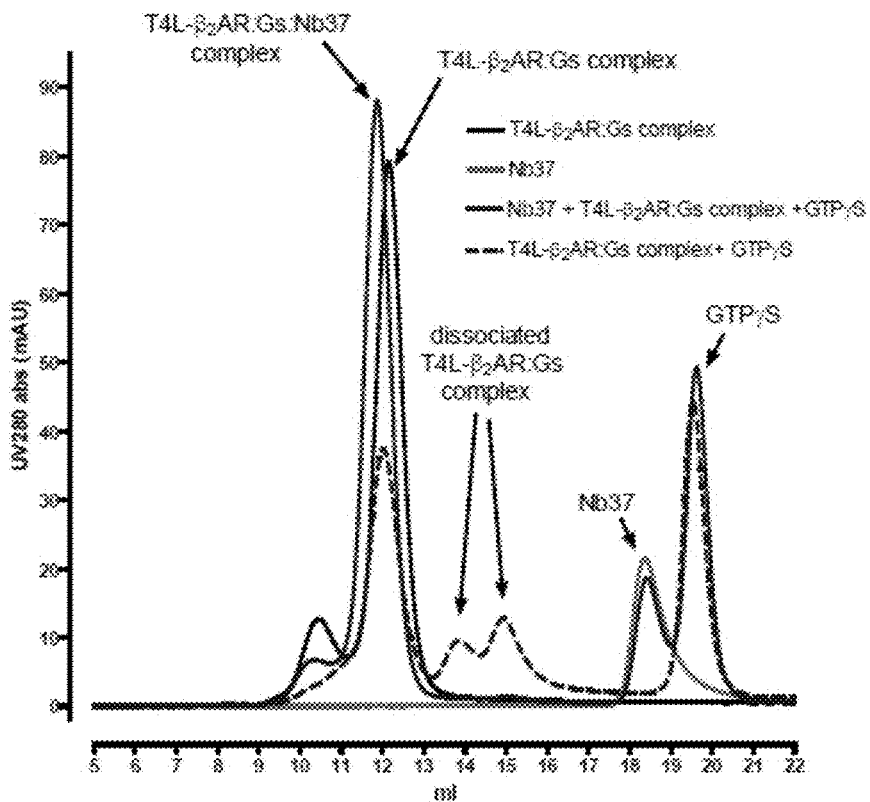

GDP, GTP and non-hydrolyzable GTP analogs disrupt the β2AR:Gs complex (FIG. 3A), causing dissociation of GPCR G protein complexes in vitro and in vivo. The mutual effects of Nbs and the non-hydrolyzable GTP analog GTPγS on the integrity of the agonist:β2AR:Gs ternary complex was analyzed by analytical size exclusion chromatography in the presence and absence of GTPγS. It was found that nanobodies 35, 36 and 37 protect the β2AR:Gs:BI167107 complex from dissociation by GTPγS (FIGS. 3D, 3E and 3G).

Example 4. Nanobody-Aided Crystallization of the β₂AR-Gs Complex

G protein-coupled receptors (GPCRs) are responsible for the majority of cellular responses to hormones and neurotransmitters as well as the senses of sight, olfaction and taste. The paradigm of GPCR signaling is the activation of a heterotrimeric GTP binding protein (G protein) by an agonist-occupied receptor. In an effort to understand the structural basis for GPCR signaling, we crystallized the β₂AR-Gs complex to solve its structure by X-ray crystallography.

One challenge for crystallogenesis was to prepare a stable β₂AR:Gs complex in detergent solution. The β₂AR and Gs couple efficiently in lipid bilayers, but not in detergents used to solubilize and purify these proteins (Example 1). It was found that a relatively stable β₂AR:Gs complex could be prepared by mixing purified GDP-Gs (approximately 100 μM final concentration) with a molar excess of purified β₂AR bound to a high affinity agonist (BI167107; Rasmussen et al., 2011) in dodecylmaltoside solution. Apyrase, a non-selective purine pyrophosphatase, was added to hydrolyze GDP released from Gs on forming a complex with the β₂AR. The complex was subsequently purified by sequential antibody affinity chromatography and size exclusion chromatography. The stability of the complex was enhanced by exchanging it into a recently developed maltose neopentyl glycol detergent (NG-310, Anatrace) (Chae et al., 2010). This complex could be incubated at room temperature for 24 hours without any noticeable degradation; however, initial efforts to crystallize the complex using sparse matrix screens in detergent micelles, bicelles and lipidic cubic phase (LCP) failed.

To further assess the quality of the complex, the protein was analyzed by single particle electron microscopy (EM). The results confirmed that the complex was monodisperse (data not shown), but revealed other possible bottlenecks for obtaining diffraction of quality crystals. First, the detergent used to stabilize the complex formed a large micelle, leaving little polar surface on the extracellular side of the β₂AR:Gs complex for the formation of crystal lattice contacts. Therefore, we replaced the unstructured amino terminus of the β₂AR with T4 lysozyme (T4L). We previously used T4L to facilitate crystallogenesis of the inactive β₂AR by inserting T4L between the cytoplasmic ends of transmembrane segments (TMs) 5 and 6 (Rosenbaum et al., 2007). This fusion protein (T4L-β₂AR) exhibited normal ligand binding and Gs coupling properties. Crystallization trials were carried out in LCP using a modified monolein (7.7 MAG, provided by Martin Caffrey) designed to accommodate the large hydrophilic component of the T4L-β₂AR:Gs complex (Misquitta et al., 2004). Although we were able to obtain small crystals that diffracted to 7 Å, we were unable to improve their quality through the use of additives and other modifications.

Another possible problem for crystallogenesis revealed by single particle EM analysis was increased variability in the positioning of the α-helical component of the Gαs subunit. Gαs consists of two domains, the ras-like GTPase domain (GαsRas), which interacts with the β₂AR and the Gβ subunit, and the α-helical domain (GαsAH) (Sprang et al., 1997). The interface of the two Gαs subdomains forms the nucleotide-binding pocket (FIG. 1), and EM 2D averages and 3D reconstructions suggest that in the absence of guanine nucleotide, GαsAH has a variable position relative to the complex of T4L-β₂AR-GαsRAS-Gβγ (FIG. 1, Panel b).

Figure 6:
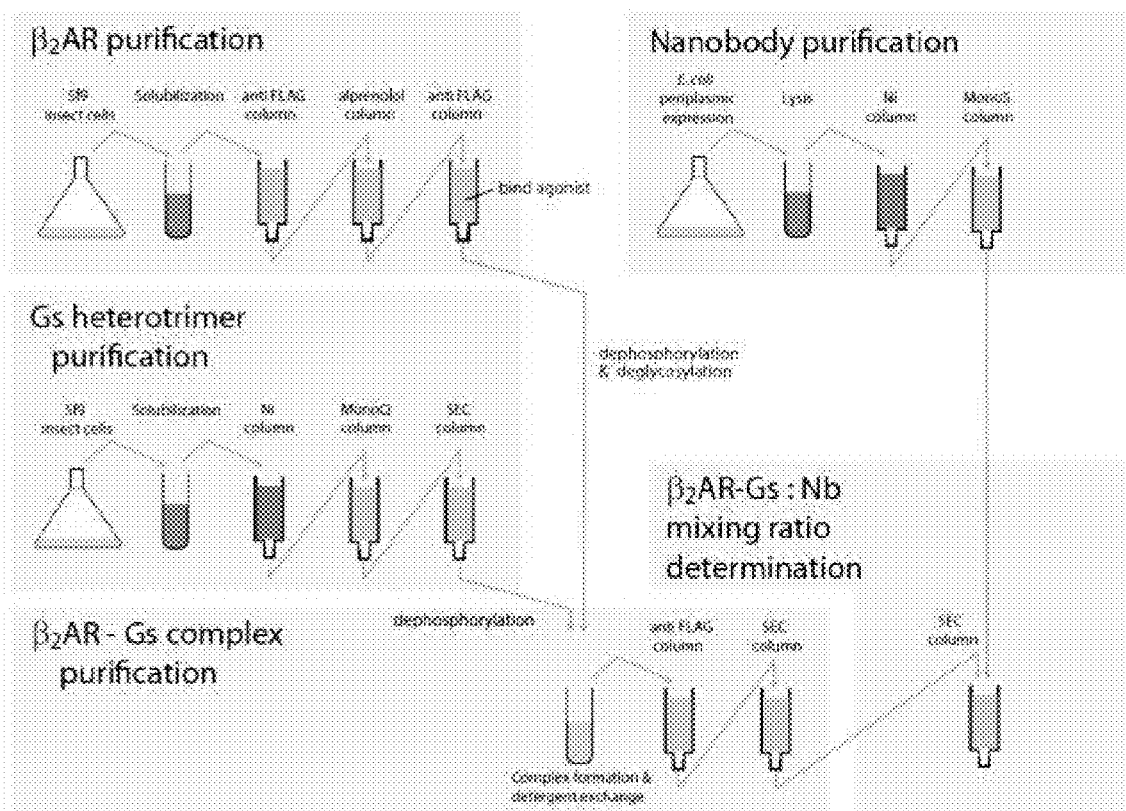
FIG. 6: Flow-chart of the purification procedures for preparing R:G complex with Nb35.
Figure 7:
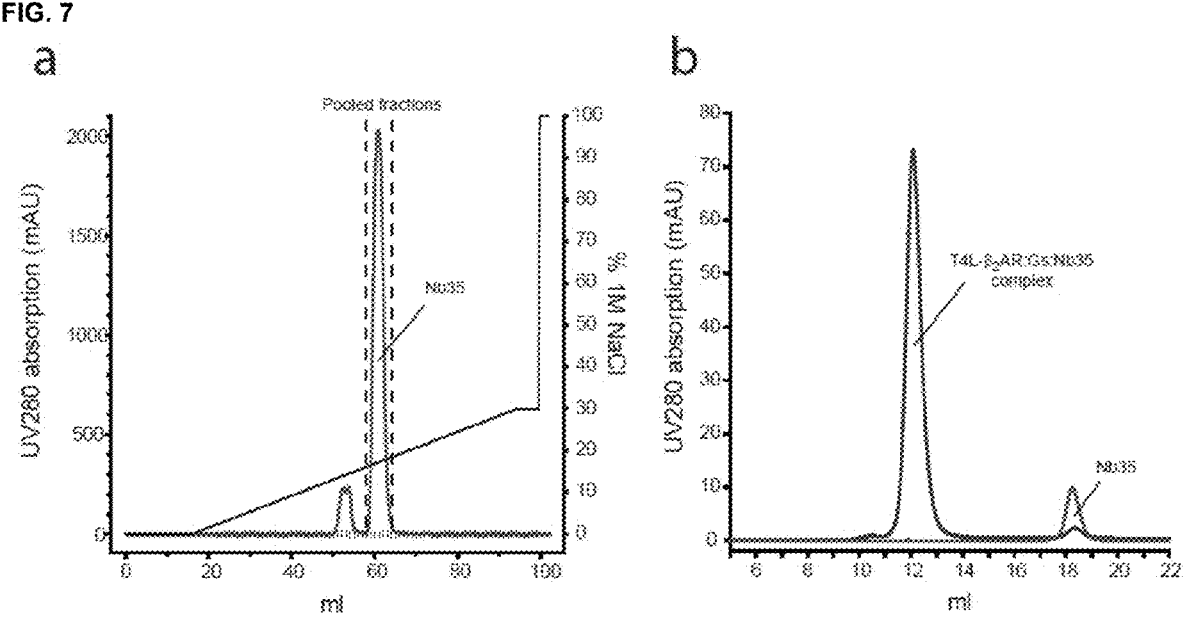
FIG. 7: Purification of Nb35 and determination of R:G:Nb mixing ratio. Panel a) Preparative ion exchange chromatography following nickel affinity chromatography purification of Nanobody 35 (Nb35). The nanobody eluted in two populations (shown in red) as a minor peak and a major homogeneous peak which was collected, spin concentrated, and used for crystallography following determination of proper mixing ratio with the R:G complex as shown in Panel b). Panel b) The agonist bound T4L-β2AR:Gs complex was mixed with slight excess of Nb35 (1 to 1.2 molar ratio of R:G complex to Nb35) on the basis of their protein concentrations and verified by analytical gel filtration.
Figure 8:
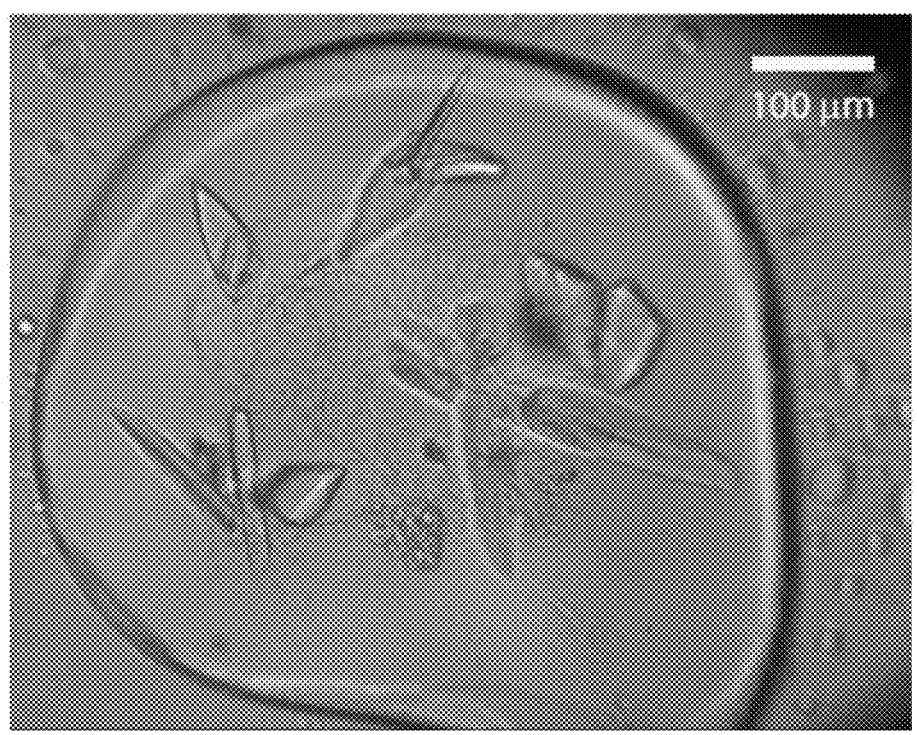
FIG. 8: Crystals of the T4L-β2AR:Gs:Nb35 complex in sponge-like mesophase.

In an effort to further facilitate crystallogenesis of the complex, we tried co-crystallization of the complex with nanobody 35. Nb35 protects the complex from dissociation by GTPγS, suggestive of a stabilizing Gs:Nb interaction (FIG. 3A). BI-167107 bound T4L-β2AR:Gs complex and Nb35 were mixed in 1:1.2 molar ratio (see FIGS. 6 and 7). The small molar excess of Nb35 was verified by analytical gel filtration (FIG. 7, Panel b). The mixture incubated for 1 hour at ROOM TEMPERATURE prior to mixing with 7.7 MAG (provided by Martin Caffrey) containing 10% cholesterol (C8667, Sigma) in 1:1 protein to lipid ratio (w/w) using the twin-syringe mixing method reported previously (Caffrey 2009). Concentration of R:G:Nb complex in 7.7 MAG was approximately 25 mg/ml. The protein:lipid mixture was delivered through a LCP dispensing robot (Gryphon, Art Robbins Instruments) in 40 nl drops to either 24-well or 96-well glass sandwich plates and overlaid en-bloc with 0.8 μl precipitant solution. Multiple crystallization leads were initially identified using in-house screens partly based on reagents from the StockOptions Salt kit (Hampton Research). Crystals for data collection were grown in 18 to 22% PEG 400, 100 mM MES pH 6.5 (FIG. 1, Panel c), 350 to 450 mM potassium nitrate, 10 mM foscarnet (FIG. 3B), 1 mM TCEP, and 10 μM BI167107. Crystals reached full size within 3-4 days at 20° C. (FIG. 8) and were picked from a sponge-like mesophase and flash-frozen without additional cryo-protectant in liquid nitrogen.

Example 5: Nb35 Facilitates Crystal Formation of the R:G Complex

Figure 9A:
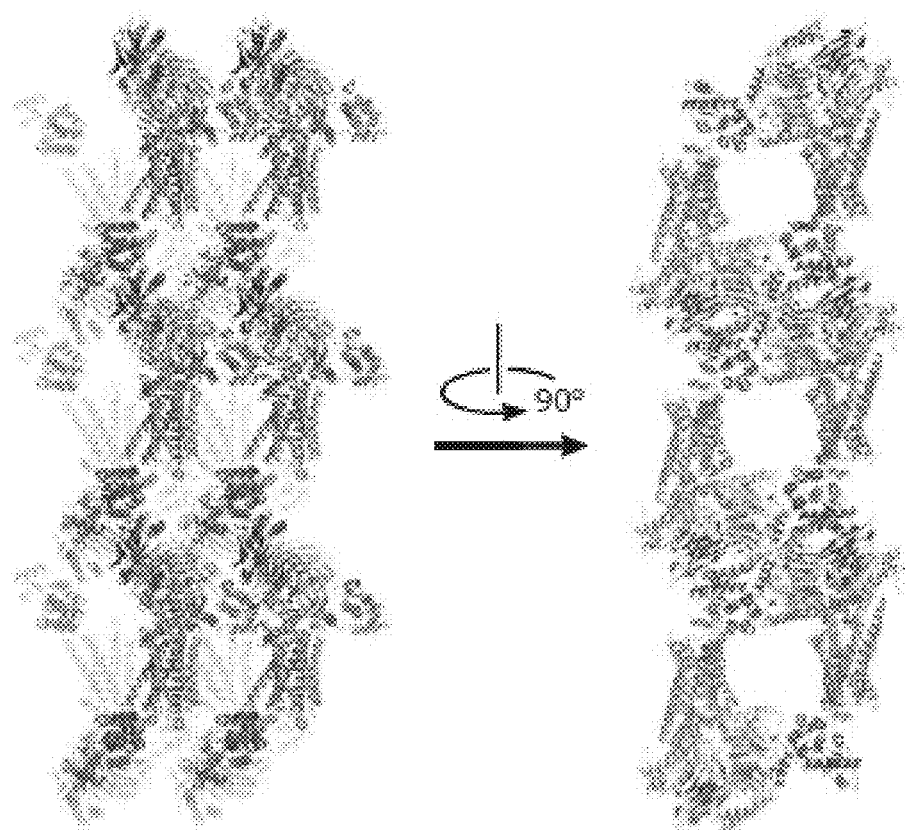
FIG. 9: Overall structure of the $\beta_2AR$:Gs complex. Panel a, Lattice packing of the complex shows alternating layers of receptor and G protein within the crystal. Abundant contacts are formed among proteins within the aqueous layers. Panel b, The overall structure of the asymmetric unit contents shows the $\beta_2AR$ (green) bound to an agonist (yellow spheres) and engaged in extensive interactions with Gs$\alpha$ (orange). G$\alpha$s together with G$\beta$ (cyan) and G$\gamma$ (purple) constitute the heterotrimeric G protein Gs. A Gs binding nanobody (Nb35, red) binds the G protein between the $\alpha$ and $\beta$ subunits. The nanobody (Nb35) facilitates crystallization, as does T4 lysozyme (magenta) fused to the amino terminus of the $\beta_2AR$. Panel c, The biological complex omitting crystallization aids, showing its location and orientation within a cell membrane.
Figure 9B:
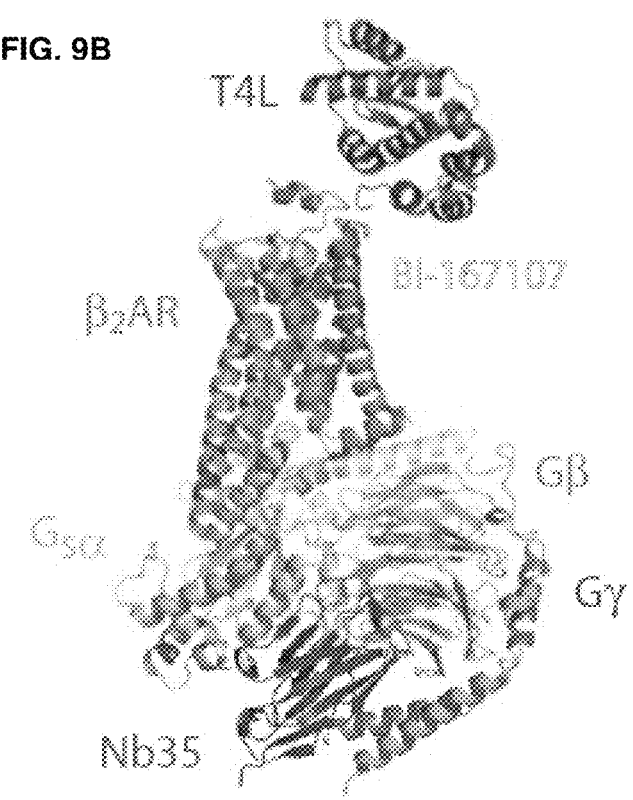
Figure 9C:
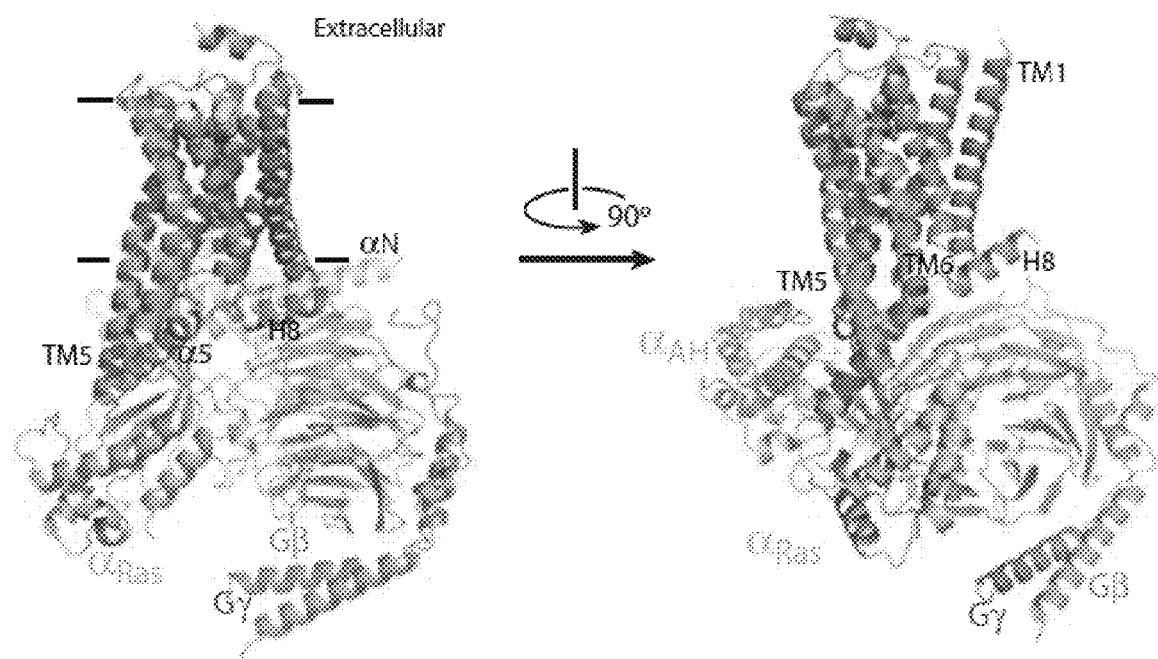

The BI-167107 bound T4L-β2AR:Gs:Nb35 complex crystallized in space group P2$_1$, with a single complex in each asymmetric unit. FIG. 9, Panel a, shows the crystallographic packing interactions. FIG. 9, Panel b, shows the structure of the complete complex including T4L and Nb35, and FIG. 9, Panel c shows the β2AR:Gs complex alone.

BI-167107 bound T4L-β2AR:Gs:Nb35 complexes are arrayed in alternating aqueous and lipidic layers with lattice contacts formed almost exclusively between soluble components of the complex, leaving receptor molecules suspended between G protein layers and widely separated from one another in the plane of the membrane. Extensive lattice contacts are formed among all the soluble proteins, likely accounting for the strong overall diffraction and remarkably clear electron density for the G protein.

Figure 10A:
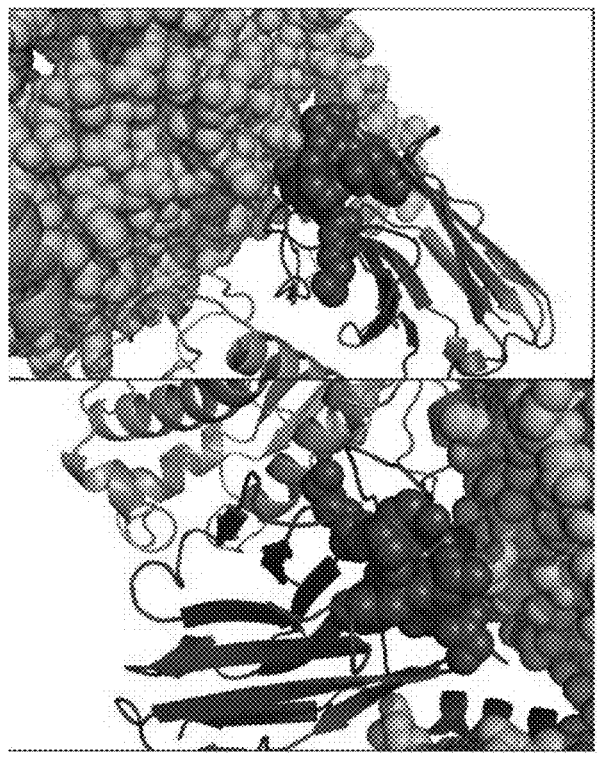
FIGS. 10A-10C: Interactions of Nb35 with Gs within the BI-167107 bound T4L-β2AR:Gs:Nb35 complex.
Figure 10B:
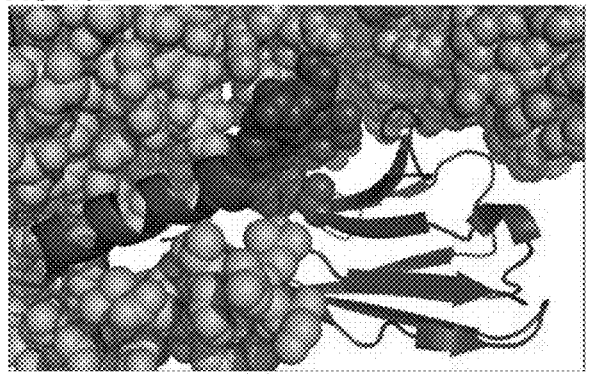
Figure 10B:
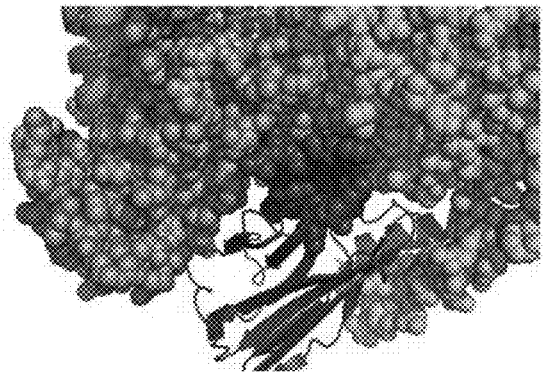
Figure 10C:
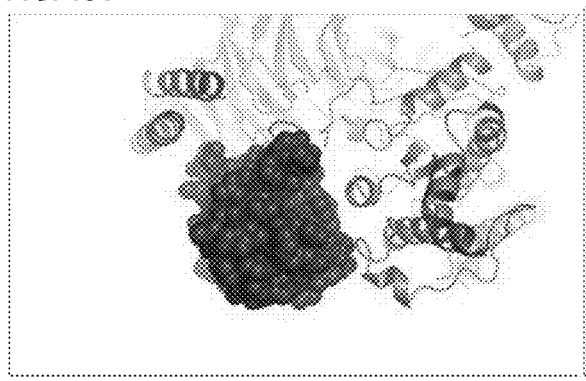
Figure 10C:
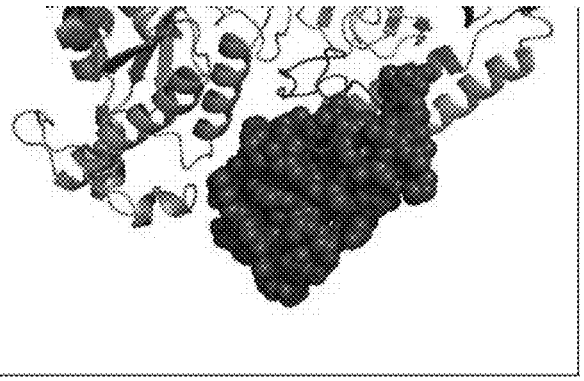
Figure 11A:
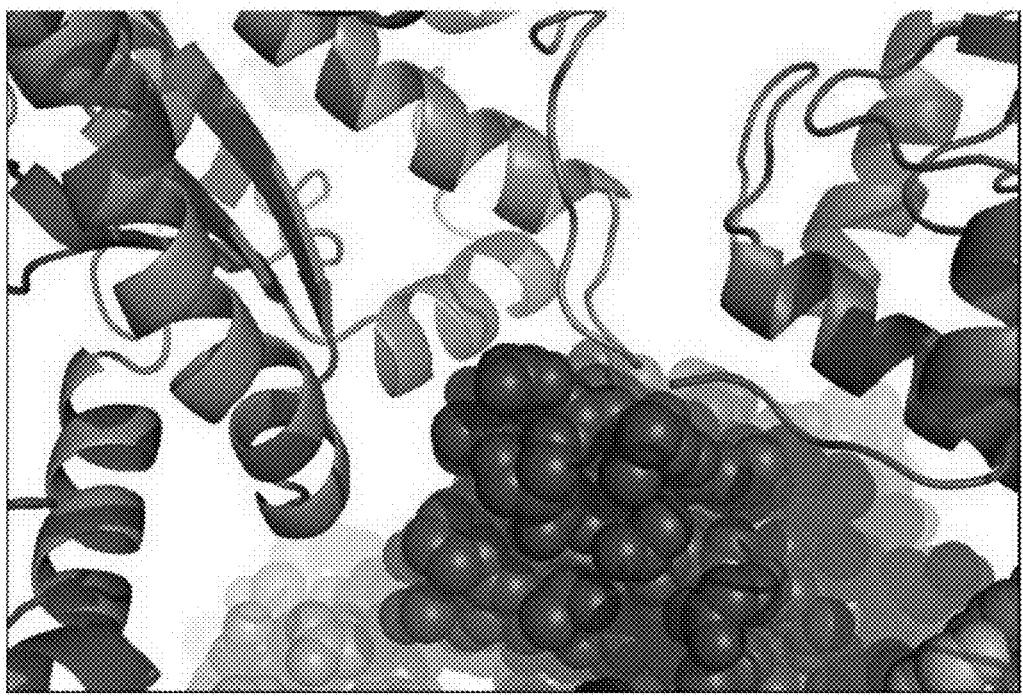
FIGS. 11A and 11B: Crystal contacts between Nb35 and GαS subunits of adjacent complexes. Crystal contacts involving Nb35 (red, space-filling representation) and GαS (orange) of the -x,y-½, -z+1 symmetry related complex (FIG. 11A) and the x,y-1,z symmetry related complex (FIG. 111B).
Figure 11B:
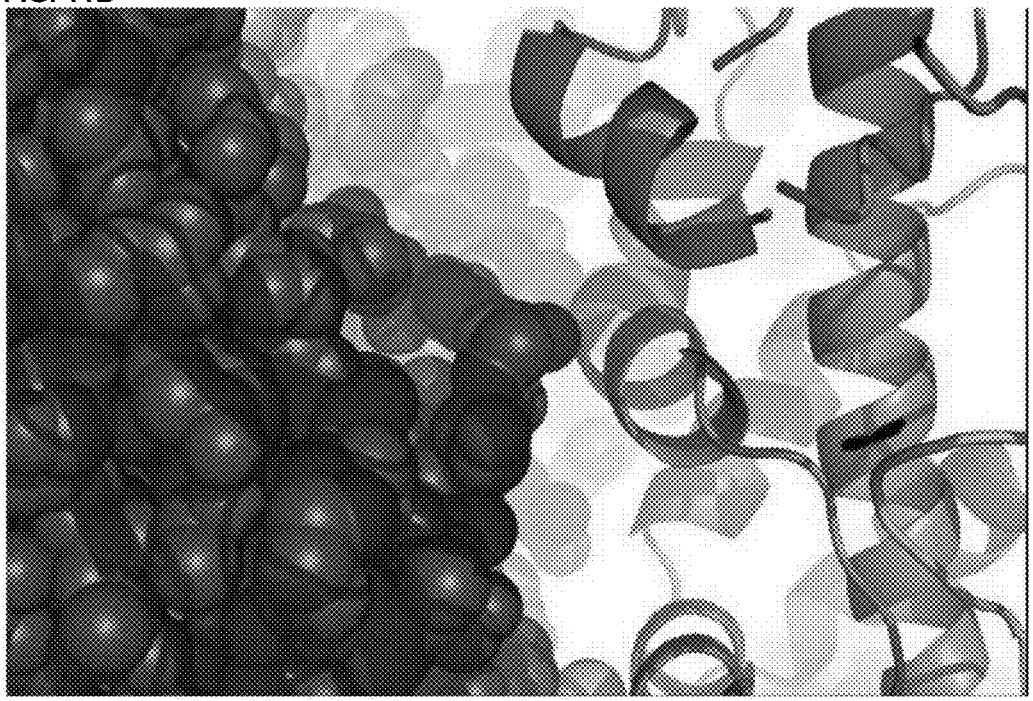

Nb35 and T4L facilitated crystal formation of the BI-167107 bound T4L-β2AR:Gs:Nb35 complex. Nb35 binds a conformational epitope on Gs and packs at the interface of Gβ and Gα subunits with complementarity-determining region (CDR, defined according to IMTG numbering; Lefranc, 2003) 1 interacting primarily with Gβ (FIG. 10A) and a long CDR3 loop interacting with both Gβ and Gα subunits (FIG. 10B). Some framework regions of Nb35 also interact with Gα from the same complex (FIG. 0C). Other framework regions from one complex interact with Gα subunits from two adjacent complexes (FIGS. 11A and 11B), contributing considerably to the crystal contacts within the crystal lattice. T4L forms relatively sparse interactions with the amino terminus of the receptor, but packs against the amino terminus of the Gβ subunit of one complex, the carboxyl terminus of the Gγ subunit of another complex, and the Gα subunit of yet another complex.

Example 6. Structure of the Active-State β$_2$AR

Figure 12A:
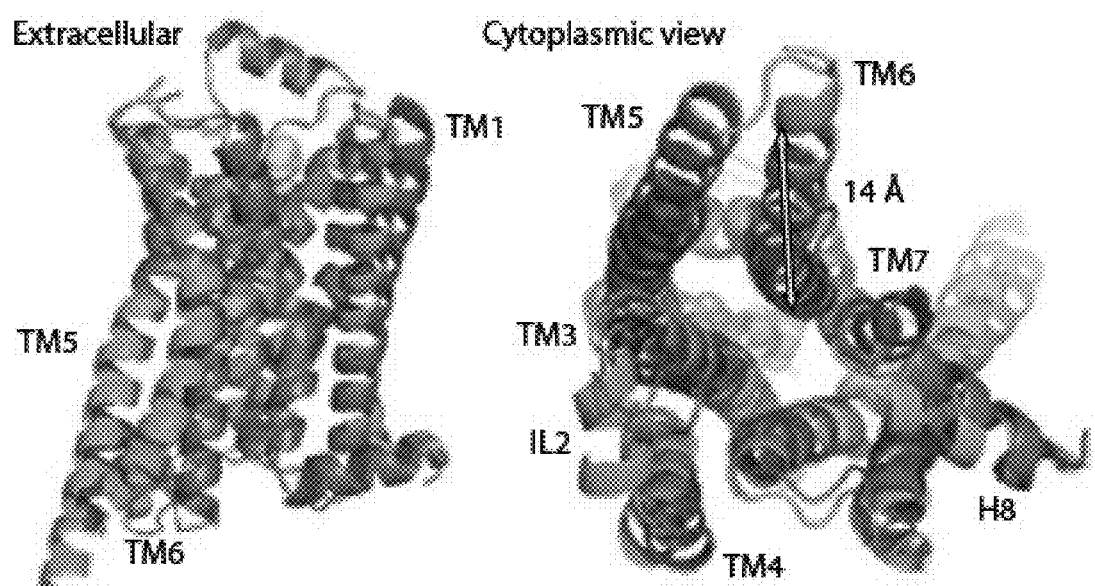
FIG. 12: Comparison of active and inactive β2AR structures. Panel a, Side and cytoplasmic views of the β2AR:Gs structure (green) compared to the inactive carazolol-bound β2AR structure (blue; Rosenbaum et al., 2007). Significant structural changes are seen for the intracellular domain of TM5 and TM6. TM5 is extended by two helical turns while TM6 is moved outward by 14 Å as measured at the α-carbons of Glu268 (yellow arrow) in the two structures. Panel b, β2AR:Gs compared with the nanobody-stabilized active state β2AR:Nb80 structure (orange, Rasmussen et al., 2011). Panel c, The positions of residues in the E/DRY and NPxxY motifs and other key residues of the β2AR:Gs and β2AR: Nb80 structures as seen from the cytoplasmic side. All residues occupy very similar positions except Arg131 which in the β2AR:Nb80 structure interacts with the nanobody.
Figure 12B:
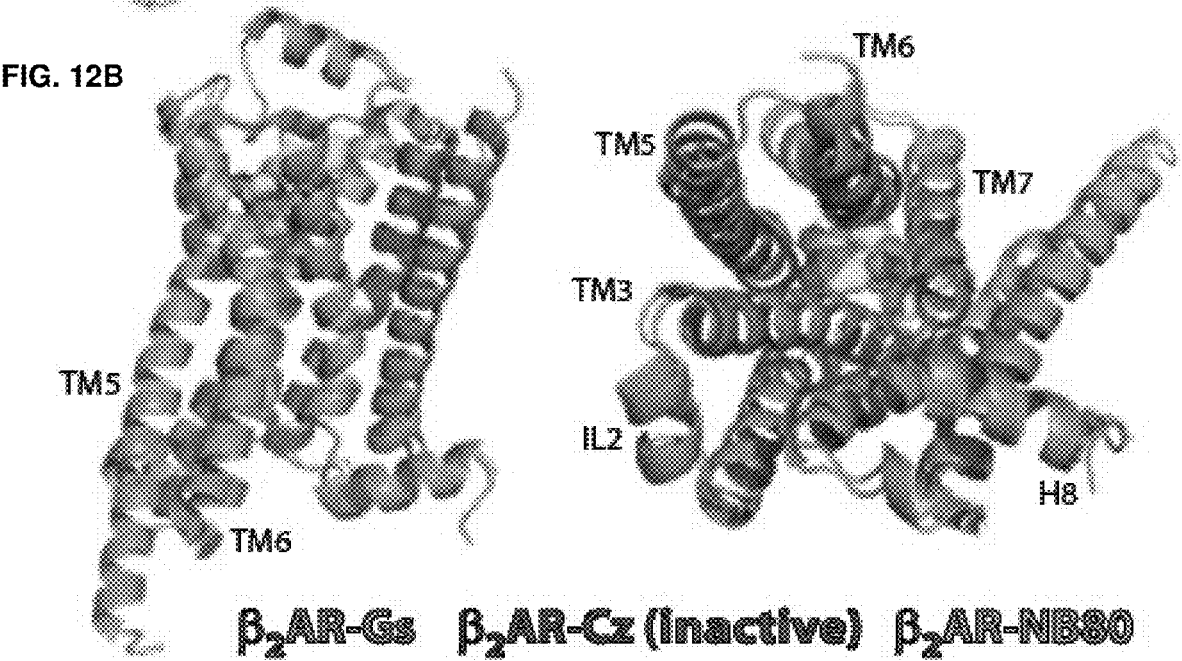
Figure 12C:
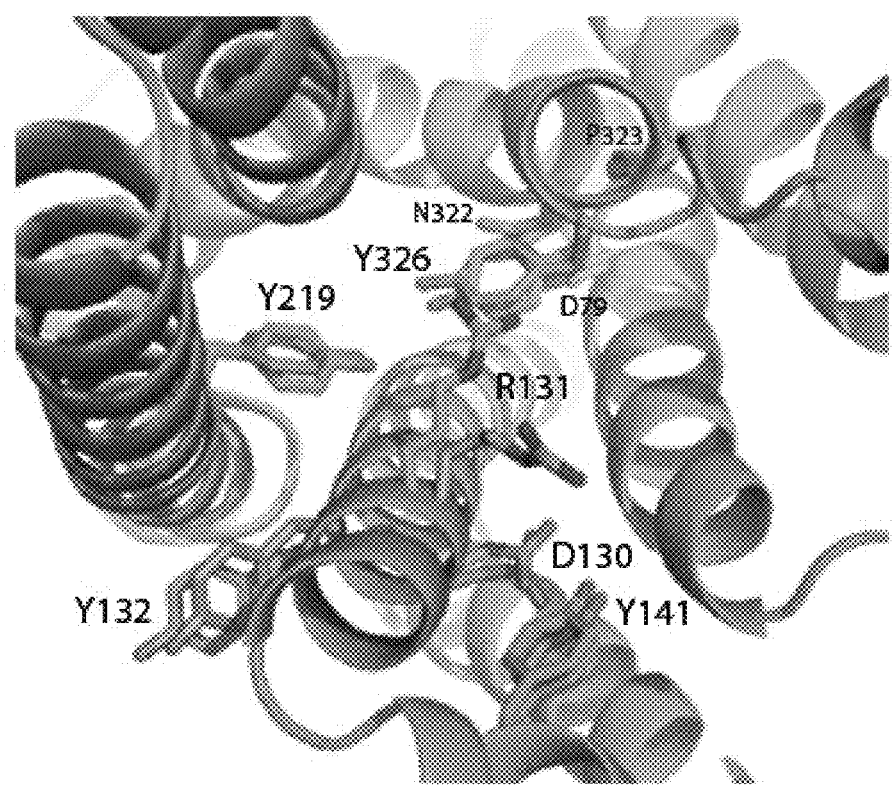
Figure 13A:
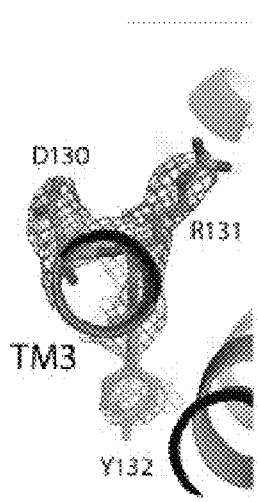
FIG. 13: Views of electron density for residues in the R:G interface. Panel a) The D/ERY motif at the cytoplasmic end of TM3. Panel b) Packing interaction between Arg131 of the E/DRY motif and Tyr391 of C-terminal GαS. Panel c) The NPxxY in the cytoplasmic end of TM7. Panel d) Interactions of Thr68 and Tyr141 with Asp130 of the E/DRY motif. Phe139 of IL2 is buried in a hydrophobic pocket in GαS. Panel e) The 1-al loop (P-loop) of GαS involved in nucleotide binding. Electron density maps are 2Fo-Fc maps contoured at 1 sigma.
Figure 13B:
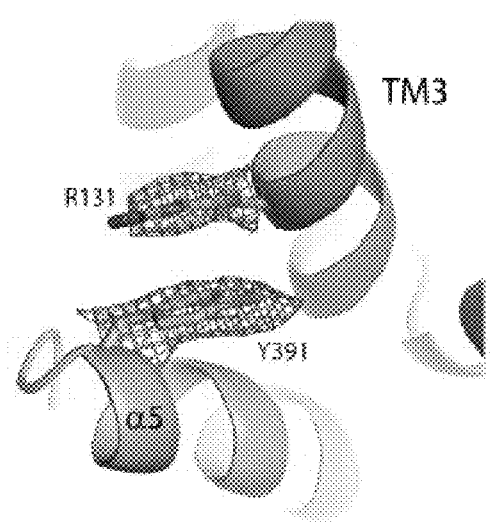
Figure 13C:
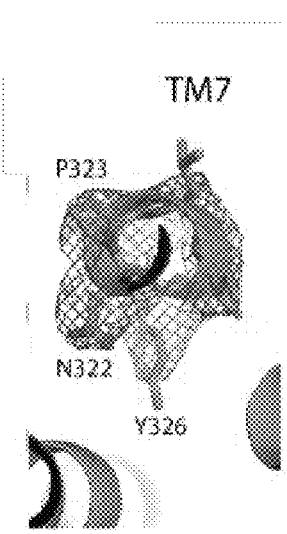
Figure 13D:
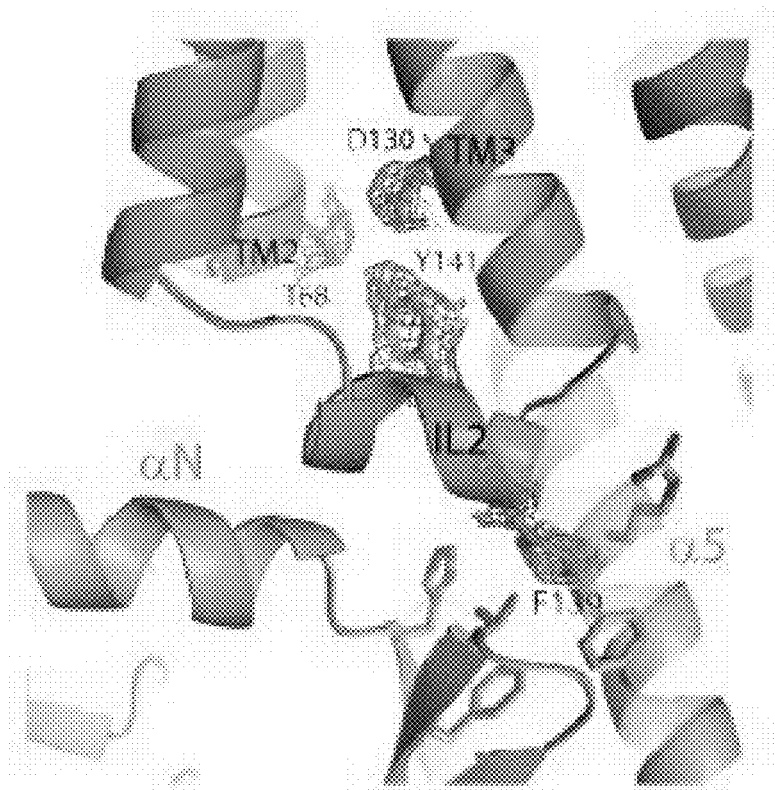
Figure 13E:
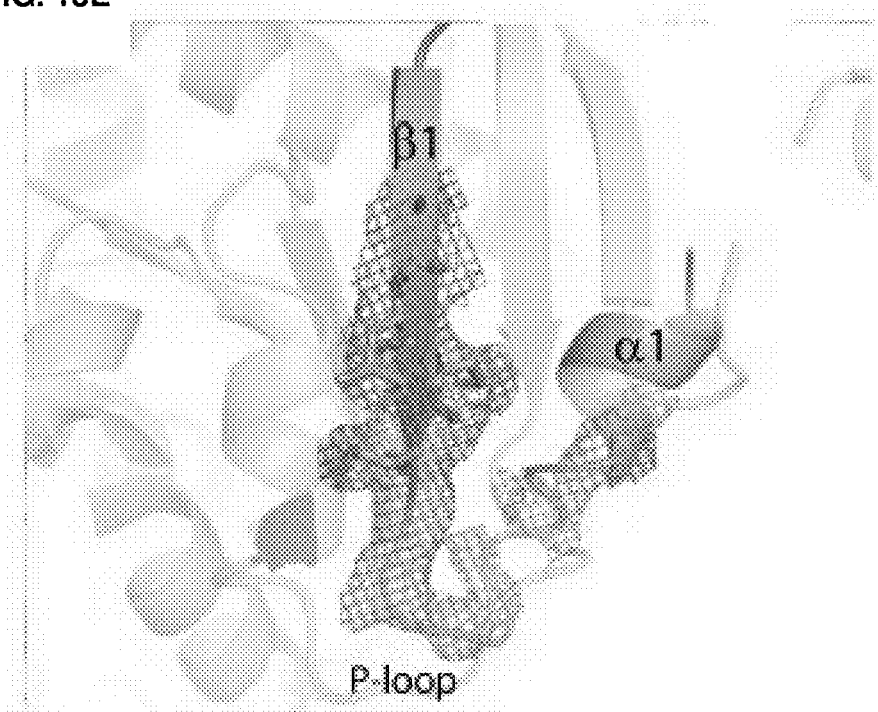

The β$_2$AR:Gs structure provides the first high-resolution insight into the mechanism of signal transduction across the plasma membrane by a GPCR, and the structural basis for the functional properties of the ternary complex. FIG. 12, Panel a, compares the structures of the agonist-bound receptor in the β$_2$AR:Gs complex and the inactive carazolol-bound β$_2$AR. The largest difference between the inactive and active structures is a 14 Å outward movement of TM6 when measured at the Cα carbon of E268. There is a smaller outward movement and extension of the cytoplasmic end of the TM5 helix by 7 residues. A stretch of 26 amino acids in the third intracellular loop (ICL3) is disordered. Another notable difference between inactive and active structures is the second intracellular loop (ICL2), which forms an extended loop in the inactive β$_2$AR structure and an α-helix in the β$_2$AR:Gs complex. This helix is also observed in the β$_2$AR-Nb80 structure (FIG. 12, Panel b); however, it may not be a feature that is unique to the active state, since it is also observed in the inactive structure of the highly homologous avian P$_1$AR (Warne et al., 2008).

The quality of the electron density maps for the β$_2$AR is highest at this β$_2$AR-GαsRas interface, and much weaker for the extracellular half, possibly due to the lack of crystal lattice contacts with the extracellular surface (FIG. 9, Panel a). As a result, we cannot confidently model the high-affinity agonist (BI-167107) in the ligand-binding pocket. However, the overall structure of the β$_2$AR in the T4L-β$_2$AR:Gs complex is very similar to our recent active-state structure of β$_2$AR stabilized by a G protein mimetic nanobody (Nb80). These structures deviate primarily at the cytoplasmic ends of TMs 5 and 6 (FIG. 12, Panel b), possibly due to the presence of T4L that replaces ICL3 in the β$_2$AR-Nb80 structure. Nonetheless, the β$_2$AR-Nb80 complex exhibits the same high affinity for the agonist isoproterenol as does the β$_2$AR:Gs complex (Rasmussen et al., 2011), consistent with high structural homology around the ligand binding pocket. The electron density maps for the β$_2$AR-Nb80 crystals provide a more reliable view of the conformational rearrangements of amino acids around the ligand-binding pocket and between the ligand-binding pocket and the Gs-coupling interface (Rasmussen et al., 2011).

FIG. 12, Panel c, shows the position of the highly conserved sequence motifs including D/ERY and NPxxY in the β$_2$AR:Gs complex compared with the β$_2$AR-Nb80 complex (see also FIG. 13). These conserved sequences have been proposed to be important for activation or for maintaining the receptor in the inactive state (Hofmann et al., 2009). The positions of these amino acids are essentially identical in these two structures demonstrating that Nb80 is a very good G protein surrogate. Only Arg131 differs between these two structures. In the β$_2$AR-Nb80 structure Arg131 interacts with Nb80, whereas in the β$_2$AR:Gs structure Arg131 packs against Tyr391 of Gαs (FIG. 13).

Figure 14:
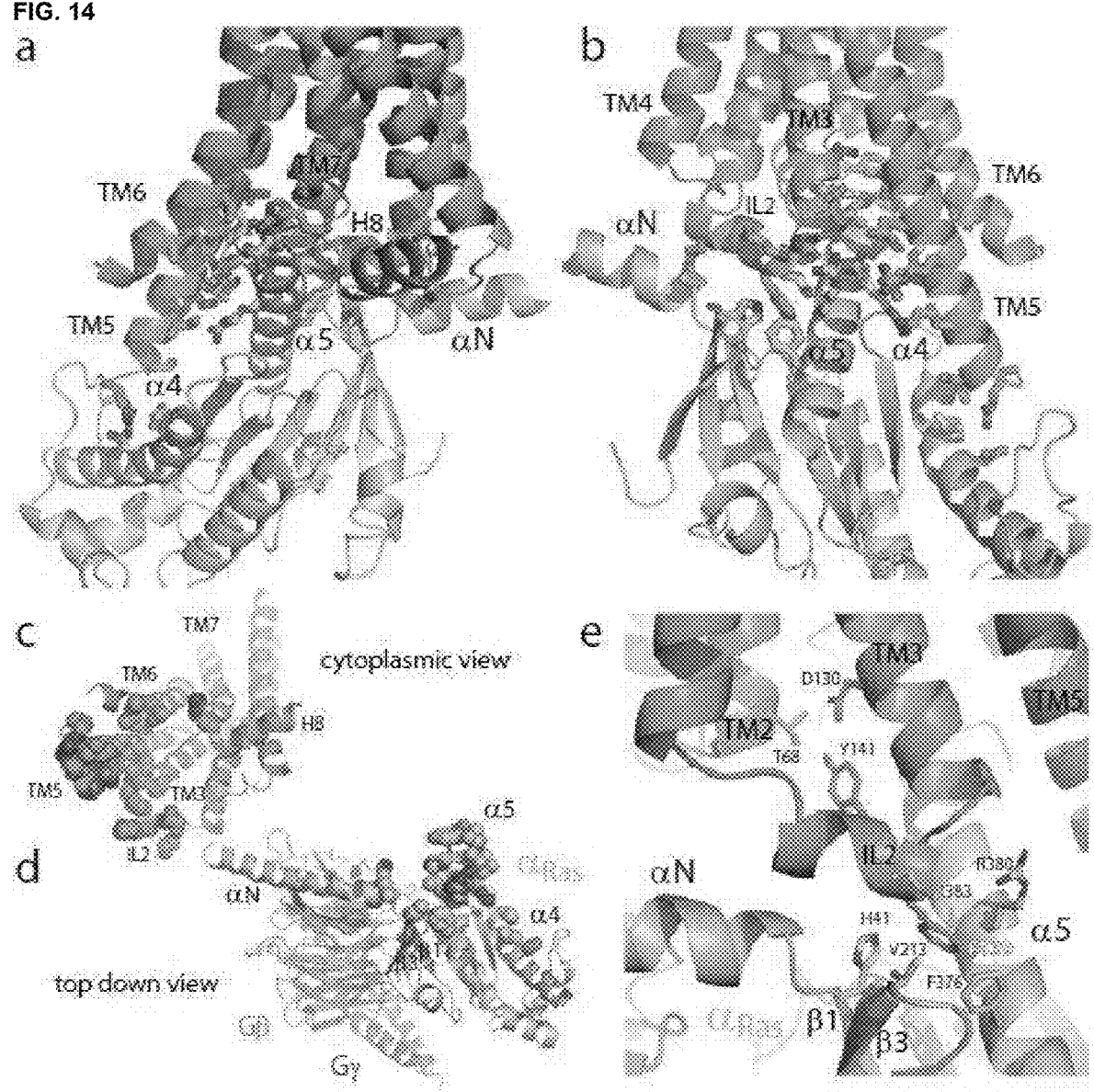
FIG. 14: Receptor:G protein interactions. Panels a and b: The α5-helix of GαS docks into a cavity formed on the intracellular side of the receptor by the opening of transmembrane helices 5 and 6. Panel a: Within the transmembrane core, the interactions are primarily non-polar. An exception involves packing of Tyr391 of the α5-helix against Arg131 of the conserved DRY sequence in TM3 (see also FIG. 13). Arg131 also packs against Tyr of the conserved NPxxY sequence in TM7. Panel b: As α5-helix exits the receptor it forms a network of polar interactions with TM5 and TM3. Panel c: A cytoplasmic view. Pandel d: A top downview. Panel e: Receptor residues Thr68 and Asp130 interact with the IL2 helix of the β₂AR via Tyr141, positioning the helix so that Phe139 of the receptor docks into a hydrophobic pocket on the G protein surface, thereby structurally linking receptor-G protein interactions with the highly conserved DRY motif of the β₂AR.

The active state of the β$_2$AR is stabilized by extensive interactions with (GαsRas) (FIG. 14). There are no direct interactions with Gβ or Gγ subunits. The total buried surface of the β$_2$AR-GαsRas interface is 2576 Å$^2$ (1300 Å$^2$ for GαsRas and 1276 Å$^2$ for the β$_2$AR). This interface is formed by ICL2, TM5 and TM6 of the β$_2$AR, and by α5-helix, the αN-β1 junction, the top of the β3-strand, and the α4-helix of GαsRas (see Table 6 for specific interactions). The β$_2$AR sequences involved in this interaction have been shown to play a role in G protein coupling; however, there is no clear consensus sequence for Gs-coupling specificity when these segments are aligned with other GPCRs. Perhaps this is not surprising considering that the β$_2$AR also couples to Gi and that many GPCRs couple to more than one G protein isoform. The structural basis for G protein coupling specificity must therefore involve more subtle features of the secondary and tertiary structure. Nevertheless, a noteworthy interaction involves Phe139, which is located at the beginning of the ICL2 helix and sits in a hydrophobic pocket formed by Gαs His41 at the beginning of the 01-strand, Val213 at the start of the β3-strand and Phe376, Arg380 and Ile383 in the α5-helix (FIG. 14, Panel e). The β$_2$AR mutant F139A displays severely impaired coupling to Gs (Moro et al., 1993). The residue corresponding to Phe139 is a Phe or Leu on almost all Gs coupled receptors, but is more variable in GPCRs known to couple to other G proteins. Of interest, the ICL2 helix is stabilized by an interaction between Asp130 of the conserved DRY sequence and Tyr141 in the middle of the ICL2 helix (FIG. 14, Panel e). Tyr141 has been shown to be a substrate for the insulin receptor tyrosine kinase (Baltensperger et al., 1996); however, the functional significance of this phosphorylation is currently unknown.

Example 7. Structure of Activated Gs

Figure 15:
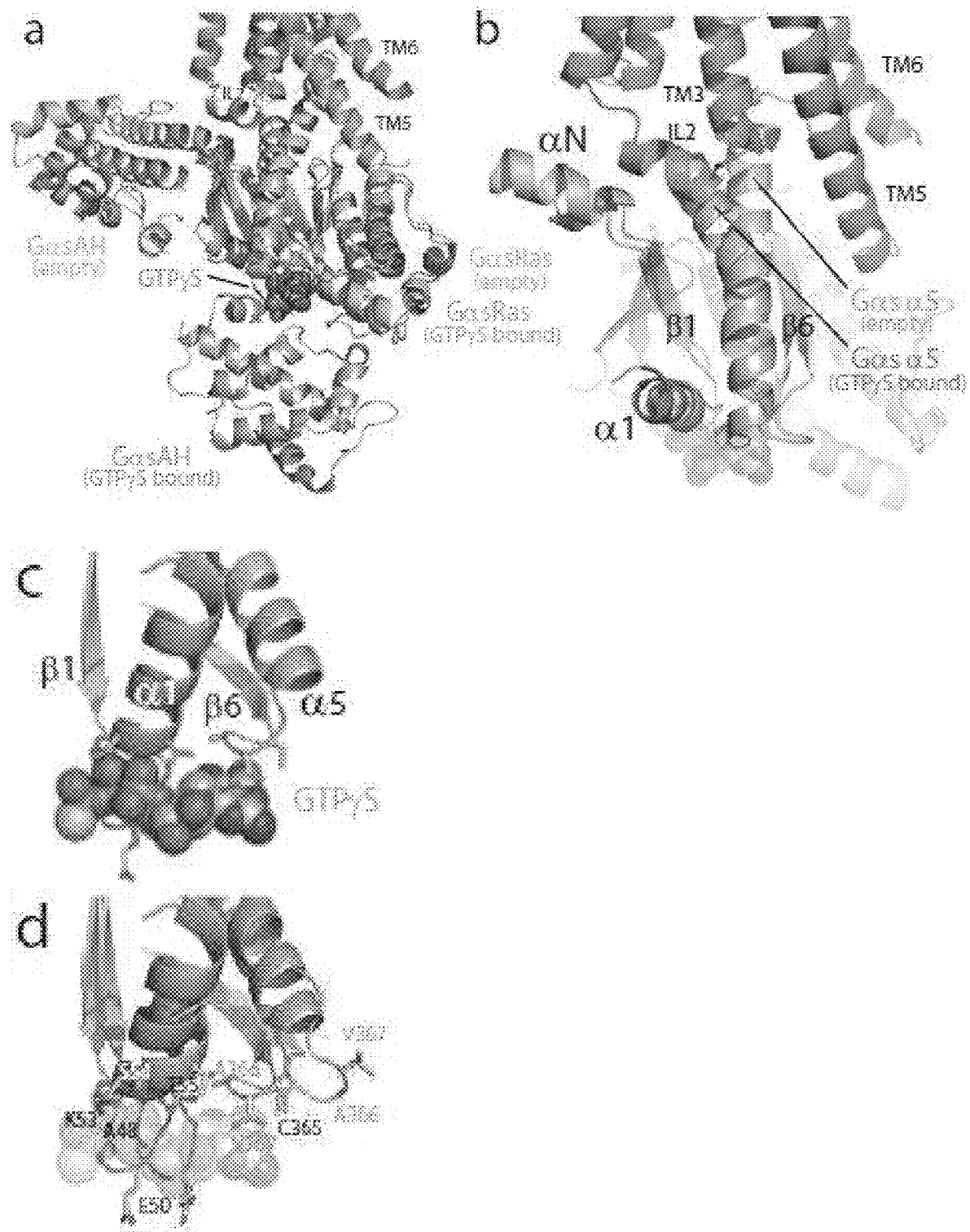
FIG. 15: Conformational changes in Gαs. Panel a, A comparison of Gαs in the β₂AR:Gs complex (orange) with the GTPγS-bound Gαs (grey) (PDB ID: 1AZT; Sunahara et al., 1997). GTPγS is shown as spheres. The helical domain of Gαs (GαsAH) exhibits a dramatic displacement relative to its position in the GTPγS-bound state. Panel b, The α5-helix of Gαs is rotated and displaced toward the β₂AR, perturbing the β6-α5 loop which otherwise forms part of the GTPγS binding pocket. Panel c, The β1-al loop (P-loop) and β6-α5 loop of Gαs interact with the phosphates and purine ring, respectively, of GTPγS in the GTPγS-Gαs structure. Panel d, The 31-al and β6-α5 loops are rearranged in the nucleotide-free β₂AR:Gs structure.

The most surprising observation in the β$_2$AR:Gs complex is the large displacement of the GαsAH relative to GαsRas (an approximately 1800 rotation about the junction between the domains) (FIG. 15, Panel a). In the crystal structure of Gαs, the nucleotide-binding pocket is formed by the interface between GαsRas and GαsAH. Guanine nucleotide binding stabilizes the interaction between these two domains. The loss of this stabilizing effect of guanine nucleotide binding is consistent with the high flexibility observed for GαsAH in single particle EM analysis of the detergent solubilized complex (data not shown). It is also in agreement with the increase in deuterium exchange at the interface between these two domains upon formation of the complex (data not shown). Recently Hamm, Hubbell and colleagues, using double electron electron resonance (DEER) spectroscopy, documented large (up to 20 Å) changes in distance between nitroxide probes positioned on the Ras and α-helical domains of Gi upon formation of a complex with light-activated rhodopsin (Van Eps 2011). Therefore, it is perhaps not surprising that GαsAH is displaced relative to GαsRas; however, its location in this crystal structure likely reflects the influence of crystal packing interactions rather than a physiological conformation.

The conformational links between the $\beta_2$AR and the nucleotide-binding pocket primarily involve the amino and carboxyl terminal helices of Gαs (FIG. 14). FIG. 15, Panel b, focuses on the region of GαsRAS that undergoes the largest conformational change when comparing the structure of GαsRAS from the Gs-$\beta_2$AR complex with that from the Gαs-GTPγS complex (Sunahara et al., 1997). The largest difference is observed for the α5 helix, which is displaced 6 Å towards the receptor and rotated as the carboxyl terminal end projects into transmembrane core of the $\beta_2$AR. Associated with this movement, the 06-α5 loop, which interacts with the guanine ring in the Gαs-GTPγS structure, is displaced outward, away from the nucleotide-binding pocket (FIG. 15, Panels b-d). The movement of a helix is also associated with changes in interactions between this helix and the β6 sheet, the αN-β1 loop, and the al helix. The β1 strand forms another link between the $\beta_2$AR and the nucleotide-binding pocket. The C-terminal end of this strand changes conformation around Gly47, and there are further changes in the β1-α1 loop (P-loop) that coordinates the γ-phosphate in the GTP-bound form (FIG. 15, Panels b-d). The observations in the crystal structure are in agreement with deuterium exchange experiments where there is enhanced deuterium exchange in the β1 sheet and the amino terminal end of the α5 helix upon formation of the nucleotide-free $\beta_2$AR:Gs complex (data not shown).

The structure of a Gs heterotrimer has not been determined, so it is not possible to directly compare the Gαs-Gβγ interface before and after formation of the $\beta_2$AR:Gs complex. Based on the structure of the GDP bound Gi heterotrimer (Wall et al., 1995), we do not observe large changes in interactions between GαsRAS and Gβγ upon formation of the complex with $\beta_2$AR. This is also consistent with deuterium exchange studies (data not shown). It should be noted that Nb35 binds at the interface between GαsRas and Gβ (FIG. 2, Panel b). Therefore, we cannot exclude the possibility that Nb35 may influence the relative orientation of the GαsRas-Gβγ interface in the crystal structure. However, single particle EM studies provide evidence that Nb35 does not disrupt interactions between GαsAH and GαsRas (data not shown).

Example 8: Nb35 and Nb37 Bind Different Epitopes on Gs and Inhibit Nucleotide Binding To investigate the effect of nanobodies (Nb35 and Nb37) on Gs alone, nanobodies were added together with bodipy-GTPγS-FL and various Gs protein preparations in 20 mM Tris-HCl, Ph 8.0, 3 mM $MgCl_2$, 1 mM DTT in a final volume of 200 μL. Samples containing a heterotrimeric Gs protein also included 0.1% DDM. Bodipy-GTPγS-FL is a stable fluorescent GTP analog ($\lambda_{ex}\cong470$ nm, $\lambda_{em}\cong515$ nm). Its fluorescence intensity increases upon G protein binding and Bodipy-GTPγS-FL can therefore be used for real-time measurements of nucleotide binding to G proteins (McEwen et al., 2001). Fluorescence was measured in a 96-well microtiter plate format on a M5 fluorescence plate reader (Molecular Precision).

Figure 16:
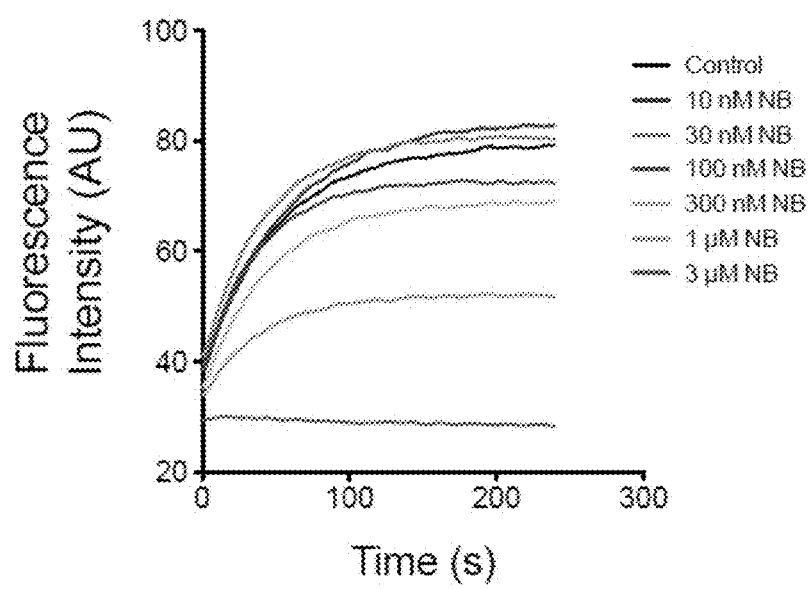
FIG. 16: Nb37 inhibits GTPγS binding to Gαs. Bodipy-GTPγS (100 nM) was incubated with 1 M purified Gαs and the fluorescence increase measured in real time in the presence of increasing concentrations of Nb37.
Figure 17:
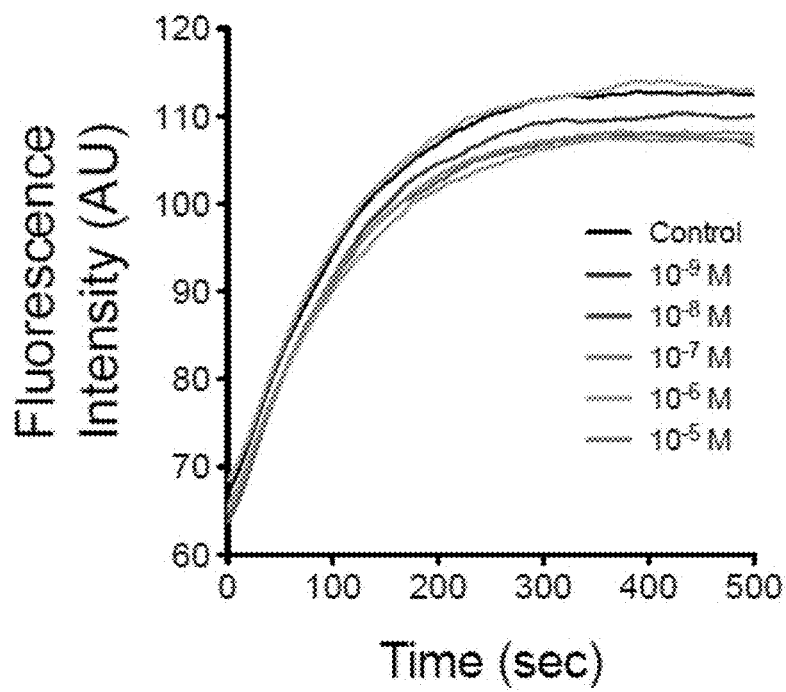
FIG. 17: Nb35 does not affect GTPγS binding to Gαs. Bodipy-GTPγS (100 nM) was incubated with 1 M purified Gαs and the fluorescence increase measured in real time in the presence of increasing concentrations of Nb35.

In a first experiment (FIG. 16), increasing amounts of Nb37 were incubated with 1 μM purified GαS and 100 nM Bodipy-GTPγS-FL and the fluorescence increase was measured on a short time scale (300 seconds) to minimize the accumulation of the hydrolysis product bodipy-phosphate (Jameson et al., 2005). The Gαs subunit of the heterotrimeric Gs protein was purified as described previously (Sunahara et al., 1997). From this experiment it appears that Nb37 blocks GTPγS binding to Gsα alone in a dose dependent manner. These results also indicate that the binding epitope of Nb37 is confined to the Gsα subunit of the heterotrimeric Gs protein. In a similar experiment (FIG. 17), increasing amounts of Nb35 were incubated with 1 μM purified GαS and 100 nM Bodipy-GTPγS-FL. Consistent with the observation that Nb35 binds an epitope composed of elements of GαsRAS and Gβ (see Example 7), Nb35 has no effect on GTPγS binding to the GαS subunit alone.

Figure 18:
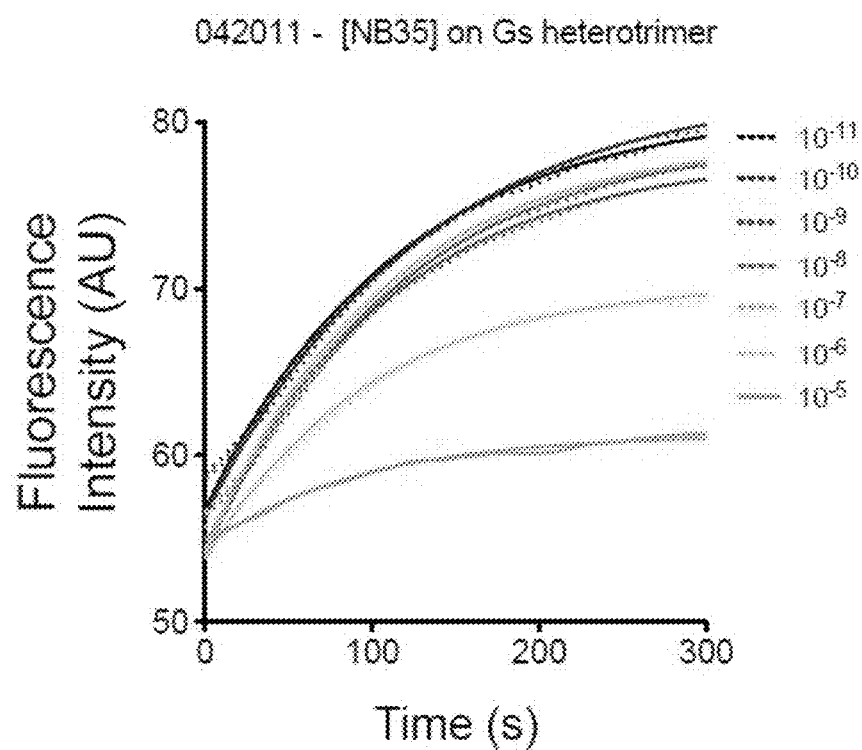
FIG. 18: Nb35 inhibits GTPγS binding to the Gsαγ heterotrimer. Bodipy-GTPγS (100 nM) was incubated with 1 M purified Gsαβγ heterotrimer and the fluorescence increase measured in real time in the presence of increasing concentrations of Nb35.

In another experiment (FIG. 18), increasing amounts of Nb35 were incubated with 1 μM of the purified Gs αβγ heterotrimer and 100 nM Bodipy-GTPγS-FL. This experiment indicates that Nb35 blocks GTPγS binding to the free Gsαβγ heterotrimer in a dose dependent manner.

Example 9. Nb35 Stabilizes Other Agonist-GPCR-Gs Complexes

The Gs alpha subunit (or Gs protein) is a heterotrimeric G protein subunit that activates the cAMP-dependent pathway by activating adenylate cyclase. The G protein-coupled receptors that couple to Gs include: 5-HT receptors types 5-HT4 and 5-HT7, ACTH receptor, Adenosine receptor types A2a and A2b, Arginine vasopressin receptor 2, β-adrenergic receptors types β1, β2 and β3, Calcitonin receptor, Calcitonin gene-related peptide receptor, Corticotropin-releasing hormone receptor, Dopamine receptors D1-like family (D1 and D5), FSH-receptor, Gastric inhibitory polypeptide receptor, Glucagon receptor, Glucagon-like peptide 1 receptor (GLP1-R), Histamine H2 receptor, Luteinizing hormone/choriogonadotropin receptor, Melanocortin receptor, Parathyroid hormone receptor 1, Prostaglandin receptor types D2 and 12, Secretin receptor, Thyrotropin receptor, amongst others.

To determine if Nanobodies that bind to Gs in the β2AR:Gs:BI167107 also stabilize other GPCR:Gs:agonist complexes, we prepared a complex of the Arginine vasopressin receptor 2 (Accession number P30518; V2R_HUMAN) in complex with Gs, Nb35 and Arginine vasopressin (AVP:NT4LV2R:Gs) and demonstrated the stability of this complex in SEC. Arginine vasopressin (AVP), also known as vasopressin, argipressin or antidiuretic hormone, is a natural ligand that activates Arginine vasopressin receptor 2.

Figure 19:
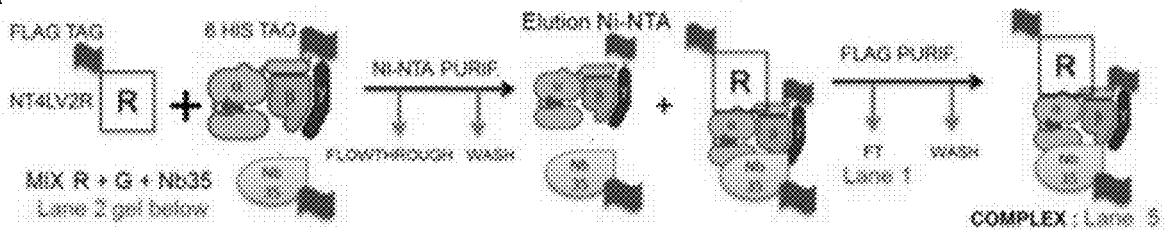
FIG. 19: Purification of a stable AVP:NT4LV2R:Gs complex. Panel A, schematic representation of the purification of the AVP:NT4LV2R:Gs complex using Ni-NTA followed by FLAG-tag affinity purification. Panel b, SEC chromatogram of the affinity purified AVP:NT4LV2R:Gs. Panel c, SDS-page to monitor the purification scheme. lane 1: flow trough of the FLAG-tag affinity column; lane 2: mix of AVP, NT4LV2R and Gs, prior to purification; lane 3: molecular marker; lane 4: AVP:NT4LV2R:Gs complex eluted from SEC; lane 5: AVP:NT4LV2R:Gs complex after Ni-NTA followed by FLAG-tag affinity purification.
Figure 19:
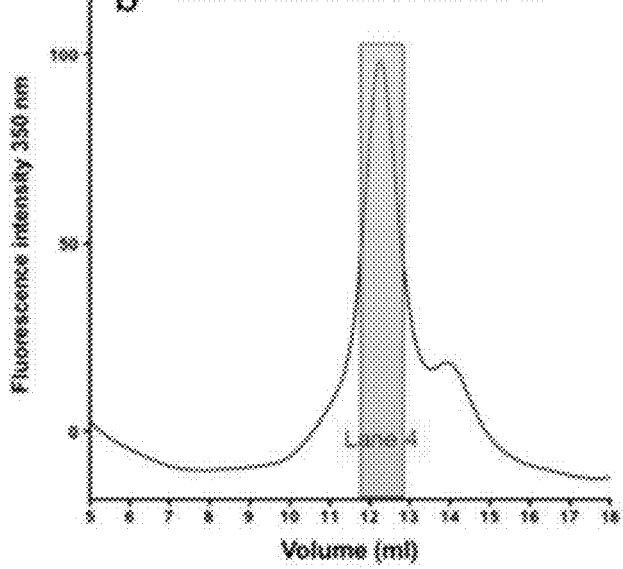
Figure 19:
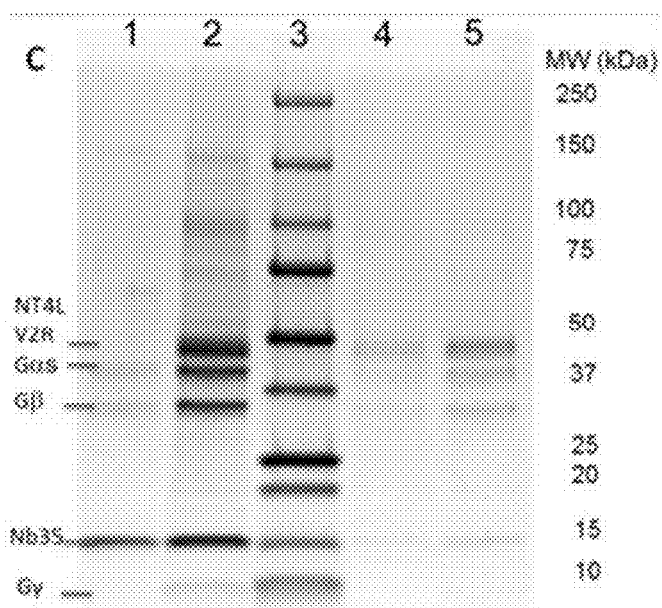

Formation of a stable complex (FIG. 19, Panel a) was accomplished by mixing His tagged Gs heterotrimer at approximately 90 μM concentration with AVP bound NT4LV2R (90 μM) and NB35 (100 μM) in 0.1 ml buffer (10 mM HEPES, pH 7.5, 100 mM NaCl, 0.1% DDM, 1 mM EDTA, 3 mM $MgCl_2$, 10 μM AVP) and incubated for 2 hours at room temperature. Next, the AVP:NT4LV2R:Gs complex was purified in two successive affinity purification steps. The purification was monitored by SDS-PAGE (FIG. 19). First, the complex was applied on a Ni-NTA column after adding 300 μl of 1% MNG in 10 mM HEPES, pH 7.5, 100 mM NaCl buffer onto the reaction mix. Following extensive washing with buffer, the complex was eluted in 0.2% MNG, 10 mM HEPES, pH 7.5, 100 mM NaCl AVP 10 μM with 200 mM imidazole. Next the complex was applied on a FLAG-tag affinity column, washed extensively in the same buffer containing 0.01% MNG and eluted with the FLAG-peptide. This procedure was monitored by SDS-PAGE (FIG. 19, Panel b) and shows that a complex containing NT4LVTR, GαS, Gβ, Gγ and Nb35 can be purified accordingly. This complex was further purified by SEC on a superdex200 column in 10 mM HEPES, pH 7.5, 100 mM NaCl, 0.01% MNG, 1 mM EDTA, 3 mM $MgCl_2$, 1 μM AVP). This procedure was monitored by SDS-PAGE (FIG. 19, Panel c) and shows that a monodisperse complex containing NT4LVTR, GαS, Gβ, Gγ and Nb35 can be purified accordingly.

Figure 20:
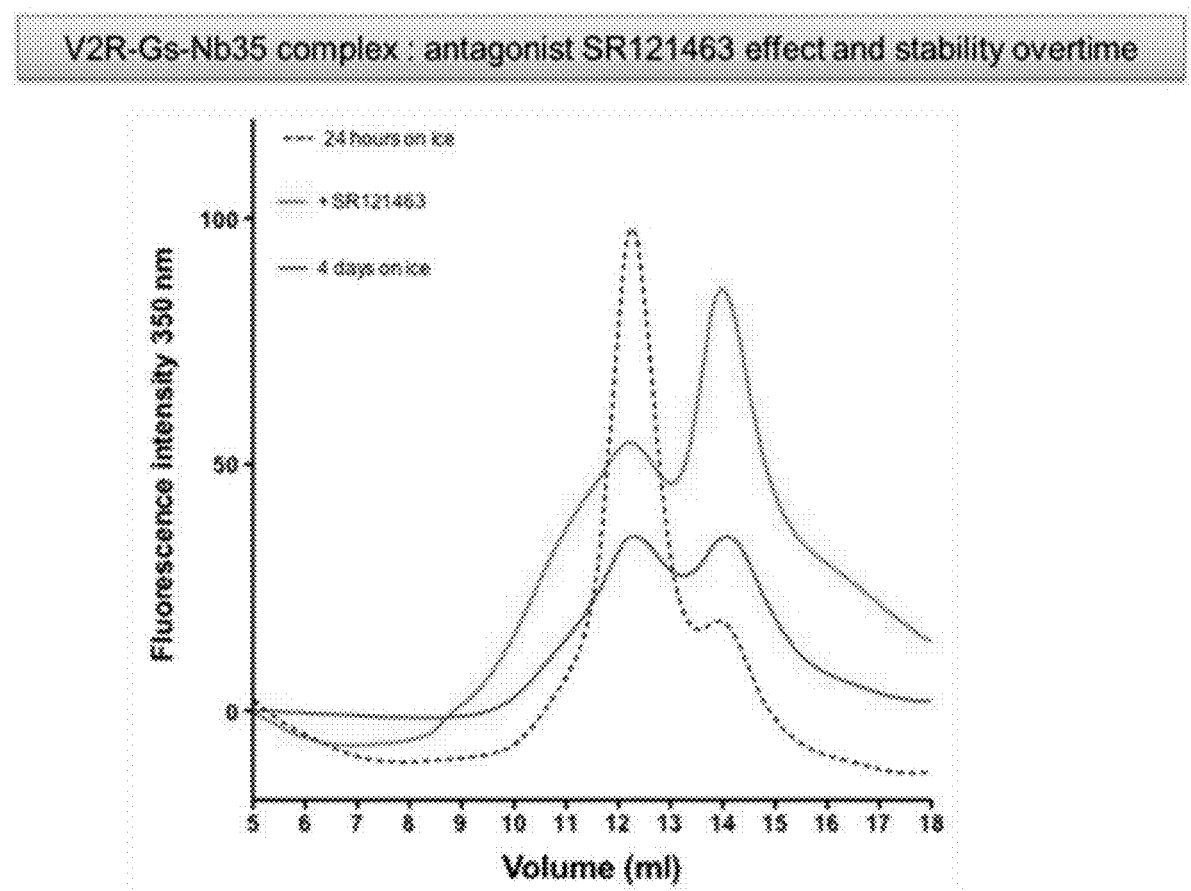
FIG. 20: Stability of the AVP:NT4LV2R:Gs complex monitored by SEC. Dashed line: SEC chromatogram of the AVP:NT4LV2R:Gs complex after 24 hours incubation on ice. Blue line: SEC chromatogram of the AVP:NT4LV2R:Gs complex after 48 hours incubation on ice. Red line, SEC chromatogram of AVP:NT4LV2R:Gs after incubation of the complex with 10 μM of the antagonist SR121463.

To confirm the stability of the AVP:NT4LV2R:Gs complex, we incubated the purified sample for 24 hours on ice and reapplied it to SEC to confirm its monodisperse character and its MW (FIG. 20). As expected, an excess amount of the antagonist SR121463 (10 μM) disrupts the AVP:NT4LV2R:Gs complex.

Example 10. Improved Screening for Agonists or Positive Allosteric Modulators Using Nanobodies Stabilizing GPCR:G Protein Complexes A Nanobody that selectively stabilizes a non-prominent conformer of GPCRs will allow more efficient screening for ligands that selectively interact with this particular low abundancy conformer. Besides, conformer selective Nanobodies could also be used to unmask allosteric or hidden drugable sites or inversely mask undesired binding pockets for drug screening. In case the particular conformer is an active state, the identified ligands will have a high probability to behave as agonists, supported by in silico docking experiments described by Costanzi & Vilar (2011). Indeed, their results indicate that activated structures favor identification of agonists over antagonists, whereas inactive structures favor identification of receptor blockers over agonists.

Evidence is provided that Nb35 stabilizes the complex between the activated β2AR and the G protein by binding the interface of Gαs and Gβγ subunits. An example of a screening assay to identify ligands that selectively interact with the low abundant active state conformer of β2AR can be a radioligand assay using Nb35 to shift β2AR population more towards its active state. Such radioligand assay can be executed similarly as the one described by Seifert and co-workers (1998) with minor modifications. We describe here an assay involving β2AR as the target of choice replacing β2AR by any other GPCR interacting with the Gαs subunit, allow implementation of similar screening methods to identify agonistic ligands against that particular GPCR. A small molecule (compound MW typically between 250 and 1000 Da) or even a fragment based (compound MW typically <250 Da) library can be screened to identify candidate agonists. The stabilization of the non-prominent conformer will increase the performance of the fragment library screens considerably, especially because the initial hits in fragment based drug screening typically have a low potency/affinity. Nb35 will selectively increase the affinity of those compounds that are specific for the selective, drugable conformer thus having a profound effect on the identification of de novo fragments.

An appropriate amount (typically 10 μg) of human β2AR homogenized membrane extracts from HEK293T cells containing the membrane anchored G protein subunits are incubated in parallel with Nb35 or a non-related Nanobody (which does not stabilize the active GPCR conformation) for 1 hour at 30° C. in incubation buffer (50 mM Hepes pH 7.4, 1 mM $CaCl_2$), 5 mM $MgCl_2$, 100 mM NaCl and 0.5% w/v BSA). Nanobodies are exogenously supplied in large molar excess (e.g., ≥1 μM) versus the adrenergic receptor. Subsequently, the Nanobody-bound membranes are added to 96-well plates containing library compounds and 2 nM of 3H-dihydroalprenolol (DHA) antagonistic radioligand. The total volume per well is adjusted with incubation buffer to 100 μl and the reaction mixture is further incubated for another hour at 30° C. Subsequently, membrane-bound radioligand is harvested using GF/C glass fiber 96-well filter plate (Perkin Elmer) presoaked in 0.3% polyethylenimine. Filter plates are washed with ice-cold wash buffer (50 mM Tris-HCl pH 7.4), and dried for 30 minutes at 50° C. After adding 25 μl of scintillation fluid (MICROSCINT™-O, Perkin Elmer), radioactivity (cpm) is measured in a Wallac MicroBeta TriLux scintillation counter. Those library compounds that significantly decrease the cpm in presence of Nb35 while not using the non-related Nanobody are considered agonistic ligands. Candidate agonistic hits identified via the primary library screening will be rescreened in a dose response manner. IC50 values of the % radioligand displacement curves for each candidate agonist in presence of Nb35 and the non-related Nanobody will be calculated using the Graphpad Prism software. To prove effective agonism of the identified de novo compounds, the dose dependent effect of these compounds in a cellular β2AR signaling assay will be evaluated. One example of such assay relies on the detection of secondary messenger molecules such as cAMP after Gαs mediated signaling (e.g., HitHunter cAMP assay technology, DiscoverX). Instead of using membrane extracts and exogenously applied Nb35, the radioligand assay could be performed on a β2AR expressing cell line co-transfected with Nb35 as an intrabody (or derived membranes) in order to shift the β2AR population to its active state. Alternatively, recombinant G protein and β2AR can be used to stabilize via Nb35 the active state of the β2AR.

Material and Methods to the Examples

Expression and Purification of βAR, Gs Heterotrimer, and Nanobody-35

An N-terminally fused T4 lysozyme-β2AR construct truncated in position 365 (T4L-β2AR, described in detail below) was expressed in Sf-9 insect cell cultures infected with recombinant baculovirus (BestBac, Expression Systems), and solubilized in n-Dodecyl-β-D-maltoside (DDM) according to methods described previously (Kobilka et al., 1995) (see FIG. 6 for purification overview). A β2AR construct truncated after residue 365 (β2AR-365; SEQ ID NO:55) was used for the majority of the analytical experiments and for deuterium exchange experiments. M1 Flag affinity chromatography (Sigma) served as the initial purification step followed by alprenolol-Sepharose chromatography for selection of functional receptor. A subsequent M1 Flag affinity chromatography step was used to exchange receptor-bound alprenolol for high-affinity agonist BI-167107. The agonist-bound receptor was eluted, dialyzed against buffer (20 mM HEPES pH7.5, 100 mM NaCl, 0.1% DDM and 10 M BI-167107), treated with lambda phosphatase (New England Biolabs), and concentrated to approximately 50 mg $ml^{-1}$ with a 50 kDa molecular weight cut off (MWCO) Millipore concentrator. Prior to spin concentration the β2AR-365 construct, but not T4L-β2AR, was treated with PNGaseF (New England Biolabs) to remove amino-terminal N-linked glycosylation. The purified receptor was routinely analyzed by SDS-PAGE/Coomassie brilliant blue staining (see FIG. 5, Panel a).

Bovine Gαs short, rat Gβ₁ fused to a His₆ tag, and rat Gγ₂ (see Table 5) were expressed in High 5 insects cells (Invitrogen) grown in Insect Xpress serum-free media (Lonza). Cultures were grown to a density of 1.5 million cells per ml and then infected with three separate *Autographa californica* nuclear polyhedrosis virus each containing the gene for one of the G protein subunits at a 1:1 multiplicity of infection (the viruses were a generous gift from Dr. Alfred Gilman). After 40-48 hours of incubation the infected cells were harvested by centrifugation and resuspended in 75 ml lysis buffer (50 mM HEPES pH 8.0, 65 mM NaCl, 1.1 mM MgCl₂, 1 mM EDTA, 1×PTT (35 g/ml phenylmethanesulfonyl fluoride, 32 g/ml tosyl phenylalanyl chloromethyl ketone, 32 g/ml tosyl lysyl chloromethyl ketone), 1×LS (3.2 g/ml leupeptin and 3.2 g/ml soybean trypsin inhibitor), 5 mM β-ME, and 10 µM GDP) per liter of culture volume. The suspension was pressurized with 600 psig N₂ for 40 minutes in a nitrogen cavitation bomb (Parr Instrument Company). After depressurization, the lysate was centrifuged to remove nuclei and unlysed cells, and then ultracentrifuged at 180,000×g for 40 minutes. The pelleted membranes were resuspended in 30 ml wash buffer (50 mM HEPES pH 8.0, 50 mM NaCl, 100 µM MgCl₂, 1×PTT, 1×LS, 5 mM R-ME, 10 µM GDP) per liter culture volume using a Dounce homogenizer and centrifuged again at 180,000×g for 40 minutes. The washed pellet was resuspended in a minimal volume of wash buffer and flash frozen with liquid nitrogen.

The frozen membranes were thawed and diluted to a total protein concentration of 5 mg/ml with fresh wash buffer. Sodium cholate detergent was added to the suspension at a final concentration of 1.0%, MgCl₂ was added to a final concentration of 5 mM, and 0.05 mg of purified protein phosphatase 5 (prepared in house) was added per liter of culture volume. The sample was stirred on ice for 40 minutes, and then centrifuged at 180,000×g for 40 minutes to remove insoluble derbies. The supernatant was diluted 5-fold with Ni-NTA load buffer (20 mM HEPES pH 8.0, 363 mM NaCl, 1.25 mM MgCl₂, 6.25 mM imidazole, 0.2% Anzergent 3-12, 1×PTT, 1×LS, 5 mM 1-ME, 10 µM GDP), taking care to add the buffer slowly to avoid dropping the cholate concentration below its critical micelle concentration too quickly. 3 ml of Ni-NTA resin (Qiagen) pre-equilibrated in Ni-NTA wash buffer 1 (20 mM HEPES pH 8.0, 300 mM NaCl, 2 mM MgCl₂, 5 mM imidazole, 0.2% Cholate, 0.15% Anzergent 3-12, 1×PTT, 1×LS, 5 mM 1-ME, 10 µM GDP) per liter culture volume was added and the sample was stirred on ice for 20 minutes. The resin was collected into a gravity column and washed with 4× column volumes of Ni-NTA wash buffer 1, Ni-NTA wash buffer 2 (20 mM HEPES pH 8.0, 50 mM NaCl, 1 mM MgCl₂, 10 mM imidazole, 0.15% Anzergent 3-12, 0.1% DDM, 1×PTT, 1×LS, 5 mM 1-ME, 10 µM GDP), and Ni-NTA wash buffer 3 (20 mM HEPES pH 8.0, 50 mM NaCl, 1 mM MgCl₂, 5 mM imidazole, 0.1% DDM, 1×PTT, 1×LS, 5 mM f-ME, 10 µM GDP). The protein was eluted with Ni-NTA elution buffer (20 mM HEPES pH 8.0, 40 mM NaCl, 1 mM MgCl₂, 200 mM imidazole, 0.1% DDM, 1×PTT, 1×LS, 5 mM f-ME, 10 µM GDP). Protein-containing fractions were pooled and MnCl2 was added to a final concentration of 100 M. 50 jg of purified lambda protein phosphatase (prepared in house) was added per liter of culture volume and the elute was incubated on ice with stirring for 30 minutes. The elute was passed through a 0.22 m filter and loaded directly onto a MonoQ HR 16/10 column (GE Healthcare) equilibrated in MonoQ buffer A (20 mM HEPES pH 8.0, 50 mM NaCl, 100 µM MgCl₂, 0.1% DDM, 5 mM f-ME, 1×PTT). The column was washed with 150 ml buffer A at 5 ml/min and bound proteins were eluted over 350 ml with a linear gradient up to 28% MonoQ buffer B (same as buffer A except with 1 M NaCl). Fractions were collected in tubes spotted with enough GDP to make a final concentration of 10 M. The Gs containing fractions were concentrated to 2 ml using a stirred ultrafiltration cell with a 10 kDa NMWL regenerated cellulose membrane (Millipore). The concentrated sample was run on a Superdex 200 prep grade XK 16/70 column (GE Healthcare) equilibrated in S200 buffer (20 mM HEPES pH 8.0, 100 mM NaCl, 1.1 mM MgCl₂, 1 mM EDTA, 0.012% DDM, 100 M TCEP, 2 M GDP). The fractions containing pure Gs were pooled, glycerol was added to 10% final concentration, and then the protein was concentrated to at least 10 mg/ml using a 30 kDa MWCO regenerated cellulose Amicon centrifugal ultrafiltration device. The concentrated sample was then aliquoted, flash frozen, and stored at −80°. A typical yield of final, purified Gs heterotrimer from 8 liters of cell culture volume was 6 mg.

Nanobody-35 (Nb35) (SEQ ID NO: 1) was expressed in the periplasm of *Escherichia coli* strain WK6, extracted, and purified by nickel affinity chromatography according to previously described methods (Rasmussen et al., 2011) followed by ion-exchange chromatography (FIG. 7a) using a Mono S 10/100 GL column (GE Healthcare). Selected Nb35 fractions were dialysis against buffer (10 mM HEPES pH 7.5, 100 mM NaCl) and concentrated to approximately 65 mg ml⁻¹ with a 10 kDa MWCO Millipore concentrator.

Protein Engineering

To increase the probability of obtaining crystals of the R:G complex we set out to increase the polar surface area of the receptors extracellular surface using two strategies. The approach was to replace the flexible and presumably unstructured N-terminus with the globular protein T4 lysozyme (T4L) used previously to crystallize and solve the carazolol bound receptor (Rosenbaum et al., 2007). The construct used here (T4L-β2AR) contained the cleavable signal sequence followed by the M1 Flag epitope (DYKDDDDA; SEQ ID NO:70), the TEV protease recognition sequence (ENLYFQG; SEQ ID NO:71), bacteriophage T4 lysozyme from N2 through Y161 including C54T and C97A mutations, and a two residue alanine linker fused to the human β₂AR sequence D29 through G365 (T4L-β2AR fusion construct defined by SEQ ID NO:69). The PNGaseF inaccessible glycosylation site of the β₂AR at N187 was mutated to Glu. M96 and M98 in the first extracellular loop were each replaced by Thr to increase the otherwise low expression level of T4L-β2AR. The threonine mutations did not affect ligand binding affinity for ³H-di-hydro-alprenolol, but caused a small, approximately two-fold decrease in affinity for isoproterenol (data not shown). Note that the wild type reference β2AR that is used here is defined by SEQ ID NO:72.

Microcrystallography Data Collection and Processing.

Data collection was performed at the Advanced Photon Source beamline 23 ID-B. Hundreds of crystals were screened, and a final dataset was compiled using diffraction wedges of typically 10 degrees from 20 strongly diffracting crystals. All data reduction was performed using HKL2000 (Otwinowski et al., 1997). Although in many cases diffraction to beyond 3 Å was seen in initial frames, radiation damage and anisotropic diffraction resulted in low completeness in higher resolution shells. Analysis of the final dataset by the UCLA diffraction anisotropy server (Strong et al., 2006) indicated that diffraction along the a* reciprocal axis was superior to that in other directions. On the basis of an F/sigF cutoff of 3 along each reciprocal space axis, reflections were subjected to an anisotropic truncation with resolution limits of 2.9, 3.2, and 3.2 Angstroms along a*, b*, and c* prior to use in refinement. Due to the low completeness in high-resolution shells, we report this structure to an overall resolution of only 3.3 Å, although it should be noted that some diffraction data to 2.9 Å was included during refinement and map calculation.

Structure Solution and Refinement

The structure was solved by molecular replacement using Phaser (McCoy et al., 2007a, b). The order of the molecular replacement search was found to be critical in solving the structure. In the order used, search models were: the structure of beta and gamma subunits from the structure of a Gi heterotrimeric G protein (PDB ID: 1GP2), Gs alpha ras domain (PDB ID: 1AZT), active-state beta2 adrenergic receptor (PDB ID: 3POG), beta2 binding nanobody (PDB ID: 3POG), T4 lysozyme (PDB ID: 2RH1), Gs alpha helical domain (PDB ID: 1AZT). Following the determination of the initial structure by molecular replacement, rigid body refinement and simulated annealing were performed in Phenix (Afonine et al., 2005) and BUSTER (Blanc et al., 2004), followed by restrained refinement and manual rebuilding in Coot (Emsley et al., 2004). After iterative refinement and manual adjustments, the structure was refined in CNS using the DEN method. Although the resolution of this structure exceeds that for which DEN is typically most useful, the presence of several poorly resolved regions indicated that the incorporation of additional information to guide refinement could provide better results. The DEN reference models used were those indicated above as molecular replacement search models, with the exception of NB35, which was well ordered and for which no higher resolution structure is available. Figures were prepared using PyMOL (The PyMOL Molecular Graphics System, Version 1.3, Schrödinger, LLC.). Refinement statistics are given in Table 7.

Binding

Membranes expressing the $\beta_2$AR or the $\beta_2$AR-Gspeptide fusion were prepared from baculovirus-infected Sf9 cells and $^3$H-dihydroalprenolol ($^3$H-DHA) binding performed as previously described (Swaminath et al., 2002). For competition binding, membranes were incubated with $^3$H-DHA (1.1 nM final) and increasing concentrations of (−)-isoproterenol (ISO) for 1 hour before harvesting onto GF/B filters. Competition data were fitted to a two-site binding model and ISO high and low Kis and fractions calculated using GraphPad prism.

Purification of NT4LV2R

The N-terminally fused T4L V2R construct (NT4L-V2R; SEQ ID NO:73) was expressed in Sf9 cells using the baculovirus system (PfastBac). Cells were infected at a density of $4 \times 10^6$ cells per ml and culture flasks were shaken at 27° C. for 48 hours. After harvesting, cells were lysed by osmotic shock in a buffer comprised of 10 mM Tris-HCl pH 7.5, 1 mM EDTA, 1 µM Tolvaptan (Sigma) and 2 mg ml$^{-1}$ iodoacetamide to block reactive cysteines. Extraction of NT4L-V2R from Sf9 membranes was done with a Dounce homogenizer in a solubilization buffer comprised of 0.5% dodecyl maltoside (DDM), 0.3% Cholate, 0.03% cholesterol hemisuccinate (CHS), 20 mM HEPES pH 7.5, 0.5 M NaCl, 30% v/v glycerol, 2 mgml$^{-1}$ iodoacetamide and 1 µM Tolvaptan. After centrifugation, nickel-NTA agarose was added to the supernatant, stirred for 2 hours, and then washed in batch with 100 g spins for 5 minutes each with a washing buffer of 0.1% DDM, 0.03% Cholate, 0.01% CHS, 20 mM HEPES pH 7.5 and 0.5 M NaCl. The resin was poured into a glass column and bound receptor was eluted in washing buffer supplemented with 300 mM imidazole. We used anti-Flag M1 affinity resin to purify NT4L-V2R further and to exchange the ligand with the agonist AVP. Ni-NTA resin eluate was loaded onto anti-Flag M1 resin and washed extensively in the presence of 10 µM AVP. Receptor was then eluted from the anti-Flag M1 affinity resin with 0.2 mgml$^{-1}$ Flag peptide and 2 mM EDTA in the presence of 1 µM AVP and concentrated using a 100 kDa MWCO concentrator.

TABLE 2

List of nanobodies

| Nanobody reference number | Nanobody short notation | SEQ ID NO: | Sequence (including C-terminal Histidine tag and EPEA tag) |
|---|---|---|---|
| CA4435 | Nb35 | 1 | QVQLQESGGGLVQPGGSLRLSCAASGFTFSNYKMNWVRQAPGKGLEWVSDISQSGASISYTGSVKGRFTISRDNAKNTLYLQMNSLKPEDTAVYYCARCPAPFTRDCFDVTSTTYAYRGQGTQVTVSSHHHHHHEPEA |
| CA4433 | Nb33 | 2 | QVQLQESGGGLVQPGGSLRLSCAASGFTFSNYVMNWVRQAPGKGLEWVSDISNGGGTTSYASSVKGRFTISRDNAKNTLYLQMNGLKPADTAVYYCARCPAPFTNDCMDITSTTYAYRGQGTQVTVSSHHHHHHEPEA |
| CA4436 | Nb36 | 3 | QVQLQESGGGSVQAGGSLRLSCTVSGTIFSVTVMGWYRQAPGKQRELVAGFTNTRNTNYVDSVKGRFTISKDSAKNTMYLQMNSLKPEDTAVYYCNVRRWGGTNWNDYWGQGTQVTVSSHHHHHHEPEA |
| CA4437 | Nb37 | 4 | QVQLQESGGGFVQAGGSLRLSCAASGSIFSKNTMAWFRQAPGKERELVAASPTGGSTAYKDSVKGRFTISRDSAKNTVLLQMNVLKPEDTAVYYCHLRQNNRGSWFHYWGQGTQVTVSSHHHHHHEPEA |

TABLE 2-continued

List of nanobodies

| Nanobody reference number | Nanobody short notation | SEQ ID NO: | Sequence (including C-terminal Histidine tag and EPEA tag) |
|---|---|---|---|
| CA4440 | Nb40 | 5 | QVQLQESGGGLVQAGGSLRLSCAVSGTIFDITPMGWYRQTPGKQREVVADLTSRGTTNYADSVKGRFTISRDNAKKMLYLQMNSLKSDDTGVYYCNVKRWGGIGWNDYWGQGTQVTVSSHHHHHHEPEA |
| CA4441 | Nb41 | 6 | QVQLQESGGGLVQSGGSLRLSCVASGFRFSNFPMMWVRQAPGKGLEWVSLISIGGSTTNYADSVKGRFTISRDNAKNTLFLQMNSLKPEDTAVYYCAKYLGRLVPPTTEGQGTQVTVSSHHHHHHEPEA |

TABLE 3

Combinations of FRs and CDRs of nanobodies

| Nanobody reference number | Nanobody short notation | FR1 | CDR1 | FR2 | CDR2 | FR3 | CDR3 | FR4 |
|---|---|---|---|---|---|---|---|---|
| CA4435 | NB35 | QVQLQESGGGLVQPGGSLRLSCAAS (SEQ ID NO: 7) | GFTFSNYK (SEQ ID NO: 13) | MNWVRQAPGKGLEWVSD (SEQ ID NO: 19) | ISQSGASI (SEQ ID NO: 25) | SYTGSVKGRFTISRDNAKNTLYLQMNSLKPEDTAVYYC (SEQ ID NO: 31) | ARCPAPFTRDCFDVTSTTYAY (SEQ ID NO: 37) | RGQGTQVTVSS (SEQ ID NO: 43) |
| CA4433 | Nb33 | QVQLQESGGGLVQPGGSLRLSCAAS (SEQ ID NO: 8) | GFTFSNYV (SEQ ID NO: 14) | MNWVRQAPGKGLEWVSD (SEQ ID NO: 20) | ISNGGGTT (SEQ ID NO: 26) | SYASSVKGRFTISRDNAKNTLYLQMNGLKPADTAVYYC (SEQ ID NO: 32) | ARCPAPFTNDCMDITSTTYAY (SEQ ID NO: 38) | RGQGTQVTVSS (SEQ ID NO: 44) |
| CA4436 | Nb36 | QVQLQESGGGSVQAGGSLRLSCTVS (SEQ ID NO: 9) | GTIFSVTV (SEQ ID NO: 15) | MGWYRQAPGKQRELVAG (SEQ ID NO: 21) | FTNTRNT (SEQ ID NO: 27) | NYVDSVKGRFTISKDSAKNTMYLQMNSLKPEDTAVYYC (SEQ ID NO: 33) | NVRRWGGTNWNDY (SEQ ID NO: 39) | WGQGTQVTVSS (SEQ ID NO: 45) |
| CA4437 | Nb37 | QVQLQESGGGFVQAGGSLRLSCAAS (SEQ ID NO: 10) | GSIFSKNT (SEQ ID NO: 16) | MAWFRQAPGKERELVAA (SEQ ID NO: 22) | SPTGGST (SEQ ID NO: 28) | AYKDSVKGRFTISRDSAKNTVLLQMNVLKPEDTAVYYC (SEQ ID NO: 34) | HLRQNNRGSWFHY (SEQ ID NO: 40) | WGQGTQVTVSS (SEQ ID NO: 46) |
| CA4440 | Nb40 | QVQLQESGGGLVQAGGSLRLSCAVS (SEQ ID NO: 11) | GTIFDITP (SEQ ID NO: 17) | MGWYRQTPGKQREVVAD (SEQ ID NO: 23) | LTSRGTT (SEQ ID NO: 29) | NYADSVKGRFTISRDNAKKMLYLQMNSLKSDDTGVYYC (SEQ ID NO: 35) | NVKRWGGIGWNDY (SEQ ID NO: 41) | WGQGTQVTVSS (SEQ ID NO: 47) |
| CA4441 | Nb41 | QVQLQESGGGLVQSGGSLRLSCVAS (SEQ ID NO: 12) | GFRFSNFP (SEQ ID NO: 18) | MMWVRQAPGKGLEWVSL (SEQ ID NO: 24) | ISIGGSTT (SEQ ID NO: 30) | NYADSVKGRFTISRDNAKNTLFLQMNSLKPEDTAVYYC (SEQ ID NO: 36) | AKYLGRLVPPTT (SEQ ID NO: 42) | EGQGTQVTVSS (SEQ ID NO: 48) |

TABLE 4

Nucleic acid sequences of nanobodies

| Nanobody reference number | Nanobody short notation | SEQ ID NO: | Nucleotide sequence of the nanobody (including nucleotide sequences of His tag and EPEA tag, which are underlined) |
|---|---|---|---|
| CA4435 | Nb35 | 49 | CAGGTGCAGCTGCAGGAGTCTGGAGGAGGCTTGGTGCAG<br>CCTGGGGGGTCTCTGAGACTCTCCTGTGCGGCCTCTGGAT<br>TCACCTTCAGCAATTATAAAATGAACTGGGTCCGCCAGG<br>CTCCAGGAAAGGGGCTCGAGTGGGTCTCAGATATTTCTC<br>AGAGTGGTGCTAGCATAAGTTACACAGGCTCCGTGAAGG<br>GCCGATTCACCATCTCCAGAGACAACGCCAAGAACACGC<br>TGTATCTACAAATGAACAGCCTGAAGCCTGAGGACACGG<br>CCGTCTATTACTGTGCCAGATGTCCGGCCCCATTCACGAG<br>AGATTGTTTTGACGTGACTAGTACCACGTATGCCTACAG<br>GGGCCAGGGGACCCAGGTCACCGTCTCCTCA<u>CACCACCA</u><br><u>TCACCATCACGAACCTGAAGCCTAG</u> |
| CA4433 | Nb33 | 50 | CAGGTGCAGCTGCAGGAGTCTGGAGGGGGCTTGGTGCAG<br>CCTGGGGGGTCTCTGAGACTCTCCTGTGCAGCCTCTGGAT<br>TCACTTTCAGTAACTATGTCATGAACTGGGTCCGCCAGG<br>CTCCAGGAAAGGGGCTCGAGTGGGTCTCAGATATTTCTA<br>ATGGCGGTGGTACCACAAGTTATGCAAGCTCCGTGAAGG<br>GCCGATTCACCATCTCCAGAGACAACGCCAAGAACACGC<br>TGTATCTGCAAATGAACGGCCTGAAGCCTGCGGACACGG<br>CCGTCTATTACTGTGCAAGATGTCCGGCCCCATTCACGA<br>ACGATTGTATGGACATAACTAGTACCACGTATGCCTACA<br>GGGGCCAGGGGACCCAGGTCACCGTCTCCTCA<u>CACCACC</u><br><u>ATCACCATCACGAACCTGAAGCCTAG</u> |
| CA4436 | Nb36 | 51 | CAGGTGCAGCTGCAGGAGTCTGGAGGAGGCTCGGTGCA<br>GGCTGGGGGGTCTCTGAGACTCTCCTGTACAGTCTCTGG<br>AACCATCTTCAGTGTCACTGTCATGGGCTGGTACCGCCA<br>GGCTCCAGGGAAGCAGCGCGAGTTGGTCGCAGGTTTTAC<br>TAATACTAGAAACACAAACTATGTAGACTCCGTGAAGGG<br>CCGCTTCACCATCTCCAAAGACAGCGCCAAGAACACGAT<br>GTATCTACAAATGAACAGCCTGAAACCTGAGGACACAGC<br>CGTCTATTACTGTAATGTACGTCGGTGGGGCGGTACGAA<br>TTGGAATGACTACTGGGGCCAGGGGACCCAGGTCACCGT<br>CTCCTCA<u>CACCACCATCACCATCACGAACCTGAAGCCTA</u><br><u>G</u> |
| CA4437 | Nb37 | 52 | CAGGTGCAGCTGCAGGAGTCTGGAGGGGGCTTCGTGCAG<br>GCTGGGGGGTCTCTGAGACTCTCCTGTGCAGCCTCTGGA<br>AGCATCTTCAGTAAGAATACCATGGCCTGGTTCCGCCAG<br>GCTCCAGGGAAGGAGCGAGAGTTGGTCGCAGCTAGTCCT<br>ACGGGTGGTAGCACAGCGTATAAAGACTCCGTGAAGGG<br>CCGATTCACCATCTCCAGAGACAGCGCCAAGAACACGGT<br>GTTGCTGCAAATGAACGTCCTGAAACCTGAGGATACTGC<br>CGTCTATTACTGTCATCTACGTCAAAATAACCGTGGTTCT<br>TGGTTCCACTACTGGGGCCAGGGGACCCAGGTCACCGTC<br>TCCTCA<u>CACCACCATCACCATCACGAACCTGAAGCCTAG</u> |
| CA4440 | Nb40 | 53 | CAGGTGCAGCTGCAGGAGTCTGGGGGAGGCTTGGTGCAG<br>GCTGGGGGGTCGCTGAGACTCTCTTGTGCAGTCTCTGGT<br>ACGATCTTCGATATCACTCCCATGGGCTGGTACCGCCAG<br>ACTCCAGGGAAGCAGCGCGAAGTGGTCGCAGATCTTACT<br>AGTCGCGGTACCACAAATTACGCAGACTCCGTGAAGGGC<br>CGGTTCACCATCTCCAGAGACAACGCCAAGAAAATGTTG<br>TATCTGCAAATGAACAGCCTGAAATCTGACGACACAGGC<br>GTGTATTACTGTAACGTGAAACGTGGGGAGGTATTGGC<br>TGGAACGACTACTGGGGCCAGGGGACCCAGGTCACCGTC<br>TCCTCA<u>CACCACCATCACCATCACGAACCTGAAGCCTAG</u> |
| CA4441 | Nb41 | 54 | CAGGTGCAGCTGCAGGAGTCTGGAGGAGGCTTGGTGCAG<br>TCTGGGGGGTCTCTGAGACTCTCCTGTGTAGCCTCTGGAT<br>TCAGATTCAGTAACTTTCCTATGATGTGGGTCCGCCAGGC<br>CCCAGGAAAGGGGCTCGAGTGGGTCTCGCTGATTAGCAT<br>TGGTGGTAGTACCACGAATTATGCGGACTCCGTGAAGGG<br>CCGATTCACCATCTCCAGAGACAACGCCAAGAACACGCT<br>GTTTCTGCAAATGAACAGCCTGAAACCTGAGGACACGGC<br>CGTGTATTACTGTGCAAAATATCTTGGTCGGCTGGTCCCA<br>CCGACTACTGAGGGCCAGGGGACCCAGGTCACCGTCTCC<br>TCA<u>ACCACCATCACCATCACGAACCTGAAGCCTAG</u> |

TABLE 5

Examples of isoforms of G protein subunits

| Protein/subunit | Accession number (SEQ ID NO:) | Isoform | AA sequence |
|---|---|---|---|
| human Gαs short | P63092 (56) | GNAS2_HUMAN | MGCLGNSKTEDQRNEEKAQREANKKIEKQL QKDKQVYRATHRLLLLGAGESGKSTIVKQM RILHVNGFNGDSEKATKVQDIKNNLKEAIETI VAAMSNLVPPVELANPENQFRVDYILSVMNV PDFDFPPEFYEHAKALWEDEGVRACYERSNE YQLIDCAQYFLDKIDVIKQADYVPSDQDLLRC RVLTSGIFETKFQVDKVNFHMFDVGGQRDER RKWIQCFNDVTAIIFVVASSSYNMVIREDNQT NRLQEALNLFKSIWNNRWLRTISVILFLNKQD LLAEKVLAGKSKIEDYFPEFARYTTPEDATPE PGEDPRVTRAKYFIRDEFLRISTASGDGRHYC YPHFTCAVDTENIRRVFNDCRDIIQRMHLRQY ELL |
| human Gαi | P63096 (57) | GNAI1_HUMAN | MGCTLSAEDKAAVERSKMIDRNLREDGEKA AREVKLLLLGAGESGKSTIVKQMKIIHEAGYS EEECKQYKAVVYSNTIQSIIAIIRAMGRLKIDF GDSARADDARQLFVLAGAAEEGFMTAELAG VIKRLWKDSGVQACFNRSREYQLNDSAAYY LNDLDRIAQPNYIPTQQDVLRTRVKTTGIVET HFTFKDLHFKMFDVGGQRSERKKWIHCFEGV TAIIFCVALSDYDLVLAEDEEMNRMHESMKL FDSICNNKWFTDTSIILFLNKKDLFEEKIKKSP LTICYPEYAGSNTYEEAAAYIQCQFEDLNKRK DTKEIYTHFTCATDTKNVQFVFDAVTDVIIKN NLKDCGLF |
| human Gαt | P11488 (58) | GNAT1_HUMAN | MGAGASAEEKHSRELEKKLKEDAEKDARTV KLLLLGAGESGKSTIVKQMKIIHQDGYSLEEC LEFIAIIYGNTLQSILAIVRAMTTLNIQYGDSA RQDDARKLMHMADTIEEGTMPKEMSDIIQRL WKDSGIQACFERASEYQLNDSAGYYLSDLER LVTPGYVPTEQDVLRSRVKTTGIIETQFSFKDL NFRMFDVGGQRSERKKWIHCFEGVTCIIFIAA LSAYDMVLVEDDEVNRMHESLHLFNSICNHR YFATTSIVLFLNKKDVFFEKIKKAHLSICFPDY DGPNTYEDAGNYIKVQFLELNMRRDVKEIYS HMTCATDTQNVKFVFDAVTDIIIKENLKDCG LF |
| Bovine Gαs short | P04896 (59) | GNAS2_BOVIN | MGCLGNSKIEDQRNEEKAQREANKKIEKQL QKDKQVYRATHRLLLLGAGESGKSTIVKQM RILHVNGFNGEGGEEDPQAARSNSDGEKATK VQDIKNNLKEAIETIVAAMSNLVPPVELANPE NQFRVDYILSVMNVPDFDFPPEFYEHAKALW EDEGVRACYERSNEYQLIDCAQYFLDKIDVIK QDDYVPSDQDLLRCRVLTSGIFETKFQVDKV NFHMFDVGGQRDERRKWIQCFNDVTAIIFVV ASSSYNMVIREDNQTNRLQEALNLFKSIWNN RWLRTISVILFLNKQDLLAEKVLAGKSKIEDY FPEFARYTTPEDATPEPGEDPRVTRAKYFIRD EFLRISTASGDGRHYCYPHFTCAVDTENIRRV FNDCRDIIQRMHLRQYELL |
| Rat Gαs short | P63095 (60) | GNAS2_RAT | MGCLGNSKIEDQRNEEKAQREANKKIEKQL QKDKQVYRATHRLLLLGAGESGKSTIVKQM RILHVNGFNGEGGEEDPQAARSNSDGEKATK VQDIKNNLKEAIETIVAAMSNLVPPVELANPE NQFRVDYILSVMNVPNFDFPPEFYEHAKALW EDEGVRACYERSNEYQLIDCAQYFLDKIDVIK QADYVPSDQDLLRCRVLTSGIFETKFQVDKV NFHMFDVGGQRDERRKWIQCFNDVTAIIFVV ASSSYNMVIREDNQTNRLQEALNLFKSIWNN RWLRTISVILFLNKQDLLAEKVLAGKSKIEDY FPEFARYTTPEDATPEPGEDPRVTRAKYFIRD EFLRISTASGDGRHYCYPHFTCAVDTENIRRV FNDCRDIIQRMHLRQYELL |
| Mouse Gαs short | P63094 (61) | GNAS2_MOUSE | MGCLGNSKTEDQRNEEKAQREANKKIEKQL QKDKQVYRATHRLLLLGAGESGKSTIVKQM RILHVNGFNGEGGEEDPQAARSNSDGEKATK VQDIKNNLKEAIETIVAAMSNLVPPVELANPE NQFRVDYILSVMNVPNFDFPPEFYEHAKALW |

TABLE 5-continued

Examples of isoforms of G protein subunits

| Protein/subunit | Accession number (SEQ ID NO:) | Isoform | AA sequence |
|---|---|---|---|
| | | | EDEGVRACYERSNEYQLIDCAQYFLDKIDVIK QADYVPSDQDLLRCRVLTSGIFETKFQVDKV NFHMFDVGGQRDERRKWIQCFNDVTAIIFVV ASSSYNMVIREDNQTNRLQEALNLFKSIWNN RWLRTISVILFLNKQDLLAEKVLAGKSKIEDY FPEFARYTTPEDATPEPGEDPRVTRAKYFIRD EFLRISTASGDGRHYCYPHFTCAVDTENIRRV FNDCRDIIQRMHLRQYELL |
| Bovine Gβ | P62871 (62) | GBB1_BOVIN | MSELDQLRQEAEQLKNQIRDARKACADATLS QITNNIDPVGRIQMRTRRTLRGHLAKIYAMH WGTDSRLLVSASQDGKLIIWDSYTTNKVHAIP LRSSWVMTCAYAPSGNYVACGGLDNICSIYN LKTREGNVRVSRELAGHTGYLSCCRFLDDNQ IVTSSGDTTCALWDIETGQQTTTFTGHTGDV MSLSLAPDTRLFVSGACDASAKLWDVREGM CRQTFTGHESDINAICFFPNGNAFATGSDDAT CRLFDLRADQELMTYSHDNIICGITSVSFSKSG RLLLAGYDDFNCNVWDALKADRAGVLAGH DNRVSCLGVTDDGMAVATGSWDSFLKIWN |
| Human Gβ | P62873 (63) | GBB1_HUMAN | MSELDQLRQEAEQLKNQIRDARKACADATLS QITNNIDPVGRIQMRTRRTLRGHLAKIYAMH WGTDSRLLVSASQDGKLIIWDSYTTNKVHAIP LRSSWVMTCAYAPSGNYVACGGLDNICSIYN LKTREGNVRVSRELAGHTGYLSCCRFLDDNQ IVTSSGDTTCALWDIETGQQTTTFTGHTGDV MSLSLAPDTRLFVSGACDASAKLWDVREGM CRQTFTGHESDINAICFFPNGNAFATGSDDAT CRLFDLRADQELMTYSHDNIICGITSVSFSKSG RLLLAGYDDFNCNVWDALKADRAGVLAGH DNRVSCLGVTDDGMAVATGSWDSFLKIWN |
| Rat Gβ | P54311 (64) | GBB1_RAT | MSELDQLRQEAEQLKNQIRDARKACADATLS QITNNIDPVGRIQMRTRRTLRGHLAKIYAMH WGTDSRLLVSASQDGKLIIWDSYTTNKVHAIP LRSSWVMTCAYAPSGNYVACGGLDNICSIYN LKTREGNVRVSRELAGHTGYLSCCRFLDDNQ IVTSSGDTTCALWDIETGQQTTTFTGHTGDV MSLSLAPDTRLFVSGACDASAKLWDVREGM CRQTFTGHESDINAICFFPNGNAFATGSDDAT CRLFDLRADQELMTYSHDNIICGITSVSFSKSG RLLLAGYDDFNCNVWDALKADRAGVLAGH DNRVSCLGVTDDGMAVATGSWDSFLKIWN |
| Mouse Gβ | P62874 (65) | GBB1_MOUSE | MSELDQLRQEAEQLKNQIRDARKACADATLS QITNNIDPVGRIQMRTRRTLRGHLAKIYAMH WGTDSRLLVSASQDGKLIIWDSYTTNKVHAIP LRSSWVMTCAYAPSGNYVACGGLDNICSIYN LKTREGNVRVSRELAGHTGYLSCCRFLDDNQ IVTSSGDTTCALWDIETGQQTTTFTGHTGDV MSLSLAPDTRLFVSGACDASAKLWDVREGM CRQTFTGHESDINAICFFPNGNAFATGSDDAT CRLFDLRADQELMTYSHDNIICGITSVSFSKSG RLLLAGYDDFNCNVWDALKADRAGVLAGH DNRVSCLGVTDDGMAVATGSWDSFLKIWN |
| Bovine Gγ | P63212 (66) | GBG2_BOVIN | MASNNTASIAQARKLVEQLKMEANIDRIKVS KAAADLMAYCEAHAKEDPLLTPVPASENPFR EKKFFCAIL |
| Mouse Gγ | P63213 (67) | GBG2_MOUSE | MASNNTASIAQARKLVEQLKMEANIDRIKVS KAAADLMAYCEAHAKEDPLLTPVPASENPFR EKKFFCAIL |
| Human Gγ | P59768 (68) | GBG2_HUMAN | MASNNTASIAQARKLVEQLKMEANIDRIKVS KAAADLMAYCEAHAKEDPLLTPVPASENP FREKKFFCAIL |

TABLE 6

Potential intermolecular interactions within the R:G interface

| | atom in β₂AR | atom in Gsα | | distance (Å) |
|---|---|---|---|---|
| TM3 | [ARG 131 CG] | [TYR 391 CE2] | | 3.6 |
| | [ALA 134 O] | [HIS 387 ND1] | | (?) |
| | [ALA 134 CB] | [HIS 387 ND1] | | (?) |
| | [ALA 134 CB] | [HIS 387 CG] | | (?) |
| | [ILE 135 O] | [GLN 384 NE2] | α5 | 2.9 |
| | [ILE 135 CD1] | [LEU 388 CD1] | | (?) |
| | [ILE 135 CD1] | [LEU 393 CD1] | | 3.5 |
| | [THR 135 O] | [ARG 380 NH2] | | 3.0 |
| IL2 | [PRO 138 O] | [ILE 383 CD1] | | 3.4 |
| | [PRO 138 CG] | [GLN 384 CG] | | 3.3 |
| | [PHE 139 CD2] | [HIS 41 NE2] | —β1 | 3.6 |
| | [PHE 139 CB] | [VAL 217 CG2] | —α4 | 3.7 |
| | [PHE 139 CE1] | [PHE 376 CZ] | | 3.3 |
| | [PHE 139 CZ] | [CYS 379 C] | | 3.0 |
| | [PHE 139 CZ] | [ARG 380 N] | α5 | 3.2 |
| | [TYR 141 CD2] | [HIS 387 NE2] | | 3.9 |
| | [GLN 142 OE1] | [HIS 387 NE2] | | 3.5 |
| | [SER 143 OG] | [ALA 39 CB] | —αN | 3.6 |
| TM5 | [VAL 222 CG1] | [LEU 393 CD1] | | 3.7 |
| | [GLU 225 OE2] | [GLN 384 NE2] | | 3.0 |
| | [ALA 226 CA] | [LEU 388 CD2] | | 3.6 |
| | [ALA 226 CB] | [LEU 393 O] | | 3.8 |
| | [GLN 229 NE2] | [ASP 381 CD1] | α5 | (?) |
| | [GLN 229 NE2] | [GLN 384 OE1] | | 3.9 |
| | [GLN 229 OE1] | [ARG 385 NE] | | 3.5 |
| | [GLN 229 CG] | [LEU 388 CD2] | | 3.1 |
| | [LEU 230 CG] | [LEU 394 CD1] | | 3.4 |
| | [LYS 232 NE] | [ASP 381 CD1] | | 3.5 |
| | [ILE 233 CD1] | [TYR 358 OH] | —β6 | 3.5 |
| | [ILE 233 CG1] | [ARG 385 NH1] | —α5 | |
| | [ARG 239 NE] | [THR 350 OG1] | —α4 | |
| TM6 | [ALA 271 CB] | [LEU 393 O] | | 3.0 |
| | [THR 274 CG2] | [GLU 392 O] | α5 | 3.4 |
| | [THR 274 CG1] | [LEU 393 CD2] | | 3.3 |
| | [LEU 275 CD2] | [LEU 393 CD2] | | (?) |

TABLE 7

Data collection and refinement statistics

Data collection*

| | |
|---|---|
| Number of crystals | 20 |
| Space group | P2₁ |
| Cell dimensions | |
| a, b, c (Å) | 119.3, 64.6, 131.2 |
| α, β, γ (°) | 90.0, 91.7, 90.0 |
| Resolution (Å) | 41-3.2 (3.26-3.20) |
| R$_{merge}$ (%) | 15.6 (55.3) |
| <I>/<σI> | 10.8 (1.8) |
| Completeness (%) | 91.2 (53.9) |
| Redundancy | 6.5 (5.0) |

Refinement

| | |
|---|---|
| Resolution (Å) | 41-3.2 |
| No. reflections | 31075 (1557 in test set) |
| R$_{work}$/R$_{free}$ (%) | 22.5/27.7 |
| No. atoms | 10277 |
| No. protein residues | 1318 |
| Anisotropic B tensor | $B_{11} = -7.0/B_{22} = 4.7/B_{33} = 2.3/B_{13} = 2.1$ |

TABLE 7-continued

Data collection and refinement statistics

Unmodelled sequences*

| | |
|---|---|
| β₂ adrenergic receptor | 29[b], 176-178, 240-264, 342-365 |
| G$_s$ α, ras domain | 1-8, 60-88, 203-204, 256-262 |
| G$_s$ γ | 1-4, 63-68 |
| T4 lysozyme | 161[c] |

Average B-factors (Å²)

| | |
|---|---|
| β₂ adrenergic receptor | 133.5 |
| G$_s$ α, ras domain | 82.8 |
| G$_s$ α, helical domain | 123.0 |
| G$_s$ β | 64.2 |
| G$_s$ γ | 85.2 |
| Nanobody 35 | 60.7 |
| T4 lysozyme | 113.7 |

R.m.s. deviation from ideality

| | |
|---|---|
| Bond length (Å) | 0.007 |
| Bond angles (°) | 0.72 |

Ramachandran statistics[d]

| | |
|---|---|
| Favored regions (%) | 95.8 |
| Allowed regions (%) | 4.2 |
| Outliers (%) | 0 |

*Highest shell statistics are in parentheses.
[a]These regions were omitted from the model due to poorly resolved electron density. Unmodeled purification tags are not included in these residue ranges.
[b]Residues 1-28 of β2AR were omitted from the construct and T4L was fused to the amino terminus of transmembrane helix 1 to facilitate crystallization.
[c]Residue of T4L was omitted from the construct.
[d]As defined by MolProbity.

REFERENCES

Afonine, P. V., Grosse-Kunstleve, R. W., & Adams, P. D. (2005). A robust bulk-solvent correction and anisotropic scaling procedure. Acta crystallographica. Section D, Biological crystallography, 61, 850-5.

Baltensperger, K. et al., The beta-adrenergic receptor is a substrate for the insulin receptor tyrosine kinase. J Biol Chem 271, 1061-1064 (1996).

Binz et al., Nature Biotech., 22: 575-582 (2004)

Blanc, E., Roversi, P., Vonrhein, C., Flensburg, C., Lea, S. M., Bricogne, G., et al. (2004). Refinement of severely incomplete structures with maximum likelihood in BUSTER-TNT. Acta crystallographica. Section D, Biological crystallography, 60, 2210-21.

Caffrey (2003). Membrane protein crystallization. J Struct. Biol. 2003 142:108-32.

Caffrey, M. & Cherezov, V. Crystallizing membrane proteins using lipidic mesophases. Nat Protoc 4, 706-731, (2009).

Chae, P. S. et al., Maltose-neopentyl glycol (MNG) amphiphiles for solubilization, stabilization and crystallization of membrane proteins. Nat Methods 7, 1003-1008 (2010).

Chelikani et al., Protein Sci. 2006 15:1433-40

Chini, B., & Parenti, M. (2009). G-protein-coupled receptors, cholesterol and palmitoylation: facts about fats. Journal of molecular endocrinology, 42(5), 371-9.

Chomczynski, P. and Sacchi, N., 1987. Single step method of RNA isolation by acid guanidium thiocyanate-phenol-chloroform extraction. Anal. Biochem. 162, p. 156.

Conrath K, Pereira A S, Martins C E, Timóteo C G, Tavares P, Spinelli S, Kinne J, Flaudrops C, Cambillau C, Muyldermans S, Moura I, Moura J J, Tegoni M, Desmyter A. Camelid nanobodies raised against an integral membrane enzyme, nitric oxide reductase. Protein Sci. 2009 March; 18(3):619-28.

Conrath K. E., M. Lauwereys, M. Galleni et al., Antimicrob Agents Chemother 45 (10), 2807 (2001).

Costanzi S, Vilar S (2011). In Silico screening for agonists and blockers of the beta(2) adrenergic receptor: Implications of inactive and activated state structures. Journal of computational chemistry 33:561-572.

Day P. W., Rasmussen S. G., Parnot C., Fung J. J., Masood A., Kobilka T. S., Yao X. J., Choi H. J., Weis W. I. and Rohrer D. K. et al., A monoclonal antibody for G protein-coupled receptor crystallography, Nat Methods 4 (2007), pp. 927-929.

Delean, A., J. M. Stadel, et al. (1980). "A TERNARY COMPLEX MODEL EXPLAINS THE AGONIST-SPECIFIC BINDING-PROPERTIES OF THE ADENYLATE CYCLASE-COUPLED BETA-ADRENERGIC-RECEPTOR." JOURNAL OF BIOLOGICAL CHEMISTRY 255 (15): 7108-7117.

Derewenda Z. S. Rational protein crystallization by mutational surface engineering, Structure (Camb) 12 (2004), pp. 529-535.

Domanska, K. et al., Atomic structure of a nanobody-trapped domain-swapped dimer of an amyloidogenic beta2-microglobulin variant. Proc Natl Acad Sci USA 108, 1314-1319, (2011).

Emsley, P. & Cowtan, K. Coot: model-building tools for molecular graphics. Acta Crystallogr D Biol Crystallogr 60, 2126-2132, (2004).

Eroglu et al., EMBO 2002 3: 491^96

Eroglu et al., Proc. Natl. Acad. Sci. 2003 100: 10219-10224

Faham et al., Crystallization of bacteriorhodopsin from bicelle formulations at room temperature. Protein Sci. 2005 14:836-40. 2005

Faham et al., Bicelle crystallization: a new method for crystallizing membrane proteins yields a monomeric bacteriorhodopsin structure. J Mol Biol. 2002-2-8; 316(1): 1-6.

Foord, S. M., T. I. Bonner, et al. (2005). "International Union of Pharmacology. XLVI. G protein-coupled receptor list." Pharmacological reviews 57(2): 279-288.

Fredriksson, R., M. C. Lagerstrom, et al. (2003). "The G-protein-coupled receptors in the human genome form five main families. Phylogenetic analysis, paralogon groups, and fingerprints." Molecular Pharmacology 63(6): 1256-1272.

Gebauer & Skerra (2009) Current opinion in chemical biology 13, 245-255

George et al., Nat Rev Drug Discov 1:808-820 (2002)

Gouaux, It's not just a phase: crystallization and X-ray structure determination of bacteriorhodopsin in lipidic cubic phases. Structure. 1998 6:5-10;

Hamers-Casterman, C., T. Atarhouch, S. Muyldermans et al., Naturally occurring antibodies devoid of light chains. Nature 363, 446-448, doi:10.1038/363446a0 (1993).

Hendrickson W A. Determination of macromolecular structures from anomalous diffraction of synchrotron radiation. Science. 1991-10-4; 254(5028):51-8.

Hofmann K. P., P. Scheerer, P. W. Hildebrand et al., Trends Biochem Sci 34 (11), 540 (2009).

Hunte C. and Michel H., Crystallization of membrane proteins mediated by antibody fragments, Curr Opin Struct Biol 12 (2002), pp. 503-508.

Jameson, E. E. et al. (2005). Real-time detection of basal and stimulated G protein GTPase activity using fluorescent GTP analogues. J Biol Chem 280, 7712-7719.

Kenakin, Trends Pharmacol Sci 25:186-192 (2002)

Kobilka et al. (2007) *Trends in pharmacological sciences* 28, 397-406.

Kobilka, B. K. Amino and carboxyl terminal modifications to facilitate the production and purification of a G protein-coupled receptor. Anal Biochem 231, 269-271 (1995).

Koide et al., J. Mol. Biol., 284: 1141-1151 (1998))

Kolakowski, L. F. (1994). "GCRDB—A G-PROTEIN-COUPLED RECEPTOR DATABASE." Receptors & Channels 2(1): 1-7.

Kolb, P., D. M. Rosenbaum, et al. (2009). "Structure-based discovery of beta(2)-adrenergic receptor ligands." Proceedings of the National Academy of Sciences of the United States of America 106(16): 6843-6848.

Kuszak, A. J., S. Pitchiaya, et al. (2009). "Purification and functional reconstitution of monomeric mu-opioid receptors: allosteric modulation of agonist binding by Gi2." The Journal of biological chemistry 284: 26732-26741.

Lagerström, M. C. and H. B. Schiöth (2008). "Structural diversity of G protein-coupled receptors and significance for drug discovery." Nature reviews. Drug discovery 7: 339-357.

Landau et al., Lipidic cubic phases: a novel concept for the crystallization of membrane proteins. Proc. Natl. Acad. Sci. 1996 93:14532-5

Lee, A. G. (2004). How lipids affect the activities of integral membrane proteins. Biochimica et biophysica acta, 1666 (1-2), 62-87.

Lee G M, Craik C S (2009). Trapping moving targets with small molecules. Science. April 10; 324(5924):213-5.

Lefranc, M. P., C. Pommie, et al. (2003). "IMGT unique numbering for immunoglobulin and T cell receptor variable domains and Ig superfamily V-like domains." Developmental and Comparative Immunology 27(1): 55-77.

Li H., Dunn J. J., Luft B. J. and Lawson C. L., Crystal structure of Lyme disease antigen outer surface protein A complexed with an Fab, Proc Natl Acad Sci USA 94 (1997), pp. 3584-3589

Luca et al., Proc. Natl. Acad. Sci. 2003 100:10706-1 1

Lynch Kevin R. (Ed) Identification and Expression of G Protein-Coupled Receptors published by John Wiley & Sons (March 1998)

Mansoor et al., Proc. Natl. Acad. Sci. 2006 103: 3060-3065

Marchese et al., Genomics 23: 609-618, 1994

McCoy, A. J. Solving structures of protein complexes by molecular replacement with Phaser. Acta Crystallogr D Biol Crystallogr 63, 32-41 (2007).

McCoy, A. J., Grosse-Kunstleve, R. W., Adams, P. D., Winn, M. D., Storoni, L. C., Read, R. J., et al. (2007). Phaser crystallographic software. Journal of applied crystallography, 40(Pt 4), 658-674.

McEwen, D. P., Gee, K. R., Kang, H. C. & Neubig, R. R. (2001) Fluorescent BODIPY-GTP analogs: real-time measurement of nucleotide binding to G proteins. Anal Biochem 291, 109-117.

Misquitta, L. V. et al., Membrane protein crystallization in lipidic mesophases with tailored bilayers. Structure 12, 2113-2124, (2004).

Moro, O., Lameh, J., Hogger, P. & Sadee, W. Hydrophobic amino acid in the i2 loop plays a key role in receptor-G protein coupling. J Biol Chem 268, 22273-22276 (1993).

Niu et al., Biophys J. 2005 89: 1833-1840

Nollert et al., Lipidic cubic phases as matrices for membrane protein crystallization Methods. 2004 34:348-53

Ostermeier C., Iwata S., Ludwig B. and Michel H., Fv fragment-mediated crystallization of the membrane protein bacterial cytochrome c oxidase, Nat Struct Biol 2 (1995), pp. 842-846.

Otwinowski, Z., & Minor, W. (1997). Processing of X-ray diffraction data collected in oscillation mode. *Methods in enzymology*, 276, 307-325.

Palczewski, K. et al., Crystal structure of rhodopsin: A G protein-coupled receptor [see comments]. Science 289, 739-745 (2000).

Probst et al., 1992, DNA Cell Biol. 1992 1: 1-20;

Qian Z M, Li H, Sun H and Ho K (2002). Targeted drug delivery via the transferring receptor-mediated endocytosis pathway. Pharmacol Rev 54, 561-587.

Rasmussen et al. (2011) Nature 469, 175-180.

Rasmussen S. G., Choi H. J., Rosenbaum D. M., Kobilka T. S., Thian F. S., Edwards P. C., Burghammer M., Ratnala V. R., Sanishvili R. and Fischetti R. F. et al., Crystal structure of the human beta2 adrenergic G-protein-coupled receptor, Nature 450 (2007), pp. 383-387.

Riechmann and Muyldermans, J. Immunol. Methods 2000; 240: 185-195.

Rios et al., Pharmacol Ther 92:71-87 (2001).

Ritter, S. L., & Hall, R. A. (2009). Fine-tuning of GPCR activity by receptor-interacting proteins. Nature reviews. Molecular cell biology, 10(12), 819-30. Nature Publishing Group. doi: 10.1038/nrm2803.)

Rosenbaum D. M., S. G. Rasmussen, and B. K. Kobilka, Nature 459 (7245), 356 (2009).

Rosenbaum, D. M. et al., Structure and function of an irreversible agonist-beta(2) adrenoceptor complex. Nature 469, 236-240 (2011).

Rosenbaum, D. M., V. Cherezov, et al. (2007). "GPCR engineering yields high-resolution structural insights into beta2-adrenergic receptor function." Science 318: 1266-1273.

Rummel et al., Lipidic Cubic Phases: New Matrices for the Three-Dimensional Crystallization of Membrane Proteins. J. Struct. Biol. 1998 121:82-91;

Sawant R, Torchilin V. Intracellular transduction using cell-penetrating peptides. Mol Biosyst. 2010 April; 6(4):628-40. Epub 2009 Dec. 21.

Seifert et al. (1998). Reconstitution of beta2-adrenoceptor-GTP-binding-protein interaction in Sf9 cells—high coupling efficiency in a beta2-adrenoceptor-G(s alpha) fusion protein. Eur. J. Biochem. 255:369-382.

Shimada et al., J. Biol. Chem. 2002 277:31774-80

Skerra, J. Molecular Recognition, 13:167-187 (2000)

Sprang, S. R. G protein mechanisms: insights from structural analysis. Annu Rev Biochem 66, 639-678 (1997).

Starovasnik et al., Proc. Natl. Acad. Sd. USA, 94: 10080-10085 (1997)

Steyaert J, Kobilka B K (2011). Nanobody stabilization of G protein-coupled receptor conformational states. Curr Opin Struct Biol. August; 21(4):567-72.

Strong, M. et al., Toward the structural genomics of complexes: crystal structure of a PE/PPE protein complex from *Mycobacterium tuberculosis*. Proc Natl Acad Sci USA 103, 8060-8065, (2006).

Sunahara, R. K., Tesmer, J. J., Gilman, A. G. & Sprang, S. R. Crystal structure of the adenylyl cyclase activator Gsalpha [see comments]. Science 278, 1943-1947 (1997).

Swaminath, G., Steenhuis, J., Kobilka, B. & Lee, T. W. Allosteric modulation of beta2-adrenergic receptor by Zn(2+). Mol Pharmacol 61, 65-72. (2002).

Tatsuya Haga (Ed), G Protein-Coupled Receptors, published by CRC Press (Sep. 24, 1999)

Van Eps, N. et al., Interaction of a G protein with an activated receptor opens the interdomain interface in the alpha subunit. Proc Natl Acad Sci USA (2011).

Wall, M. A. et al., The structure of the G protein heterotrimer Gial b1 g 2. Cell 83, 1047-1058 (1995).

Warne, T. et al., Structure of a beta1-adrenergic G-protein-coupled receptor. Nature 454, 486-491, (2008).

Watson, S. (Ed). G-Protein Linked Receptor Factsbook, published by Academic Press (1st edition; 1994).

Wess Jurgen (Ed), Structure-Function Analysis of G Protein-Coupled Receptors published by Wiley-Liss (1 st edition; Oct. 15, 1999)

Whorton, M. R. et al., A monomeric G protein-coupled receptor isolated in a high-density lipoprotein particle efficiently activates its G protein. Proc Natl Acad Sci USA 104, 7682-7687 (2007).

Whorton, M. R., S. G. F. Rasmussen, et al. (2009). "The effect of ligand efficacy on the formation and stability of a GPCR-G protein complex." PNAS 106: 1-6.

---

What is claimed is:

1. A method for identifying a test compound that binds to a GPCR/G-protein complex, the method comprising:
   determining that a protein binding domain binds to the G-protein in the GPCR/G-protein complex and stabilizes the GPCR/G-protein complex, wherein the protein binding domain is a nanobody;
   forming a complex of the GPCR, the G-protein, and the protein binding domain;
   contacting the complex with the test compound; and
   determining binding between the test compound and the complex.

2. The method according to claim 1, further comprising: determining that the test compound binds to the GPCR in the complex.

3. The method according to claim 1, further comprising: determining that the test compound binds to the G-protein in the complex.

4. The method according to claim 1, wherein the test compound is selected from the group consisting of a polypeptide, a peptide, a small molecule, a natural product, a peptidomimetic, a nucleic acid, a lipid, a lipopeptide, a carbohydrate, an antibody or an antigen-binding fragment thereof, a heavy chain antibody (hcAb), a single domain antibody (sdAb), a minibody, a variable domain derived from a camelid heavy chain antibody, a variable domain of an immunoglobulin new antigen receptor ($V_{NAR}$), and a protein scaffold.

5. The method according to claim 4, wherein the antigen-binding fragment thereof is selected from the group consisting of a Fab, a Fab', a F(ab')2, an Fd, a single-chain Fvs (scFv), a single-chain antibody, a disulfide-linked Fv (dsFv), a fragment comprising a VL domain and a fragment comprising a VH domain.

6. The method according to claim 4, wherein the protein scaffold is selected from the group consisting of an alphabody, a protein A, a protein G, a designed ankyrin-repeat domain (DARPin), a fibronectin-type III repeat, an anticalin, a knottin, and an engineered CH2 domain.

7. The method according to claim 1, wherein the protein binding domain binds to an intracellular domain of the GPCR/G-protein complex.

8. The method according to claim 1, wherein the protein binding domain binds to an intracellular domain of the G-protein.

9. The method according to claim 8, wherein the protein binding domain binds to a conformational epitope at the interface between the alpha and beta subunits of the G-protein.

10. The method according to claim 1, wherein the protein binding domain (a) is derived from an immunoglobulin, (b) comprises an amino acid sequence comprising 4 framework regions and 3 complementary determining regions or any suitable fragment thereof, (c) is derived from a camelid antibody, and/or (d) comprises a nanobody sequence or any suitable fragment thereof.

11. The method according to claim 1, wherein the test compound has higher affinity that for the GPRC/G-protein/protein binding domain complex than the same complex in the absence of the protein binding domain.

* * * * *

SEQUENCE LISTING

```
<160> NUMBER OF SEQ ID NOS: 73

<210> SEQ ID NO 1
<211> LENGTH: 138
<212> TYPE: PRT
<213> ORGANISM: Lama glama

<400> SEQUENCE: 1

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Lys Met Asn Trp Val Arg Gln Ala Pro Gly Lys Gly Leu Glu Trp Val
        35                  40                  45

Ser Asp Ile Ser Gln Ser Gly Ala Ser Ile Ser Tyr Thr Gly Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95
```

Ala Arg Cys Pro Ala Pro Phe Thr Arg Asp Cys Phe Asp Val Thr Ser
                100                 105                 110

Thr Thr Tyr Ala Tyr Arg Gly Gln Gly Thr Gln Val Thr Val Ser Ser
            115                 120                 125

His His His His His His Glu Pro Glu Ala
    130                 135

<210> SEQ ID NO 2
<211> LENGTH: 138
<212> TYPE: PRT
<213> ORGANISM: Lama glama

<400> SEQUENCE: 2

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Val Met Asn Trp Val Arg Gln Ala Pro Gly Lys Gly Leu Glu Trp Val
        35                  40                  45

Ser Asp Ile Ser Asn Gly Gly Gly Thr Thr Ser Tyr Ala Ser Ser Val
50                  55                  60

Lys Gly Arg Phe Thr Ile Ser Arg Asp Asn Ala Lys Asn Thr Leu Tyr
65                  70                  75                  80

Leu Gln Met Asn Gly Leu Lys Pro Ala Asp Thr Ala Val Tyr Tyr Cys
                85                  90                  95

Ala Arg Cys Pro Ala Pro Phe Thr Asn Asp Cys Met Asp Ile Thr Ser
                100                 105                 110

Thr Thr Tyr Ala Tyr Arg Gly Gln Gly Thr Gln Val Thr Val Ser Ser
            115                 120                 125

His His His His His His Glu Pro Glu Ala
    130                 135

<210> SEQ ID NO 3
<211> LENGTH: 129
<212> TYPE: PRT
<213> ORGANISM: Lama glama

<400> SEQUENCE: 3

Gln Val Gln Leu Gln Glu Ser Gly Gly Gly Ser Val Gln Ala Gly Gly
1               5                   10                  15

Ser Leu Arg Leu Ser Cys Thr Val Ser Gly Thr Ile Phe Ser Val Thr
            20                  25                  30

Val Met Gly Trp Tyr Arg Gln Ala Pro Gly Lys Gln Arg Glu Leu Val
        35                  40                  45

Ala Gly Phe Thr Asn Thr Arg Asn Thr Asn Tyr Val Asp Ser Val Lys
50                  55                  60

Gly Arg Phe Thr Ile Ser Lys Asp Ser Ala Lys Asn Thr Met Tyr Leu
65                  70                  75                  80

Gln Met Asn Ser Leu Lys Pro Glu Asp Thr Ala Val Tyr Tyr Cys Asn
                85                  90                  95

Val Arg Arg Trp Gly Gly Thr Asn Trp Asn Asp Tyr Trp Gly Gln Gly
                100                 105                 110

Thr Gln Val Thr Val Ser Ser His His His His His His Glu Pro Glu
            115                 120                 125

Ala

<210> SEQ ID NO 4
<211> LENGTH: 129
<212> TYPE: PRT
<213> ORGANISM: Lama glama

<400> SEQUENCE: 4

Gln Val Gln Leu Gln Glu Ser Gly Gly Gly Phe Val Gln Ala Gly Gly
1               5                   10                  15

Ser Leu Arg Leu Ser Cys Ala Ala Ser Gly Ser Ile Phe Ser Lys Asn
            20                  25                  30

Thr Met Ala Trp Phe Arg Gln Ala Pro Gly Lys Glu Arg Glu Leu Val
        35                  40                  45

Ala Ala Ser Pro Thr Gly Gly Ser Thr Ala Tyr Lys Asp Ser Val Lys
    50                  55                  60

Gly Arg Phe Thr Ile Ser Arg Asp Ser Ala Lys Asn Thr Val Leu Leu
65                  70                  75                  80

Gln Met Asn Val Leu Lys Pro Glu Asp Thr Ala Val Tyr Tyr Cys His
                85                  90                  95

Leu Arg Gln Asn Asn Arg Gly Ser Trp Phe His Tyr Trp Gly Gln Gly
            100                 105                 110

Thr Gln Val Thr Val Ser Ser His His His His His Glu Pro Glu
        115                 120                 125

Ala

<210> SEQ ID NO 5
<211> LENGTH: 129
<212> TYPE: PRT
<213> ORGANISM: Lama glama

<400> SEQUENCE: 5

Gln Val Gln Leu Gln Glu Ser Gly Gly Gly Leu Val Gln Ala Gly Gly
1               5                   10                  15

Ser Leu Arg Leu Ser Cys Ala Val Ser Gly Thr Ile Phe Asp Ile Thr
            20                  25                  30

Pro Met Gly Trp Tyr Arg Gln Thr Pro Gly Lys Gln Arg Glu Val Val
        35                  40                  45

Ala Asp Leu Thr Ser Arg Gly Thr Thr Asn Tyr Ala Asp Ser Val Lys
    50                  55                  60

Gly Arg Phe Thr Ile Ser Arg Asp Asn Ala Lys Lys Met Leu Tyr Leu
65                  70                  75                  80

Gln Met Asn Ser Leu Lys Ser Asp Thr Gly Val Tyr Tyr Cys Asn
                85                  90                  95

Val Lys Arg Trp Gly Gly Ile Gly Trp Asn Asp Tyr Trp Gly Gln Gly
            100                 105                 110

Thr Gln Val Thr Val Ser Ser His His His His His Glu Pro Glu
        115                 120                 125

Ala

<210> SEQ ID NO 6
<211> LENGTH: 129
<212> TYPE: PRT
<213> ORGANISM: Lama glama

<400> SEQUENCE: 6

Gln Val Gln Leu Gln Glu Ser Gly Gly Gly Leu Val Gln Ser Gly Gly
1               5                   10                  15

```
Ser Leu Arg Leu Ser Cys Val Ala Ser Gly Phe Arg Phe Ser Asn Phe
            20                  25                  30

Pro Met Met Trp Val Arg Gln Ala Pro Gly Lys Gly Leu Glu Trp Val
        35                  40                  45

Ser Leu Ile Ser Ile Gly Gly Ser Thr Thr Asn Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Asn Ser Leu Lys Pro Glu Asp Thr Ala Val Tyr Tyr Cys
                85                  90                  95

Ala Lys Tyr Leu Gly Arg Leu Val Pro Pro Thr Thr Glu Gly Gln Gly
            100                 105                 110

Thr Gln Val Thr Val Ser Ser His His His His His His Glu Pro Glu
            115                 120                 125

Ala
```

<210> SEQ ID NO 7
<211> LENGTH: 25
<212> TYPE: PRT
<213> ORGANISM: Lama glama

<400> SEQUENCE: 7

```
Gln Val Gln Leu Gln Glu Ser Gly Gly Gly Leu Val Gln Pro Gly Gly
1               5                   10                  15

Ser Leu Arg Leu Ser Cys Ala Ala Ser
            20                  25
```

<210> SEQ ID NO 8
<211> LENGTH: 25
<212> TYPE: PRT
<213> ORGANISM: Lama glama

<400> SEQUENCE: 8

```
Gln Val Gln Leu Gln Glu Ser Gly Gly Gly Leu Val Gln Pro Gly Gly
1               5                   10                  15

Ser Leu Arg Leu Ser Cys Ala Ala Ser
            20                  25
```

<210> SEQ ID NO 9
<211> LENGTH: 25
<212> TYPE: PRT
<213> ORGANISM: Lama glama

<400> SEQUENCE: 9

```
Gln Val Gln Leu Gln Glu Ser Gly Gly Gly Ser Val Gln Ala Gly Gly
1               5                   10                  15

Ser Leu Arg Leu Ser Cys Thr Val Ser
            20                  25
```

<210> SEQ ID NO 10
<211> LENGTH: 25
<212> TYPE: PRT
<213> ORGANISM: Lama glama

<400> SEQUENCE: 10

```
Gln Val Gln Leu Gln Glu Ser Gly Gly Gly Phe Val Gln Ala Gly Gly
1               5                   10                  15

Ser Leu Arg Leu Ser Cys Ala Ala Ser
            20                  25
```

<210> SEQ ID NO 11
<211> LENGTH: 25
<212> TYPE: PRT
<213> ORGANISM: Lama glama

<400> SEQUENCE: 11

Gln Val Gln Leu Gln Glu Ser Gly Gly Gly Leu Val Gln Ala Gly Gly
1               5                   10                  15

Ser Leu Arg Leu Ser Cys Ala Val Ser
            20                  25

<210> SEQ ID NO 12
<211> LENGTH: 25
<212> TYPE: PRT
<213> ORGANISM: Lama glama

<400> SEQUENCE: 12

Gln Val Gln Leu Gln Glu Ser Gly Gly Gly Leu Val Gln Ser Gly Gly
1               5                   10                  15

Ser Leu Arg Leu Ser Cys Val Ala Ser
            20                  25

<210> SEQ ID NO 13
<211> LENGTH: 8
<212> TYPE: PRT
<213> ORGANISM: Lama glama

<400> SEQUENCE: 13

Gly Phe Thr Phe Ser Asn Tyr Lys
1               5

<210> SEQ ID NO 14
<211> LENGTH: 8
<212> TYPE: PRT
<213> ORGANISM: Lama glama

<400> SEQUENCE: 14

Gly Phe Thr Phe Ser Asn Tyr Val
1               5

<210> SEQ ID NO 15
<211> LENGTH: 8
<212> TYPE: PRT
<213> ORGANISM: Lama glama

<400> SEQUENCE: 15

Gly Thr Ile Phe Ser Val Thr Val
1               5

<210> SEQ ID NO 16
<211> LENGTH: 8
<212> TYPE: PRT
<213> ORGANISM: Lama glama

<400> SEQUENCE: 16

Gly Ser Ile Phe Ser Lys Asn Thr
1               5

<210> SEQ ID NO 17
<211> LENGTH: 8
<212> TYPE: PRT
<213> ORGANISM: Lama glama

<400> SEQUENCE: 17

```
Gly Thr Ile Phe Asp Ile Thr Pro
1               5
```

<210> SEQ ID NO 18
<211> LENGTH: 8
<212> TYPE: PRT
<213> ORGANISM: Lama glama

<400> SEQUENCE: 18

```
Gly Phe Arg Phe Ser Asn Phe Pro
1               5
```

<210> SEQ ID NO 19
<211> LENGTH: 17
<212> TYPE: PRT
<213> ORGANISM: Lama glama

<400> SEQUENCE: 19

```
Met Asn Trp Val Arg Gln Ala Pro Gly Lys Gly Leu Glu Trp Val Ser
1               5                   10                  15

Asp
```

<210> SEQ ID NO 20
<211> LENGTH: 17
<212> TYPE: PRT
<213> ORGANISM: Lama glama

<400> SEQUENCE: 20

```
Met Asn Trp Val Arg Gln Ala Pro Gly Lys Gly Leu Glu Trp Val Ser
1               5                   10                  15

Asp
```

<210> SEQ ID NO 21
<211> LENGTH: 17
<212> TYPE: PRT
<213> ORGANISM: Lama glama

<400> SEQUENCE: 21

```
Met Gly Trp Tyr Arg Gln Ala Pro Gly Lys Gln Arg Glu Leu Val Ala
1               5                   10                  15

Gly
```

<210> SEQ ID NO 22
<211> LENGTH: 17
<212> TYPE: PRT
<213> ORGANISM: Lama glama

<400> SEQUENCE: 22

```
Met Ala Trp Phe Arg Gln Ala Pro Gly Lys Glu Arg Glu Leu Val Ala
1               5                   10                  15

Ala
```

<210> SEQ ID NO 23
<211> LENGTH: 17
<212> TYPE: PRT
<213> ORGANISM: Lama glama

<400> SEQUENCE: 23

```
Met Gly Trp Tyr Arg Gln Thr Pro Gly Lys Gln Arg Glu Val Val Ala
1               5                   10                  15

Asp
```

<210> SEQ ID NO 24
<211> LENGTH: 17
<212> TYPE: PRT
<213> ORGANISM: Lama glama

<400> SEQUENCE: 24

Met Met Trp Val Arg Gln Ala Pro Gly Lys Gly Leu Glu Trp Val Ser
1               5                   10                  15

Leu

<210> SEQ ID NO 25
<211> LENGTH: 8
<212> TYPE: PRT
<213> ORGANISM: Lama glama

<400> SEQUENCE: 25

Ile Ser Gln Ser Gly Ala Ser Ile
1               5

<210> SEQ ID NO 26
<211> LENGTH: 8
<212> TYPE: PRT
<213> ORGANISM: Lama glama

<400> SEQUENCE: 26

Ile Ser Asn Gly Gly Gly Thr Thr
1               5

<210> SEQ ID NO 27
<211> LENGTH: 7
<212> TYPE: PRT
<213> ORGANISM: Lama glama

<400> SEQUENCE: 27

Phe Thr Asn Thr Arg Asn Thr
1               5

<210> SEQ ID NO 28
<211> LENGTH: 7
<212> TYPE: PRT
<213> ORGANISM: Lama glama

<400> SEQUENCE: 28

Ser Pro Thr Gly Gly Ser Thr
1               5

<210> SEQ ID NO 29
<211> LENGTH: 7
<212> TYPE: PRT
<213> ORGANISM: Lama glama

<400> SEQUENCE: 29

Leu Thr Ser Arg Gly Thr Thr
1               5

<210> SEQ ID NO 30
<211> LENGTH: 8
<212> TYPE: PRT
<213> ORGANISM: Lama glama

<400> SEQUENCE: 30

Ile Ser Ile Gly Gly Ser Thr Thr
1               5

```
<210> SEQ ID NO 31
<211> LENGTH: 38
<212> TYPE: PRT
<213> ORGANISM: Lama glama

<400> SEQUENCE: 31

Ser Tyr Thr Gly Ser Val Lys Gly Arg Phe Thr Ile Ser Arg Asp Asn
1               5                   10                  15

Ala Lys Asn Thr Leu Tyr Leu Gln Met Asn Ser Leu Lys Pro Glu Asp
            20                  25                  30

Thr Ala Val Tyr Tyr Cys
        35

<210> SEQ ID NO 32
<211> LENGTH: 38
<212> TYPE: PRT
<213> ORGANISM: Lama glama

<400> SEQUENCE: 32

Ser Tyr Ala Ser Ser Val Lys Gly Arg Phe Thr Ile Ser Arg Asp Asn
1               5                   10                  15

Ala Lys Asn Thr Leu Tyr Leu Gln Met Asn Gly Leu Lys Pro Ala Asp
            20                  25                  30

Thr Ala Val Tyr Tyr Cys
        35

<210> SEQ ID NO 33
<211> LENGTH: 38
<212> TYPE: PRT
<213> ORGANISM: Lama glama

<400> SEQUENCE: 33

Asn Tyr Val Asp Ser Val Lys Gly Arg Phe Thr Ile Ser Lys Asp Ser
1               5                   10                  15

Ala Lys Asn Thr Met Tyr Leu Gln Met Asn Ser Leu Lys Pro Glu Asp
            20                  25                  30

Thr Ala Val Tyr Tyr Cys
        35

<210> SEQ ID NO 34
<211> LENGTH: 38
<212> TYPE: PRT
<213> ORGANISM: Lama glama

<400> SEQUENCE: 34

Ala Tyr Lys Asp Ser Val Lys Gly Arg Phe Thr Ile Ser Arg Asp Ser
1               5                   10                  15

Ala Lys Asn Thr Val Leu Leu Gln Met Asn Val Leu Lys Pro Glu Asp
            20                  25                  30

Thr Ala Val Tyr Tyr Cys
        35

<210> SEQ ID NO 35
<211> LENGTH: 38
<212> TYPE: PRT
<213> ORGANISM: Lama glama

<400> SEQUENCE: 35

Asn Tyr Ala Asp Ser Val Lys Gly Arg Phe Thr Ile Ser Arg Asp Asn
1               5                   10                  15
```

```
Ala Lys Lys Met Leu Tyr Leu Gln Met Asn Ser Leu Lys Ser Asp Asp
            20                  25                  30

Thr Gly Val Tyr Tyr Cys
            35

<210> SEQ ID NO 36
<211> LENGTH: 38
<212> TYPE: PRT
<213> ORGANISM: Lama glama

<400> SEQUENCE: 36

Asn Tyr Ala Asp Ser Val Lys Gly Arg Phe Thr Ile Ser Arg Asp Asn
1               5                   10                  15

Ala Lys Asn Thr Leu Phe Leu Gln Met Asn Ser Leu Lys Pro Glu Asp
            20                  25                  30

Thr Ala Val Tyr Tyr Cys
            35

<210> SEQ ID NO 37
<211> LENGTH: 21
<212> TYPE: PRT
<213> ORGANISM: Lama glama

<400> SEQUENCE: 37

Ala Arg Cys Pro Ala Pro Phe Thr Arg Asp Cys Phe Asp Val Thr Ser
1               5                   10                  15

Thr Thr Tyr Ala Tyr
            20

<210> SEQ ID NO 38
<211> LENGTH: 21
<212> TYPE: PRT
<213> ORGANISM: Lama glama

<400> SEQUENCE: 38

Ala Arg Cys Pro Ala Pro Phe Thr Asn Asp Cys Met Asp Ile Thr Ser
1               5                   10                  15

Thr Thr Tyr Ala Tyr
            20

<210> SEQ ID NO 39
<211> LENGTH: 13
<212> TYPE: PRT
<213> ORGANISM: Lama glama

<400> SEQUENCE: 39

Asn Val Arg Arg Trp Gly Gly Thr Asn Trp Asn Asp Tyr
1               5                   10

<210> SEQ ID NO 40
<211> LENGTH: 13
<212> TYPE: PRT
<213> ORGANISM: Lama glama

<400> SEQUENCE: 40

His Leu Arg Gln Asn Asn Arg Gly Ser Trp Phe His Tyr
1               5                   10

<210> SEQ ID NO 41
<211> LENGTH: 13
<212> TYPE: PRT
<213> ORGANISM: Lama glama
```

<400> SEQUENCE: 41

Asn Val Lys Arg Trp Gly Gly Ile Gly Trp Asn Asp Tyr
1               5                   10

<210> SEQ ID NO 42
<211> LENGTH: 12
<212> TYPE: PRT
<213> ORGANISM: Lama glama

<400> SEQUENCE: 42

Ala Lys Tyr Leu Gly Arg Leu Val Pro Pro Thr Thr
1               5                   10

<210> SEQ ID NO 43
<211> LENGTH: 11
<212> TYPE: PRT
<213> ORGANISM: Lama glama

<400> SEQUENCE: 43

Arg Gly Gln Gly Thr Gln Val Thr Val Ser Ser
1               5                   10

<210> SEQ ID NO 44
<211> LENGTH: 11
<212> TYPE: PRT
<213> ORGANISM: Lama glama

<400> SEQUENCE: 44

Arg Gly Gln Gly Thr Gln Val Thr Val Ser Ser
1               5                   10

<210> SEQ ID NO 45
<211> LENGTH: 11
<212> TYPE: PRT
<213> ORGANISM: Lama glama

<400> SEQUENCE: 45

Trp Gly Gln Gly Thr Gln Val Thr Val Ser Ser
1               5                   10

<210> SEQ ID NO 46
<211> LENGTH: 11
<212> TYPE: PRT
<213> ORGANISM: Lama glama

<400> SEQUENCE: 46

Trp Gly Gln Gly Thr Gln Val Thr Val Ser Ser
1               5                   10

<210> SEQ ID NO 47
<211> LENGTH: 11
<212> TYPE: PRT
<213> ORGANISM: Lama glama

<400> SEQUENCE: 47

Trp Gly Gln Gly Thr Gln Val Thr Val Ser Ser
1               5                   10

<210> SEQ ID NO 48
<211> LENGTH: 11
<212> TYPE: PRT
<213> ORGANISM: Lama glama

<400> SEQUENCE: 48

```
Glu Gly Gln Gly Thr Gln Val Thr Val Ser Ser
1               5                   10
```

<210> SEQ ID NO 49
<211> LENGTH: 417
<212> TYPE: PRT
<213> ORGANISM: Lama glama

<400> SEQUENCE: 49

```
Cys Ala Gly Gly Thr Gly Cys Ala Gly Cys Thr Gly Cys Ala Gly Gly
1               5                   10                  15

Ala Gly Thr Cys Thr Gly Gly Ala Gly Gly Ala Gly Gly Cys Thr Thr
                20                  25                  30

Gly Gly Thr Gly Cys Ala Gly Cys Cys Thr Gly Gly Gly Gly Gly Gly
                35                  40                  45

Thr Cys Thr Cys Thr Gly Ala Gly Ala Cys Thr Cys Thr Cys Cys Thr
            50                  55                  60

Gly Thr Gly Cys Gly Gly Cys Cys Thr Cys Thr Gly Gly Ala Thr Thr
65                  70                  75                  80

Cys Ala Cys Cys Thr Thr Cys Ala Gly Cys Ala Ala Thr Thr Ala Thr
                85                  90                  95

Ala Ala Ala Ala Thr Gly Ala Ala Cys Thr Gly Gly Thr Cys Cys
                100                 105                 110

Gly Cys Cys Ala Gly Gly Cys Thr Cys Cys Ala Gly Gly Ala Ala Ala
            115                 120                 125

Gly Gly Gly Gly Cys Thr Cys Gly Ala Gly Thr Gly Gly Gly Thr Cys
            130                 135                 140

Thr Cys Ala Gly Ala Thr Ala Thr Thr Cys Thr Cys Ala Gly Ala
145                 150                 155                 160

Gly Thr Gly Gly Thr Gly Cys Thr Ala Gly Cys Ala Thr Ala Ala Gly
                165                 170                 175

Thr Thr Ala Cys Ala Cys Ala Gly Cys Thr Cys Cys Gly Thr Gly
                180                 185                 190

Ala Ala Gly Gly Gly Cys Cys Gly Ala Thr Thr Cys Ala Cys Cys Ala
            195                 200                 205

Thr Cys Thr Cys Cys Ala Gly Ala Gly Ala Cys Ala Ala Cys Gly Cys
210                 215                 220

Cys Ala Ala Gly Ala Ala Cys Ala Cys Gly Cys Thr Gly Thr Ala Thr
225                 230                 235                 240

Cys Thr Ala Cys Ala Ala Ala Thr Gly Ala Ala Cys Ala Gly Cys Cys
                245                 250                 255

Thr Gly Ala Ala Gly Cys Cys Thr Gly Ala Gly Gly Ala Cys Ala Cys
                260                 265                 270

Gly Gly Cys Cys Gly Thr Cys Thr Ala Thr Thr Ala Cys Thr Gly Thr
            275                 280                 285

Gly Cys Cys Ala Gly Ala Thr Gly Thr Cys Gly Gly Cys Cys Cys
            290                 295                 300

Cys Ala Thr Thr Cys Ala Cys Gly Ala Gly Ala Thr Ala Thr Gly
305                 310                 315                 320

Thr Thr Thr Thr Gly Ala Cys Gly Thr Gly Ala Cys Thr Gly Thr
                325                 330                 335

Ala Cys Cys Ala Cys Gly Thr Ala Thr Gly Cys Thr Ala Cys Ala
                340                 345                 350

Gly Gly Gly Gly Cys Cys Ala Gly Gly Gly Ala Cys Cys Cys Ala
```

```
                355                 360                 365
Gly Gly Thr Cys Ala Cys Cys Gly Thr Cys Thr Cys Cys Thr Cys Ala
            370                 375                 380
Cys Ala Cys Cys Ala Cys Cys Ala Thr Cys Ala Cys Cys Ala Thr Cys
385                 390                 395                 400
Ala Cys Gly Ala Ala Cys Cys Thr Gly Ala Gly Cys Cys Thr Ala
                405                 410                 415
Gly

<210> SEQ ID NO 50
<211> LENGTH: 417
<212> TYPE: PRT
<213> ORGANISM: Lama glama

<400> SEQUENCE: 50

Cys Ala Gly Gly Thr Gly Cys Ala Gly Cys Thr Gly Cys Ala Gly Gly
1               5                   10                  15
Ala Gly Thr Cys Thr Gly Gly Ala Gly Gly Gly Gly Cys Thr Thr
            20                  25                  30
Gly Gly Thr Gly Cys Ala Gly Cys Cys Thr Gly Gly Gly Gly Gly
        35                  40                  45
Thr Cys Thr Cys Thr Gly Ala Gly Ala Cys Thr Cys Thr Cys Cys Thr
50                  55                  60
Gly Thr Gly Cys Ala Gly Cys Cys Thr Cys Thr Gly Gly Ala Thr Thr
65                  70                  75                  80
Cys Ala Cys Thr Thr Thr Cys Ala Gly Thr Ala Ala Cys Thr Ala Thr
            85                  90                  95
Gly Thr Cys Ala Thr Gly Ala Ala Cys Thr Gly Gly Gly Thr Cys Cys
            100                 105                 110
Gly Cys Cys Ala Gly Gly Cys Thr Cys Cys Ala Gly Gly Ala Ala Ala
        115                 120                 125
Gly Gly Gly Gly Cys Thr Cys Gly Ala Gly Thr Gly Gly Thr Cys
    130                 135                 140
Thr Cys Ala Gly Ala Thr Ala Thr Thr Thr Cys Thr Ala Ala Thr Gly
145                 150                 155                 160
Gly Cys Gly Gly Thr Gly Gly Thr Ala Cys Cys Ala Cys Ala Ala Gly
            165                 170                 175
Thr Thr Ala Thr Gly Cys Ala Ala Gly Cys Thr Cys Cys Gly Thr Gly
            180                 185                 190
Ala Ala Gly Gly Gly Cys Cys Gly Ala Thr Thr Cys Ala Cys Cys Ala
        195                 200                 205
Thr Cys Thr Cys Ala Gly Ala Gly Ala Cys Ala Ala Cys Gly Cys
    210                 215                 220
Cys Ala Ala Gly Ala Ala Cys Ala Cys Gly Cys Thr Gly Thr Ala Thr
225                 230                 235                 240
Cys Thr Gly Cys Ala Ala Ala Thr Gly Ala Ala Cys Gly Gly Cys Cys
            245                 250                 255
Thr Gly Ala Ala Gly Cys Cys Thr Gly Cys Gly Gly Ala Cys Ala Cys
            260                 265                 270
Gly Gly Cys Cys Gly Thr Cys Thr Ala Thr Ala Cys Thr Gly Thr
        275                 280                 285
Gly Cys Ala Ala Gly Ala Thr Gly Thr Cys Gly Gly Cys Cys
    290                 295                 300
Cys Ala Thr Thr Cys Ala Cys Gly Ala Ala Cys Gly Ala Thr Thr Gly
```

```
                305                 310                 315                 320
Thr Ala Thr Gly Gly Ala Cys Ala Thr Ala Ala Cys Thr Ala Gly Thr
                325                 330                 335

Ala Cys Cys Ala Cys Gly Thr Ala Thr Gly Cys Cys Thr Ala Cys Ala
                340                 345                 350

Gly Gly Gly Gly Cys Cys Ala Gly Gly Ala Cys Cys Cys Ala
                355                 360                 365

Gly Gly Thr Cys Ala Cys Cys Gly Thr Thr Cys Cys Thr Cys Ala
                370                 375                 380

Cys Ala Cys Cys Ala Cys Cys Ala Thr Cys Ala Cys Ala Thr Cys
385                 390                 395                 400

Ala Cys Gly Ala Ala Cys Cys Thr Gly Ala Ala Gly Cys Cys Thr Ala
                405                 410                 415

Gly

<210> SEQ ID NO 51
<211> LENGTH: 390
<212> TYPE: PRT
<213> ORGANISM: Lama glama

<400> SEQUENCE: 51

Cys Ala Gly Gly Thr Gly Cys Ala Gly Cys Thr Gly Cys Ala Gly Gly
1               5                   10                  15

Ala Gly Thr Cys Thr Gly Gly Ala Gly Gly Ala Gly Gly Cys Thr Cys
                20                  25                  30

Gly Gly Thr Gly Cys Ala Gly Gly Cys Thr Gly Gly Gly Gly Gly
            35                  40                  45

Thr Cys Thr Cys Thr Gly Ala Gly Ala Cys Thr Cys Thr Cys Cys Thr
        50                  55                  60

Gly Thr Ala Cys Ala Gly Thr Cys Thr Cys Thr Gly Gly Ala Ala Cys
65                  70                  75                  80

Cys Ala Thr Cys Thr Thr Cys Ala Gly Thr Gly Thr Cys Ala Cys Thr
                85                  90                  95

Gly Thr Cys Ala Thr Gly Gly Gly Cys Thr Gly Gly Thr Ala Cys Cys
                100                 105                 110

Gly Cys Cys Ala Gly Gly Cys Thr Cys Cys Ala Gly Gly Gly Ala Ala
            115                 120                 125

Gly Cys Ala Gly Cys Gly Gly Ala Gly Thr Thr Gly Gly Thr Cys
            130                 135                 140

Gly Cys Ala Gly Gly Thr Thr Thr Thr Ala Cys Thr Ala Ala Thr Ala
145                 150                 155                 160

Cys Thr Ala Gly Ala Ala Ala Cys Ala Cys Ala Ala Ala Cys Thr Ala
                165                 170                 175

Thr Gly Thr Ala Gly Ala Cys Thr Cys Cys Gly Thr Gly Ala Ala Gly
                180                 185                 190

Gly Gly Cys Cys Gly Cys Thr Thr Cys Ala Cys Cys Ala Thr Cys Thr
            195                 200                 205

Cys Cys Ala Ala Ala Gly Ala Cys Ala Gly Cys Gly Cys Ala Ala
            210                 215                 220

Gly Ala Ala Cys Ala Cys Gly Ala Thr Gly Thr Ala Thr Cys Thr Ala
225                 230                 235                 240

Cys Ala Ala Ala Thr Gly Ala Ala Cys Ala Gly Cys Cys Thr Gly Ala
                245                 250                 255

Ala Ala Cys Cys Thr Gly Ala Gly Gly Ala Cys Ala Cys Ala Gly Cys
```

```
                   260                 265                 270
Cys Gly Thr Cys Thr Ala Thr Thr Ala Cys Thr Gly Thr Ala Ala Thr
                   275                 280                 285
Gly Thr Ala Cys Gly Thr Cys Gly Gly Thr Gly Gly Gly Cys Gly
                   290                 295                 300
Gly Thr Ala Cys Gly Ala Ala Thr Thr Gly Gly Ala Ala Thr Gly Ala
305                                310                 315                 320
Cys Thr Ala Cys Thr Gly Gly Gly Cys Ala Gly Gly Gly
                   325                 330                 335
Ala Cys Cys Cys Ala Gly Gly Thr Cys Ala Cys Gly Thr Cys Thr
                   340                 345                 350
Cys Cys Thr Cys Ala Cys Ala Cys Cys Ala Cys Ala Thr Cys Ala
                   355                 360                 365
Cys Cys Ala Thr Cys Ala Cys Gly Ala Ala Cys Cys Thr Gly Ala Ala
                   370                 375                 380
Gly Cys Cys Thr Ala Gly
385                 390

<210> SEQ ID NO 52
<211> LENGTH: 390
<212> TYPE: PRT
<213> ORGANISM: Lama glama

<400> SEQUENCE: 52

Cys Ala Gly Gly Thr Gly Cys Ala Gly Cys Thr Gly Cys Ala Gly Gly
1                   5                   10                  15
Ala Gly Thr Cys Thr Gly Gly Ala Gly Gly Gly Gly Cys Thr Thr
                    20                  25                  30
Cys Gly Thr Gly Cys Ala Gly Gly Cys Thr Gly Gly Gly Gly Gly
                    35                  40                  45
Thr Cys Thr Cys Thr Gly Ala Gly Ala Cys Thr Cys Thr Cys Cys Thr
50                                  55                  60
Gly Thr Gly Cys Ala Gly Cys Cys Thr Cys Thr Gly Gly Ala Ala Gly
65                  70                  75                  80
Cys Ala Thr Cys Thr Thr Cys Ala Gly Thr Ala Ala Gly Ala Ala Thr
                    85                  90                  95
Ala Cys Cys Ala Thr Gly Gly Cys Cys Thr Gly Gly Thr Thr Cys Cys
                    100                 105                 110
Gly Cys Cys Ala Gly Gly Cys Thr Cys Cys Ala Gly Gly Gly Ala Ala
                    115                 120                 125
Gly Gly Ala Gly Cys Gly Ala Gly Ala Gly Thr Thr Gly Gly Thr Cys
                    130                 135                 140
Gly Cys Ala Gly Cys Thr Ala Gly Thr Cys Thr Ala Cys Gly Gly
145                                 150                 155                 160
Gly Thr Gly Gly Thr Ala Gly Cys Ala Cys Ala Gly Cys Gly Thr Ala
                    165                 170                 175
Thr Ala Ala Ala Gly Ala Cys Thr Cys Cys Gly Thr Gly Ala Ala Gly
                    180                 185                 190
Gly Gly Cys Cys Gly Ala Thr Thr Cys Ala Cys Cys Ala Thr Cys Thr
                    195                 200                 205
Cys Cys Ala Gly Ala Gly Ala Cys Ala Gly Cys Gly Cys Cys Ala Ala
                    210                 215                 220
Gly Ala Ala Cys Ala Cys Gly Gly Thr Gly Thr Thr Gly Cys Thr Gly
225                                 230                 235                 240
```

```
Cys Ala Ala Ala Thr Gly Ala Ala Cys Gly Thr Cys Thr Gly Ala
                245                 250                 255

Ala Ala Cys Cys Thr Gly Ala Gly Gly Ala Thr Ala Cys Thr Gly Cys
            260                 265                 270

Cys Gly Thr Cys Thr Ala Thr Thr Ala Cys Thr Gly Thr Cys Ala Thr
        275                 280                 285

Cys Thr Ala Cys Gly Thr Cys Ala Ala Ala Thr Ala Ala Cys Cys
290                 295                 300

Gly Thr Gly Gly Thr Thr Cys Thr Thr Gly Thr Thr Cys Cys Ala
305                 310                 315                 320

Cys Thr Ala Cys Thr Gly Gly Gly Cys Cys Ala Gly Gly Gly Gly
            325                 330                 335

Ala Cys Cys Cys Ala Gly Gly Thr Cys Ala Cys Cys Gly Thr Cys Thr
            340                 345                 350

Cys Cys Thr Cys Ala Cys Ala Cys Cys Ala Cys Cys Ala Thr Cys Ala
        355                 360                 365

Cys Cys Ala Thr Cys Ala Cys Gly Ala Ala Cys Cys Thr Gly Ala Ala
        370                 375                 380

Gly Cys Cys Thr Ala Gly
385                 390

<210> SEQ ID NO 53
<211> LENGTH: 390
<212> TYPE: PRT
<213> ORGANISM: Lama glama

<400> SEQUENCE: 53

Cys Ala Gly Gly Thr Gly Cys Ala Gly Cys Thr Gly Cys Ala Gly Gly
1               5                   10                  15

Ala Gly Thr Cys Thr Gly Gly Gly Gly Gly Ala Gly Gly Cys Thr Thr
            20                  25                  30

Gly Gly Thr Gly Cys Ala Gly Gly Cys Thr Gly Gly Gly Gly Gly
        35                  40                  45

Thr Cys Gly Cys Thr Gly Ala Gly Ala Cys Thr Cys Thr Cys Thr Thr
50                  55                  60

Gly Thr Gly Cys Ala Gly Cys Cys Thr Cys Thr Gly Gly Thr Ala Cys
65                  70                  75                  80

Gly Ala Thr Cys Thr Thr Cys Gly Ala Thr Ala Thr Cys Ala Cys Thr
                85                  90                  95

Cys Cys Cys Ala Thr Gly Gly Cys Thr Gly Gly Thr Ala Cys Cys
            100                 105                 110

Gly Cys Cys Ala Gly Ala Cys Thr Cys Cys Ala Gly Gly Gly Ala Ala
        115                 120                 125

Gly Cys Ala Gly Cys Gly Cys Gly Ala Ala Gly Gly Gly Thr Cys
        130                 135                 140

Gly Cys Ala Gly Ala Thr Cys Thr Thr Ala Cys Thr Ala Gly Thr Cys
145                 150                 155                 160

Gly Cys Gly Gly Thr Ala Cys Ala Cys Ala Ala Ala Thr Thr Ala
            165                 170                 175

Cys Gly Cys Ala Gly Ala Cys Thr Cys Cys Gly Thr Gly Ala Ala Gly
        180                 185                 190

Gly Gly Cys Cys Gly Gly Thr Thr Cys Ala Cys Cys Ala Thr Cys Thr
        195                 200                 205

Cys Cys Ala Gly Ala Gly Ala Cys Ala Ala Cys Gly Cys Cys Ala Ala
210                 215                 220
```

```
Gly Ala Ala Ala Thr Gly Thr Thr Gly Thr Ala Thr Cys Thr Gly
225                 230                 235                 240

Cys Ala Ala Ala Thr Gly Ala Ala Cys Ala Gly Cys Cys Thr Gly Ala
                245                 250                 255

Ala Ala Thr Cys Thr Gly Ala Cys Gly Ala Cys Ala Cys Ala Gly Gly
                260                 265                 270

Cys Gly Thr Gly Thr Ala Thr Thr Ala Cys Thr Gly Thr Ala Ala Cys
                275                 280                 285

Gly Thr Gly Ala Ala Ala Cys Gly Gly Thr Gly Gly Gly Ala Gly
            290                 295                 300

Gly Thr Ala Thr Thr Gly Gly Cys Thr Gly Gly Ala Ala Cys Gly Ala
305                 310                 315                 320

Cys Thr Ala Cys Thr Gly Gly Gly Cys Cys Ala Gly Gly Gly
                325                 330                 335

Ala Cys Cys Cys Ala Gly Gly Thr Cys Ala Cys Cys Gly Thr Cys Thr
                340                 345                 350

Cys Cys Thr Cys Ala Cys Ala Cys Cys Ala Cys Cys Ala Thr Cys Ala
                355                 360                 365

Cys Cys Ala Thr Cys Ala Cys Gly Ala Ala Cys Cys Thr Gly Ala Ala
                370                 375                 380

Gly Cys Cys Thr Ala Gly
385                 390

<210> SEQ ID NO 54
<211> LENGTH: 390
<212> TYPE: PRT
<213> ORGANISM: Lama glama

<400> SEQUENCE: 54

Cys Ala Gly Gly Thr Gly Cys Ala Gly Cys Thr Gly Cys Ala Gly Gly
1               5                   10                  15

Ala Gly Thr Cys Thr Gly Gly Ala Gly Gly Ala Gly Gly Cys Thr Thr
                20                  25                  30

Gly Gly Thr Gly Cys Ala Gly Thr Cys Thr Gly Gly Gly Gly Gly
            35                  40                  45

Thr Cys Thr Cys Thr Gly Ala Gly Ala Cys Thr Cys Thr Cys Cys Thr
50                  55                  60

Gly Thr Gly Thr Ala Gly Cys Cys Thr Cys Thr Gly Gly Ala Thr Thr
65                  70                  75                  80

Cys Ala Gly Ala Thr Cys Ala Gly Thr Ala Ala Cys Thr Thr Thr
                85                  90                  95

Cys Cys Thr Ala Thr Gly Ala Thr Gly Gly Gly Thr Cys Cys
                100                 105                 110

Gly Cys Cys Ala Gly Gly Cys Cys Cys Ala Gly Gly Ala Ala Ala
            115                 120                 125

Gly Gly Gly Gly Cys Thr Cys Gly Ala Gly Thr Gly Gly Thr Cys
            130                 135                 140

Thr Cys Gly Cys Thr Gly Ala Thr Thr Ala Gly Cys Ala Thr Thr Gly
145                 150                 155                 160

Gly Thr Gly Gly Thr Ala Gly Thr Ala Cys Ala Cys Gly Ala Ala
                165                 170                 175

Thr Thr Ala Thr Gly Cys Gly Ala Cys Thr Cys Cys Gly Thr Gly
            180                 185                 190

Ala Ala Gly Gly Gly Cys Cys Gly Ala Thr Thr Cys Ala Cys Cys Ala
```

```
        195                 200                 205

Thr Cys Thr Cys Cys Ala Gly Ala Gly Ala Cys Ala Ala Cys Gly Cys
    210                 215                 220

Cys Ala Ala Gly Ala Ala Cys Ala Cys Gly Cys Thr Gly Thr Thr Thr
225                 230                 235                 240

Cys Thr Gly Cys Ala Ala Ala Thr Gly Ala Ala Cys Ala Gly Cys Cys
                245                 250                 255
Thr Gly Ala Ala Ala Cys Cys Thr Gly Ala Gly Gly Ala Cys Ala Cys
            260                 265                 270

Gly Gly Cys Cys Gly Thr Gly Thr Ala Thr Thr Ala Cys Thr Gly Thr
        275                 280                 285
Gly Cys Ala Ala Ala Ala Thr Ala Thr Cys Thr Thr Gly Gly Thr Cys
    290                 295                 300

Gly Gly Cys Thr Gly Gly Thr Cys Cys Cys Ala Cys Cys Gly Ala Cys
305                 310                 315                 320

Thr Ala Cys Thr Gly Ala Gly Gly Gly Cys Cys Ala Gly Gly Gly Gly
                325                 330                 335
Ala Cys Cys Cys Ala Gly Gly Thr Cys Ala Cys Cys Gly Thr Cys Thr
            340                 345                 350
Cys Cys Thr Cys Ala Cys Ala Cys Cys Ala Cys Cys Ala Thr Cys Ala
        355                 360                 365
Cys Cys Ala Thr Cys Ala Cys Gly Ala Ala Cys Cys Thr Gly Ala Ala
    370                 375                 380

Gly Cys Cys Thr Ala Gly
385                 390

<210> SEQ ID NO 55
<211> LENGTH: 1095
<212> TYPE: PRT
<213> ORGANISM: Artificial
<220> FEATURE:
<223> OTHER INFORMATION: Beta2AR construct

<400> SEQUENCE: 55

Gly Gly Gly Cys Ala Ala Cys Cys Cys Gly Gly Gly Ala Ala Cys Gly
1               5                   10                  15
Gly Cys Ala Gly Cys Gly Cys Cys Thr Thr Cys Thr Thr Gly Cys Thr
            20                  25                  30

Gly Gly Cys Ala Cys Cys Cys Ala Ala Thr Ala Gly Ala Ala Gly Cys
        35                  40                  45
Cys Ala Thr Gly Cys Gly Cys Cys Gly Gly Ala Cys Cys Ala Cys Gly
    50                  55                  60

Ala Cys Gly Thr Cys Ala Cys Gly Cys Ala Gly Cys Ala Ala Ala Gly
65                  70                  75                  80

Gly Gly Ala Cys Gly Ala Gly Gly Thr Gly Thr Gly Gly Gly Thr Gly
                85                  90                  95

Gly Thr Gly Gly Gly Cys Ala Thr Gly Gly Gly Cys Ala Thr Cys Gly
            100                 105                 110

Thr Cys Ala Thr Gly Thr Cys Thr Cys Thr Cys Ala Thr Cys Gly Thr
        115                 120                 125

Cys Cys Thr Gly Gly Cys Cys Ala Thr Cys Gly Thr Gly Thr Thr Thr
    130                 135                 140

Gly Gly Cys Ala Ala Thr Gly Thr Gly Cys Thr Gly Gly Thr Cys Ala
145                 150                 155                 160

Thr Cys Ala Cys Ala Gly Cys Cys Ala Thr Thr Gly Cys Cys Ala Ala
```

-continued

```
                165                 170                 175

Gly Thr Thr Cys Gly Ala Gly Cys Gly Thr Cys Thr Gly Cys Ala Gly
            180                 185                 190

Ala Cys Gly Gly Thr Cys Ala Cys Cys Ala Ala Cys Thr Ala Cys Thr
        195                 200                 205

Thr Cys Ala Thr Cys Ala Cys Thr Thr Cys Ala Cys Thr Gly Gly Cys
    210                 215                 220

Cys Thr Gly Thr Gly Cys Thr Gly Ala Thr Cys Thr Gly Gly Thr Cys
225                 230                 235                 240

Ala Thr Gly Gly Gly Cys Cys Thr Gly Gly Cys Ala Gly Thr Gly Gly
                245                 250                 255

Thr Gly Cys Cys Cys Thr Thr Thr Gly Gly Gly Gly Cys Cys Gly Cys
            260                 265                 270

Cys Cys Ala Thr Ala Thr Thr Cys Thr Thr Ala Thr Gly Ala Ala Ala
        275                 280                 285

Ala Thr Gly Thr Gly Gly Ala Cys Thr Thr Thr Thr Gly Gly Cys Ala
    290                 295                 300

Ala Cys Thr Thr Cys Thr Gly Gly Thr Gly Cys Gly Ala Gly Thr Thr
305                 310                 315                 320

Thr Thr Gly Gly Ala Cys Thr Thr Cys Cys Ala Thr Thr Gly Ala Thr
                325                 330                 335

Gly Thr Gly Cys Thr Gly Thr Gly Cys Gly Thr Cys Ala Cys Gly Gly
            340                 345                 350

Cys Cys Ala Gly Cys Ala Thr Thr Gly Ala Gly Ala Cys Cys Cys Thr
        355                 360                 365

Gly Thr Gly Cys Gly Thr Gly Ala Thr Cys Gly Cys Ala Gly Thr Gly
    370                 375                 380

Gly Ala Thr Cys Gly Cys Thr Ala Cys Thr Thr Thr Gly Cys Cys Ala
385                 390                 395                 400

Thr Thr Ala Cys Thr Thr Cys Ala Cys Cys Thr Thr Thr Cys Ala Ala
                405                 410                 415

Gly Thr Ala Cys Cys Ala Gly Ala Gly Cys Cys Thr Gly Cys Thr Gly
            420                 425                 430

Ala Cys Cys Ala Ala Gly Ala Ala Thr Ala Ala Gly Gly Cys Cys Cys
        435                 440                 445

Gly Gly Gly Thr Gly Ala Thr Cys Ala Thr Thr Cys Thr Gly Ala Thr
    450                 455                 460

Gly Gly Thr Gly Thr Gly Gly Ala Thr Thr Gly Thr Gly Thr Cys Ala
465                 470                 475                 480

Gly Gly Cys Cys Thr Thr Ala Cys Cys Thr Cys Cys Thr Thr Cys Thr
                485                 490                 495

Thr Gly Cys Cys Cys Ala Thr Thr Cys Ala Gly Ala Thr Gly Cys Ala
            500                 505                 510

Cys Thr Gly Gly Thr Ala Cys Cys Gly Gly Gly Cys Cys Ala Cys Cys
        515                 520                 525

Cys Ala Cys Cys Ala Gly Gly Ala Ala Gly Cys Cys Ala Thr Cys Ala
    530                 535                 540

Ala Cys Thr Gly Cys Thr Ala Thr Gly Cys Cys Gly Ala Gly Gly Ala
545                 550                 555                 560

Gly Ala Cys Cys Thr Gly Cys Thr Gly Thr Gly Ala Cys Thr Thr Cys
                565                 570                 575

Thr Thr Cys Ala Cys Gly Ala Ala Cys Cys Ala Ala Gly Cys Cys Thr
            580                 585                 590
```

-continued

```
Ala Thr Gly Cys Cys Ala Thr Thr Gly Cys Cys Thr Cys Thr Thr Cys
        595                 600                 605

Cys Ala Thr Cys Gly Thr Gly Thr Cys Cys Thr Thr Cys Thr Ala Cys
    610                 615                 620

Gly Thr Thr Cys Cys Cys Cys Thr Gly Gly Thr Gly Ala Thr Cys Ala
625                 630                 635                 640

Thr Gly Gly Thr Cys Thr Thr Cys Gly Thr Cys Thr Ala Cys Thr Cys
                645                 650                 655

Cys Ala Gly Gly Gly Thr Cys Thr Thr Thr Cys Ala Gly Gly Ala Gly
            660                 665                 670

Gly Cys Cys Ala Ala Ala Ala Gly Gly Cys Ala Gly Cys Thr Cys Cys
        675                 680                 685

Ala Gly Ala Ala Gly Ala Thr Thr Gly Ala Cys Ala Ala Ala Thr Cys
    690                 695                 700

Thr Gly Ala Gly Gly Gly Cys Cys Gly Cys Thr Thr Cys Cys Ala Thr
705                 710                 715                 720

Gly Thr Cys Cys Ala Gly Ala Ala Cys Cys Thr Thr Ala Gly Cys Cys
                725                 730                 735

Ala Gly Gly Thr Gly Gly Ala Gly Cys Ala Gly Gly Ala Thr Gly Gly
            740                 745                 750

Gly Cys Gly Gly Ala Cys Gly Gly Gly Gly Cys Ala Thr Gly Gly Ala
        755                 760                 765

Cys Thr Cys Cys Gly Cys Ala Gly Ala Thr Cys Thr Thr Cys Cys Ala
    770                 775                 780

Ala Gly Thr Thr Cys Thr Gly Cys Thr Thr Gly Ala Ala Gly Gly Ala
785                 790                 795                 800

Gly Cys Ala Cys Ala Ala Ala Gly Cys Cys Cys Thr Cys Ala Ala Gly
                805                 810                 815

Ala Cys Gly Thr Thr Ala Gly Gly Cys Ala Thr Cys Ala Thr Cys Ala
            820                 825                 830

Thr Gly Gly Gly Cys Ala Cys Thr Thr Thr Cys Ala Cys Cys Cys Thr
        835                 840                 845

Cys Thr Gly Cys Thr Gly Gly Cys Thr Gly Cys Cys Cys Thr Thr Cys
    850                 855                 860

Thr Thr Cys Ala Thr Cys Gly Thr Thr Ala Ala Cys Ala Thr Thr Gly
865                 870                 875                 880

Thr Gly Cys Ala Thr Gly Thr Gly Ala Thr Cys Cys Ala Gly Gly Ala
                885                 890                 895

Thr Ala Ala Cys Cys Thr Cys Ala Thr Cys Cys Gly Thr Ala Ala Gly
            900                 905                 910

Gly Ala Ala Gly Thr Thr Thr Ala Cys Ala Thr Cys Cys Thr Cys Cys
        915                 920                 925

Thr Ala Ala Ala Thr Thr Gly Gly Ala Thr Ala Gly Gly Cys Thr Ala
    930                 935                 940

Thr Gly Thr Cys Ala Ala Thr Thr Cys Thr Gly Gly Thr Thr Thr Cys
945                 950                 955                 960

Ala Ala Thr Cys Cys Cys Cys Thr Thr Ala Thr Cys Thr Ala Cys Thr
                965                 970                 975

Gly Cys Cys Gly Gly Ala Gly Cys Cys Cys Ala Gly Ala Thr Thr Thr
            980                 985                 990

Cys Ala Gly Gly Ala Thr Thr Gly  Cys Cys Thr Thr Cys  Cys Ala Gly
        995                 1000                 1005
```

```
Gly Ala Gly Cys Thr Thr Cys Thr Gly Thr Cys Cys Thr Gly
    1010            1015                1020

Cys Gly Cys Ala Gly Gly Thr Cys Thr Thr Cys Thr Thr Thr Gly
    1025            1030                1035

Ala Ala Gly Gly Cys Cys Thr Ala Thr Gly Gly Ala Ala Thr
    1040            1045                1050

Gly Gly Cys Thr Ala Cys Thr Cys Cys Ala Gly Cys Ala Ala Cys
    1055            1060                1065

Gly Gly Cys Ala Ala Cys Ala Cys Ala Gly Gly Gly Ala Gly
    1070            1075                1080

Cys Ala Gly Ala Gly Thr Gly Gly Ala Thr Ala Ala
    1085            1090                1095
```

<210> SEQ ID NO 56
<211> LENGTH: 380
<212> TYPE: PRT
<213> ORGANISM: Homo sapiens

<400> SEQUENCE: 56

```
Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
            20                  25                  30

Asp Lys Gln Val Tyr Arg Ala Thr His Arg Leu Leu Leu Leu Gly Ala
        35                  40                  45

Gly Glu Ser Gly Lys Ser Thr Ile Val Lys Gln Met Arg Ile Leu His
    50                  55                  60

Val Asn Gly Phe Asn Gly Asp Ser Glu Lys Ala Thr Lys Val Gln Asp
65                  70                  75                  80

Ile Lys Asn Asn Leu Lys Glu Ala Ile Glu Thr Ile Val Ala Ala Met
                85                  90                  95

Ser Asn Leu Val Pro Pro Val Glu Leu Ala Asn Pro Glu Asn Gln Phe
            100                 105                 110

Arg Val Asp Tyr Ile Leu Ser Val Met Asn Val Pro Asp Phe Asp Phe
        115                 120                 125

Pro Pro Glu Phe Tyr Glu His Ala Lys Ala Leu Trp Glu Asp Glu Gly
    130                 135                 140

Val Arg Ala Cys Tyr Glu Arg Ser Asn Glu Tyr Gln Leu Ile Asp Cys
145                 150                 155                 160

Ala Gln Tyr Phe Leu Asp Lys Ile Asp Val Ile Lys Gln Ala Asp Tyr
                165                 170                 175

Val Pro Ser Asp Gln Asp Leu Leu Arg Cys Arg Val Leu Thr Ser Gly
            180                 185                 190

Ile Phe Glu Thr Lys Phe Gln Val Asp Lys Val Asn Phe His Met Phe
        195                 200                 205

Asp Val Gly Gly Gln Arg Asp Glu Arg Arg Lys Trp Ile Gln Cys Phe
    210                 215                 220

Asn Asp Val Thr Ala Ile Ile Phe Val Val Ala Ser Ser Ser Tyr Asn
225                 230                 235                 240

Met Val Ile Arg Glu Asp Asn Gln Thr Asn Arg Leu Gln Glu Ala Leu
                245                 250                 255

Asn Leu Phe Lys Ser Ile Trp Asn Asn Arg Trp Leu Arg Thr Ile Ser
            260                 265                 270

Val Ile Leu Phe Leu Asn Lys Gln Asp Leu Leu Ala Glu Lys Val Leu
        275                 280                 285
```

```
Ala Gly Lys Ser Lys Ile Glu Asp Tyr Phe Pro Glu Phe Ala Arg Tyr
    290                 295                 300

Thr Thr Pro Glu Asp Ala Thr Pro Glu Pro Gly Glu Asp Pro Arg Val
305                 310                 315                 320

Thr Arg Ala Lys Tyr Phe Ile Arg Asp Glu Phe Leu Arg Ile Ser Thr
                325                 330                 335

Ala Ser Gly Asp Gly Arg His Tyr Cys Tyr Pro His Phe Thr Cys Ala
            340                 345                 350

Val Asp Thr Glu Asn Ile Arg Arg Val Phe Asn Asp Cys Arg Asp Ile
        355                 360                 365

Ile Gln Arg Met His Leu Arg Gln Tyr Glu Leu Leu
    370                 375                 380

<210> SEQ ID NO 57
<211> LENGTH: 354
<212> TYPE: PRT
<213> ORGANISM: Homo sapiens

<400> SEQUENCE: 57

Met Gly Cys Thr Leu Ser Ala Glu Asp Lys Ala Ala Val Glu Arg Ser
1               5                   10                  15

Lys Met Ile Asp Arg Asn Leu Arg Glu Asp Gly Glu Lys Ala Ala Arg
            20                  25                  30

Glu Val Lys Leu Leu Leu Leu Gly Ala Gly Glu Ser Gly Lys Ser Thr
        35                  40                  45

Ile Val Lys Gln Met Lys Ile Ile His Glu Ala Gly Tyr Ser Glu Glu
    50                  55                  60

Glu Cys Lys Gln Tyr Lys Ala Val Val Tyr Ser Asn Thr Ile Gln Ser
65                  70                  75                  80

Ile Ile Ala Ile Ile Arg Ala Met Gly Arg Leu Lys Ile Asp Phe Gly
                85                  90                  95

Asp Ser Ala Arg Ala Asp Asp Ala Arg Gln Leu Phe Val Leu Ala Gly
            100                 105                 110

Ala Ala Glu Glu Gly Phe Met Thr Ala Glu Leu Ala Gly Val Ile Lys
        115                 120                 125

Arg Leu Trp Lys Asp Ser Gly Val Gln Ala Cys Phe Asn Arg Ser Arg
    130                 135                 140

Glu Tyr Gln Leu Asn Asp Ser Ala Ala Tyr Tyr Leu Asn Asp Leu Asp
145                 150                 155                 160

Arg Ile Ala Gln Pro Asn Tyr Ile Pro Thr Gln Gln Asp Val Leu Arg
                165                 170                 175

Thr Arg Val Lys Thr Thr Gly Ile Val Glu Thr His Phe Thr Phe Lys
            180                 185                 190

Asp Leu His Phe Lys Met Phe Asp Val Gly Gly Gln Arg Ser Glu Arg
        195                 200                 205

Lys Lys Trp Ile His Cys Phe Glu Gly Val Thr Ala Ile Ile Phe Cys
    210                 215                 220

Val Ala Leu Ser Asp Tyr Asp Leu Val Leu Ala Glu Asp Glu Glu Met
225                 230                 235                 240

Asn Arg Met His Glu Ser Met Lys Leu Phe Asp Ser Ile Cys Asn Asn
                245                 250                 255

Lys Trp Phe Thr Asp Thr Ser Ile Ile Leu Phe Leu Asn Lys Lys Asp
            260                 265                 270

Leu Phe Glu Glu Lys Ile Lys Lys Ser Pro Leu Thr Ile Cys Tyr Pro
```

```
                275                 280                 285
Glu Tyr Ala Gly Ser Asn Thr Tyr Glu Glu Ala Ala Tyr Ile Gln
            290                 295                 300
Cys Gln Phe Glu Asp Leu Asn Lys Arg Lys Asp Thr Lys Glu Ile Tyr
305                 310                 315                 320
Thr His Phe Thr Cys Ala Thr Asp Thr Lys Asn Val Gln Phe Val Phe
                325                 330                 335
Asp Ala Val Thr Asp Val Ile Ile Lys Asn Asn Leu Lys Asp Cys Gly
                340                 345                 350
Leu Phe

<210> SEQ ID NO 58
<211> LENGTH: 350
<212> TYPE: PRT
<213> ORGANISM: Homo sapiens

<400> SEQUENCE: 58

Met Gly Ala Gly Ala Ser Ala Glu Glu Lys His Ser Arg Glu Leu Glu
1               5                   10                  15
Lys Lys Leu Lys Glu Asp Ala Glu Lys Asp Ala Arg Thr Val Lys Leu
            20                  25                  30
Leu Leu Leu Gly Ala Gly Glu Ser Gly Lys Ser Thr Ile Val Lys Gln
        35                  40                  45
Met Lys Ile Ile His Gln Asp Gly Tyr Ser Leu Glu Glu Cys Leu Glu
    50                  55                  60
Phe Ile Ala Ile Ile Tyr Gly Asn Thr Leu Gln Ser Ile Leu Ala Ile
65                  70                  75                  80
Val Arg Ala Met Thr Thr Leu Asn Ile Gln Tyr Gly Asp Ser Ala Arg
                85                  90                  95
Gln Asp Asp Ala Arg Lys Leu Met His Met Ala Asp Thr Ile Glu Glu
            100                 105                 110
Gly Thr Met Pro Lys Glu Met Ser Asp Ile Ile Gln Arg Leu Trp Lys
        115                 120                 125
Asp Ser Gly Ile Gln Ala Cys Phe Glu Arg Ala Ser Glu Tyr Gln Leu
130                 135                 140
Asn Asp Ser Ala Gly Tyr Tyr Leu Ser Asp Leu Glu Arg Leu Val Thr
145                 150                 155                 160
Pro Gly Tyr Val Pro Thr Glu Gln Asp Val Leu Arg Ser Arg Val Lys
                165                 170                 175
Thr Thr Gly Ile Ile Glu Thr Gln Phe Ser Phe Lys Asp Leu Asn Phe
            180                 185                 190
Arg Met Phe Asp Val Gly Gly Gln Arg Ser Glu Arg Lys Lys Trp Ile
        195                 200                 205
His Cys Phe Glu Gly Val Thr Cys Ile Ile Phe Ile Ala Ala Leu Ser
    210                 215                 220
Ala Tyr Asp Met Val Leu Val Glu Asp Asp Glu Val Asn Arg Met His
225                 230                 235                 240
Glu Ser Leu His Leu Phe Asn Ser Ile Cys Asn His Arg Tyr Phe Ala
                245                 250                 255
Thr Thr Ser Ile Val Leu Phe Leu Asn Lys Lys Asp Val Phe Phe Glu
            260                 265                 270
Lys Ile Lys Lys Ala His Leu Ser Ile Cys Phe Pro Asp Tyr Asp Gly
        275                 280                 285
Pro Asn Thr Tyr Glu Asp Ala Gly Asn Tyr Ile Lys Val Gln Phe Leu
```

```
            290                 295                 300
Glu Leu Asn Met Arg Arg Asp Val Lys Glu Ile Tyr Ser His Met Thr
305                 310                 315                 320

Cys Ala Thr Asp Thr Gln Asn Val Lys Phe Val Phe Asp Ala Val Thr
                325                 330                 335

Asp Ile Ile Lys Glu Asn Leu Lys Asp Cys Gly Leu Phe
            340                 345                 350

<210> SEQ ID NO 59
<211> LENGTH: 394
<212> TYPE: PRT
<213> ORGANISM: Bos taurus

<400> SEQUENCE: 59

Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
                20                  25                  30

Asp Lys Gln Val Tyr Arg Ala Thr His Arg Leu Leu Leu Leu Gly Ala
            35                  40                  45

Gly Glu Ser Gly Lys Ser Thr Ile Val Lys Gln Met Arg Ile Leu His
50                  55                  60

Val Asn Gly Phe Asn Gly Glu Gly Gly Glu Glu Asp Pro Gln Ala Ala
65                  70                  75                  80

Arg Ser Asn Ser Asp Gly Glu Lys Ala Thr Lys Val Gln Asp Ile Lys
                85                  90                  95

Asn Asn Leu Lys Glu Ala Ile Glu Thr Ile Val Ala Ala Met Ser Asn
            100                 105                 110

Leu Val Pro Pro Val Glu Leu Ala Asn Pro Glu Asn Gln Phe Arg Val
        115                 120                 125

Asp Tyr Ile Leu Ser Val Met Asn Val Pro Asp Phe Asp Phe Pro Pro
    130                 135                 140

Glu Phe Tyr Glu His Ala Lys Ala Leu Trp Glu Asp Glu Gly Val Arg
145                 150                 155                 160

Ala Cys Tyr Glu Arg Ser Asn Glu Tyr Gln Leu Ile Asp Cys Ala Gln
                165                 170                 175

Tyr Phe Leu Asp Lys Ile Asp Val Ile Lys Gln Asp Asp Tyr Val Pro
            180                 185                 190

Ser Asp Gln Asp Leu Leu Arg Cys Arg Val Leu Thr Ser Gly Ile Phe
        195                 200                 205

Glu Thr Lys Phe Gln Val Asp Lys Val Asn Phe His Met Phe Asp Val
    210                 215                 220

Gly Gly Gln Arg Asp Glu Arg Arg Lys Trp Ile Gln Cys Phe Asn Asp
225                 230                 235                 240

Val Thr Ala Ile Ile Phe Val Val Ala Ser Ser Ser Tyr Asn Met Val
                245                 250                 255

Ile Arg Glu Asp Asn Gln Thr Asn Arg Leu Gln Glu Ala Leu Asn Leu
            260                 265                 270

Phe Lys Ser Ile Trp Asn Asn Arg Trp Leu Arg Thr Ile Ser Val Ile
        275                 280                 285

Leu Phe Leu Asn Lys Gln Asp Leu Leu Ala Glu Lys Val Leu Ala Gly
    290                 295                 300

Lys Ser Lys Ile Glu Asp Tyr Phe Pro Glu Phe Ala Arg Tyr Thr Thr
305                 310                 315                 320
```

```
Pro Glu Asp Ala Thr Pro Glu Pro Gly Glu Asp Pro Arg Val Thr Arg
                325                 330                 335

Ala Lys Tyr Phe Ile Arg Asp Glu Phe Leu Arg Ile Ser Thr Ala Ser
            340                 345                 350

Gly Asp Gly Arg His Tyr Cys Tyr Pro His Phe Thr Cys Ala Val Asp
        355                 360                 365

Thr Glu Asn Ile Arg Arg Val Phe Asn Asp Cys Arg Asp Ile Ile Gln
    370                 375                 380

Arg Met His Leu Arg Gln Tyr Glu Leu Leu
385                 390
```

<210> SEQ ID NO 60
<211> LENGTH: 394
<212> TYPE: PRT
<213> ORGANISM: Rattus norvegicus

<400> SEQUENCE: 60

```
Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
            20                  25                  30

Asp Lys Gln Val Tyr Arg Ala Thr His Arg Leu Leu Leu Leu Gly Ala
        35                  40                  45

Gly Glu Ser Gly Lys Ser Thr Ile Val Lys Gln Met Arg Ile Leu His
    50                  55                  60

Val Asn Gly Phe Asn Gly Glu Gly Gly Glu Glu Asp Pro Gln Ala Ala
65                  70                  75                  80

Arg Ser Asn Ser Asp Gly Glu Lys Ala Thr Lys Val Gln Asp Ile Lys
                85                  90                  95

Asn Asn Leu Lys Glu Ala Ile Glu Thr Ile Val Ala Ala Met Ser Asn
            100                 105                 110

Leu Val Pro Pro Val Glu Leu Ala Asn Pro Glu Asn Gln Phe Arg Val
        115                 120                 125

Asp Tyr Ile Leu Ser Val Met Asn Val Pro Asn Phe Asp Phe Pro Pro
    130                 135                 140

Glu Phe Tyr Glu His Ala Lys Ala Leu Trp Glu Asp Glu Gly Val Arg
145                 150                 155                 160

Ala Cys Tyr Glu Arg Ser Asn Glu Tyr Gln Leu Ile Asp Cys Ala Gln
                165                 170                 175

Tyr Phe Leu Asp Lys Ile Asp Val Ile Lys Gln Ala Asp Tyr Val Pro
            180                 185                 190

Ser Asp Gln Asp Leu Leu Arg Cys Arg Val Leu Thr Ser Gly Ile Phe
        195                 200                 205

Glu Thr Lys Phe Gln Val Asp Lys Val Asn Phe His Met Phe Asp Val
    210                 215                 220

Gly Gly Gln Arg Asp Glu Arg Arg Lys Trp Ile Gln Cys Phe Asn Asp
225                 230                 235                 240

Val Thr Ala Ile Ile Phe Val Val Ala Ser Ser Ser Tyr Asn Met Val
                245                 250                 255

Ile Arg Glu Asp Asn Gln Thr Asn Arg Leu Gln Glu Ala Leu Asn Leu
            260                 265                 270

Phe Lys Ser Ile Trp Asn Asn Arg Trp Leu Arg Thr Ile Ser Val Ile
        275                 280                 285

Leu Phe Leu Asn Lys Gln Asp Leu Leu Ala Glu Lys Val Leu Ala Gly
    290                 295                 300
```

```
Lys Ser Lys Ile Glu Asp Tyr Phe Pro Glu Phe Ala Arg Tyr Thr Thr
305                 310                 315                 320

Pro Glu Asp Ala Thr Pro Glu Pro Gly Glu Asp Pro Arg Val Thr Arg
                325                 330                 335

Ala Lys Tyr Phe Ile Arg Asp Glu Phe Leu Arg Ile Ser Thr Ala Ser
                340                 345                 350

Gly Asp Gly Arg His Tyr Cys Tyr Pro His Phe Thr Cys Ala Val Asp
            355                 360                 365

Thr Glu Asn Ile Arg Arg Val Phe Asn Asp Cys Arg Asp Ile Ile Gln
        370                 375                 380

Arg Met His Leu Arg Gln Tyr Glu Leu Leu
385                 390

<210> SEQ ID NO 61
<211> LENGTH: 394
<212> TYPE: PRT
<213> ORGANISM: Mus musculus

<400> SEQUENCE: 61

Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
            20                  25                  30

Asp Lys Gln Val Tyr Arg Ala Thr His Arg Leu Leu Leu Leu Gly Ala
        35                  40                  45

Gly Glu Ser Gly Lys Ser Thr Ile Val Lys Gln Met Arg Ile Leu His
    50                  55                  60

Val Asn Gly Phe Asn Gly Glu Gly Gly Glu Glu Asp Pro Gln Ala Ala
65                  70                  75                  80

Arg Ser Asn Ser Asp Gly Glu Lys Ala Thr Lys Val Gln Asp Ile Lys
                85                  90                  95

Asn Asn Leu Lys Glu Ala Ile Glu Thr Ile Val Ala Ala Met Ser Asn
            100                 105                 110

Leu Val Pro Pro Val Glu Leu Ala Asn Pro Glu Asn Gln Phe Arg Val
        115                 120                 125

Asp Tyr Ile Leu Ser Val Met Asn Val Pro Asn Phe Asp Phe Pro Pro
    130                 135                 140

Glu Phe Tyr Glu His Ala Lys Ala Leu Trp Glu Asp Glu Gly Val Arg
145                 150                 155                 160

Ala Cys Tyr Glu Arg Ser Asn Glu Tyr Gln Leu Ile Asp Cys Ala Gln
                165                 170                 175

Tyr Phe Leu Asp Lys Ile Asp Val Ile Lys Gln Ala Asp Tyr Val Pro
            180                 185                 190

Ser Asp Gln Asp Leu Leu Arg Cys Arg Val Leu Thr Ser Gly Ile Phe
        195                 200                 205

Glu Thr Lys Phe Gln Val Asp Lys Val Asn Phe His Met Phe Asp Val
    210                 215                 220

Gly Gly Gln Arg Asp Glu Arg Arg Lys Trp Ile Gln Cys Phe Asn Asp
225                 230                 235                 240

Val Thr Ala Ile Ile Phe Val Val Ala Ser Ser Tyr Asn Met Val
                245                 250                 255

Ile Arg Glu Asp Asn Gln Thr Asn Arg Leu Gln Glu Ala Leu Asn Leu
            260                 265                 270

Phe Lys Ser Ile Trp Asn Asn Arg Trp Leu Arg Thr Ile Ser Val Ile
```

```
                   275                 280                 285
Leu Phe Leu Asn Lys Gln Asp Leu Leu Ala Glu Lys Val Leu Ala Gly
            290                 295                 300
Lys Ser Lys Ile Glu Asp Tyr Phe Pro Glu Phe Ala Arg Tyr Thr Thr
305                 310                 315                 320
Pro Glu Asp Ala Thr Pro Glu Pro Gly Glu Asp Pro Arg Val Thr Arg
                325                 330                 335
Ala Lys Tyr Phe Ile Arg Asp Glu Phe Leu Arg Ile Ser Thr Ala Ser
            340                 345                 350
Gly Asp Gly Arg His Tyr Cys Tyr Pro His Phe Thr Cys Ala Val Asp
                355                 360                 365
Thr Glu Asn Ile Arg Arg Val Phe Asn Asp Cys Arg Asp Ile Ile Gln
            370                 375                 380
Arg Met His Leu Arg Gln Tyr Glu Leu Leu
385                 390

<210> SEQ ID NO 62
<211> LENGTH: 340
<212> TYPE: PRT
<213> ORGANISM: Bos taurus

<400> SEQUENCE: 62

Met Ser Glu Leu Asp Gln Leu Arg Gln Glu Ala Glu Gln Leu Lys Asn
1               5                   10                  15
Gln Ile Arg Asp Ala Arg Lys Ala Cys Ala Asp Ala Thr Leu Ser Gln
            20                  25                  30
Ile Thr Asn Asn Ile Asp Pro Val Gly Arg Ile Gln Met Arg Thr Arg
        35                  40                  45
Arg Thr Leu Arg Gly His Leu Ala Lys Ile Tyr Ala Met His Trp Gly
    50                  55                  60
Thr Asp Ser Arg Leu Leu Val Ser Ala Ser Gln Asp Gly Lys Leu Ile
65                  70                  75                  80
Ile Trp Asp Ser Tyr Thr Thr Asn Lys Val His Ala Ile Pro Leu Arg
                85                  90                  95
Ser Ser Trp Val Met Thr Cys Ala Tyr Ala Pro Ser Gly Asn Tyr Val
            100                 105                 110
Ala Cys Gly Gly Leu Asp Asn Ile Cys Ser Ile Tyr Asn Leu Lys Thr
        115                 120                 125
Arg Glu Gly Asn Val Arg Val Ser Arg Glu Leu Ala Gly His Thr Gly
    130                 135                 140
Tyr Leu Ser Cys Cys Arg Phe Leu Asp Asp Asn Gln Ile Val Thr Ser
145                 150                 155                 160
Ser Gly Asp Thr Thr Cys Ala Leu Trp Asp Ile Glu Thr Gly Gln Gln
                165                 170                 175
Thr Thr Thr Phe Thr Gly His Thr Gly Asp Val Met Ser Leu Ser Leu
            180                 185                 190
Ala Pro Asp Thr Arg Leu Phe Val Ser Gly Ala Cys Asp Ala Ser Ala
        195                 200                 205
Lys Leu Trp Asp Val Arg Glu Gly Met Cys Arg Gln Thr Phe Thr Gly
    210                 215                 220
His Glu Ser Asp Ile Asn Ala Ile Cys Phe Phe Pro Asn Gly Asn Ala
225                 230                 235                 240
Phe Ala Thr Gly Ser Asp Asp Ala Thr Cys Arg Leu Phe Asp Leu Arg
                245                 250                 255
```

```
Ala Asp Gln Glu Leu Met Thr Tyr Ser His Asp Asn Ile Ile Cys Gly
            260                 265                 270

Ile Thr Ser Val Ser Phe Ser Lys Ser Gly Arg Leu Leu Leu Ala Gly
        275                 280                 285

Tyr Asp Asp Phe Asn Cys Asn Val Trp Asp Ala Leu Lys Ala Asp Arg
    290                 295                 300

Ala Gly Val Leu Ala Gly His Asp Asn Arg Val Ser Cys Leu Gly Val
305                 310                 315                 320

Thr Asp Asp Gly Met Ala Val Ala Thr Gly Ser Trp Asp Ser Phe Leu
                325                 330                 335

Lys Ile Trp Asn
            340

<210> SEQ ID NO 63
<211> LENGTH: 340
<212> TYPE: PRT
<213> ORGANISM: Homo sapiens

<400> SEQUENCE: 63

Met Ser Glu Leu Asp Gln Leu Arg Gln Glu Ala Glu Gln Leu Lys Asn
1               5                   10                  15

Gln Ile Arg Asp Ala Arg Lys Ala Cys Ala Asp Ala Thr Leu Ser Gln
            20                  25                  30

Ile Thr Asn Asn Ile Asp Pro Val Gly Arg Ile Gln Met Arg Thr Arg
        35                  40                  45

Arg Thr Leu Arg Gly His Leu Ala Lys Ile Tyr Ala Met His Trp Gly
    50                  55                  60

Thr Asp Ser Arg Leu Leu Val Ser Ala Ser Gln Asp Gly Lys Leu Ile
65                  70                  75                  80

Ile Trp Asp Ser Tyr Thr Thr Asn Lys Val His Ala Ile Pro Leu Arg
                85                  90                  95

Ser Ser Trp Val Met Thr Cys Ala Tyr Ala Pro Ser Gly Asn Tyr Val
            100                 105                 110

Ala Cys Gly Gly Leu Asp Asn Ile Cys Ser Ile Tyr Asn Leu Lys Thr
        115                 120                 125

Arg Glu Gly Asn Val Arg Val Ser Arg Glu Leu Ala Gly His Thr Gly
    130                 135                 140

Tyr Leu Ser Cys Cys Arg Phe Leu Asp Asp Asn Gln Ile Val Thr Ser
145                 150                 155                 160

Ser Gly Asp Thr Thr Cys Ala Leu Trp Asp Ile Glu Thr Gly Gln Gln
                165                 170                 175

Thr Thr Thr Phe Thr Gly His Thr Gly Asp Val Met Ser Leu Ser Leu
            180                 185                 190

Ala Pro Asp Thr Arg Leu Phe Val Ser Gly Ala Cys Asp Ala Ser Ala
        195                 200                 205

Lys Leu Trp Asp Val Arg Glu Gly Met Cys Arg Gln Thr Phe Thr Gly
    210                 215                 220

His Glu Ser Asp Ile Asn Ala Ile Cys Phe Phe Pro Asn Gly Asn Ala
225                 230                 235                 240

Phe Ala Thr Gly Ser Asp Asp Ala Thr Cys Arg Leu Phe Asp Leu Arg
                245                 250                 255

Ala Asp Gln Glu Leu Met Thr Tyr Ser His Asp Asn Ile Ile Cys Gly
            260                 265                 270

Ile Thr Ser Val Ser Phe Ser Lys Ser Gly Arg Leu Leu Leu Ala Gly
        275                 280                 285
```

```
Tyr Asp Asp Phe Asn Cys Asn Val Trp Asp Ala Leu Lys Ala Asp Arg
            290                 295                 300

Ala Gly Val Leu Ala Gly His Asp Asn Arg Val Ser Cys Leu Gly Val
305                 310                 315                 320

Thr Asp Asp Gly Met Ala Val Ala Thr Gly Ser Trp Asp Ser Phe Leu
                325                 330                 335

Lys Ile Trp Asn
            340

<210> SEQ ID NO 64
<211> LENGTH: 340
<212> TYPE: PRT
<213> ORGANISM: Rattus norvegicus

<400> SEQUENCE: 64

Met Ser Glu Leu Asp Gln Leu Arg Gln Glu Ala Glu Gln Leu Lys Asn
1               5                   10                  15

Gln Ile Arg Asp Ala Arg Lys Ala Cys Ala Asp Ala Thr Leu Ser Gln
                20                  25                  30

Ile Thr Asn Asn Ile Asp Pro Val Gly Arg Ile Gln Met Arg Thr Arg
            35                  40                  45

Arg Thr Leu Arg Gly His Leu Ala Lys Ile Tyr Ala Met His Trp Gly
        50                  55                  60

Thr Asp Ser Arg Leu Leu Val Ser Ala Ser Gln Asp Gly Lys Leu Ile
65                  70                  75                  80

Ile Trp Asp Ser Tyr Thr Thr Asn Lys Val His Ala Ile Pro Leu Arg
                85                  90                  95

Ser Ser Trp Val Met Thr Cys Ala Tyr Ala Pro Ser Gly Asn Tyr Val
            100                 105                 110

Ala Cys Gly Gly Leu Asp Asn Ile Cys Ser Ile Tyr Asn Leu Lys Thr
        115                 120                 125

Arg Glu Gly Asn Val Arg Val Ser Arg Glu Leu Ala Gly His Thr Gly
    130                 135                 140

Tyr Leu Ser Cys Cys Arg Phe Leu Asp Asp Asn Gln Ile Val Thr Ser
145                 150                 155                 160

Ser Gly Asp Thr Thr Cys Ala Leu Trp Asp Ile Glu Thr Gly Gln Gln
                165                 170                 175

Thr Thr Thr Phe Thr Gly His Thr Gly Asp Val Met Ser Leu Ser Leu
            180                 185                 190

Ala Pro Asp Thr Arg Leu Phe Val Ser Gly Ala Cys Asp Ala Ser Ala
        195                 200                 205

Lys Leu Trp Asp Val Arg Glu Gly Met Cys Arg Gln Thr Phe Thr Gly
    210                 215                 220

His Glu Ser Asp Ile Asn Ala Ile Cys Phe Phe Pro Asn Gly Asn Ala
225                 230                 235                 240

Phe Ala Thr Gly Ser Asp Asp Ala Thr Cys Arg Leu Phe Asp Leu Arg
                245                 250                 255

Ala Asp Gln Glu Leu Met Thr Tyr Ser His Asp Asn Ile Ile Cys Gly
            260                 265                 270

Ile Thr Ser Val Ser Phe Ser Lys Ser Gly Arg Leu Leu Leu Ala Gly
        275                 280                 285

Tyr Asp Asp Phe Asn Cys Asn Val Trp Asp Ala Leu Lys Ala Asp Arg
    290                 295                 300

Ala Gly Val Leu Ala Gly His Asp Asn Arg Val Ser Cys Leu Gly Val
```

```
                305                 310                 315                 320
Thr Asp Asp Gly Met Ala Val Ala Thr Gly Ser Trp Asp Ser Phe Leu
                    325                 330                 335
Lys Ile Trp Asn
            340

<210> SEQ ID NO 65
<211> LENGTH: 340
<212> TYPE: PRT
<213> ORGANISM: Mus musculus

<400> SEQUENCE: 65

Met Ser Glu Leu Asp Gln Leu Arg Gln Glu Ala Glu Gln Leu Lys Asn
1               5                   10                  15
Gln Ile Arg Asp Ala Arg Lys Ala Cys Ala Asp Ala Thr Leu Ser Gln
                20                  25                  30
Ile Thr Asn Asn Ile Asp Pro Val Gly Arg Ile Gln Met Arg Thr Arg
            35                  40                  45
Arg Thr Leu Arg Gly His Leu Ala Lys Ile Tyr Ala Met His Trp Gly
        50                  55                  60
Thr Asp Ser Arg Leu Leu Val Ser Ala Ser Gln Asp Gly Lys Leu Ile
65                  70                  75                  80
Ile Trp Asp Ser Tyr Thr Thr Asn Lys Val His Ala Ile Pro Leu Arg
                85                  90                  95
Ser Ser Trp Val Met Thr Cys Ala Tyr Ala Pro Ser Gly Asn Tyr Val
                100                 105                 110
Ala Cys Gly Gly Leu Asp Asn Ile Cys Ser Ile Tyr Asn Leu Lys Thr
            115                 120                 125
Arg Glu Gly Asn Val Arg Val Ser Arg Glu Leu Ala Gly His Thr Gly
        130                 135                 140
Tyr Leu Ser Cys Cys Arg Phe Leu Asp Asp Asn Gln Ile Val Thr Ser
145                 150                 155                 160
Ser Gly Asp Thr Thr Cys Ala Leu Trp Asp Ile Glu Thr Gly Gln Gln
                165                 170                 175
Thr Thr Thr Phe Thr Gly His Thr Gly Asp Val Met Ser Leu Ser Leu
            180                 185                 190
Ala Pro Asp Thr Arg Leu Phe Val Ser Gly Ala Cys Asp Ala Ser Ala
        195                 200                 205
Lys Leu Trp Asp Val Arg Glu Gly Met Cys Arg Gln Thr Phe Thr Gly
210                 215                 220
His Glu Ser Asp Ile Asn Ala Ile Cys Phe Phe Pro Asn Gly Asn Ala
225                 230                 235                 240
Phe Ala Thr Gly Ser Asp Asp Ala Thr Cys Arg Leu Phe Asp Leu Arg
                245                 250                 255
Ala Asp Gln Glu Leu Met Thr Tyr Ser His Asp Asn Ile Ile Cys Gly
            260                 265                 270
Ile Thr Ser Val Ser Phe Ser Lys Ser Gly Arg Leu Leu Leu Ala Gly
        275                 280                 285
Tyr Asp Asp Phe Asn Cys Asn Val Trp Asp Ala Leu Lys Ala Asp Arg
290                 295                 300
Ala Gly Val Leu Ala Gly His Asp Asn Arg Val Ser Cys Leu Gly Val
305                 310                 315                 320
Thr Asp Asp Gly Met Ala Val Ala Thr Gly Ser Trp Asp Ser Phe Leu
                325                 330                 335
```

```
Lys Ile Trp Asn
            340

<210> SEQ ID NO 66
<211> LENGTH: 71
<212> TYPE: PRT
<213> ORGANISM: Bos taurus

<400> SEQUENCE: 66

Met Ala Ser Asn Asn Thr Ala Ser Ile Ala Gln Ala Arg Lys Leu Val
1               5                   10                  15

Glu Gln Leu Lys Met Glu Ala Asn Ile Asp Arg Ile Lys Val Ser Lys
            20                  25                  30

Ala Ala Ala Asp Leu Met Ala Tyr Cys Glu Ala His Ala Lys Glu Asp
        35                  40                  45

Pro Leu Leu Thr Pro Val Pro Ala Ser Glu Asn Pro Phe Arg Glu Lys
    50                  55                  60

Lys Phe Phe Cys Ala Ile Leu
65                  70

<210> SEQ ID NO 67
<211> LENGTH: 71
<212> TYPE: PRT
<213> ORGANISM: Mus musculus

<400> SEQUENCE: 67

Met Ala Ser Asn Asn Thr Ala Ser Ile Ala Gln Ala Arg Lys Leu Val
1               5                   10                  15

Glu Gln Leu Lys Met Glu Ala Asn Ile Asp Arg Ile Lys Val Ser Lys
            20                  25                  30

Ala Ala Ala Asp Leu Met Ala Tyr Cys Glu Ala His Ala Lys Glu Asp
        35                  40                  45

Pro Leu Leu Thr Pro Val Pro Ala Ser Glu Asn Pro Phe Arg Glu Lys
    50                  55                  60

Lys Phe Phe Cys Ala Ile Leu
65                  70

<210> SEQ ID NO 68
<211> LENGTH: 71
<212> TYPE: PRT
<213> ORGANISM: Homo sapiens

<400> SEQUENCE: 68

Met Ala Ser Asn Asn Thr Ala Ser Ile Ala Gln Ala Arg Lys Leu Val
1               5                   10                  15

Glu Gln Leu Lys Met Glu Ala Asn Ile Asp Arg Ile Lys Val Ser Lys
            20                  25                  30

Ala Ala Ala Asp Leu Met Ala Tyr Cys Glu Ala His Ala Lys Glu Asp
        35                  40                  45

Pro Leu Leu Thr Pro Val Pro Ala Ser Glu Asn Pro Phe Arg Glu Lys
    50                  55                  60

Lys Phe Phe Cys Ala Ile Leu
65                  70

<210> SEQ ID NO 69
<211> LENGTH: 514
<212> TYPE: PRT
<213> ORGANISM: Artificial
<220> FEATURE:
<223> OTHER INFORMATION: T4L-Beta2AR fusion construct
```

<400> SEQUENCE: 69

Asp Tyr Lys Asp Asp Asp Ala Glu Asn Leu Tyr Phe Gln Gly Asn
1               5                   10                  15

Ile Phe Glu Met Leu Arg Ile Asp Glu Gly Leu Arg Leu Lys Ile Tyr
            20                  25                  30

Lys Asp Thr Glu Gly Tyr Tyr Thr Ile Gly Ile Gly His Leu Leu Thr
            35                  40                  45

Lys Ser Pro Ser Leu Asn Ala Ala Lys Ser Glu Leu Asp Lys Ala Ile
    50                  55                  60

Gly Arg Asn Thr Asn Gly Val Ile Thr Lys Asp Glu Ala Glu Lys Leu
65                  70                  75                  80

Phe Asn Gln Asp Val Asp Ala Ala Val Arg Gly Ile Leu Arg Asn Ala
                85                  90                  95

Lys Leu Lys Pro Val Tyr Asp Ser Leu Asp Ala Val Arg Arg Ala Ala
            100                 105                 110

Leu Ile Asn Met Val Phe Gln Met Gly Glu Thr Gly Val Ala Gly Phe
            115                 120                 125

Thr Asn Ser Leu Arg Met Leu Gln Gln Lys Arg Trp Asp Glu Ala Ala
130                 135                 140

Val Asn Leu Ala Lys Ser Arg Trp Tyr Asn Gln Thr Pro Asn Arg Ala
145                 150                 155                 160

Lys Arg Val Ile Thr Thr Phe Arg Thr Gly Thr Trp Asp Ala Tyr Ala
                165                 170                 175

Ala Asp Glu Val Trp Val Gly Met Gly Ile Val Met Ser Leu Ile
            180                 185                 190

Val Leu Ala Ile Val Phe Gly Asn Val Leu Val Ile Thr Ala Ile Ala
            195                 200                 205

Lys Phe Glu Arg Leu Gln Thr Val Thr Asn Tyr Phe Ile Thr Ser Leu
210                 215                 220

Ala Cys Ala Asp Leu Val Met Gly Leu Ala Val Val Pro Phe Gly Ala
225                 230                 235                 240

Ala His Ile Leu Thr Lys Thr Trp Thr Phe Gly Asn Phe Trp Cys Glu
                245                 250                 255

Phe Trp Thr Ser Ile Asp Val Leu Cys Val Thr Ala Ser Ile Glu Thr
            260                 265                 270

Leu Cys Val Ile Ala Val Asp Arg Tyr Phe Ala Ile Thr Ser Pro Phe
            275                 280                 285

Lys Tyr Gln Ser Leu Leu Thr Lys Asn Lys Ala Arg Val Ile Ile Leu
290                 295                 300

Met Val Trp Ile Val Ser Gly Leu Thr Ser Phe Leu Pro Ile Gln Met
305                 310                 315                 320

His Trp Tyr Arg Ala Thr His Gln Glu Ala Ile Asn Cys Tyr Ala Glu
                325                 330                 335

Glu Thr Cys Cys Asp Phe Phe Thr Asn Gln Ala Tyr Ala Ile Ala Ser
            340                 345                 350

Ser Ile Val Ser Phe Tyr Val Pro Leu Val Ile Met Val Phe Val Tyr
            355                 360                 365

Ser Arg Val Phe Gln Glu Ala Lys Arg Gln Leu Gln Lys Ile Asp Lys
            370                 375                 380

Ser Glu Gly Arg Phe His Val Gln Asn Leu Ser Gln Val Glu Gln Asp
385                 390                 395                 400

Gly Arg Thr Gly His Gly Leu Arg Arg Ser Ser Lys Phe Cys Leu Lys

```
                          405                 410                 415
Glu His Lys Ala Leu Lys Thr Leu Gly Ile Ile Met Gly Thr Phe Thr
                420                 425                 430

Leu Cys Trp Leu Pro Phe Phe Ile Val Asn Ile Val His Val Ile Gln
            435                 440                 445

Asp Asn Leu Ile Arg Lys Glu Val Tyr Ile Leu Leu Asn Trp Ile Gly
        450                 455                 460

Tyr Val Asn Ser Gly Phe Asn Pro Leu Ile Tyr Cys Arg Ser Pro Asp
465                 470                 475                 480

Phe Arg Ile Ala Phe Gln Glu Leu Leu Cys Leu Arg Arg Ser Ser Leu
                485                 490                 495

Lys Ala Tyr Gly Asn Gly Tyr Ser Ser Asn Gly Asn Thr Gly Glu Gln
            500                 505                 510

Ser Gly

<210> SEQ ID NO 70
<211> LENGTH: 8
<212> TYPE: PRT
<213> ORGANISM: Artificial
<220> FEATURE:
<223> OTHER INFORMATION: M1 Flag epitope

<400> SEQUENCE: 70

Asp Tyr Lys Asp Asp Asp Asp Ala
1               5

<210> SEQ ID NO 71
<211> LENGTH: 7
<212> TYPE: PRT
<213> ORGANISM: Artificial
<220> FEATURE:
<223> OTHER INFORMATION: TEV protease recognition sequence

<400> SEQUENCE: 71

Glu Asn Leu Tyr Phe Gln Gly
1               5

<210> SEQ ID NO 72
<211> LENGTH: 413
<212> TYPE: PRT
<213> ORGANISM: Homo sapiens

<400> SEQUENCE: 72

Met Gly Gln Pro Gly Asn Gly Ser Ala Phe Leu Leu Ala Pro Asn Gly
1               5                   10                  15

Ser His Ala Pro Asp His Asp Val Thr Gln Glu Arg Asp Glu Val Trp
            20                  25                  30

Val Val Gly Met Gly Ile Val Met Ser Leu Ile Val Leu Ala Ile Val
        35                  40                  45

Phe Gly Asn Val Leu Val Ile Thr Ala Ile Ala Lys Phe Glu Arg Leu
    50                  55                  60

Gln Thr Val Thr Asn Tyr Phe Ile Thr Ser Leu Ala Cys Ala Asp Leu
65                  70                  75                  80

Val Met Gly Leu Ala Val Val Pro Phe Gly Ala Ala His Ile Leu Met
                85                  90                  95

Lys Met Trp Thr Phe Gly Asn Phe Trp Cys Glu Phe Trp Thr Ser Ile
            100                 105                 110

Asp Val Leu Cys Val Thr Ala Ser Ile Glu Thr Leu Cys Val Ile Ala
        115                 120                 125
```

Val Asp Arg Tyr Phe Ala Ile Thr Ser Pro Phe Lys Tyr Gln Ser Leu
            130                 135                 140

Leu Thr Lys Asn Lys Ala Arg Val Ile Ile Leu Met Val Trp Ile Val
145                 150                 155                 160

Ser Gly Leu Thr Ser Phe Leu Pro Ile Gln Met His Trp Tyr Arg Ala
            165                 170                 175

Thr His Gln Glu Ala Ile Asn Cys Tyr Ala Asn Glu Thr Cys Cys Asp
            180                 185                 190

Phe Phe Thr Asn Gln Ala Tyr Ala Ile Ala Ser Ser Ile Val Ser Phe
            195                 200                 205

Tyr Val Pro Leu Val Ile Met Val Phe Val Tyr Ser Arg Val Phe Gln
            210                 215                 220

Glu Ala Lys Arg Gln Leu Gln Lys Ile Asp Lys Ser Glu Gly Arg Phe
225                 230                 235                 240

His Val Gln Asn Leu Ser Gln Val Glu Gln Asp Gly Arg Thr Gly His
            245                 250                 255

Gly Leu Arg Arg Ser Ser Lys Phe Cys Leu Lys Glu His Lys Ala Leu
            260                 265                 270

Lys Thr Leu Gly Ile Ile Met Gly Thr Phe Thr Leu Cys Trp Leu Pro
            275                 280                 285

Phe Phe Ile Val Asn Ile Val His Val Ile Gln Asp Asn Leu Ile Arg
            290                 295                 300

Lys Glu Val Tyr Ile Leu Leu Asn Trp Ile Gly Tyr Val Asn Ser Gly
305                 310                 315                 320

Phe Asn Pro Leu Ile Tyr Cys Arg Ser Pro Asp Phe Arg Ile Ala Phe
            325                 330                 335

Gln Glu Leu Leu Cys Leu Arg Arg Ser Ser Leu Lys Ala Tyr Gly Asn
            340                 345                 350

Gly Tyr Ser Ser Asn Gly Asn Thr Gly Glu Gln Ser Gly Tyr His Val
            355                 360                 365

Glu Gln Glu Lys Glu Asn Lys Leu Leu Cys Glu Asp Leu Pro Gly Thr
            370                 375                 380

Glu Asp Phe Val Gly His Gln Gly Thr Val Pro Ser Asp Asn Ile Asp
385                 390                 395                 400

Ser Gln Gly Arg Asn Cys Ser Thr Asn Asp Ser Leu Leu
            405                 410

<210> SEQ ID NO 73
<211> LENGTH: 539
<212> TYPE: PRT
<213> ORGANISM: Artificial Sequence
<220> FEATURE:
<223> OTHER INFORMATION: N-terminal T4LV2R construct

<400> SEQUENCE: 73

Asp Tyr Lys Asp Asp Asp Ala Gly Leu Met Ala Ser Thr Thr Ser
1               5                   10                  15

Ala Val Pro Gly His Pro Ser Leu Pro Ser Leu Pro Ser Asn Ser Ser
            20                  25                  30

Gln Glu Arg Pro Leu Asp Thr Asn Ile Phe Glu Met Leu Arg Ile Asp
            35                  40                  45

Glu Gly Leu Arg Leu Lys Ile Tyr Lys Asp Thr Glu Gly Tyr Tyr Thr
            50                  55                  60

Ile Gly Ile Gly His Leu Leu Thr Lys Ser Pro Ser Leu Asn Ala Ala
65                  70                  75                  80

-continued

```
Lys Ser Glu Leu Asp Lys Ala Ile Gly Arg Asn Thr Asn Gly Val Ile
                 85                  90                  95

Thr Lys Asp Glu Ala Glu Lys Leu Phe Asn Gln Asp Val Asp Ala Ala
            100                 105                 110

Val Arg Gly Ile Leu Arg Asn Ala Lys Leu Lys Pro Val Tyr Asp Ser
            115                 120                 125

Leu Asp Ala Val Arg Arg Ala Ala Leu Ile Asn Met Val Phe Gln Met
        130                 135                 140

Gly Glu Thr Gly Val Ala Gly Phe Thr Asn Ser Leu Arg Met Leu Gln
145                 150                 155                 160

Gln Lys Arg Trp Asp Glu Ala Ala Val Asn Leu Ala Lys Ser Arg Trp
                165                 170                 175

Tyr Asn Gln Thr Pro Asn Arg Ala Lys Arg Val Ile Thr Thr Phe Arg
            180                 185                 190

Thr Gly Thr Trp Asp Ala Tyr Arg Asp Pro Leu Leu Ala Arg Ala Glu
        195                 200                 205

Leu Ala Leu Leu Ser Ile Val Phe Val Ala Val Ala Leu Ser Asn Gly
    210                 215                 220

Leu Val Leu Ala Ala Leu Ala Arg Arg Gly Arg Arg Gly His Trp Ala
225                 230                 235                 240

Pro Ile His Val Phe Ile Gly His Leu Cys Leu Ala Asp Leu Ala Val
                245                 250                 255

Ala Leu Phe Gln Val Leu Pro Gln Leu Ala Trp Lys Ala Thr Asp Arg
            260                 265                 270

Phe Arg Gly Pro Asp Ala Leu Cys Arg Ala Val Lys Tyr Leu Gln Met
        275                 280                 285

Val Gly Met Tyr Ala Ser Ser Tyr Met Ile Leu Ala Met Thr Leu Asp
    290                 295                 300

Arg His Arg Ala Ile Cys Arg Pro Met Leu Ala Tyr Arg His Gly Ser
305                 310                 315                 320

Gly Ala His Trp Asn Arg Pro Val Leu Val Ala Trp Ala Phe Ser Leu
                325                 330                 335

Leu Leu Ser Leu Pro Gln Leu Phe Ile Phe Ala Gln Arg Asn Val Glu
            340                 345                 350

Gly Gly Ser Gly Val Thr Asp Cys Trp Ala Cys Phe Ala Glu Pro Trp
        355                 360                 365

Gly Arg Arg Thr Tyr Val Thr Trp Ile Ala Leu Met Val Phe Val Ala
    370                 375                 380

Pro Thr Leu Gly Ile Ala Ala Cys Gln Val Leu Ile Phe Arg Glu Ile
385                 390                 395                 400

His Ala Ser Leu Val Pro Gly Pro Ser Glu Arg Pro Gly Gly Arg Arg
                405                 410                 415

Arg Gly Arg Arg Thr Gly Ser Pro Gly Glu Gly Ala His Val Ser Ala
            420                 425                 430

Ala Val Ala Lys Thr Val Arg Met Thr Leu Val Ile Val Val Val Tyr
        435                 440                 445

Val Leu Cys Trp Ala Pro Phe Phe Leu Val Gln Leu Trp Ala Ala Trp
    450                 455                 460

Asp Pro Glu Ala Pro Leu Glu Gly Ala Pro Phe Val Leu Leu Met Leu
465                 470                 475                 480

Leu Ala Ser Leu Asn Ser Cys Thr Asn Pro Trp Ile Tyr Ala Ser Phe
                485                 490                 495
```

-continued

```
Ser Ser Ser Val Ser Ser Glu Leu Arg Ser Leu Leu Cys Cys Ala Arg
            500             505                 510

Gly Arg Thr Pro Pro Ser Leu Gly Pro Gln Asp Glu Ser Cys Thr Thr
        515                 520                 525

Ala Ser Ser Ser Leu Ala Lys Asp Thr Ser Ser
    530                 535
```